(12) United States Patent
Lafleche et al.

(10) Patent No.: US 12,090,091 B2
(45) Date of Patent: Sep. 17, 2024

(54) PATIENT SUPPORT APPARATUS AND ACCESSORIES THEREFOR

(71) Applicant: Stryker Corporation, Kalamazoo, MI (US)

(72) Inventors: Patrick Lafleche, Kalamazoo, MI (US); James K. Galer, Byron Center, MI (US); Justin Raymond, Jackson, MI (US); Bradley Sommer, Portage, MI (US); Nicole L. Schriemer, Portage, MI (US); Thomas J. Africa, Lebanon, OH (US); Alison Adams Zdan Shields, Portage, MI (US); Annali V. Evling, Portage, MI (US); Sherry L. Jones, Pataskala, OH (US); Lauren C. Angell, Pataskala, OH (US); Ciara Nichole Poolman, Kalamazoo, MI (US)

(73) Assignee: Stryker Corporation, Portage, MI (US)

( * ) Notice: Subject to any disclaimer, the term of this patent is extended or adjusted under 35 U.S.C. 154(b) by 233 days.

(21) Appl. No.: 17/320,688

(22) Filed: May 14, 2021

(65) Prior Publication Data
US 2021/0353476 A1  Nov. 18, 2021

Related U.S. Application Data

(60) Provisional application No. 63/114,217, filed on Nov. 16, 2020, provisional application No. 63/108,600, (Continued)

(51) Int. Cl.
*A61G 1/04* (2006.01)
*A61F 5/37* (2006.01)
*A61G 1/044* (2006.01)

(52) U.S. Cl.
CPC .............. *A61G 1/04* (2013.01); *A61F 5/37* (2013.01); *A61G 1/044* (2013.01); *A61G 2200/14* (2013.01)

(58) Field of Classification Search
CPC . A61G 1/00; A61G 1/04; A61G 1/044; A61G 2200/00; A61G 2200/10;
(Continued)

(56) References Cited

U.S. PATENT DOCUMENTS 2,137,012 A   11/1938  Ellen
2,475,631 A   7/1949   Joshua et al.
(Continued)

FOREIGN PATENT DOCUMENTS

DE   202007016952 U1 *  5/2009  .......... A61F 5/3776
EP   3137031 B1          1/2018
(Continued)

OTHER PUBLICATIONS

US 11,730,654 B2, 08/2023, Wilkie (withdrawn)
International Search report and Written Opinion for Application PCT/US2021/032466, dated Aug. 30, 2021, 13 pages.

*Primary Examiner* — Michelle J Lee
(74) *Attorney, Agent, or Firm* — Warner Norcross + Judd LLP

(57) ABSTRACT

A method of securing a pediatric patient to a patient transport apparatus includes providing an adult harness, coupling the adult harness to the patient support and the frame, providing a pediatric restraint assembly, and coupling the pediatric restraint assembly to the adult harness wherein the pediatric restraint assembly moves with the adult harness.

20 Claims, 111 Drawing Sheets

Related U.S. Application Data filed on Nov. 2, 2020, provisional application No. 63/026,391, filed on May 18, 2020.

(58) Field of Classification Search
CPC .... A61G 2200/14; A61G 7/05; A61G 7/0504; A61F 5/37; A61F 5/3707; A61F 5/3769–3792; B64D 25/00–06; A47D 13/08; A47D 13/086; A47D 15/00; A47D 15/005–008

See application file for complete search history.

(56) References Cited

U.S. PATENT DOCUMENTS

| | | | |
|---|---|---|---|
| 2,741,412 | A | 4/1956 | Hinkle |
| D217,895 | S | 6/1970 | Burleson |
| 4,172,453 | A | 10/1979 | Leckie |
| 4,211,218 | A | 7/1980 | Kendrick |
| 4,226,474 | A | 7/1980 | Rupert et al. |
| D285,383 | S | 9/1986 | Anthony |
| 4,627,428 | A | 12/1986 | Brooks |
| D296,047 | S | 6/1988 | Kucera et al. |
| 4,775,183 | A | 10/1988 | Tsuge et al. |
| 4,832,053 | A | 5/1989 | McCarthy |
| 4,840,144 | A | 6/1989 | Voorhees et al. |
| 4,977,630 | A | 12/1990 | Oswalt et al. |
| 4,979,520 | A | 12/1990 | Boone, Jr. et al. |
| D314,533 | S | 2/1991 | Fossum |
| 5,014,374 | A | 5/1991 | Williams |
| 5,014,724 | A | 5/1991 | Miller |
| 5,056,533 | A | 10/1991 | Solano |
| 5,088,137 | A | 2/1992 | Rose |
| 5,103,537 | A | 4/1992 | Snyder et al. |
| 5,137,334 | A | 8/1992 | Cheney et al. |
| 5,211,186 | A * | 5/1993 | Shoemaker ............ A61G 1/044 5/628 |
| 5,216,772 | A | 6/1993 | Clute |
| 5,366,271 | A | 11/1994 | Johnston et al. |
| 5,383,711 | A | 1/1995 | Houghteling |
| D356,658 | S | 3/1995 | Bernart |
| D357,435 | S | 4/1995 | Cook |
| D364,126 | S | 11/1995 | Ochiai et al. |
| 5,496,092 | A * | 3/1996 | Williams ............ B60N 2/2812 297/256.13 |
| 5,580,126 | A | 12/1996 | Sedlack |
| 5,673,969 | A | 10/1997 | Frazier |
| D389,286 | S | 1/1998 | Celestina-Krevh et al. |
| 5,733,004 | A | 3/1998 | Celestina-Krevh et al. |
| 5,836,650 | A | 11/1998 | Warner, Jr. et al. |
| 5,964,502 | A | 10/1999 | Stephens |
| 6,109,698 | A | 8/2000 | Perez |
| 6,363,936 | B1 | 4/2002 | McCormick et al. |
| 6,457,774 | B2 | 10/2002 | Baloga |
| 6,648,416 | B2 | 11/2003 | O'Connor et al. |
| D491,735 | S | 6/2004 | Kamiki |
| 6,772,764 | B2 | 8/2004 | Chapman |
| 6,863,350 | B1 | 3/2005 | McCulley et al. |
| 6,898,811 | B2 | 5/2005 | Zucker et al. |
| 6,916,066 | B2 | 7/2005 | Sedlack |
| 6,932,429 | B2 | 8/2005 | Kamiki |
| 6,948,219 | B2 | 9/2005 | Kakuda et al. |
| 6,966,087 | B2 | 11/2005 | Robinette |
| 6,968,845 | B2 | 11/2005 | Dubats |
| 6,969,120 | B2 | 11/2005 | Levin |
| 7,140,692 | B2 | 11/2006 | Stoll |
| 7,188,899 | B1 | 3/2007 | McClellan-Derrickson |
| 7,281,285 | B2 | 10/2007 | Zucker et al. |
| 7,300,410 | B1 | 11/2007 | Weber |
| 7,347,494 | B2 * | 3/2008 | Boyle ............ B60N 2/2806 297/254 |
| 7,360,543 | B1 | 4/2008 | Coleman et al. |
| 7,464,989 | B2 | 12/2008 | Merrill |
| 7,469,965 | B2 | 12/2008 | Glover et al. |
| 7,488,038 | B2 | 2/2009 | Boyle et al. |
| 7,644,986 | B2 | 1/2010 | Berger et al. |
| 7,752,722 | B2 | 7/2010 | Calkin |
| 7,770,969 | B2 | 8/2010 | Boyle et al. |
| 7,861,341 | B2 | 1/2011 | Ayette et al. |
| 7,862,117 | B2 | 1/2011 | Hutchinson et al. |
| 7,878,584 | B2 | 2/2011 | Hu et al. |
| 8,001,634 | B2 | 8/2011 | Ayette et al. |
| 8,087,725 | B2 | 1/2012 | Hutchinson et al. |
| 8,096,613 | B2 | 1/2012 | Gibson et al. |
| 8,113,584 | B2 | 2/2012 | Boyle et al. |
| 8,123,294 | B2 | 2/2012 | Hutchinson et al. |
| 8,210,617 | B2 | 7/2012 | Aaron et al. |
| 8,214,975 | B2 | 7/2012 | Calkin |
| 8,220,112 | B2 | 7/2012 | Hofmann et al. |
| D666,525 | S | 9/2012 | Anderson et al. |
| D673,880 | S | 1/2013 | Boothby et al. |
| 8,382,202 | B2 | 2/2013 | Gillett et al. |
| 8,387,844 | B2 | 3/2013 | Wrigley et al. |
| D683,262 | S | 5/2013 | Fitzpatrick et al. |
| 8,439,439 | B2 | 5/2013 | Meeker et al. |
| D699,553 | S | 2/2014 | Geller |
| 8,667,629 | B2 | 3/2014 | Mohr et al. |
| 8,794,709 | B2 | 8/2014 | Kennedy |
| 9,113,721 | B2 | 8/2015 | Dignitti et al. |
| D739,303 | S | 9/2015 | Kinskey |
| 9,120,403 | B2 | 9/2015 | Hutchinson |
| 9,192,248 | B2 | 11/2015 | Wigzell et al. |
| D748,013 | S | 1/2016 | Spater |
| 9,687,083 | B1 | 6/2017 | Romero |
| D815,982 | S | 4/2018 | Chang |
| 10,016,066 | B2 | 7/2018 | Howard |
| 10,080,694 | B1 | 9/2018 | Scheenstra et al. |
| 10,085,902 | B2 | 10/2018 | Chia et al. |
| 10,172,736 | B1 | 1/2019 | Kayser |
| 10,292,878 | B2 | 5/2019 | Perez |
| 10,335,328 | B2 | 7/2019 | Scheenstra et al. |
| D863,101 | S | 10/2019 | Chang |
| 10,464,449 | B2 | 11/2019 | Geist |
| 10,575,658 | B2 | 3/2020 | Romero |
| D896,046 | S | 9/2020 | Spater |
| D896,695 | S | 9/2020 | Falvai |
| 10,786,091 | B2 | 9/2020 | Howard |
| 10,793,031 | B1 | 10/2020 | Daniels et al. |
| D903,527 | S | 12/2020 | Spater |
| D920,159 | S | 5/2021 | Power, II et al. |
| 11,077,822 | B2 | 8/2021 | Macaluso et al. |
| D931,141 | S | 9/2021 | Kosh |
| 11,167,718 | B2 | 11/2021 | Archibald et al. |
| 11,173,812 | B2 | 11/2021 | Maciejczyk |
| 11,186,208 | B2 | 11/2021 | Qian et al. |
| 11,241,344 | B2 | 2/2022 | King et al. |
| 11,439,528 | B2 | 9/2022 | Gilbert, Jr. |
| 11,447,050 | B2 | 9/2022 | Yan et al. |
| 11,447,051 | B2 | 9/2022 | Yan et al. |
| 11,498,460 | B1 | 11/2022 | Rumler |
| 11,517,485 | B2 | 12/2022 | Saxon et al. |
| 11,590,865 | B2 | 2/2023 | Maciejczyk |
| 11,653,721 | B2 | 5/2023 | Jessup et al. |
| 2004/0026901 | A1 | 2/2004 | Yann et al. |
| 2004/0045089 | A1 * | 3/2004 | Zucker ............ A61G 1/04 5/628 |
| 2007/0001495 | A1 * | 1/2007 | Boyle ............ B60N 2/2806 297/484 |
| 2007/0182235 | A1 | 8/2007 | Fonseca De Arruda et al. |
| 2010/0077550 | A1 | 4/2010 | Bertozzi |
| 2010/0163059 | A1 | 7/2010 | Tierney et al. |
| 2010/0175702 | A1 | 7/2010 | West |
| 2010/0242971 | A1 | 9/2010 | McGuigan et al. |
| 2014/0125110 | A1 * | 5/2014 | Kennedy ............ B64D 11/0612 297/483 |
| 2015/0313778 | A1 * | 11/2015 | Chia ............ A61G 1/044 128/876 |
| 2016/0338886 | A1 | 11/2016 | Schroeder et al. |
| 2018/0022241 | A1 | 1/2018 | Jewkes |
| 2019/0126790 | A1 | 5/2019 | Maciejczyk |
| 2019/0247219 | A1 | 8/2019 | Xu et al. |
| 2020/0046583 | A1 | 2/2020 | King et al. |
| 2020/0100930 | A1 | 4/2020 | Gilbert, Jr. |
| 2021/0100699 | A1 | 4/2021 | Scheenstra et al. |

(56) References Cited

U.S. PATENT DOCUMENTS

| | | |
|---|---|---|
| 2022/0160557 A1 | 5/2022 | King et al. |
| 2023/0189968 A1 | 6/2023 | Brechting et al. |
| 2023/0191961 A1 | 6/2023 | Maciejczyk |

FOREIGN PATENT DOCUMENTS

| | | | |
|---|---|---|---|
| KR | 200213740 Y1 | 2/2001 | |
| WO | 97/015469 A1 | 5/1997 | |
| WO | 9947028 A1 | 9/1999 | |
| WO | 0224137 A1 | 3/2002 | |
| WO | 2012/053420 A1 | 4/2012 | |
| WO | 2013014401 A1 | 1/2013 | |
| WO | 2013/158580 A2 | 10/2013 | |
| WO | 2013184007 A1 | 12/2013 | |
| WO | WO-2015030668 A1 * | 3/2015 | ............... A61G 1/04 |
| WO | 2016079350 A1 | 5/2016 | |
| WO | 2021/236443 A1 | 11/2021 | |

* cited by examiner

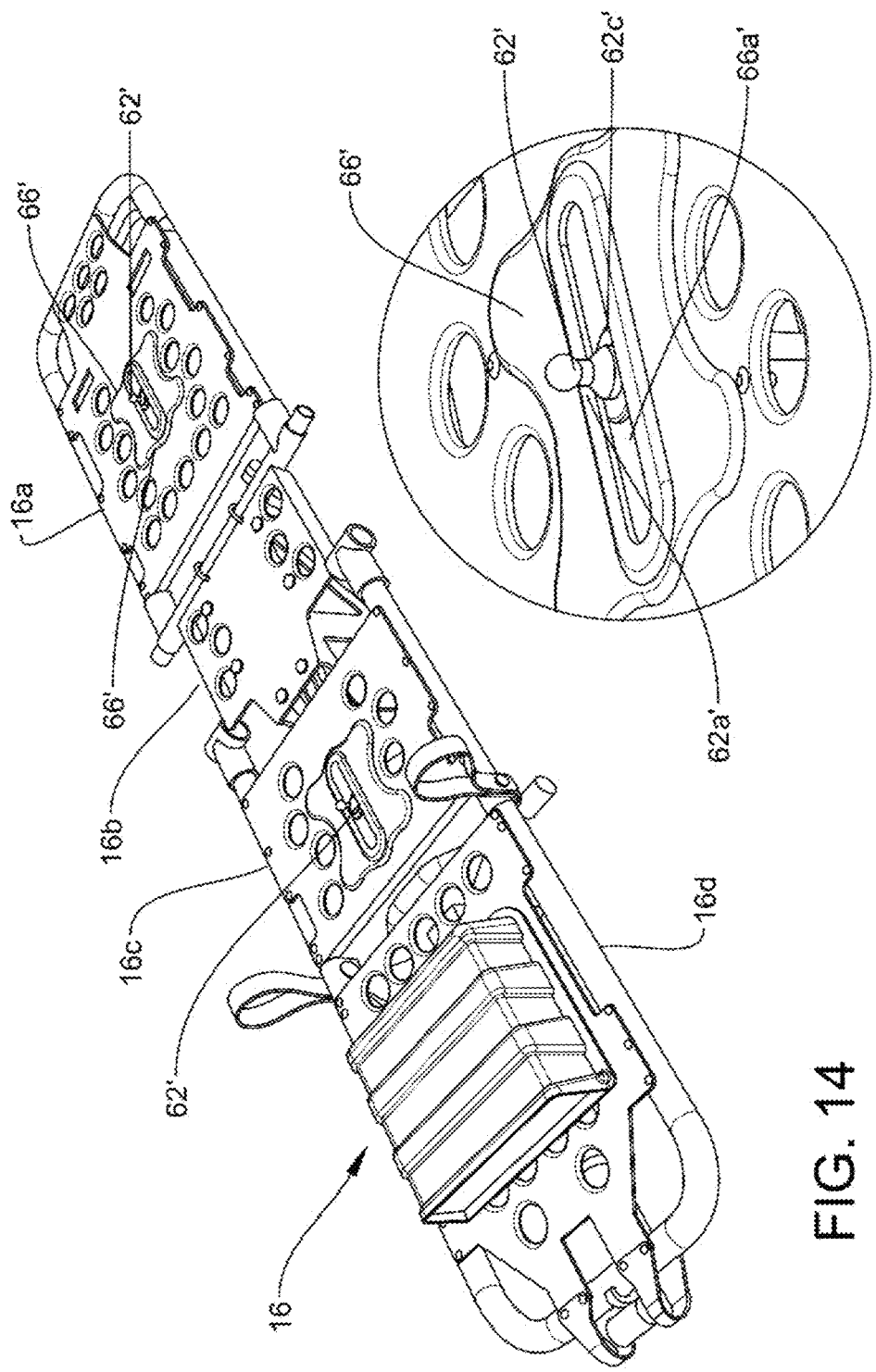

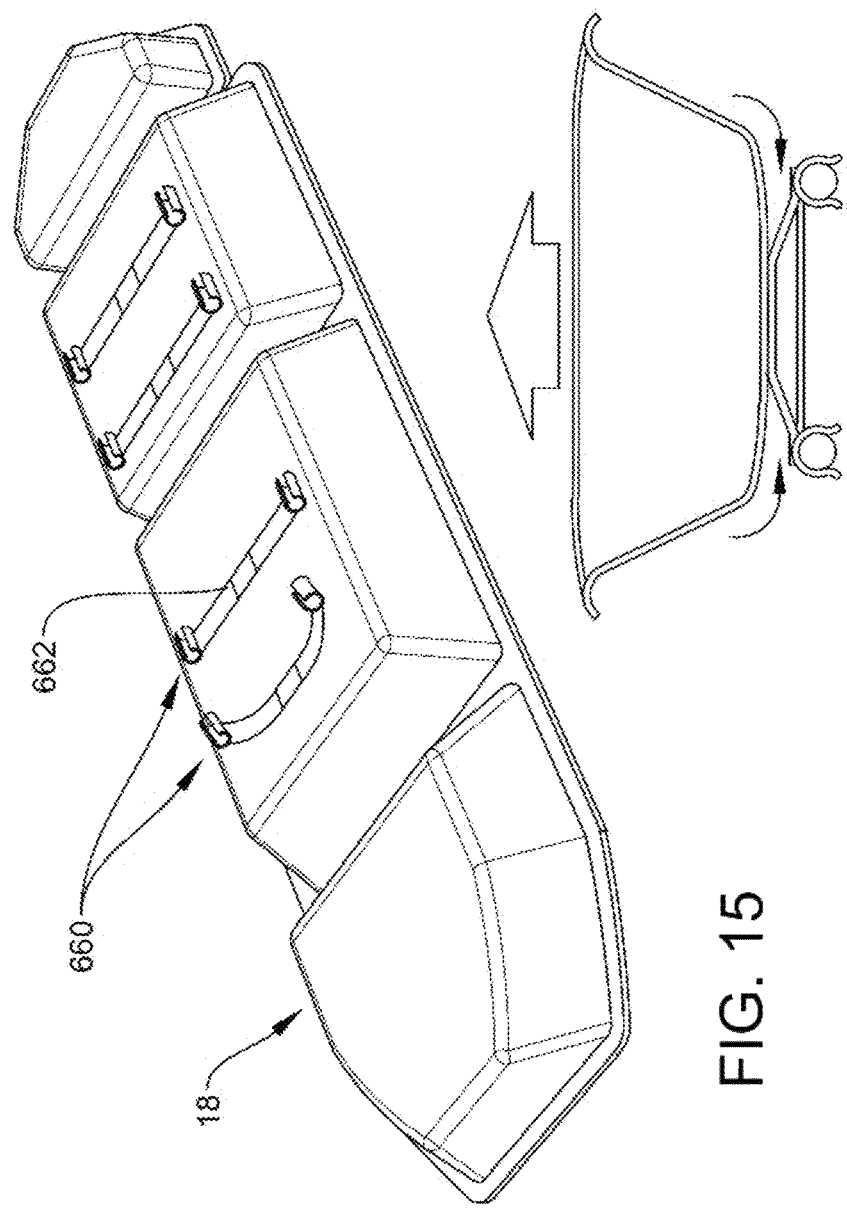
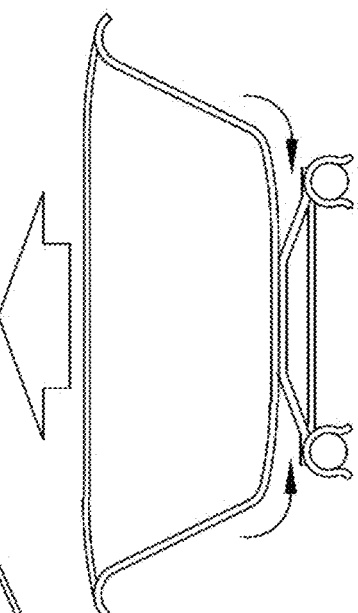
FIG. 15
FIG. 16

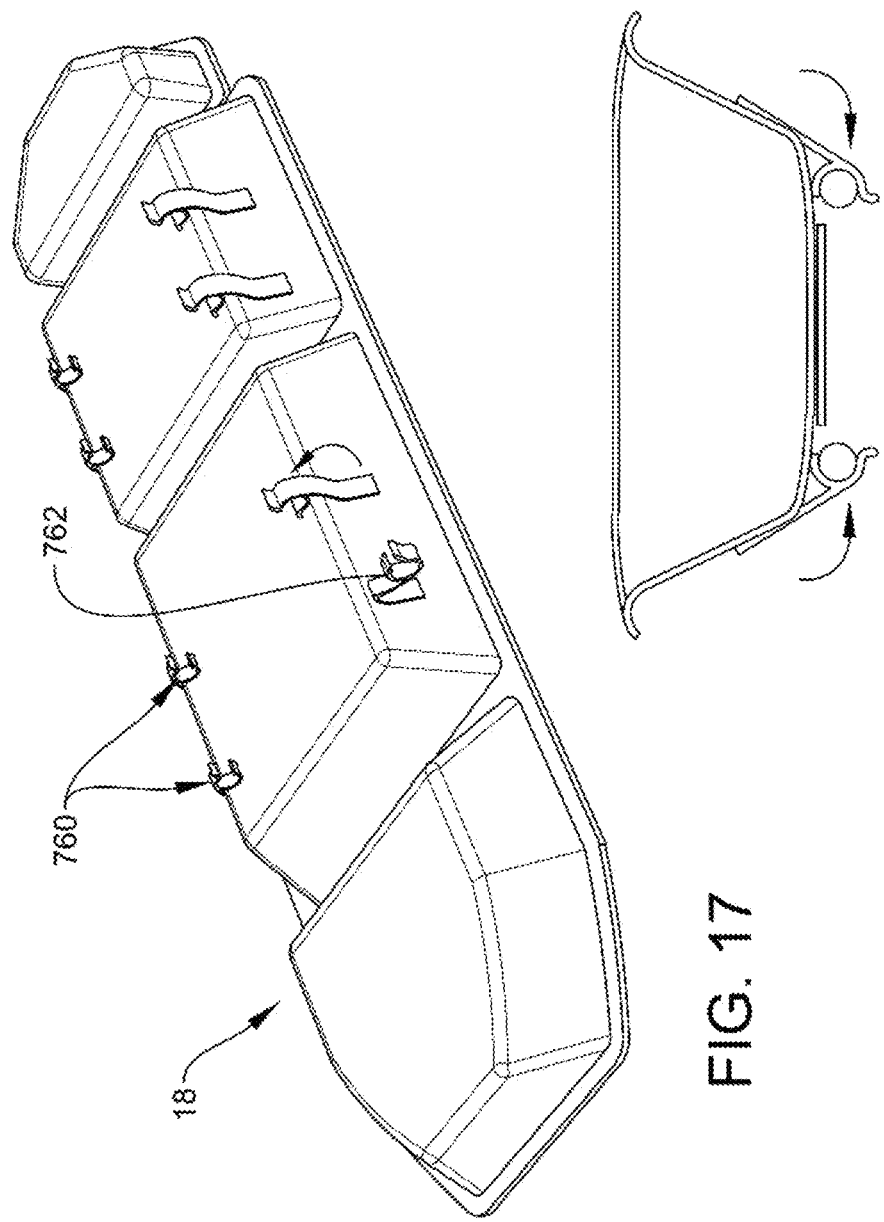

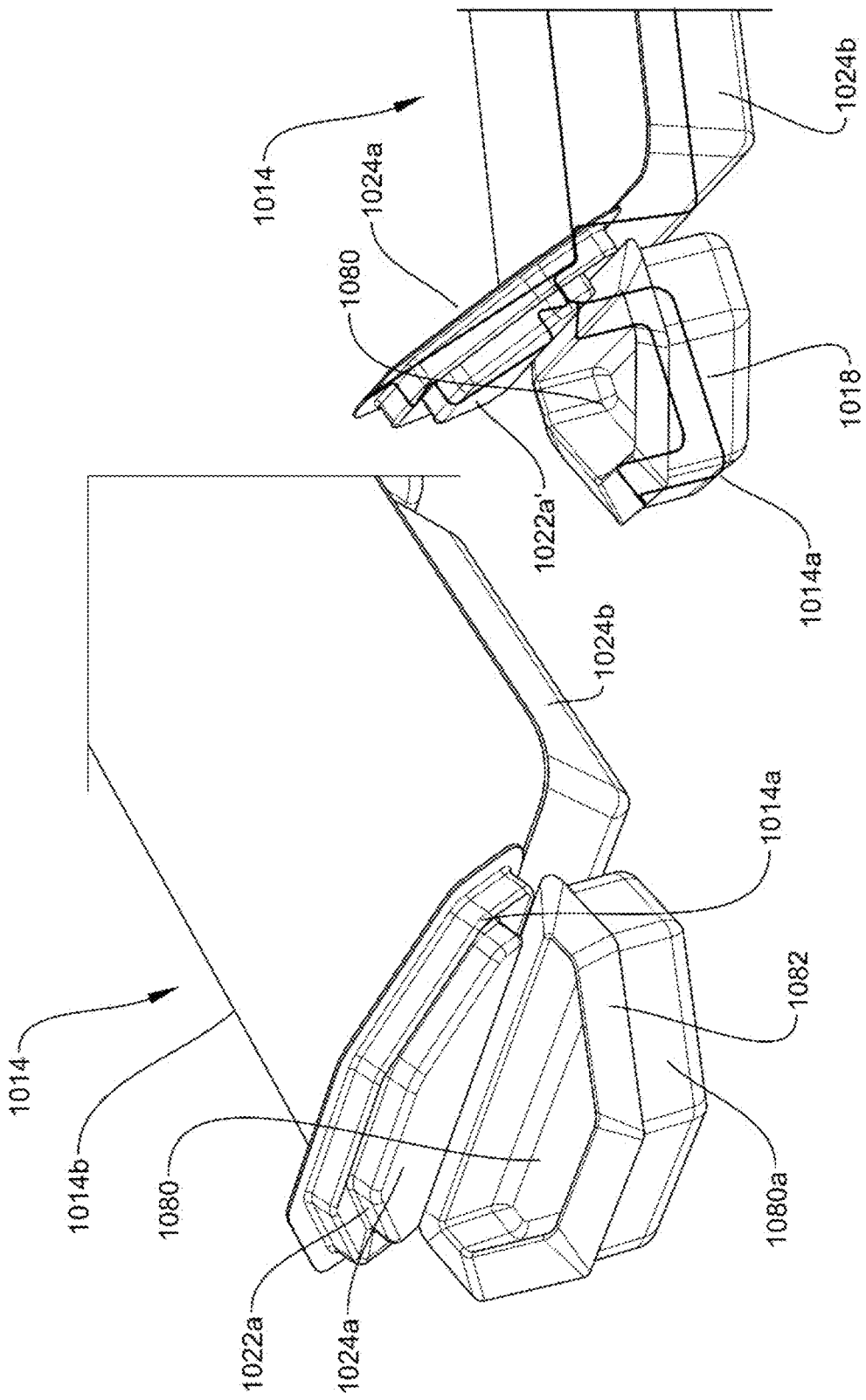

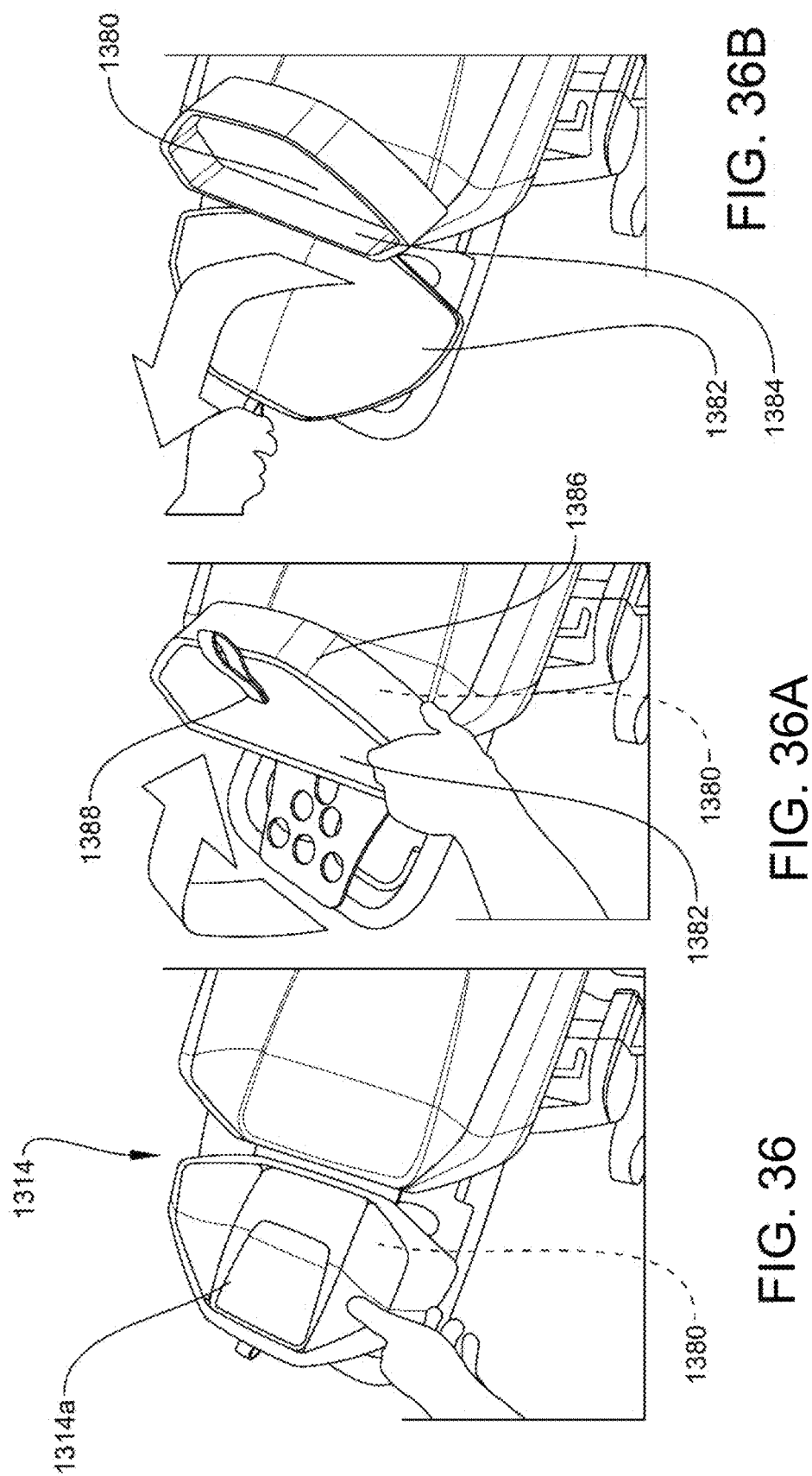

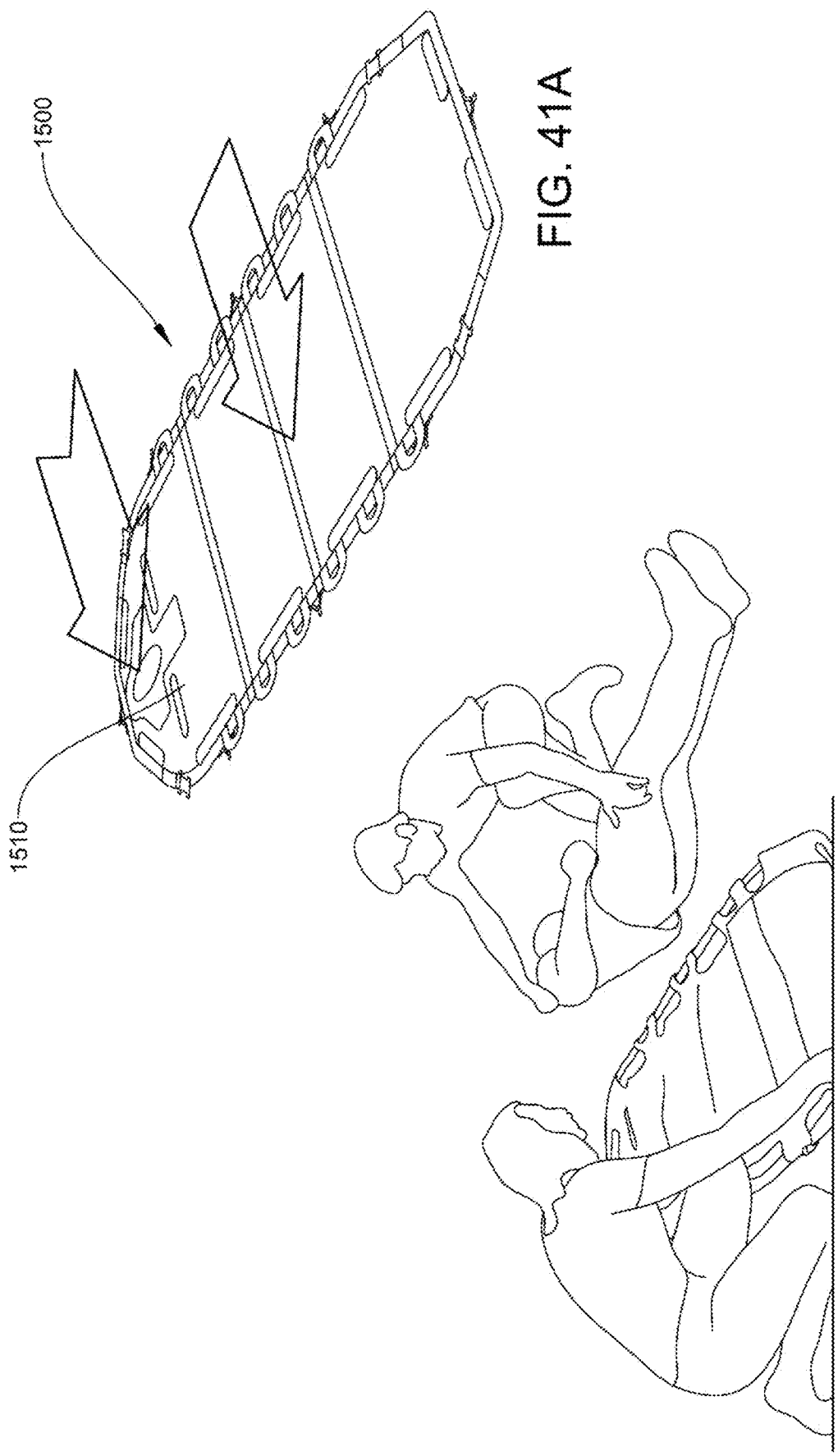

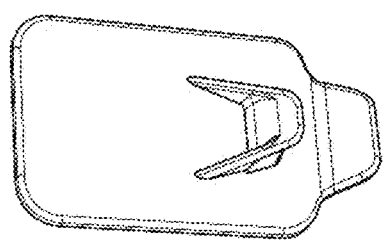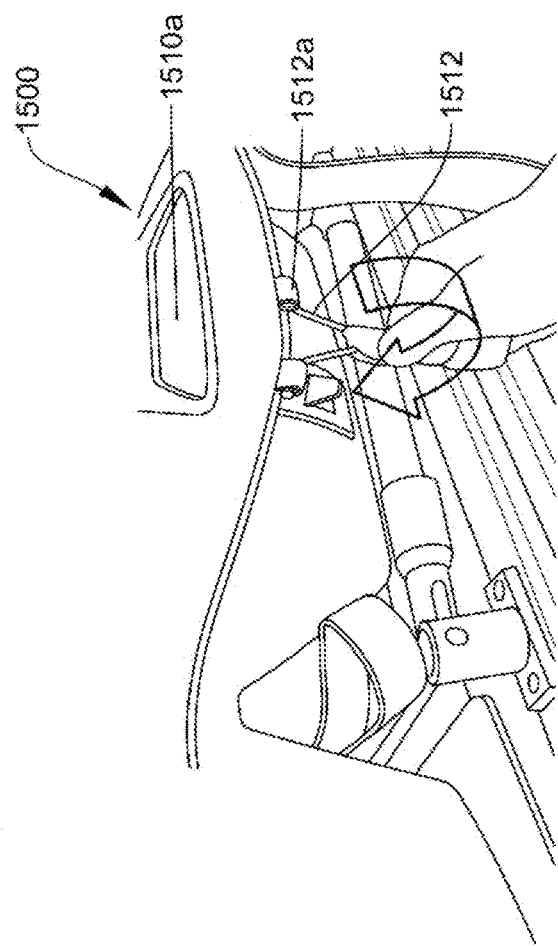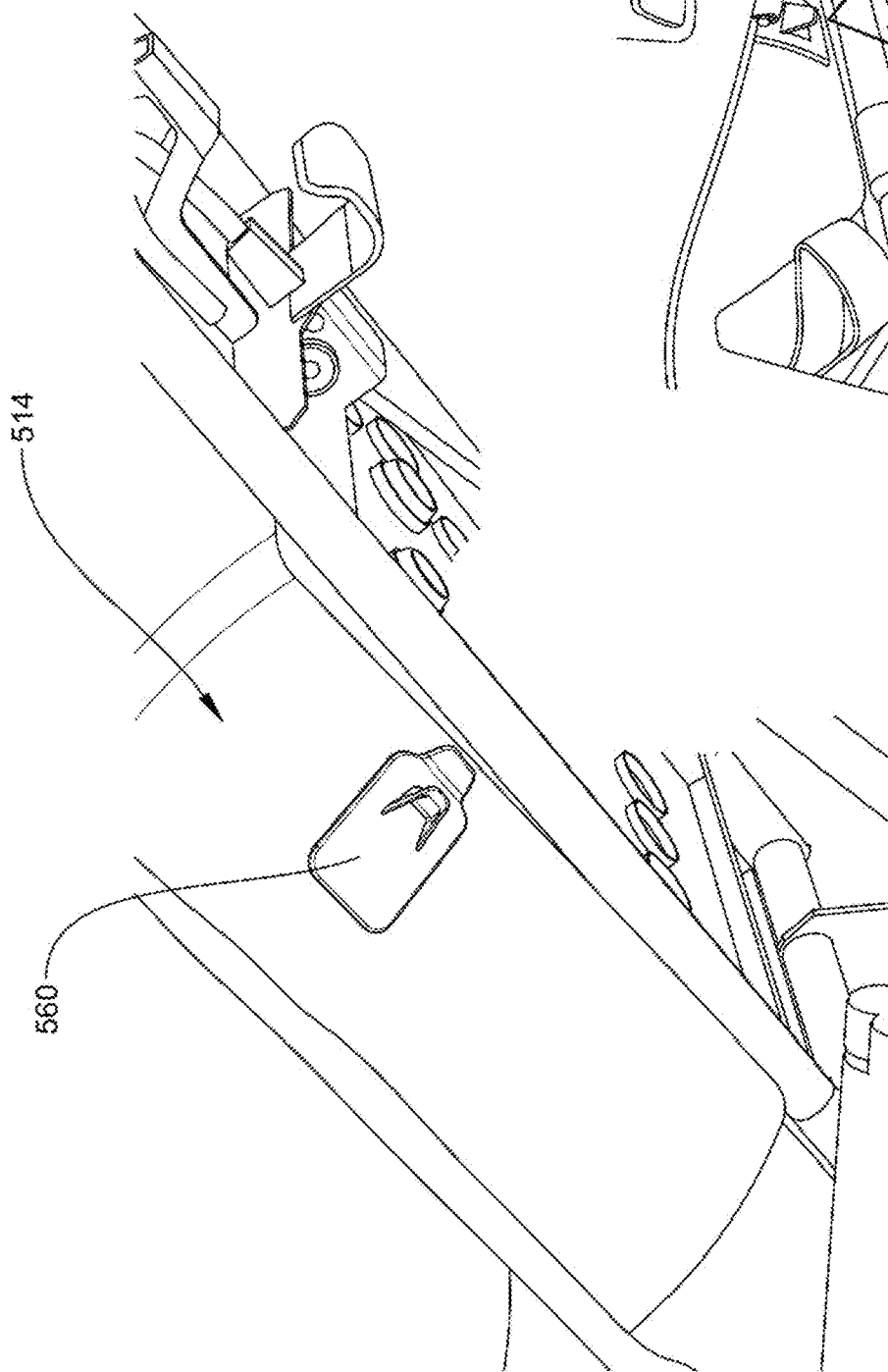

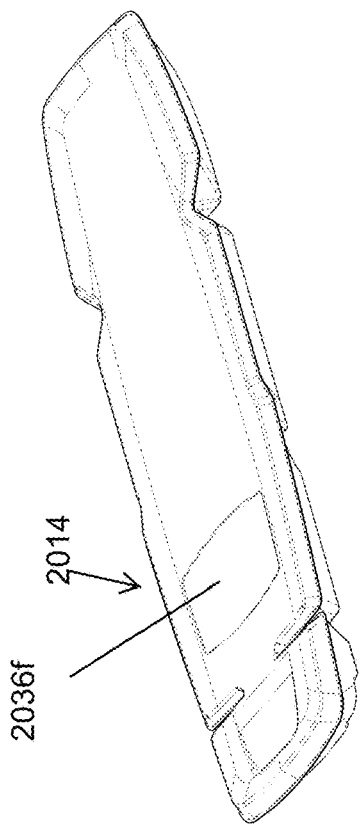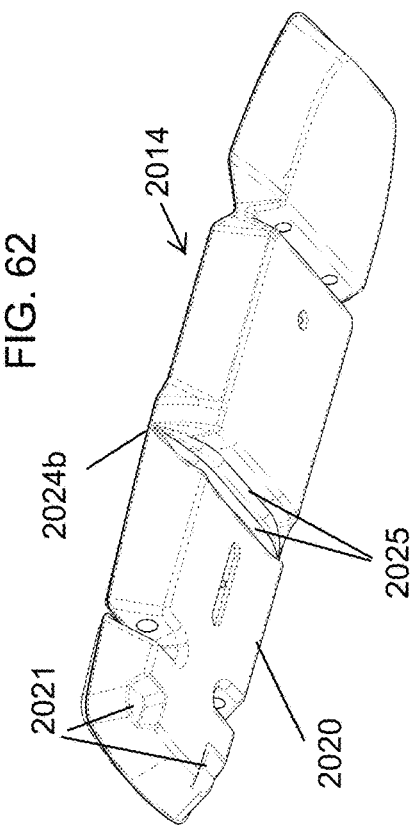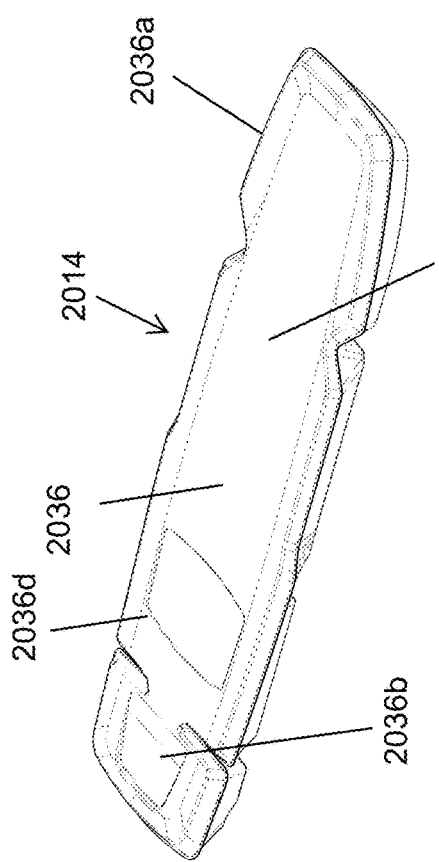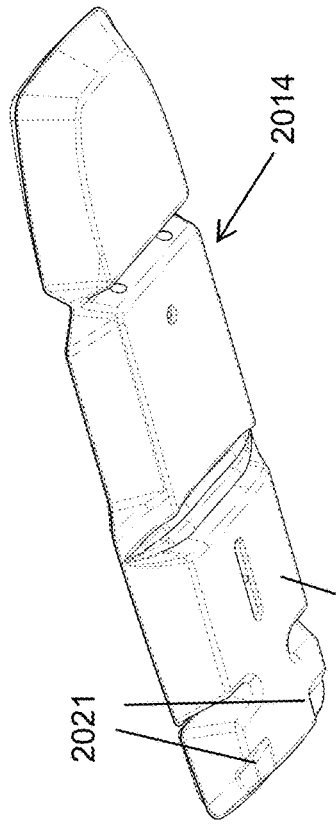

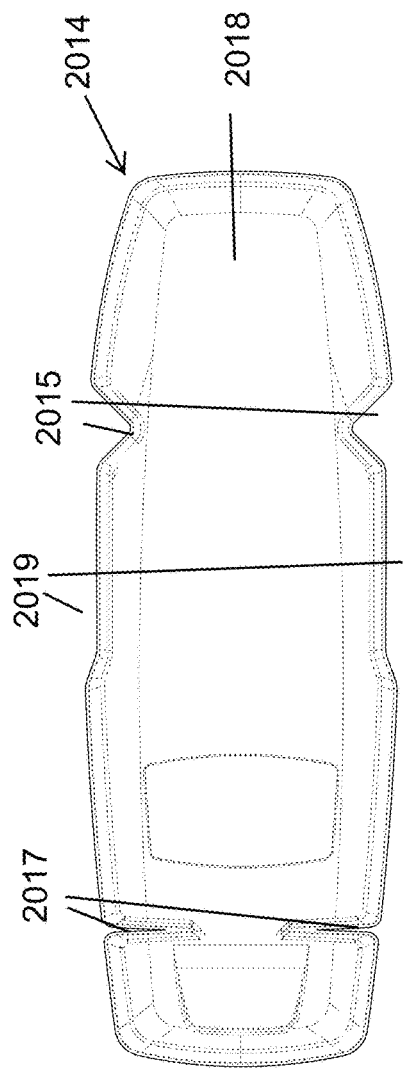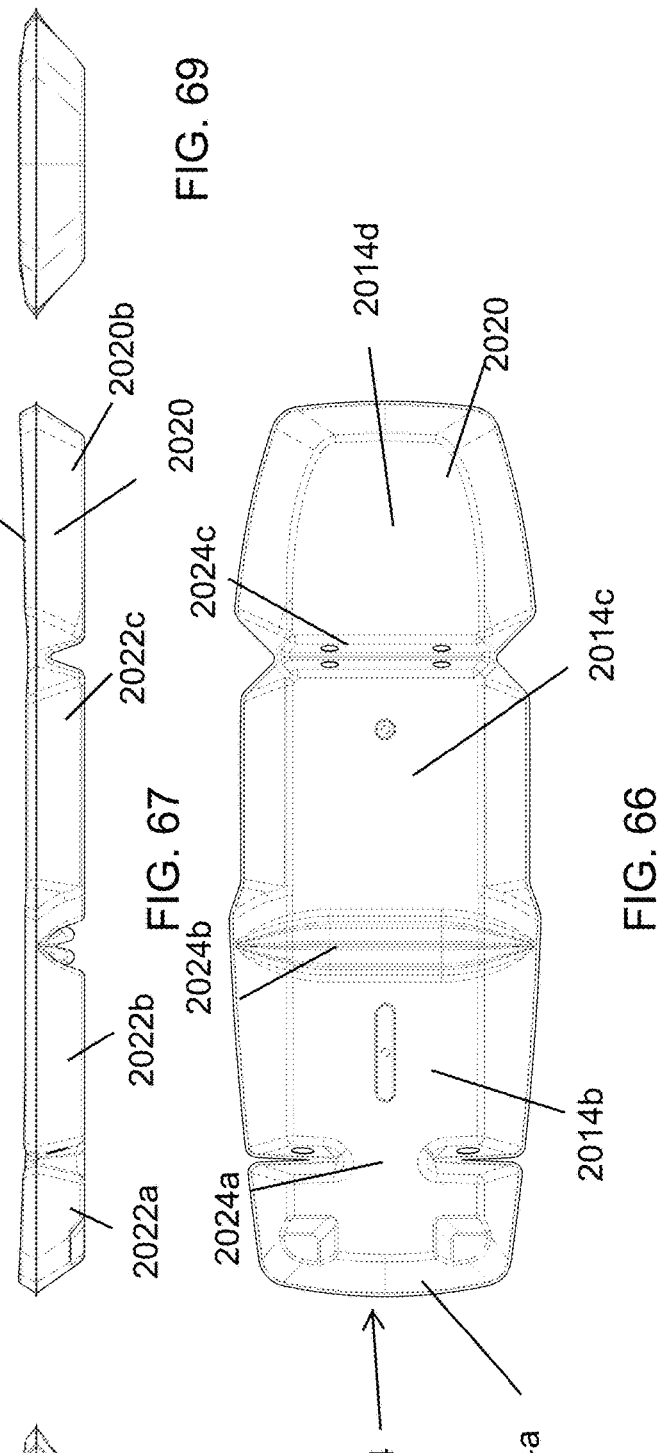

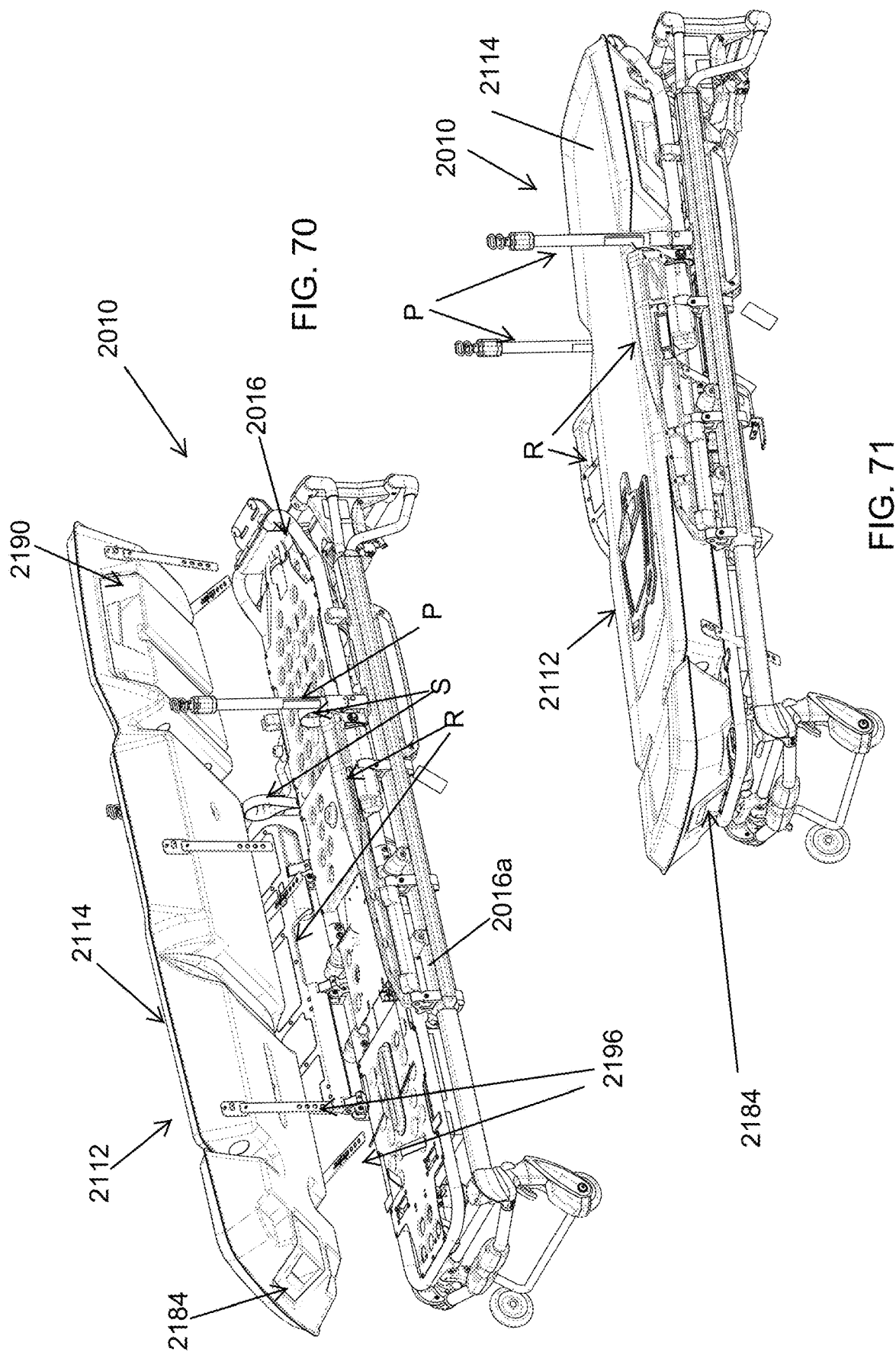

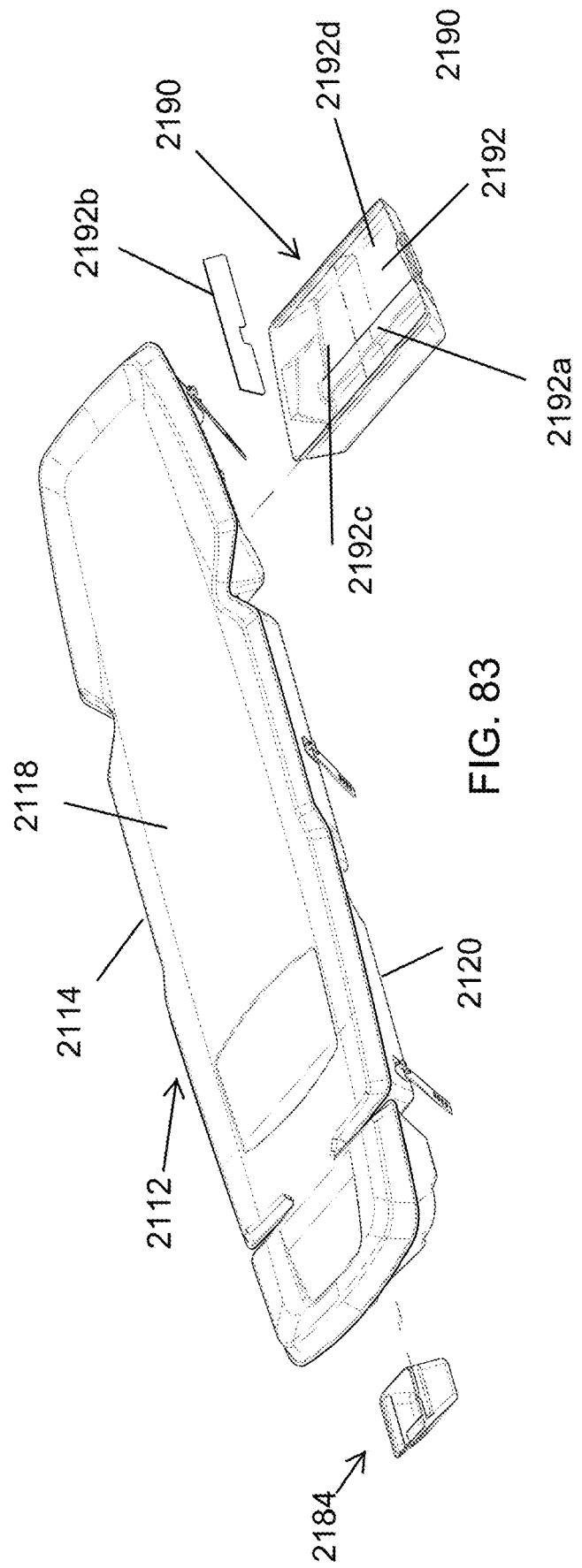

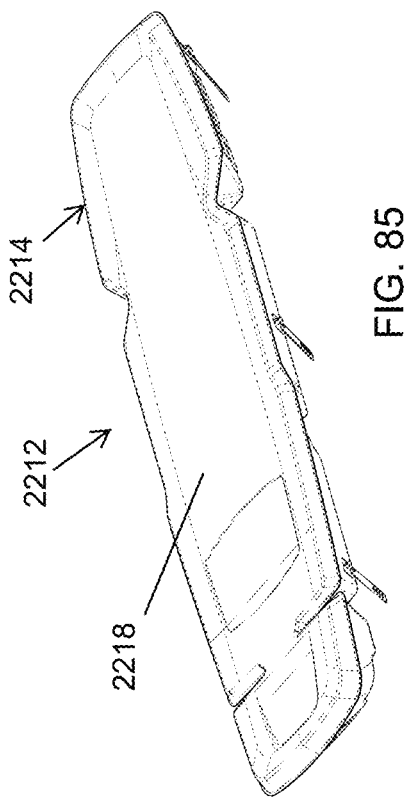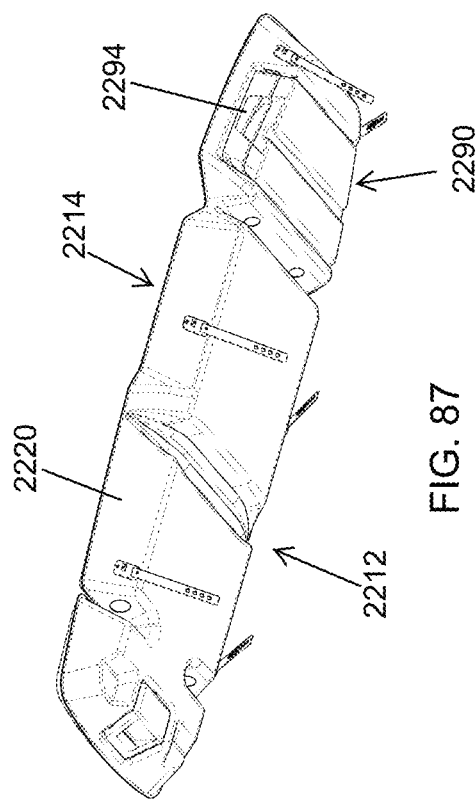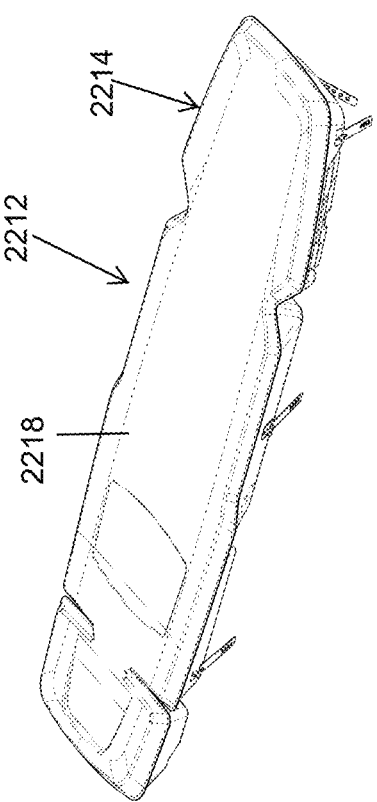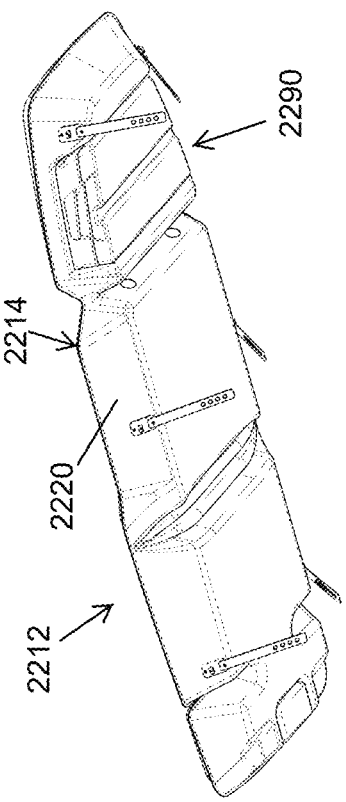

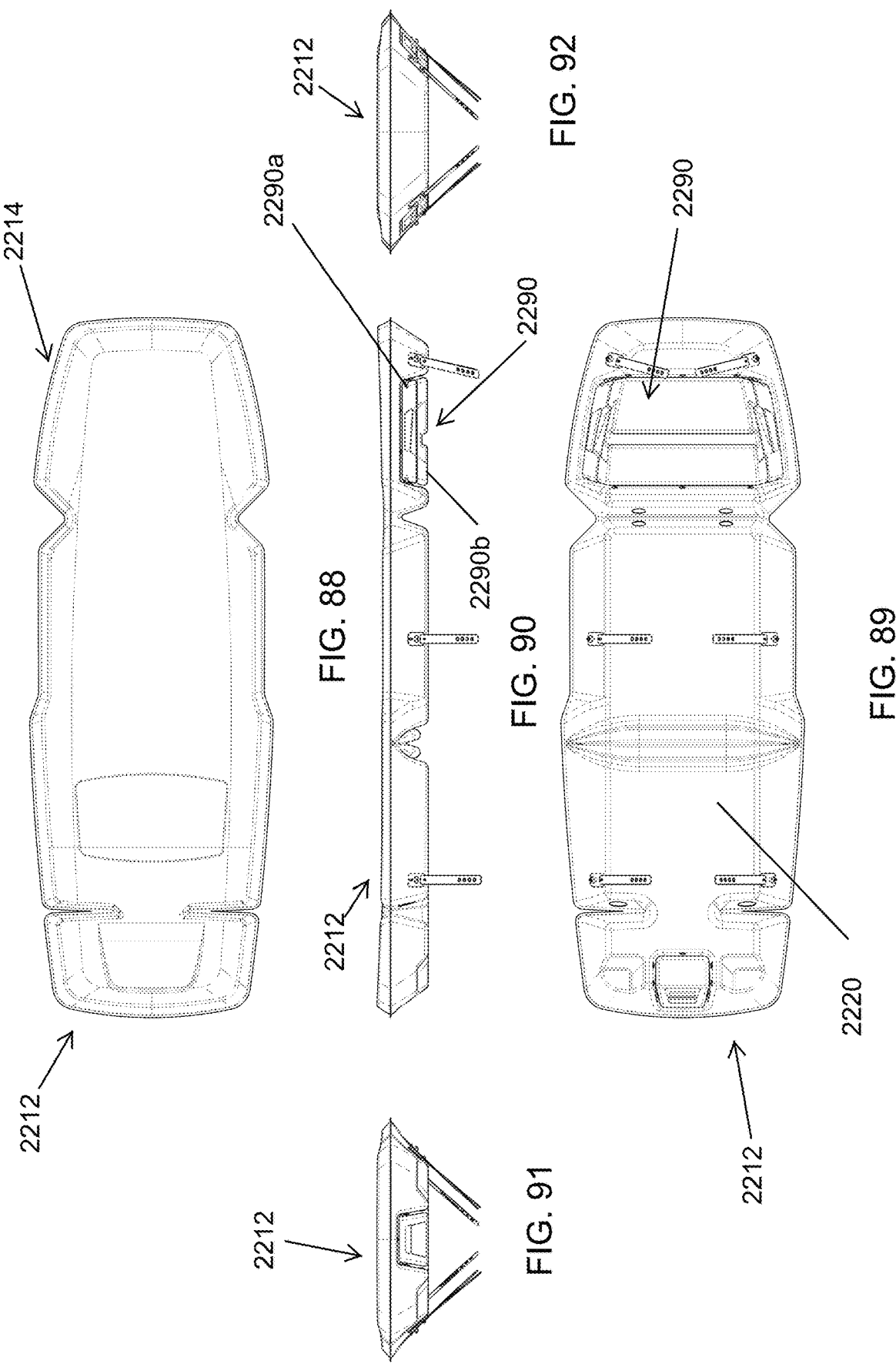

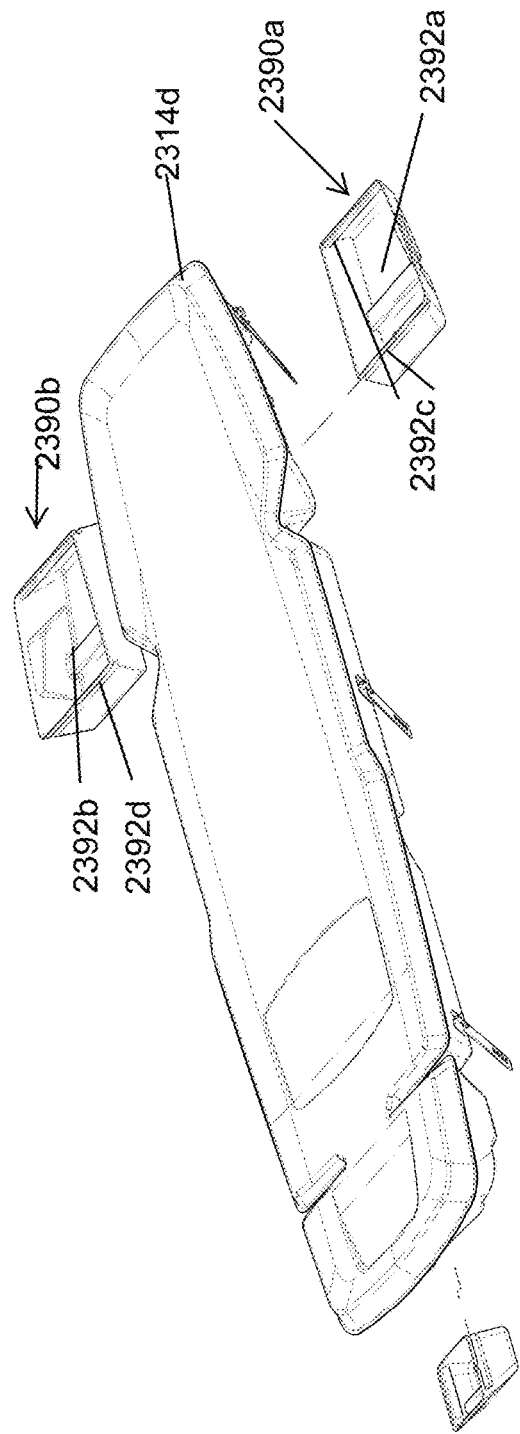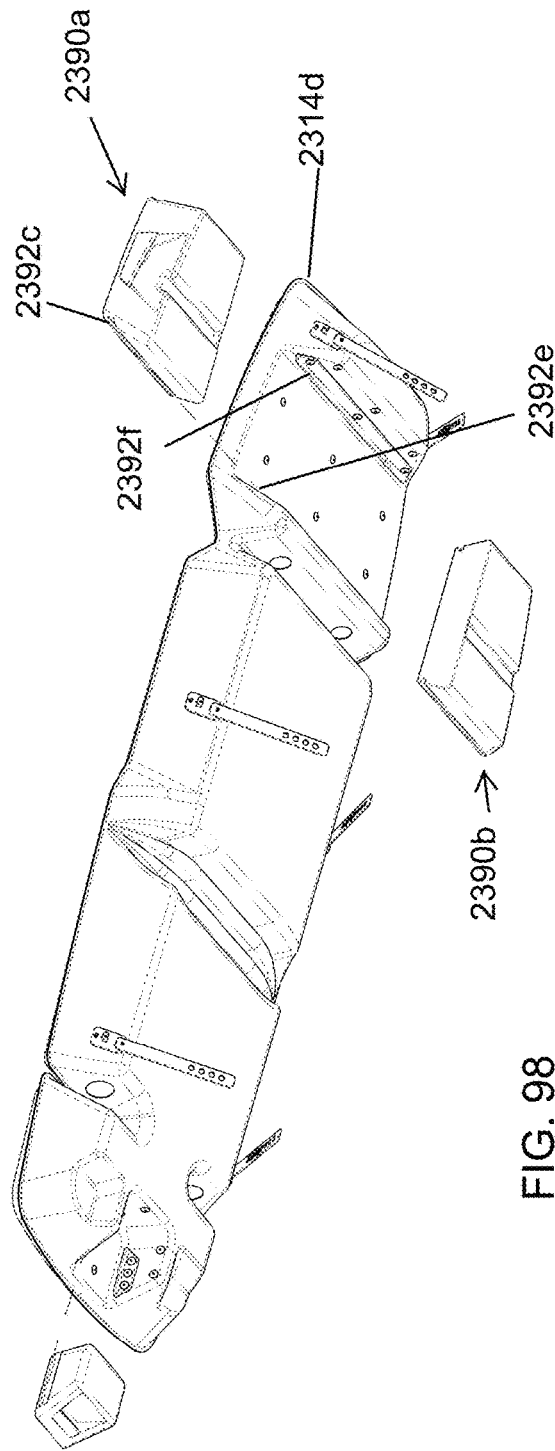
FIG. 97
FIG. 98

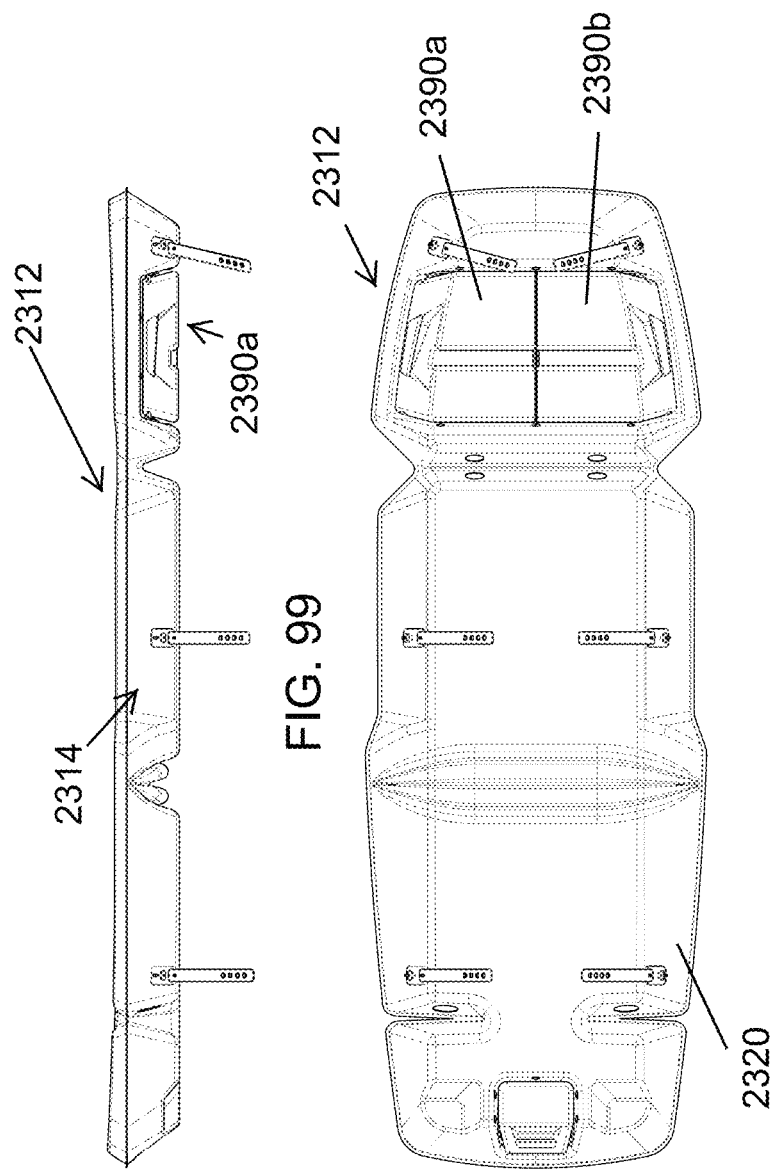

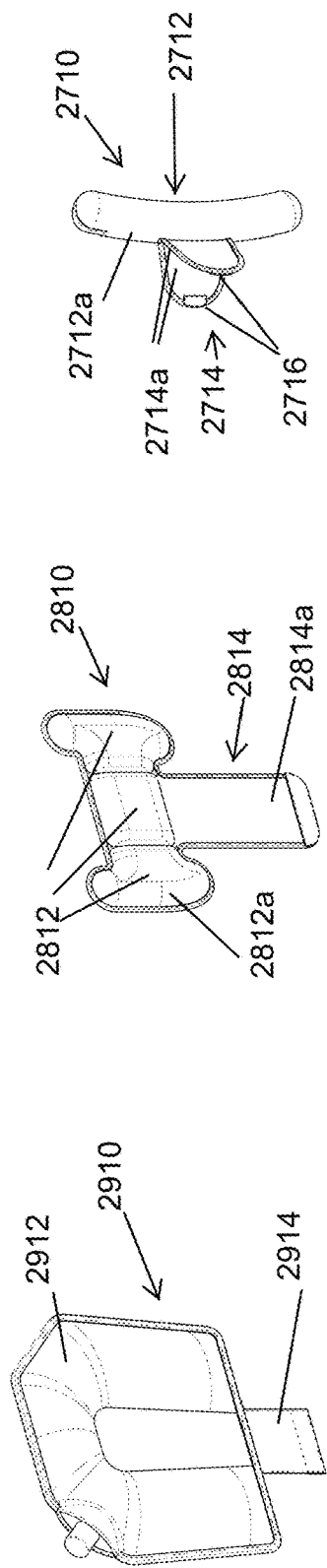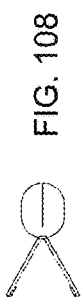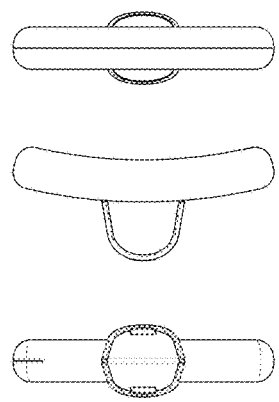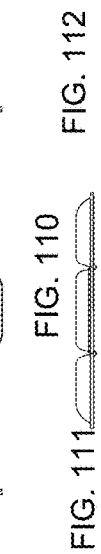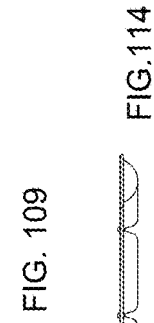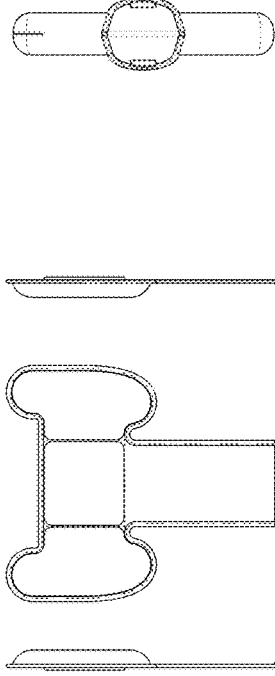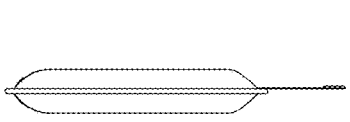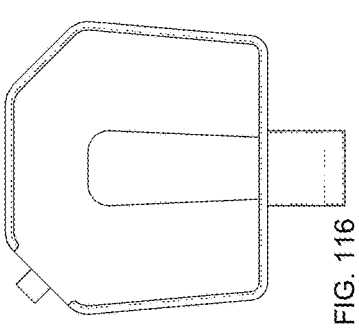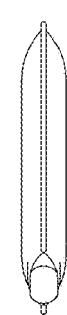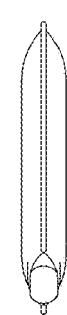

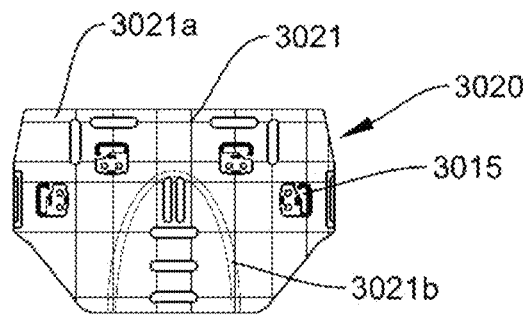
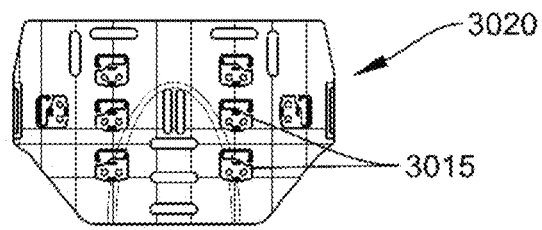
FIG. 133A  FIG. 133B
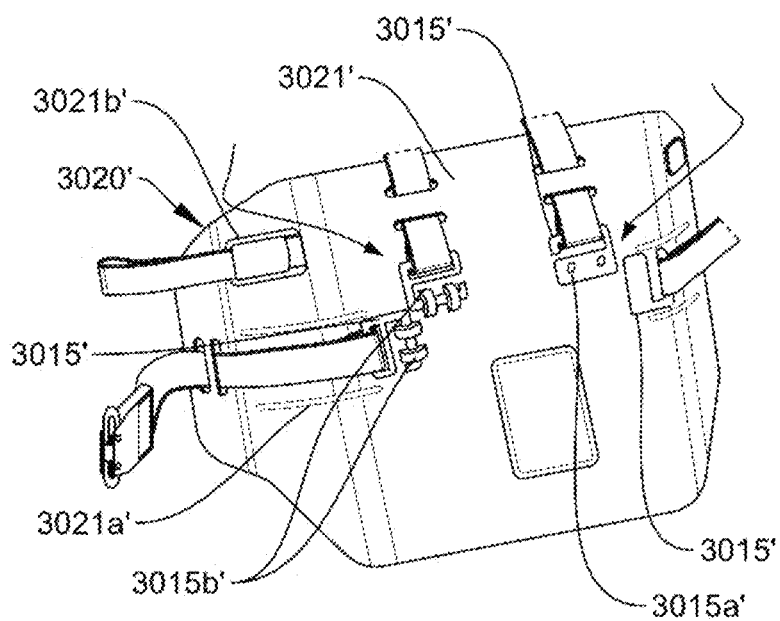
FIG. 133C

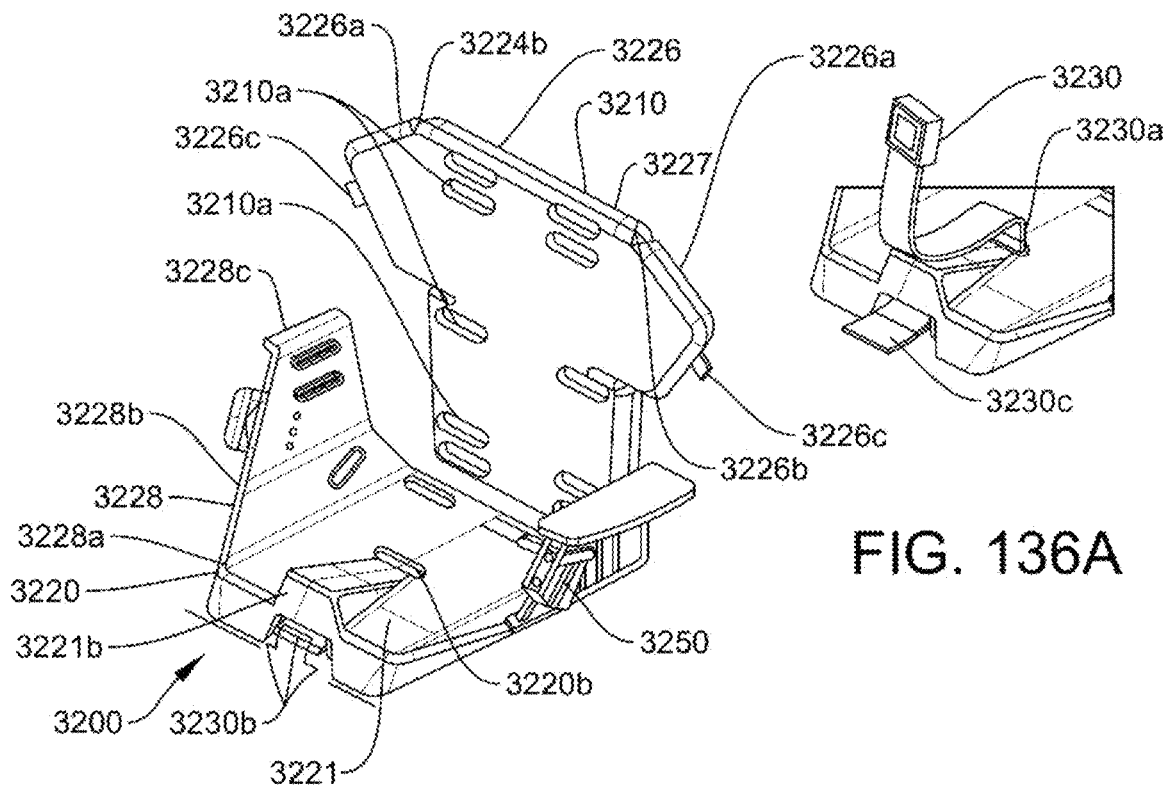
FIG. 136A
FIG. 136
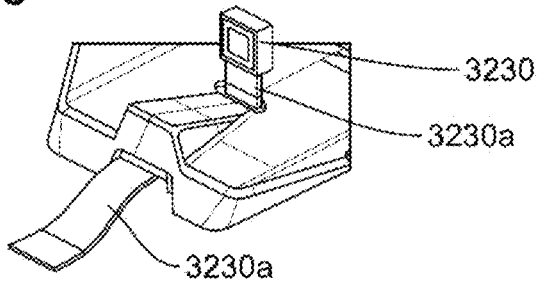
FIG. 136B
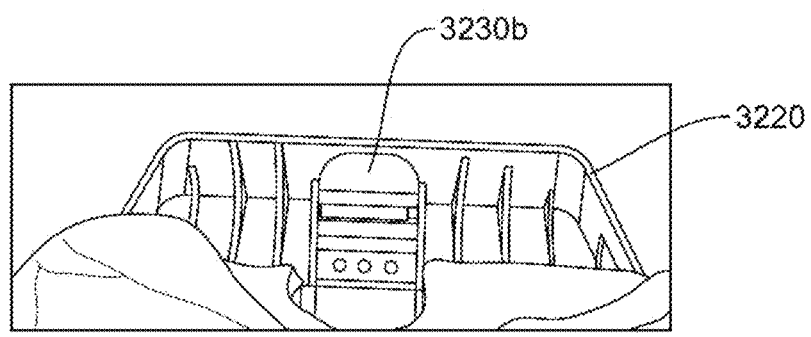
FIG. 136C

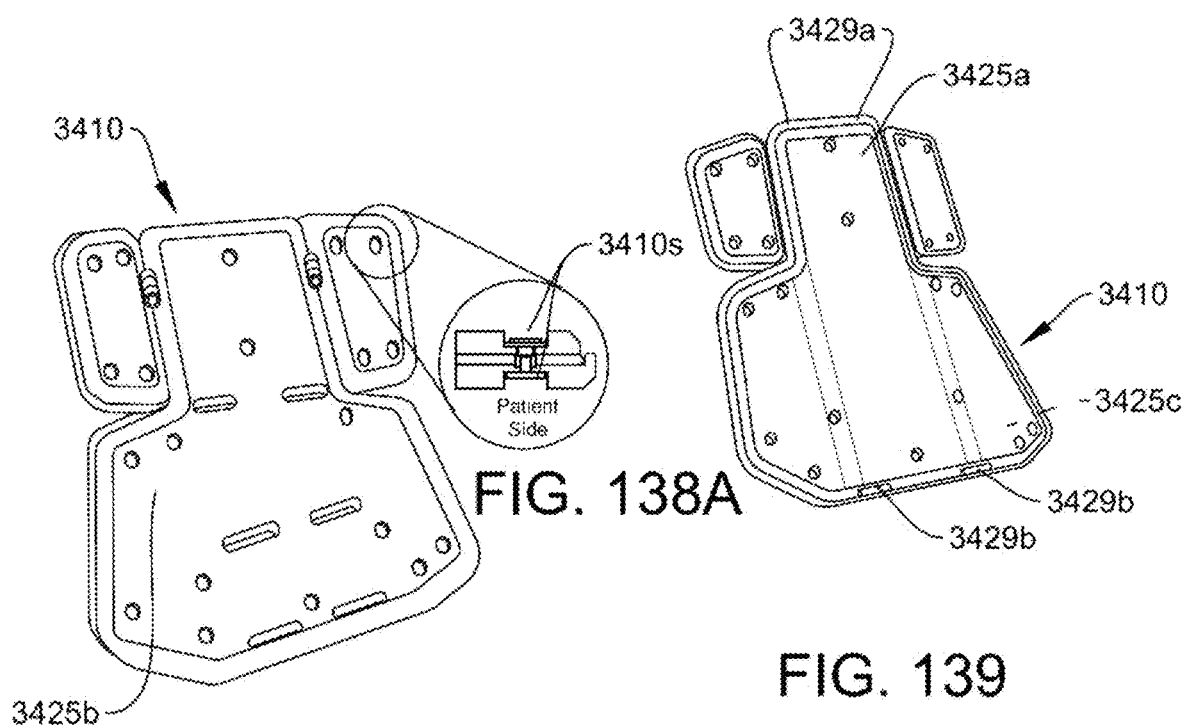
FIG. 138A
FIG. 138
FIG. 139
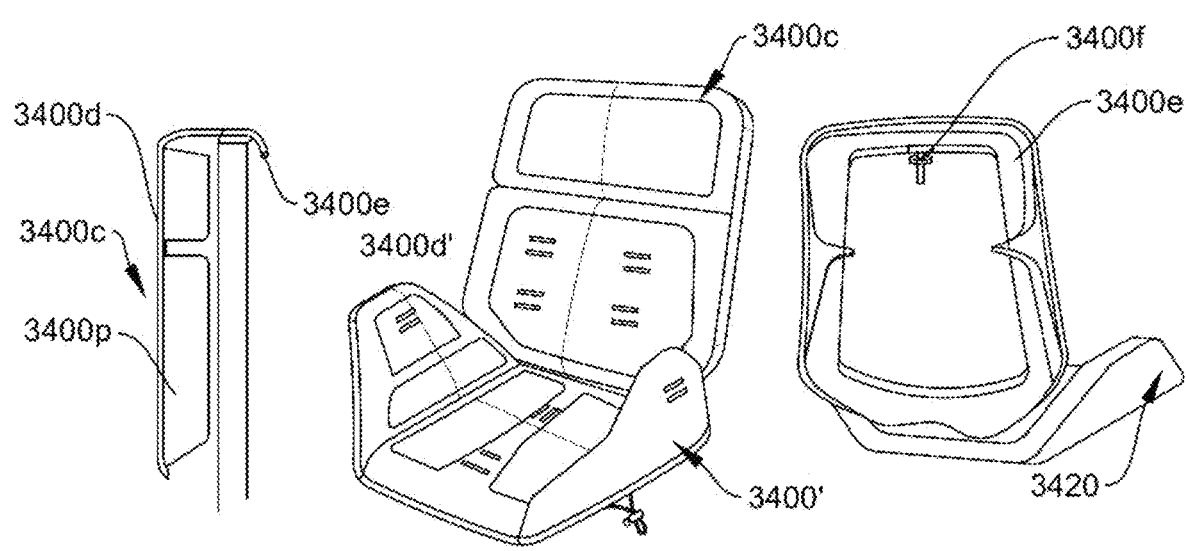
FIG. 142  FIG. 140  FIG. 141

PATIENT SUPPORT APPARATUS AND ACCESSORIES THEREFOR

This application claims the benefit of U.S. Provisional Applications Ser. No. 63/026,391, entitled PATIENT SUPPORT APPARATUS AND SUPPORT SURFACE SYSTEM THEREFOR (P636), filed on May 18, 2020, Ser. No. 63/108,600, entitled PATIENT SUPPORT APPARATUS AND SUPPORT SURFACE SYSTEM THEREFOR (P636A), filed on Nov. 2, 2020, and Ser. No. 63/114,217, entitled PATIENT SUPPORT APPARATUS AND SUPPORT SURFACE SYSTEM THEREFOR (P636B), filed on Nov. 16, 2020, all commonly owned by Stryker Corporation of Kalamazoo, Michigan, and which are incorporated herein by reference in their entireties.

TECHNICAL FIELD AND BACKGROUND

The present invention relates to a transport apparatus, such as an emergency cot or stretcher or the like, and, more particularly, to a patient support surface system that works with the transport apparatus to provide improved support for and handling of a patient.

SUMMARY

In one embodiment, a support surface for a transport apparatus includes a patient support surface that is segmented into articulatable patient support surface sections. The patient support surface is formed by a bottom cover and a top cover, which respectively form the lower surface and the upper surface of the patient support surface. The bottom cover is pre-formed into at least two adjacent cavities, with each cavity receiving a cushion section, and each cavity joined to the adjacent cavity by a hinge, such as a living hinge or mechanical hinge, so that the support surface can be articulated about the hinge. Each cushion section is formed from one or more cushioning materials that vary in their properties along their respective cross-sections to vary the immersion and/or pressure distribution characteristics of the patient support surface.

In one embodiment, at least one of the cushion sections is formed from multiple layers of cushioning material, such as foam, gel, three dimensional material, beads, and/or a bladder or bladders or a combination thereof.

In one embodiment, the multiple layers may be arranged vertically and/or horizontally.

In one embodiment, the bottom cover is formed from a polymer film and pre-formed by molding, such as thermoforming, blow molding, injection molding, rotational molding, or structural foam molding, for example.

In one embodiment, the bottom cover is flexible. For example, suitable materials include urethane films, urethane laminates or coated fabric, or polyolefin. In another embodiment, the bottom cover is rigid. Suitable materials for a rigid construction include structural polymer materials, such as ABS, polyethylene, HIPS, HDPE, PET, or PETG, or the like, or composites thereof, including fiberglass.

In one embodiment, the top cover is formed from a continuous sheet that extends over each of the cavities and is joined with the bottom cover around the upper perimeter of the bottom cover and, further, joined with the bottom cover around the upper perimeters of each of the cavities. In another embodiment, the construction may be inverted and/or both covers may be thermoformed and joined along the sides of the patient support surface, for example somewhere in the middle of the sides.

In any of the above, the top cover may be joined with the bottom cover by a seal, such as formed by welding, including RF welding. In one embodiment, the seal is formed by a seam tape that is glued over the sewn, joined edges of the top cover and the bottom cover. For example, in one embodiment, the perimeter edges of the top and bottom covers are sealed by welding or stitching, which is then covered with binding and seam tape.

Optionally, the top cover or the bottom cover may include one or more valves to allow pressure above a prescribed level to escape from within the patient support surface. For example, this valve may be a vent or a mechanical pressure relief valve, including umbrella valves or duckbill valves. The vent may be formed from a fluid-proof vent or breathable fabric patch.

Optionally, a valve may be provided for each section associated with each cavity of the patient support surface.

In any of the above, as noted, the top cover may be continuous to form a continuous upper surface that is easily cleaned.

In one embodiment, the top cover is formed with channels, such as by thermoforming, embossing, compression molding, or the like. The channels may aid in directing fluid and/or may be provided for markings or tactile or visual guides for patient positioning, or simply for aesthetic purposes, such as branding or the like.

In one embodiment, a patient support surface for an EMS cot or stretcher is configured to promote pressure redistribution and safe patient handling through varying the cushioning layers either vertically or horizontally or both.

For example, at least one section of the patent support surface incorporates a foam crib and a plurality of cushioning layers of varying stiffness supported in the foam crib.

In one embodiment, at least one section of the patient support surface incorporates a wedge having greater stiffness than the surrounding cushioning layer or layers (with the exception of the crib) to reduce patient migration along the length of the patient support surface.

In another embodiment, a patient support surface for an EMS cot or stretcher, which includes at least one articulatable section, is formed with a thermoformed bottom cover, which eliminates the need for corner seams or joints between sections and can create a living hinge between the sections.

In another embodiment, a patient support surface for an EMS cot or stretcher includes a continuous top cover formed from impermeable material that is sealed with a bottom cover to form an impervious barrier to the cushion section between the top and bottom covers to prevent fluid ingress into the patient support surface, and hence the cushion section, to reduce infection spread.

For example in one embodiment, the perimeter edges of the top and bottom covers are sealed by welding or stitching and then covered by binding and seam tape.

In another embodiment, a patient support surface for an EMS cot or stretcher incorporates a plurality of attachment points to allow for various attachable/detachable elements or accessories to be fixed to the patient support surface.

In another embodiment, a patient support surface for an EMS cot or stretcher is formed from various layers with different color coatings that are intended to wear away over the life of the patient support surface due to mechanical wear or chemical cleaning to indicate the end of the service life.

In another embodiment, a patient support surface for an EMS cot or stretcher is formed with one or more spaces or areas accessible by the user for storage of equipment and/or supplies.

In any of the above patient support surfaces, the various support surface sections may be attached by a hinge, but still be removable to either service or tailor the support surface to suit the patient or the use of the patient support surface.

In another embodiment, a patient support surface for an EMS cot or stretcher incorporates temperature control into the support surface for therapeutic or comfort purposes, for example, by using one or a plurality of thermodynamic devices, which may be powered by an onboard power supply on the transport apparatus.

In one embodiment, a transport apparatus includes a deck, a pair of side rails, and a patient support surface. The patient support surface has an outer perimeter and is formed by a bottom cover and a top cover, which respectively form the lower surface and the upper surface of the patient support surface. The bottom cover is pre-formed into at least two adjacent cavities, with each cavity receiving a cushion section, and each cavity joined to the adjacent cavity by a hinge, such as a living hinge or mechanical hinge, so that the support surface can be articulated about the hinge to accommodate changes in the deck configuration. The upper surface includes a raise rim that extends around the outer perimeter of the patient support surface.

In one embodiment, the outer perimeter of the patient support surface is configured to reduce interference with the side rails when they are raised.

In another embodiment, the outer perimeter of the patient support surface is configured to reduce interference with the side rails over one range of motion but to permit the side rails to urge the patient support surface to curl at its outer perimeter over a second range of motion to thereby cradle a patient supported therein.

For example, the outer perimeter of the patient support surface may have a tapered recess that extends inwardly toward the patient support surface.

In another embodiment, the bottom cover includes at least one recess to form a storage space. For example, a compartment may be mounted in the recess, which forms the storage space. For example, the compartment may be configured as a drawer and may be deployed from one or both lateral sides of the support surface.

In one embodiment, the support surface includes two compartments—either separate or as a compartment assembly.

In any of the above, as noted, the top cover may be continuous to form a continuous upper surface that is easily cleaned.

In one embodiment, the top cover is formed with one or more recessed regions, for example, at the head end and/or under the patient's torso or patient's torso and/or legs.

In other embodiments, a pediatric restraint assembly is configured to releasably mount to an adult harness and/or to a transport apparatus frame.

In one aspect, the pediatric restraint assembly includes a pediatric harness that is configured to releasably mount to an adult harness and/or to a transport apparatus frame.

For example, the pediatric restraint assembly may include at least a back panel and a seat panel.

In one embodiment, the pediatric harness passes through the back panel to anchor the pediatric patient and the pediatric restraint assembly to the adult harness and/or to the transport apparatus frame.

In another aspect, the pediatric restraint assembly may include at least a back panel and a pediatric harness that secures the pediatric patient to the back panel and an anchor strap or straps to anchor the panel to the adult harness and/or to the transport apparatus frame.

In one embodiment, when mounted to the adult harness, an adult may be also secured to the transport apparatus via the adult harness, so that the pediatric patient and adult can move together with the adult harness.

These and other objects, advantages, purposes and features of the invention will become more apparent from the study of the following description taken in conjunction with the drawings.

BRIEF DESCRIPTION OF DRAWINGS

FIG. 14 is a perspective view of the cot illustrating another embodiment of a releasable coupler for releasably coupling the patient support surface to the deck of the transport apparatus and an optional storage compartment as part of the patient support surface system;

FIG. 14A is an enlarged perspective of view the releasable coupler of FIG. 14;

FIG. 15 is a bottom perspective of another embodiment of releasable couplers for releasably coupling the patient support surface to the deck of the transport apparatus;

FIG. 16 is an end view illustrating the releasable couplers of FIG. 15 coupling the patient support surface to the deck;

FIG. 17 is a bottom perspective of another embodiment of releasable couplers for releasably coupling the patient support surface to the deck of the transport apparatus;

FIG. 18 is an end view illustrating the releasable couplers of FIG. 17 coupling the patient support surface to the deck;

FIG. 31 is a perspective view of another embodiment of the patient support surface incorporating a storage compartment at the head end of the patient support surface as a part of the patient support surface system;

FIG. 32 is another perspective view of the patient support surface of FIG. 31;

FIG. 36 is a perspective view of another embodiment of the patient support surface incorporating a storage compartment at the head end of the patient support surface as a part of the patient support surface system, which is accessible from the head end of the patient support surface when the head section of the patient support surface is raised;

FIG. 36A is an enlarged partial perspective view of the head end of the patient support surface when the head section of the patient support surface is raised;

FIG. 36B is another enlarged partial perspective view of the head end of the patient support surface;

FIG. 41 is an illustration of how the cover can be used when placed under a patient to transfer the patient;

FIG. 41A is a perspective view of the cover;

FIG. 46 is a similar view to FIG. 45 with the cover removed to show a coupler mounted to the side of the patient support surface;

FIG. 46A is a similar view to FIG. 45 but with the cover added to illustrate how the cover may be coupled to the patient support surface using the coupler;

FIG. 46B is an enlarged perspective of the coupler of FIG. 46;

FIG. 61 is a top perspective view of the patient support surface system of FIG. 60;

FIG. 62 is another top perspective view of the patient support surface system of FIG. 60;

FIG. 63 is a bottom perspective view of the patient support surface system of FIG. 60;

FIG. 64 is another bottom perspective view of the patient support surface system of FIG. 60;

FIG. 65 is a top plan view of the patient support surface system of FIG. 60;

FIG. 66 is a bottom plan view of the patient support surface system of FIG. 60;

FIG. 67 is a side elevation view of the patient support surface system of FIG. 65;

FIG. 68 is a head end elevation view of the patient support surface system of FIG. 65;

FIG. 69 is a foot end elevation view of the patient support surface system of FIG. 65;

FIG. 70 is an exploded perspective view of the transport apparatus and the patient support surface system illustrating the bottom perspective view of another embodiment of the patient support surface system;

FIG. 71 is a top perspective view of the transport apparatus and the patient support surface system of FIG. 70;

FIG. 83 is a top exploded perspective view of another embodiment of the storage compartment of the patient support surface system;

FIG. 84 is a top perspective view of another embodiment of the patient support surface system incorporating multiple storage compartments;

FIG. 85 is another top perspective view of the patient support surface system of FIG. 84;

FIG. 86 is a bottom perspective view of the patient support surface system of FIG. 84;

FIG. 87 is another bottom perspective view of the patient support surface system of FIG. 84;

FIG. 88 is a top plan view of the patient support surface system of FIG. 84;

FIG. 89 is a bottom plan view of the patient support surface system of FIG. 84;

FIG. 90 is a side elevation view of the patient support surface system of FIG. 84;

FIG. 91 is a head end elevation view of the patient support surface system of FIG. 84;

FIG. 92 is a foot end elevation view of the patient support surface system of FIG. 84;

FIG. 93 is a top and partially exploded perspective view of the patient support surface system of FIG. 84 with the storage compartments extended;

FIG. 94 is a bottom and partially exploded perspective view of the patient support surface system of FIG. 93;

FIG. 95 is a bottom perspective view of another embodiment of a patient support surface system with multiple storage compartments;

FIG. 96 is another bottom perspective view of the patient support surface system of FIG. 95;

FIG. 97 is a top exploded perspective view of the patient support surface system of FIG. 95;

FIG. 98 is a bottom exploded perspective view of the patient support surface system of FIG. 97;

FIG. 99 is a side elevation view of the patient support surface system of FIG. 95;

FIG. 100 is a bottom plan view of the patient support surface system of FIG. 95;

FIG. 101 is a perspective view of a pediatric restraint assembly for a pediatric patient;

FIG. 102 is an enlarged view of a coupler for coupling the pediatric restraint assembly of FIG. 101 to a transport apparatus, such as an emergency cot;

FIG. 102A is enlarged view of the straps of the pediatric restraint assembly of FIG. 101;

Figure 101:
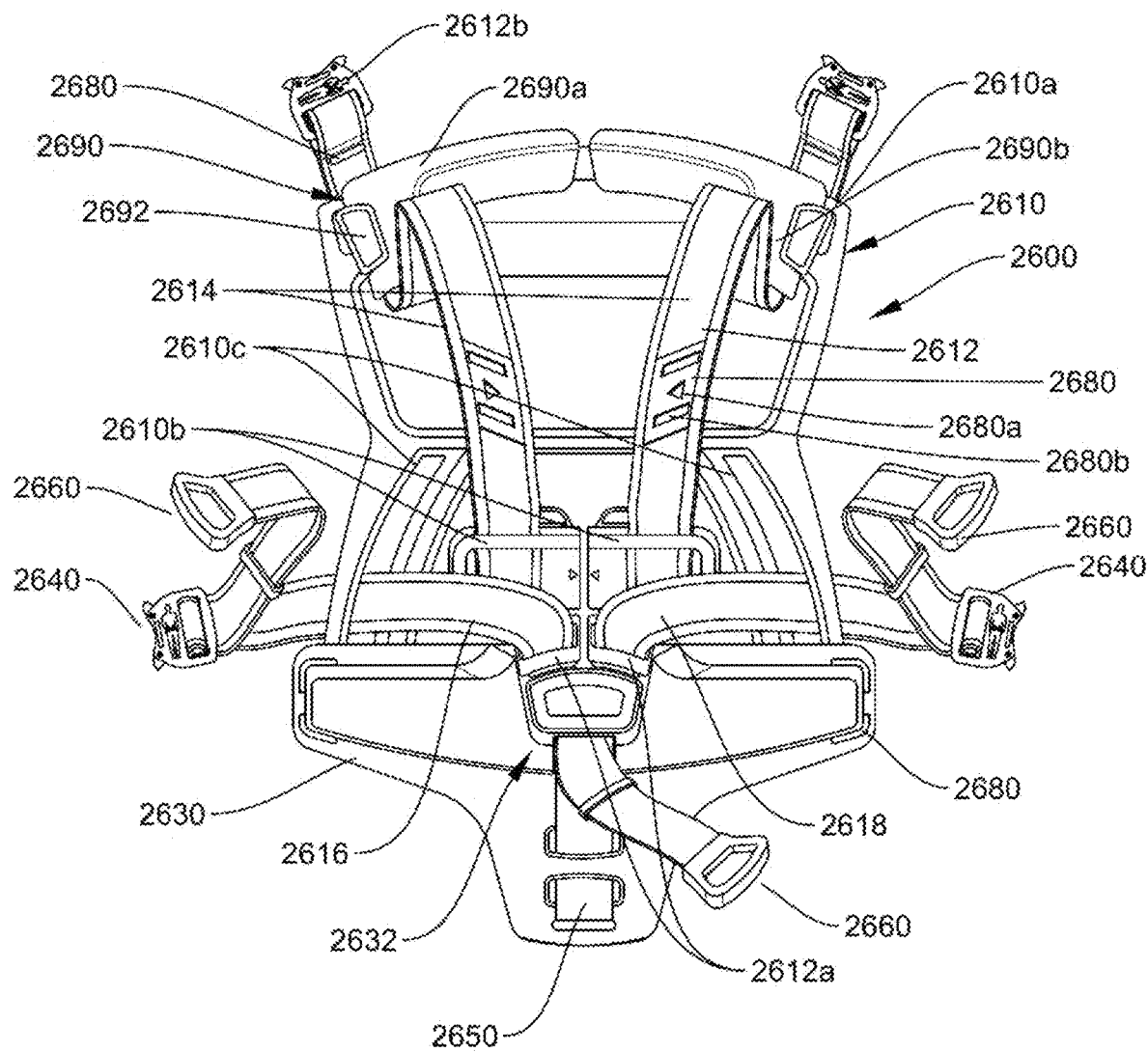
Figure 121:
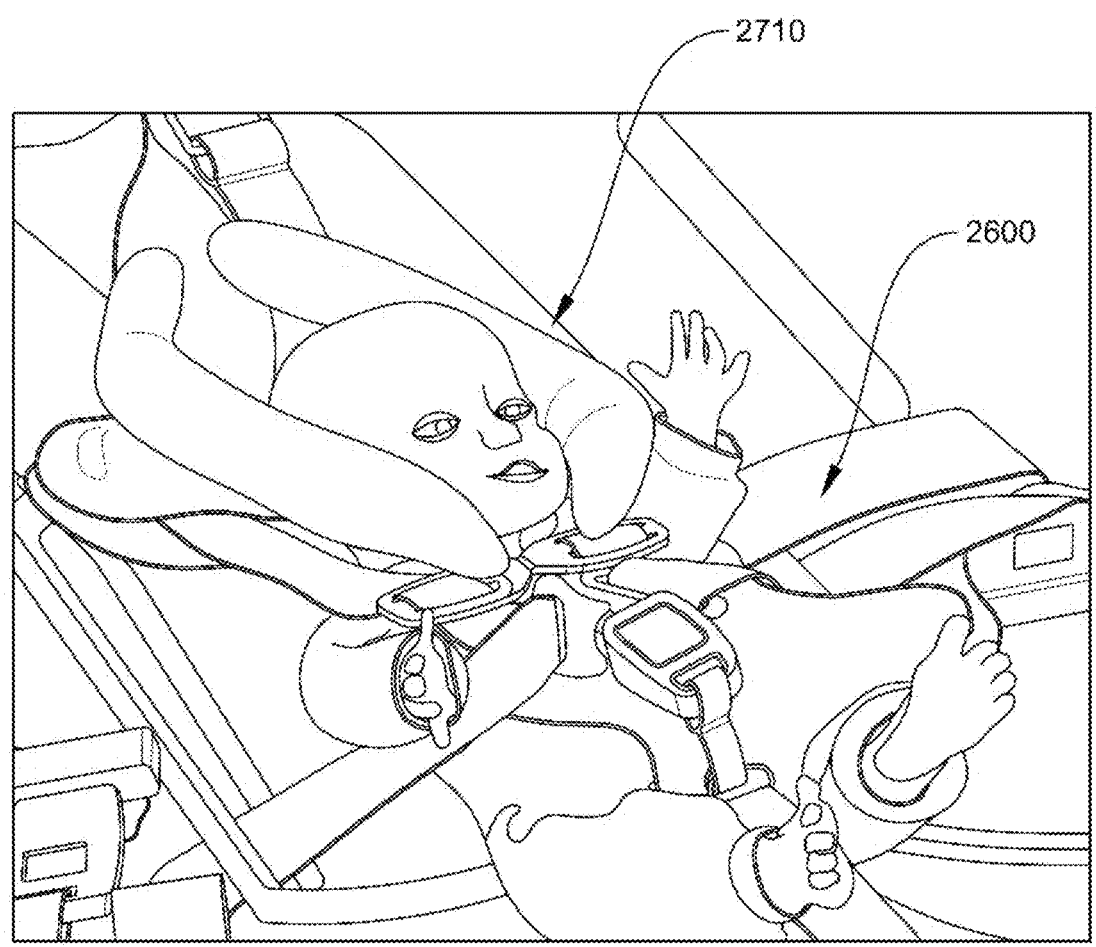
Figure 122:
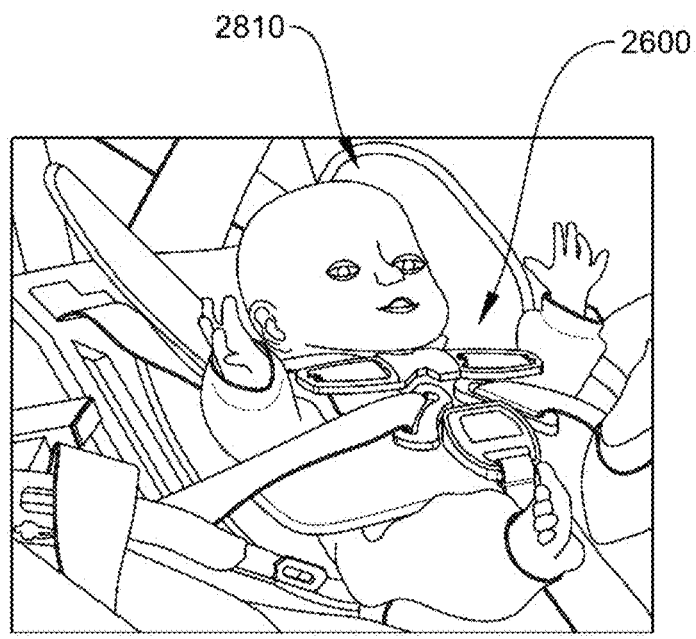
Figure 123:
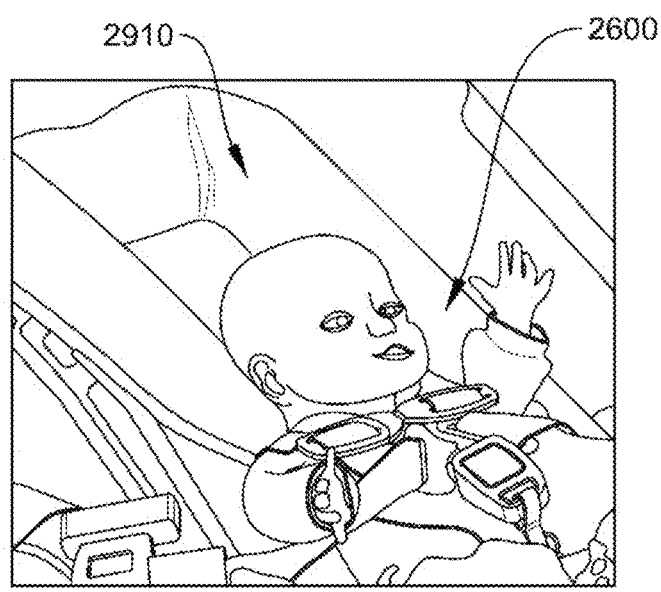
Figure 124:
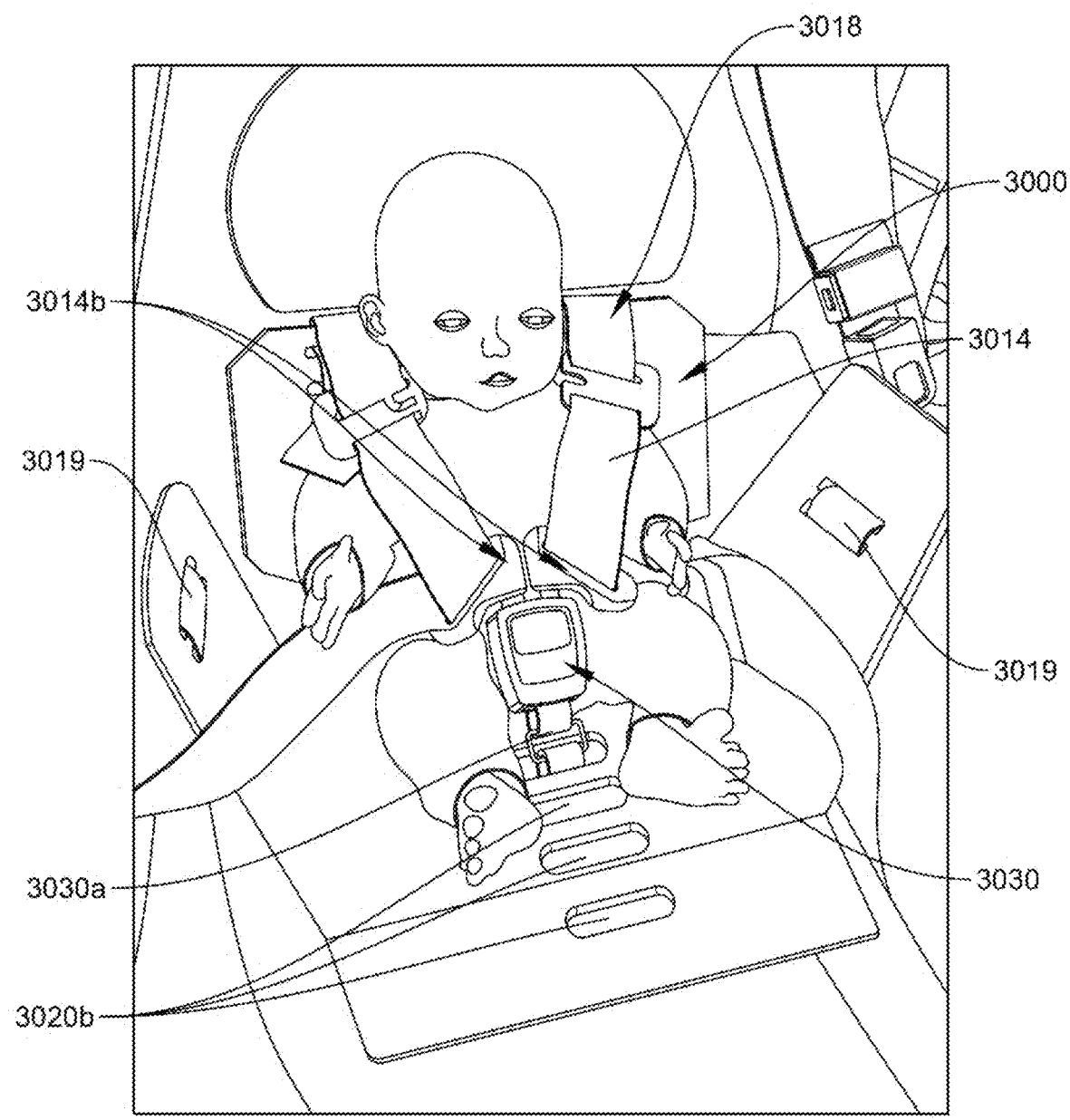
Figure 124A:
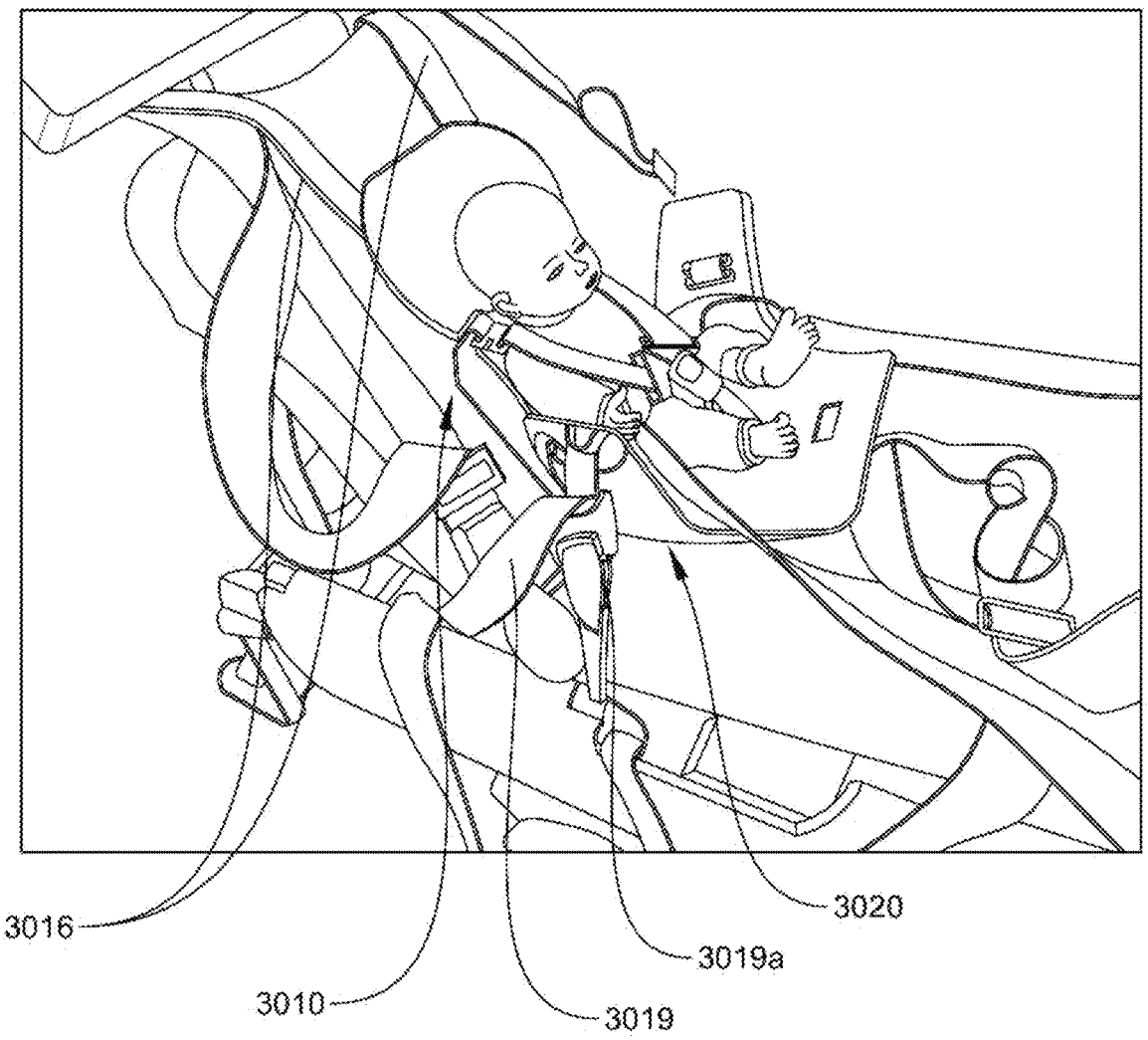
Figure 124B:
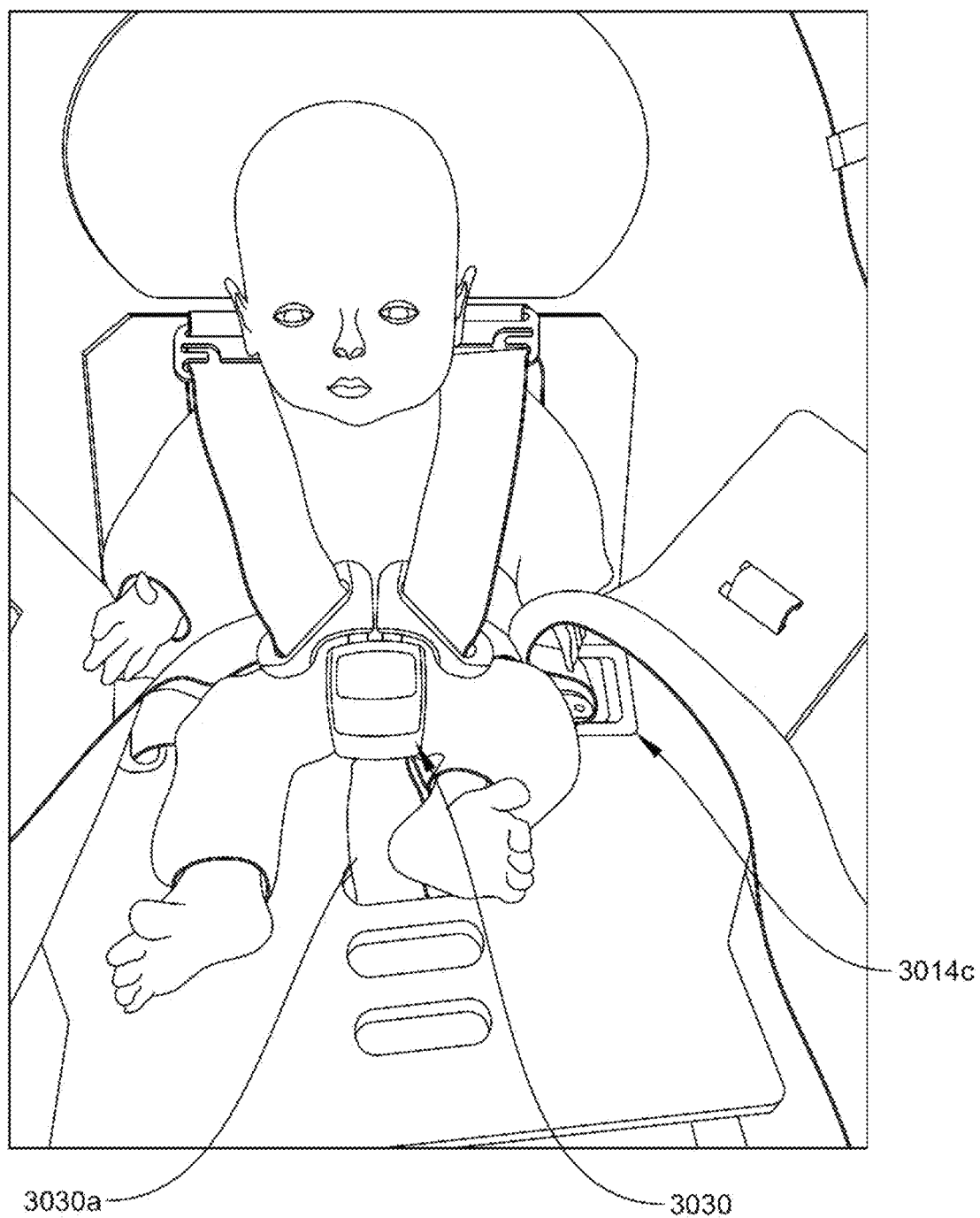
Figure 125:
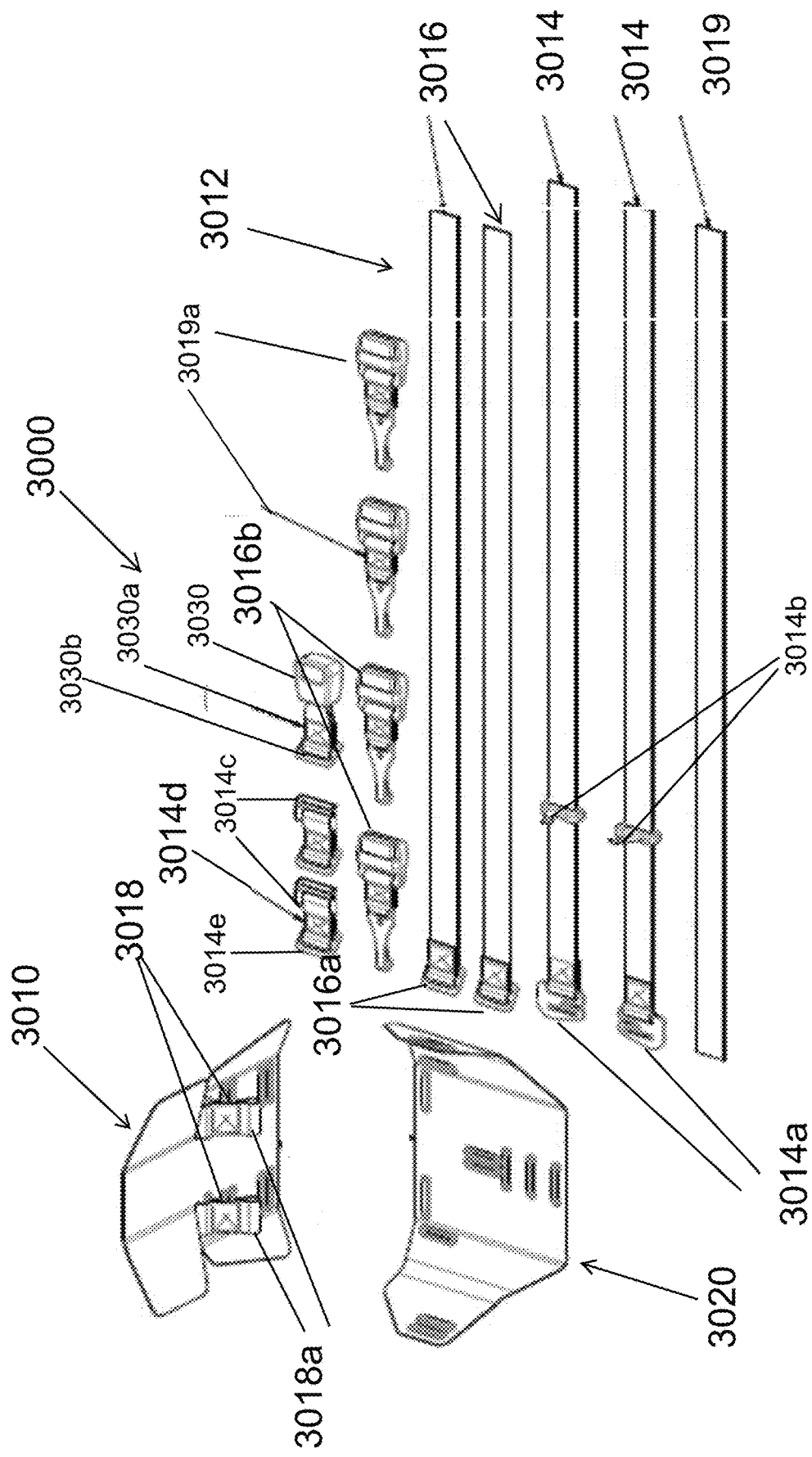
Figure 126:
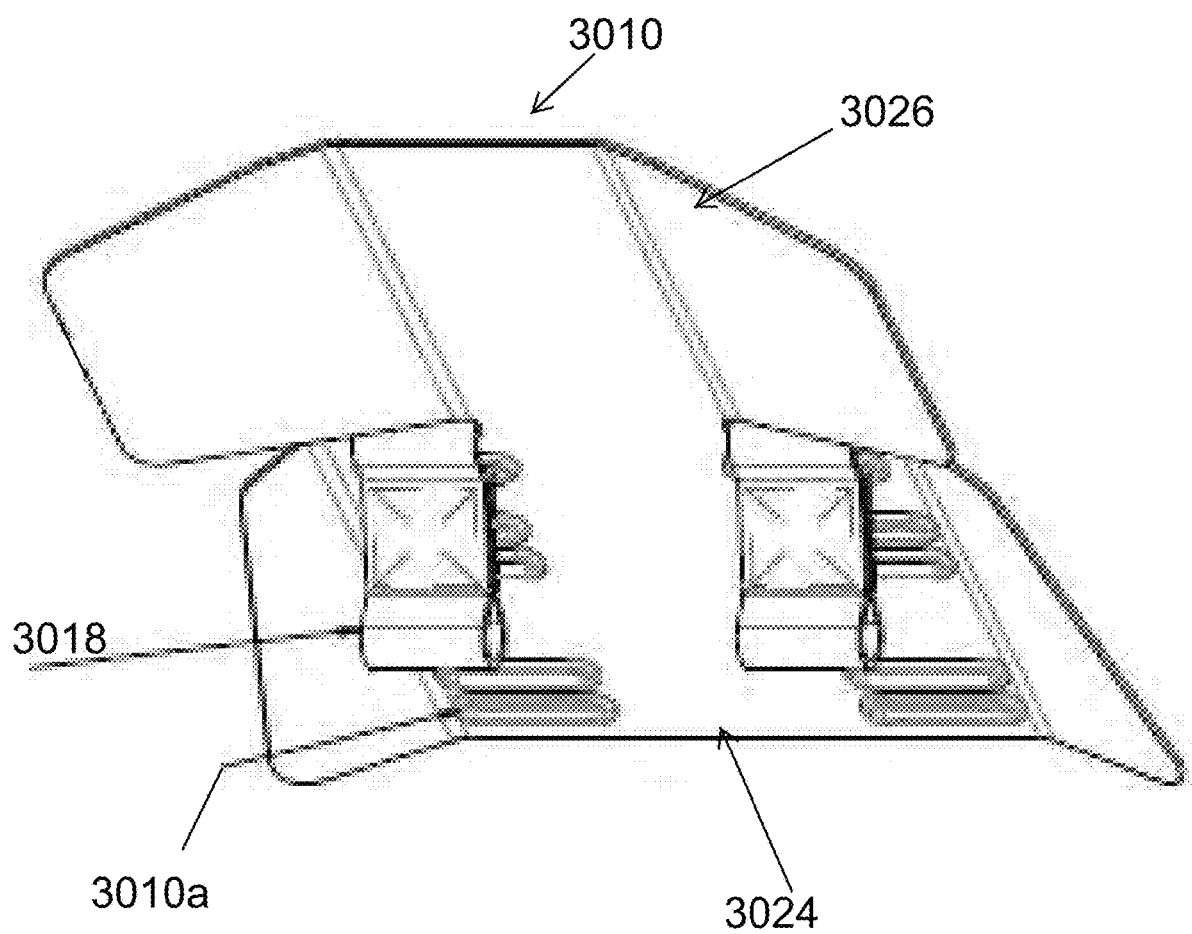
Figure 127:
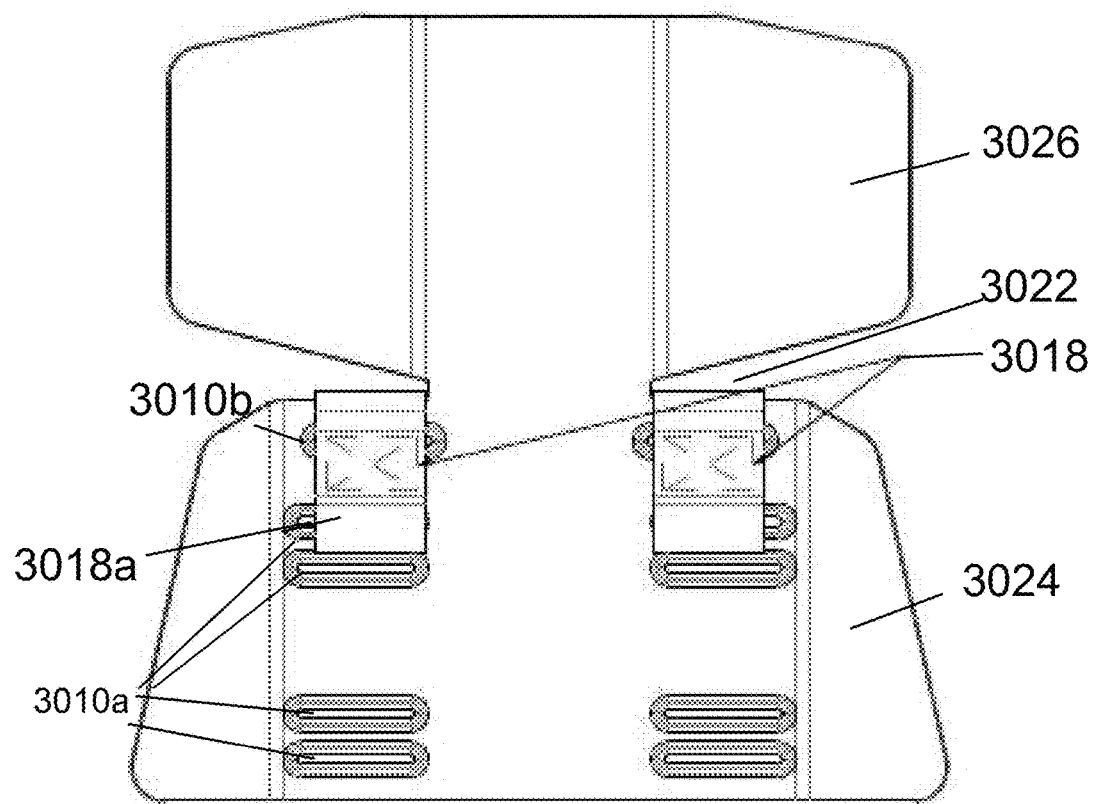
Figure 128:
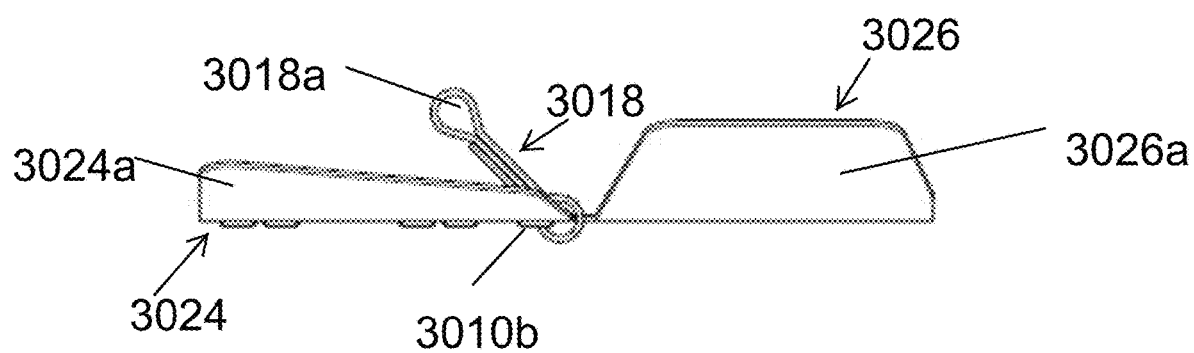
Figure 129:
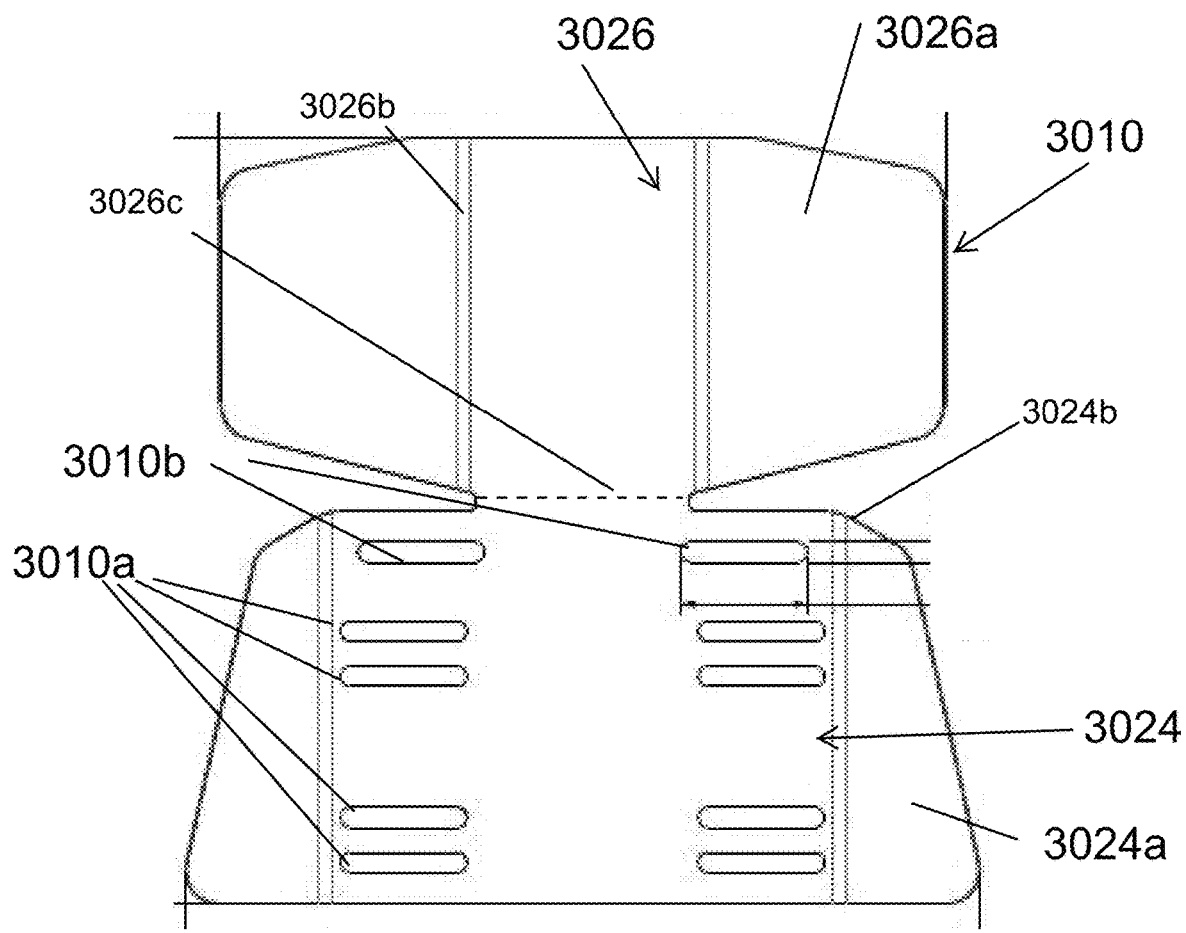
Figure 130:
Figure 131:
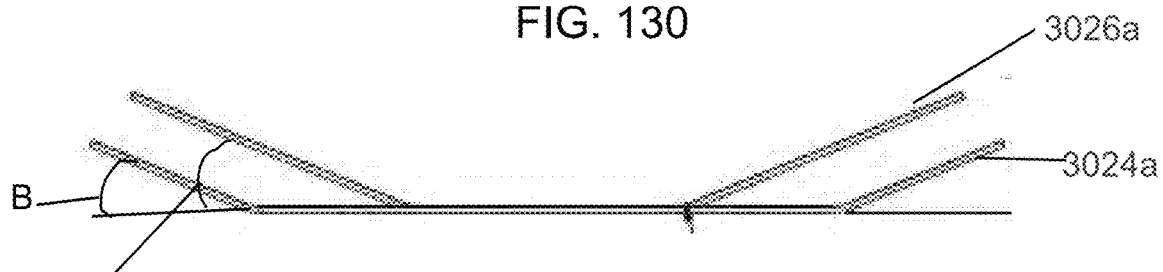
Figure 132:
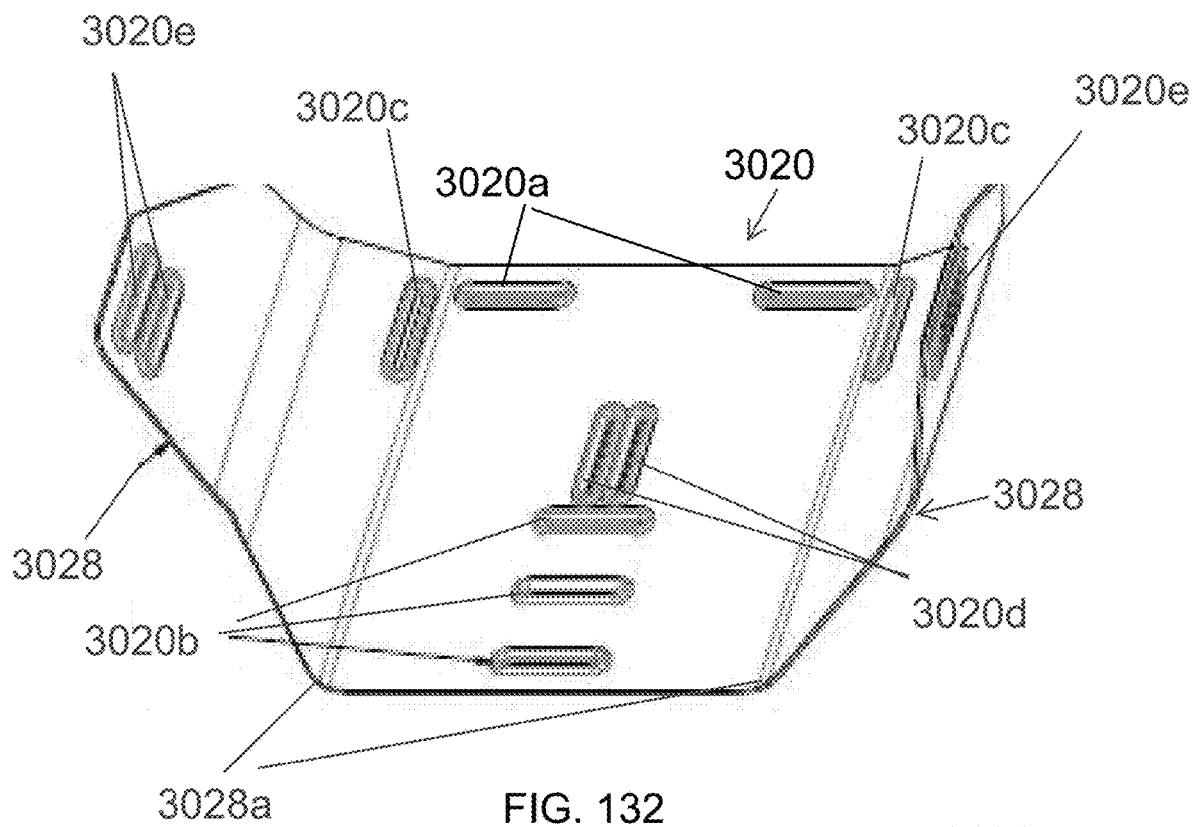
Figure 133:
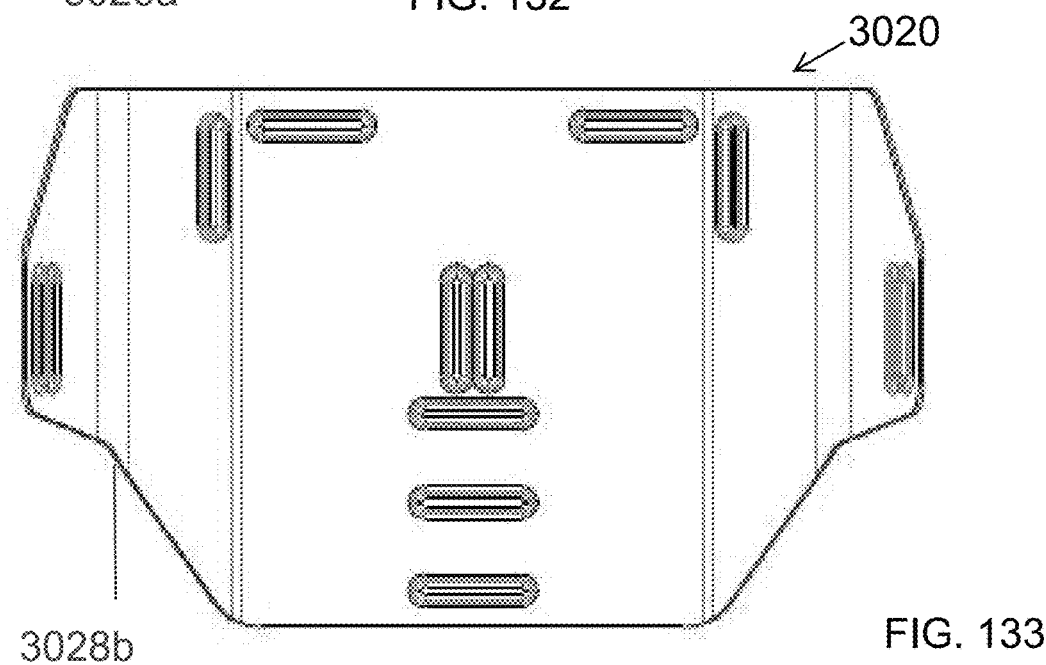
Figure 132A:
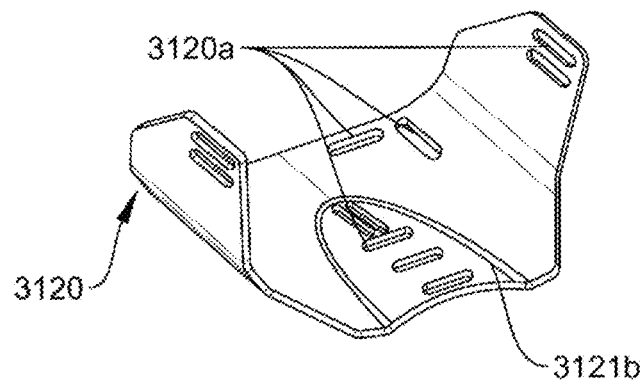
Figure 132B:
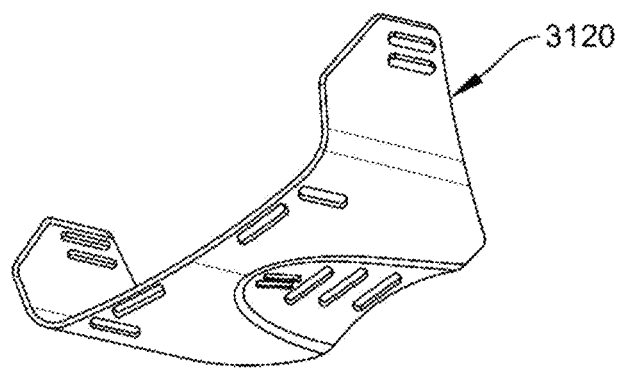
Figure 132C:
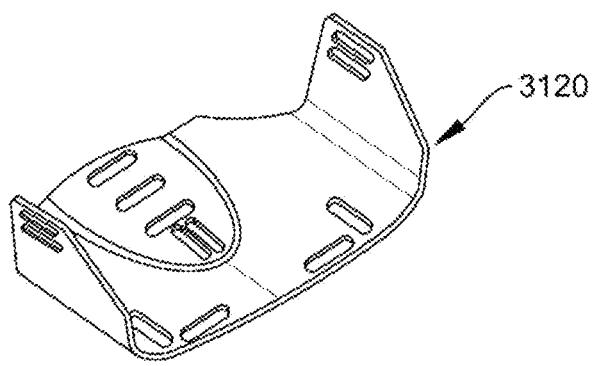
Figure 134:
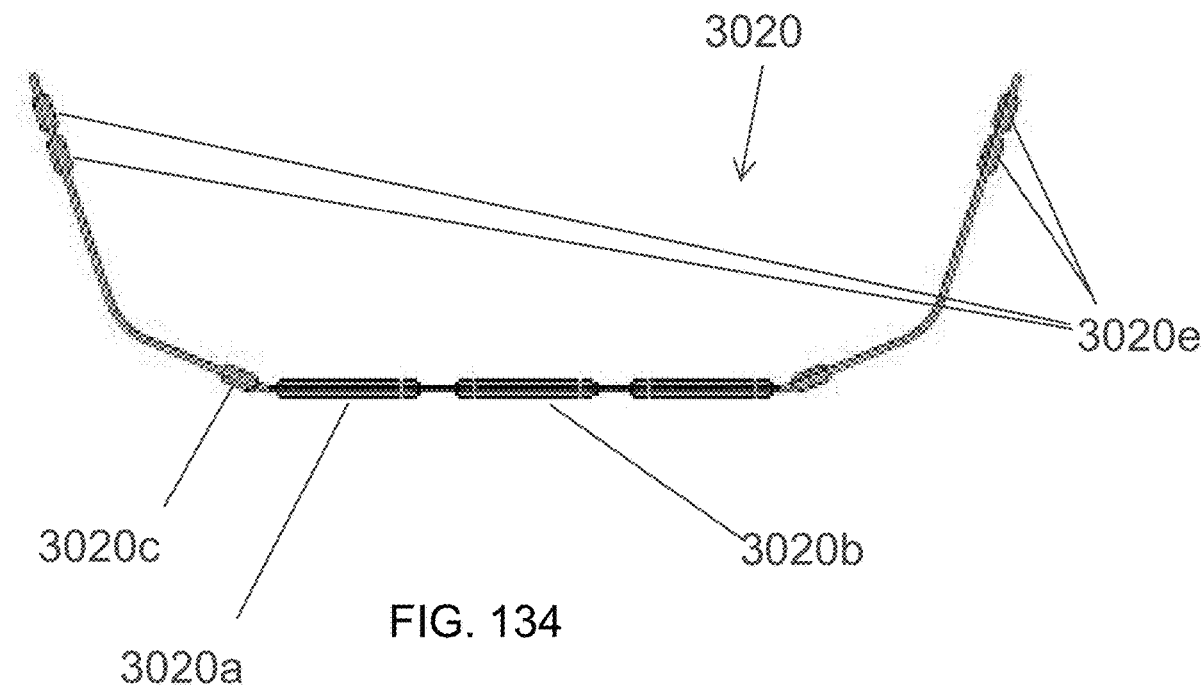
Figure 135:
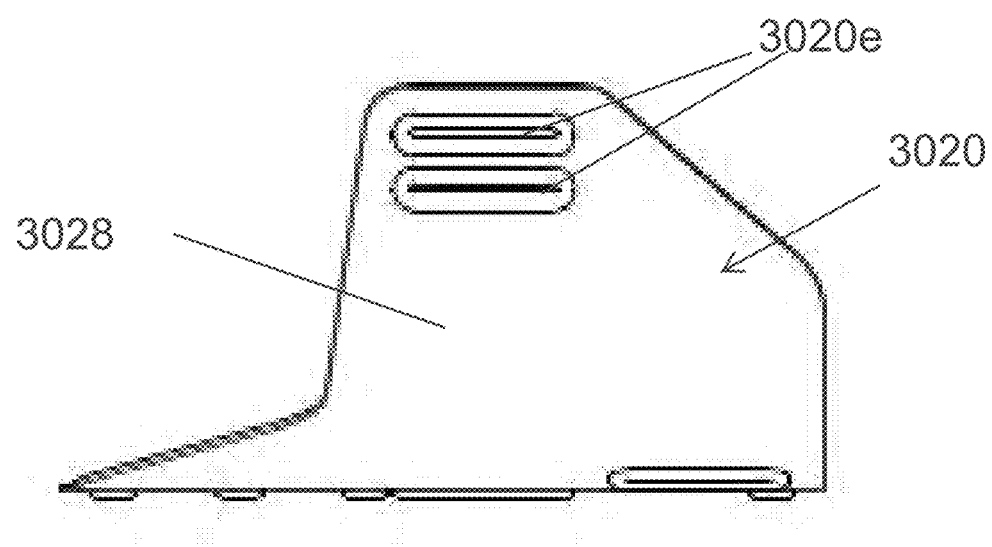
Figure 135A:
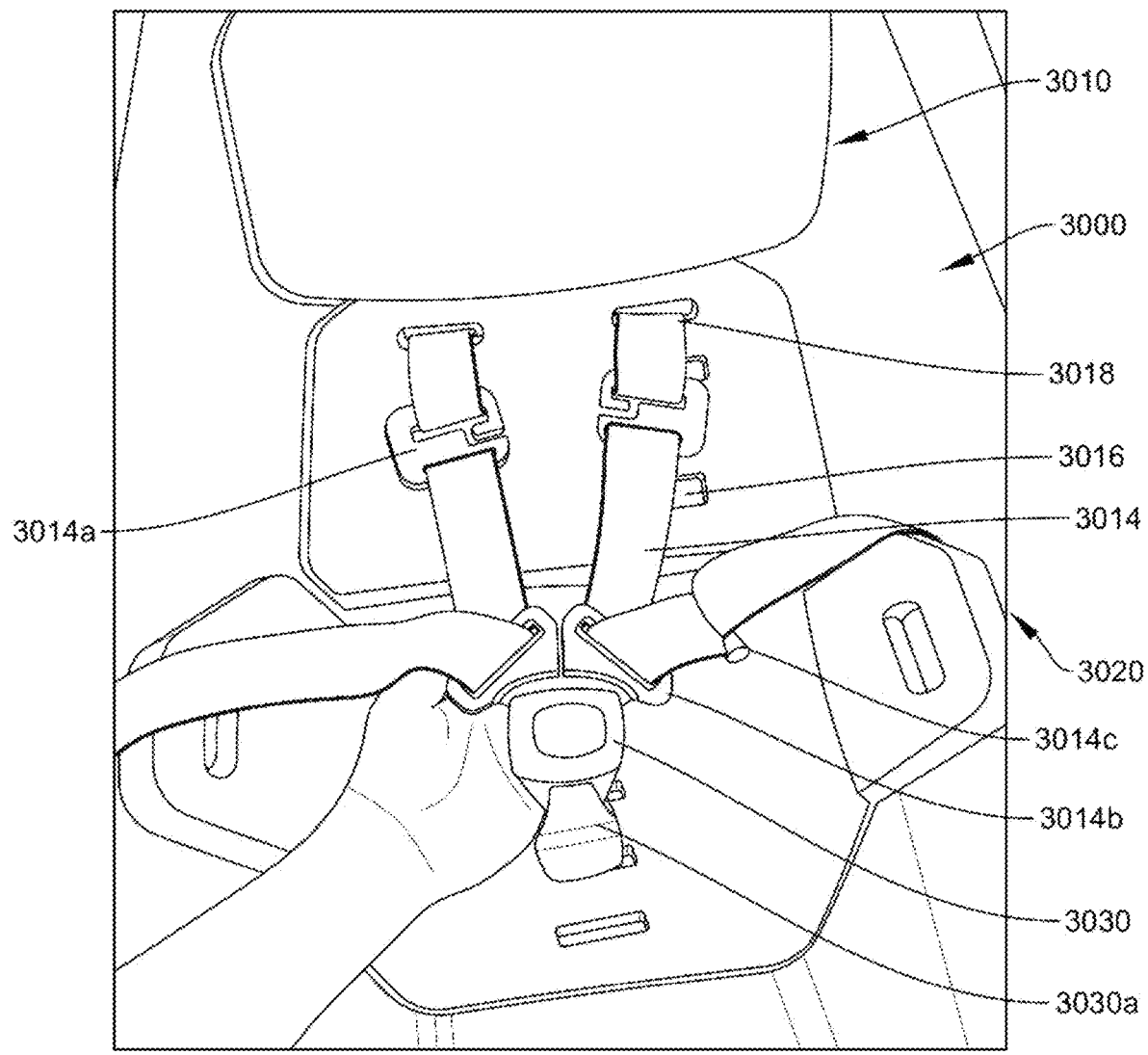
Figure 135B:
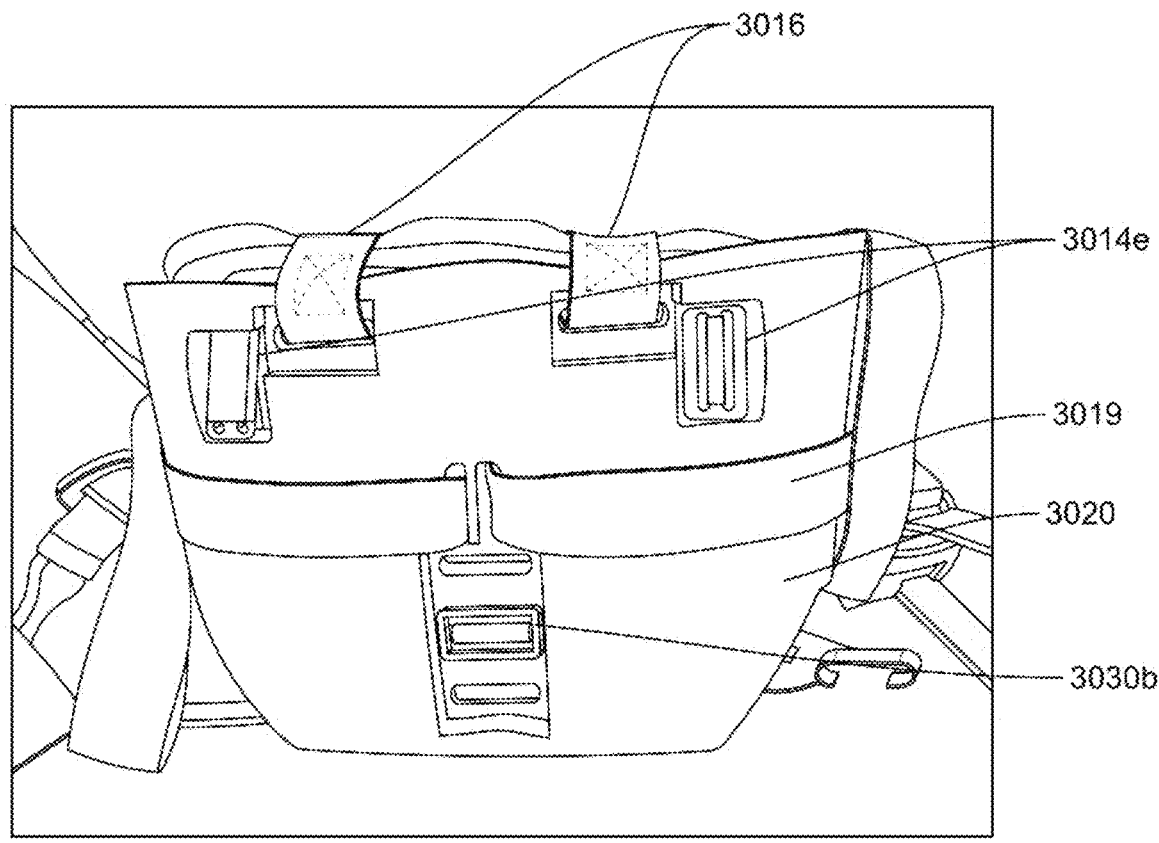
Figure 135C:
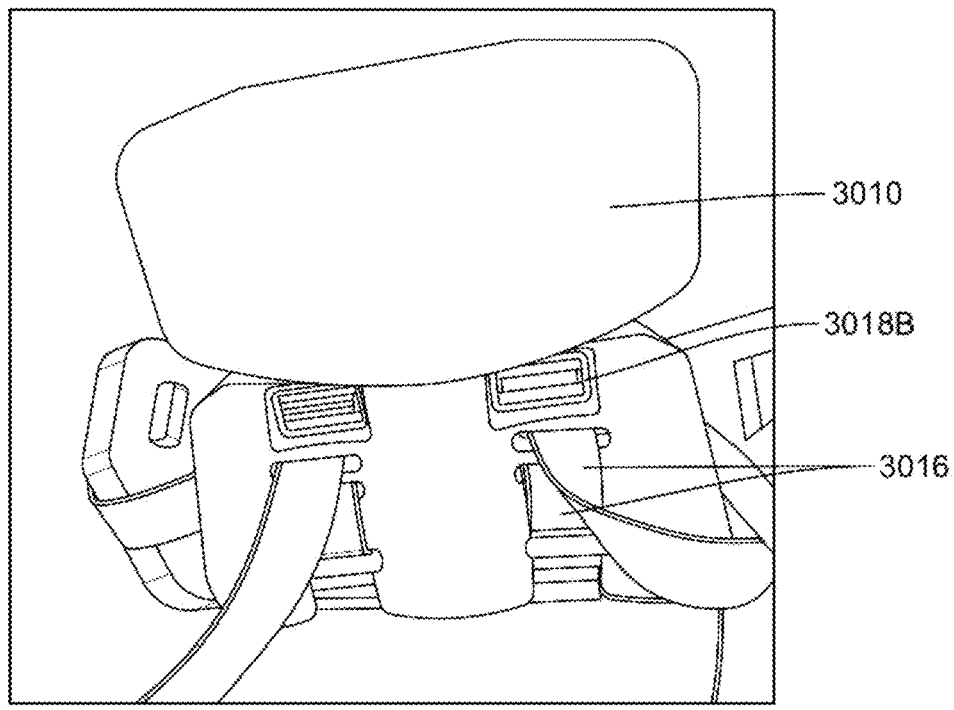
Figure 136D:
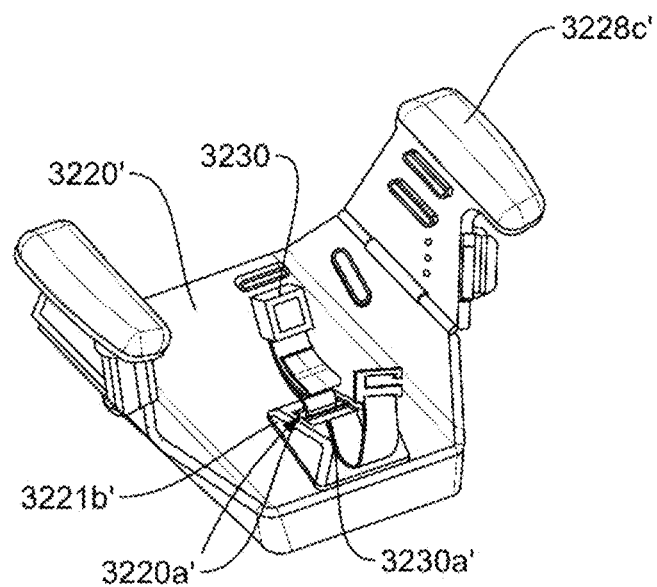
Figure 136E:
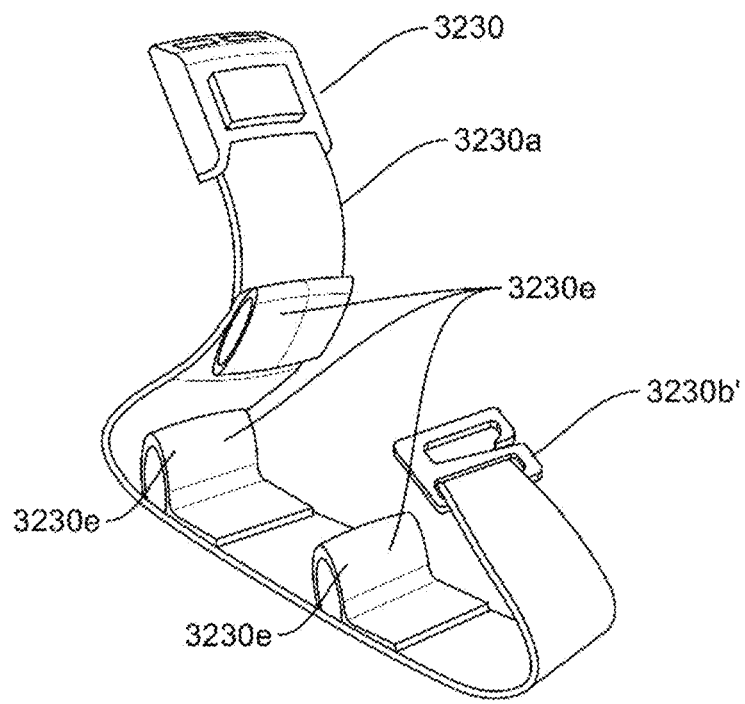
Figure 136G:
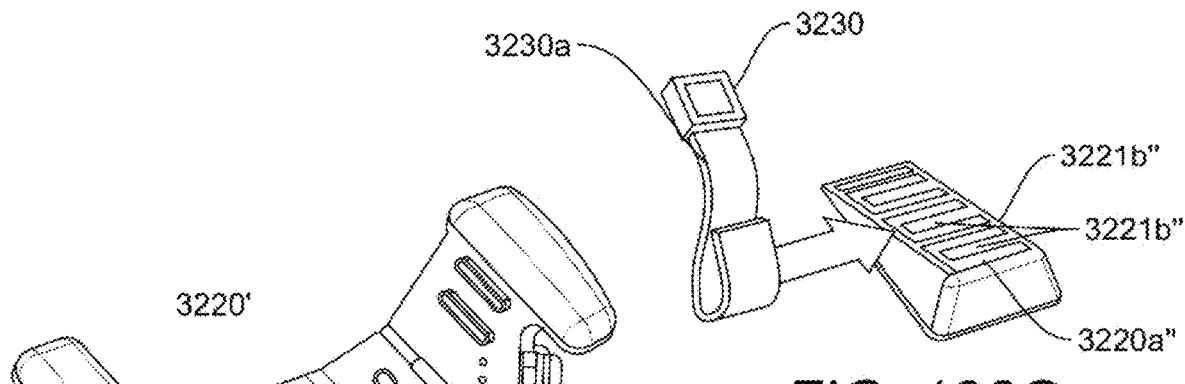
Figures 136F, 136H:
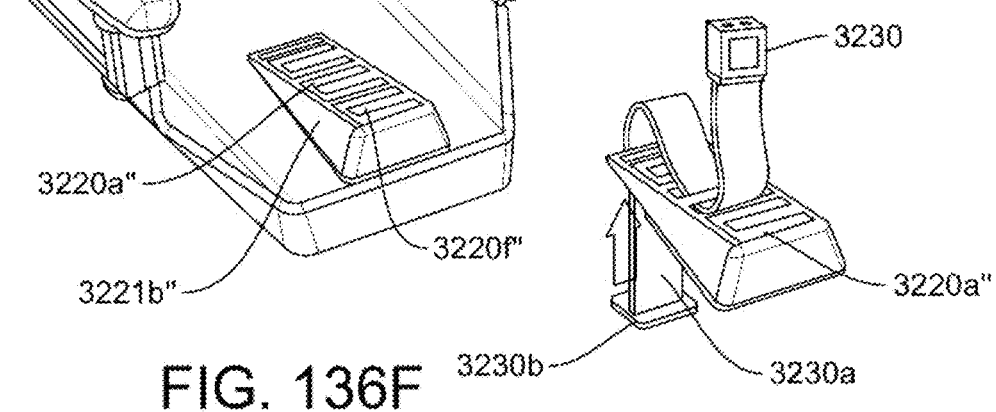
Figure 136J:
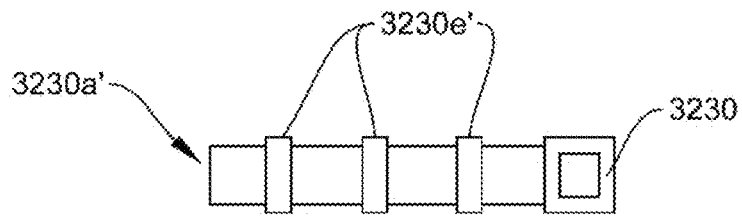
Figure 136K:
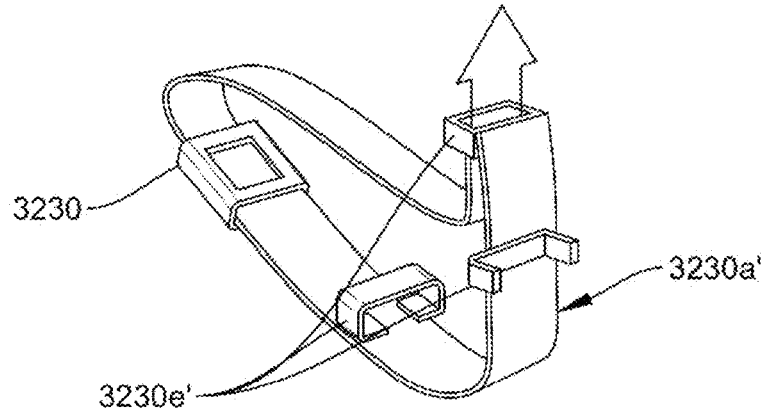
Figure 137:
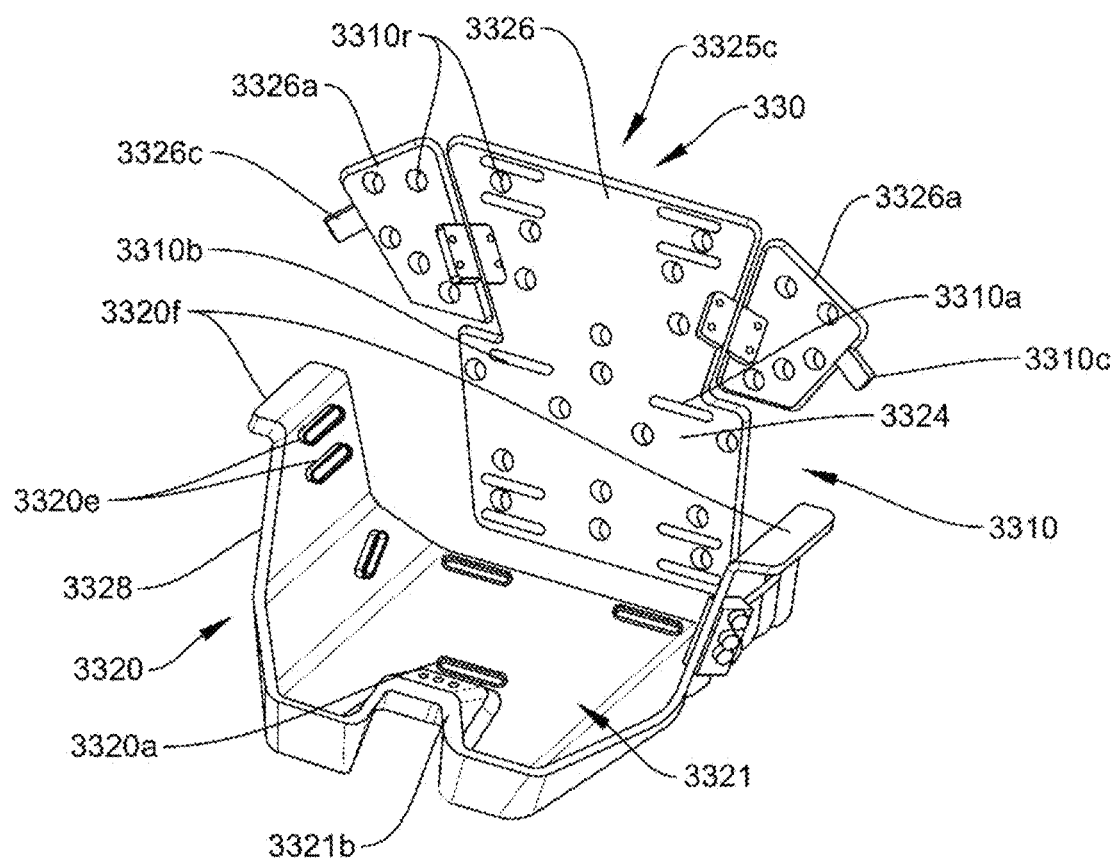
Figure 137A:
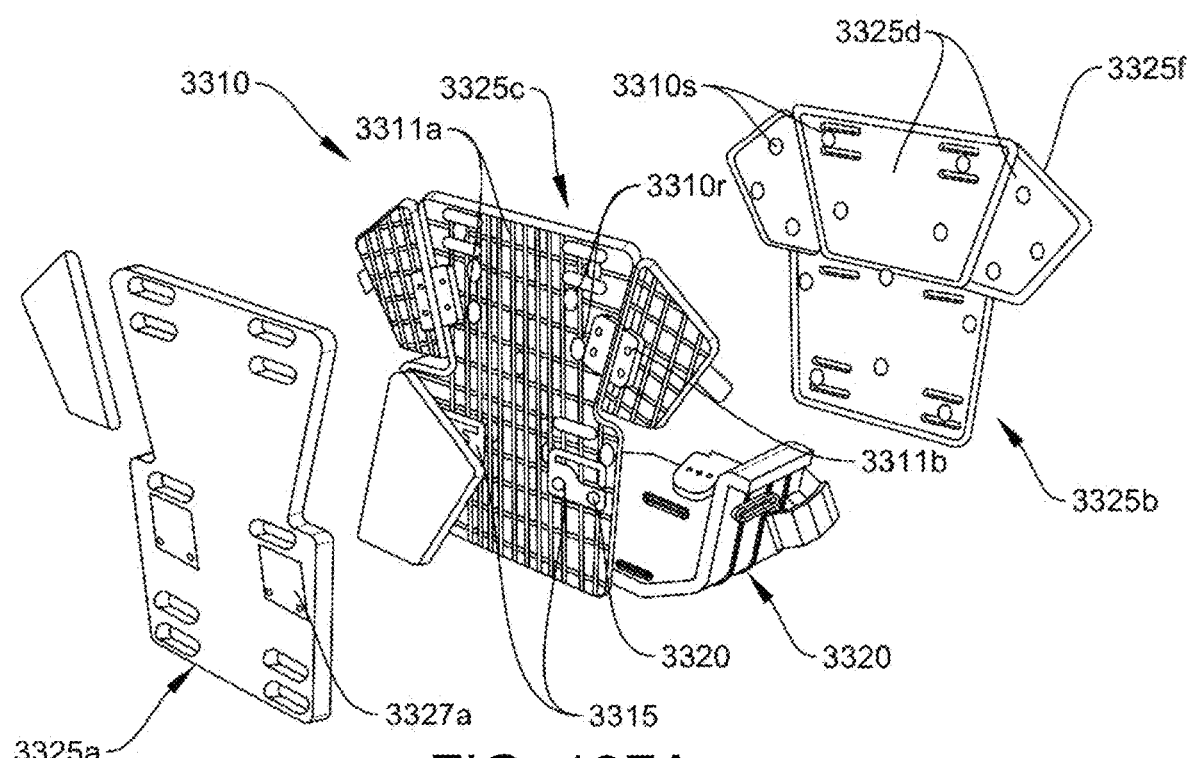
Figure 137B:
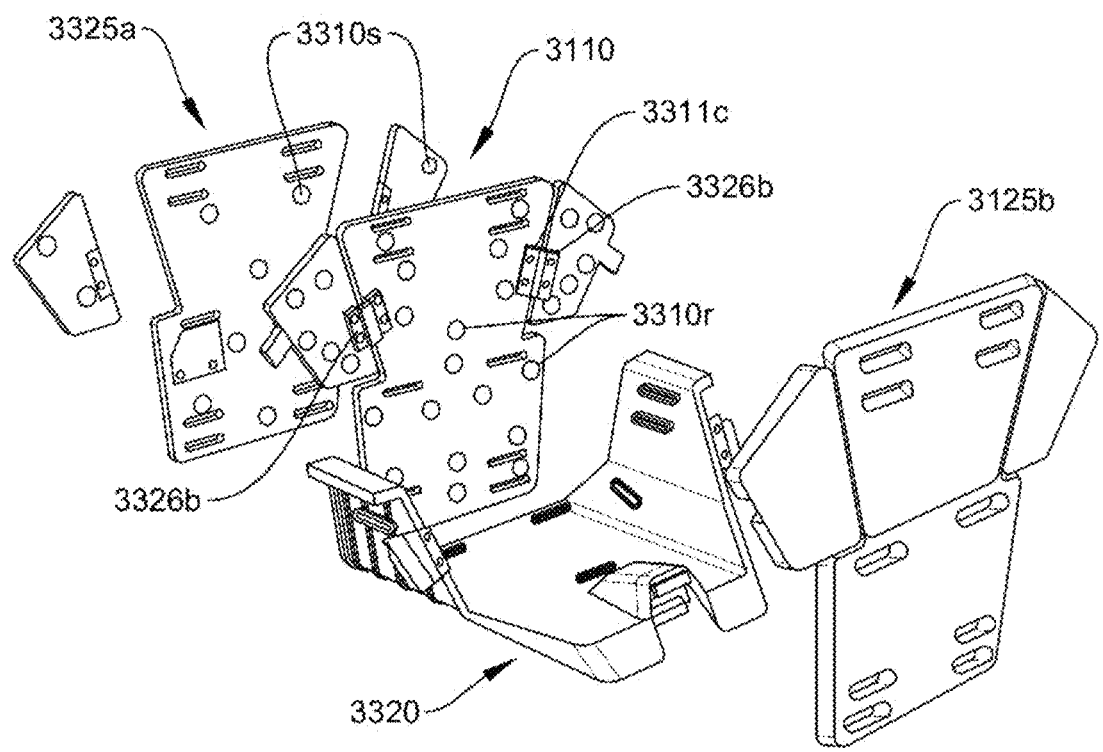
Figure 143:
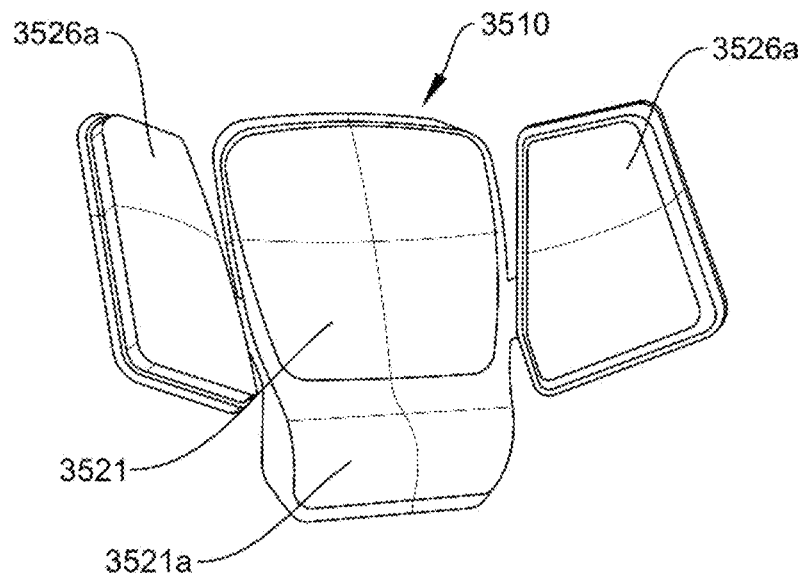
Figure 143A:
Figure 143B:
Figure 143C:
Figure 144:
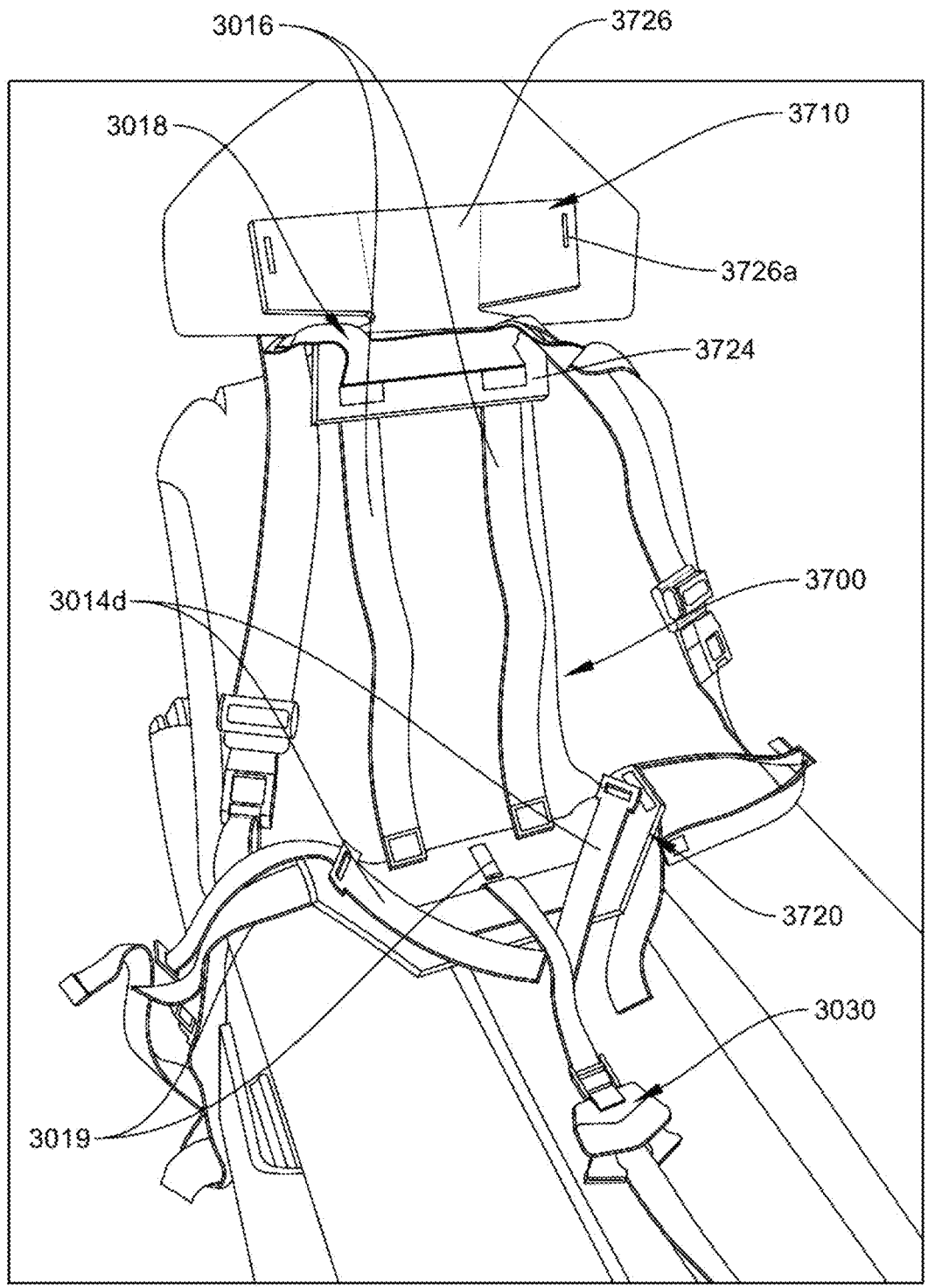
Figure 145:
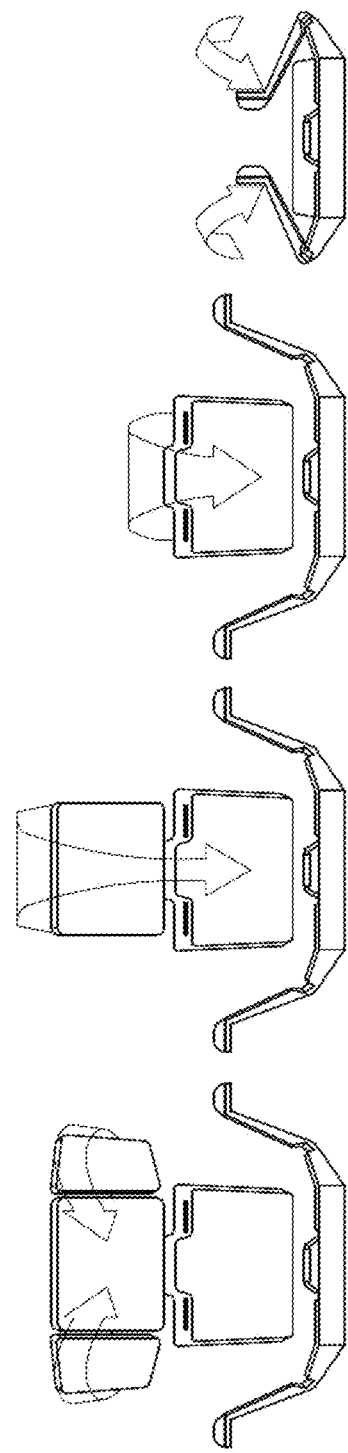
Figure 145A:
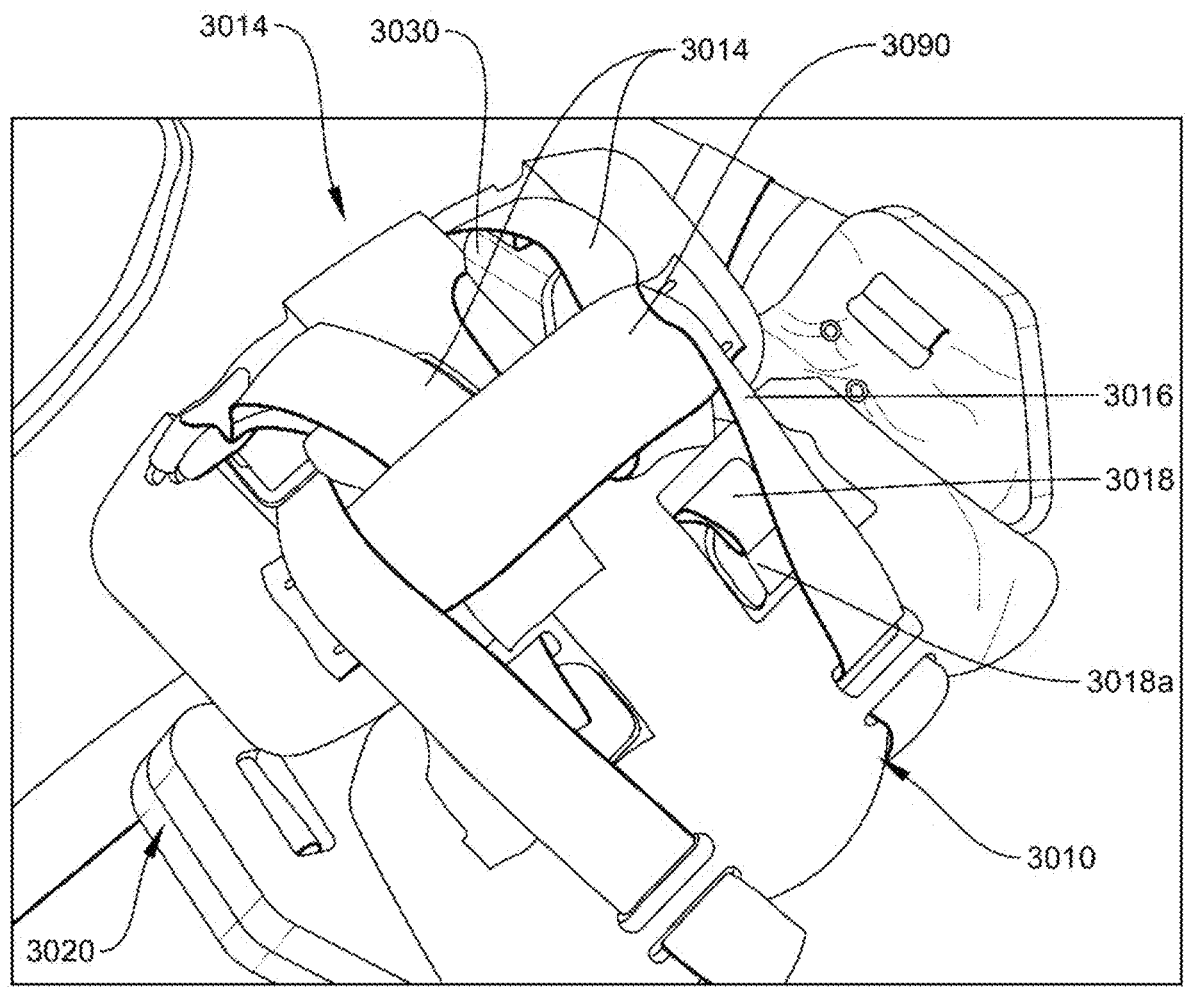
Figure 145B:
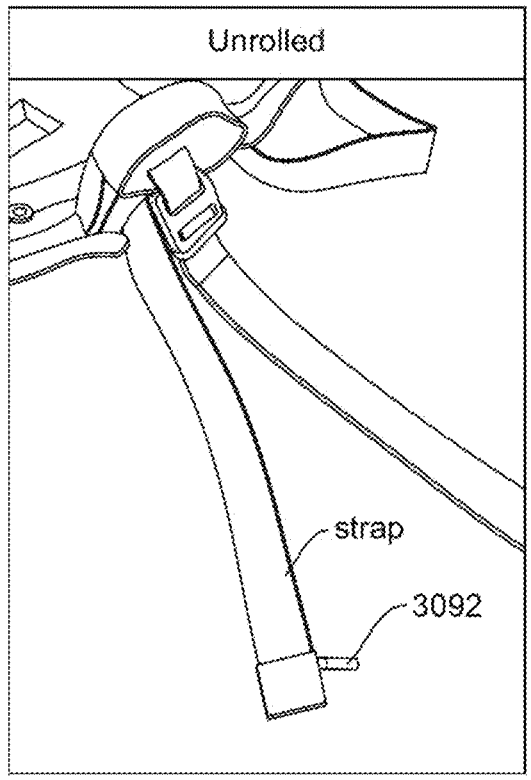
Figure 145C:
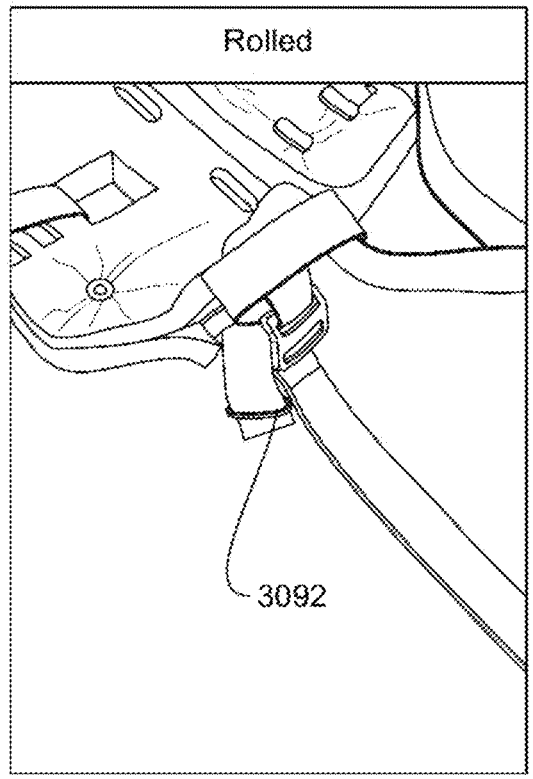
Figure 145D:
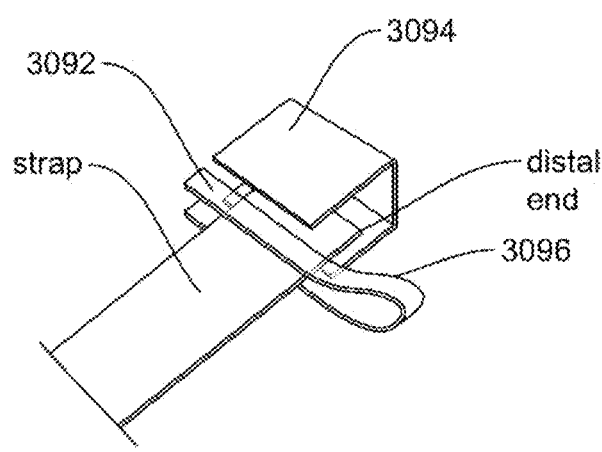
Figure 145E:
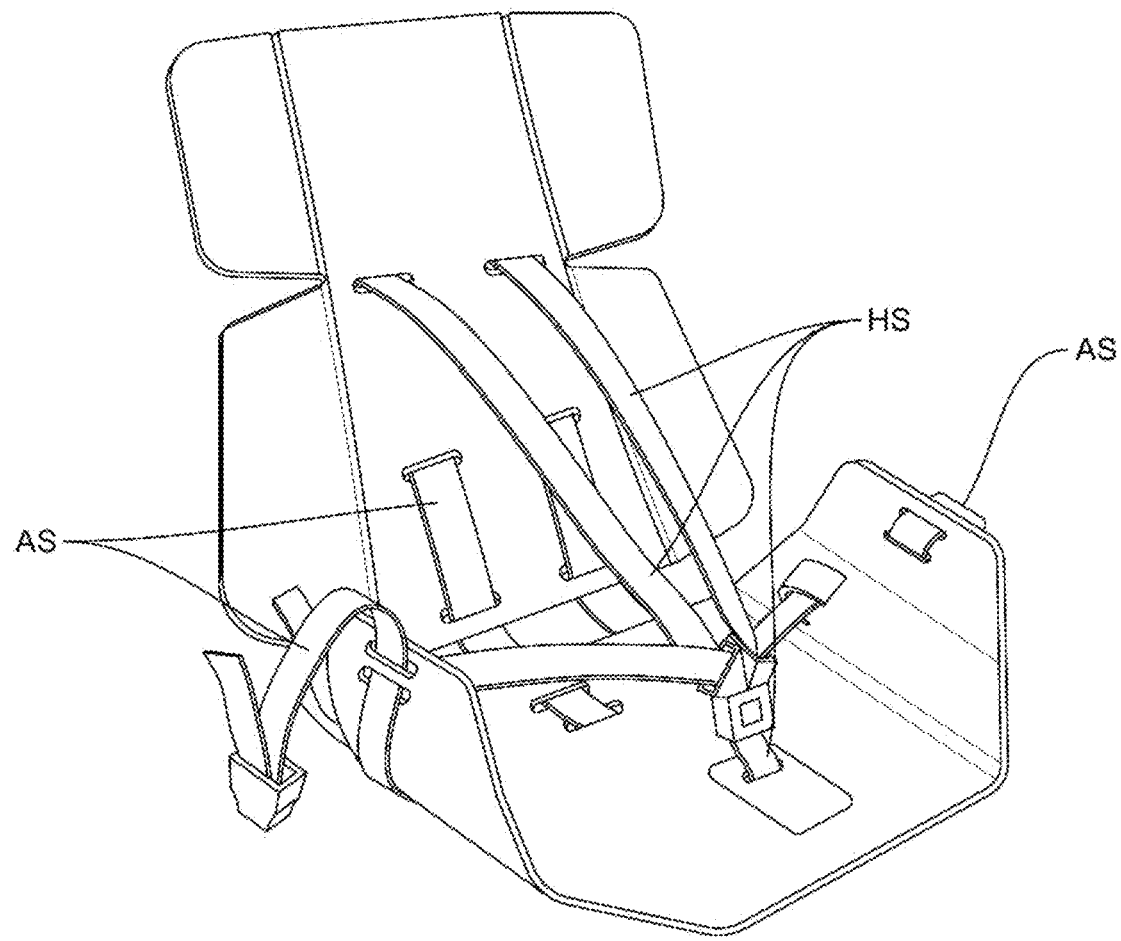
Figure 146A:
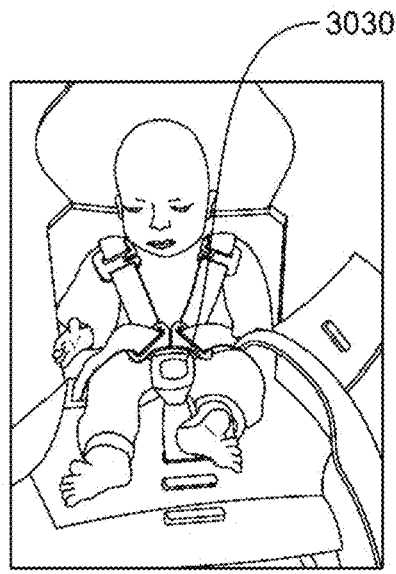
Figure 146B:
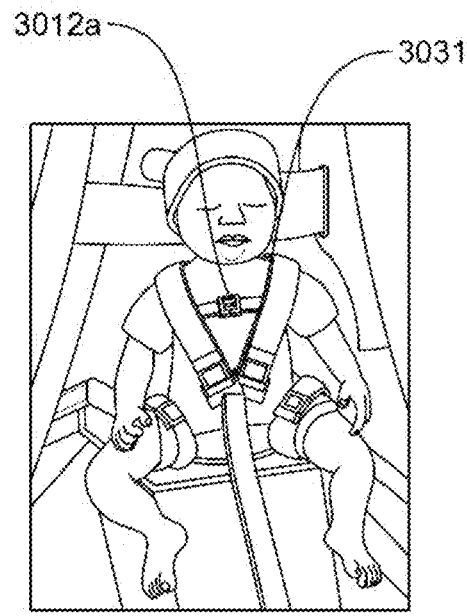
Figure 146C:
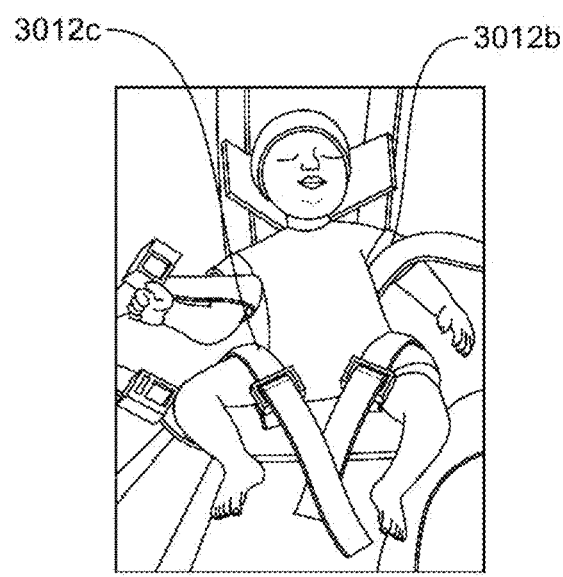
Figure 146D:
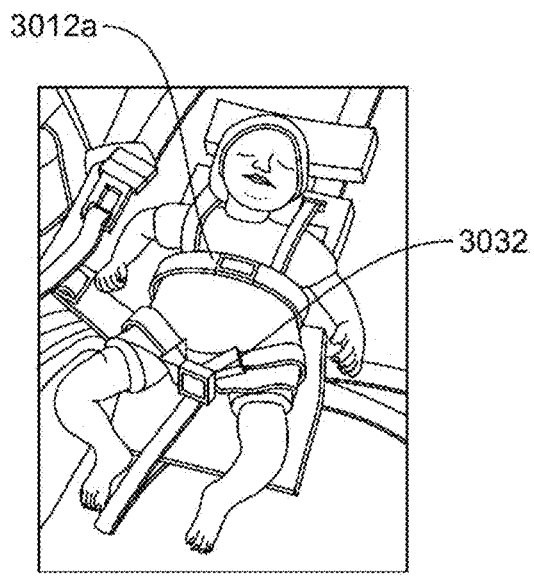
Figure 147:
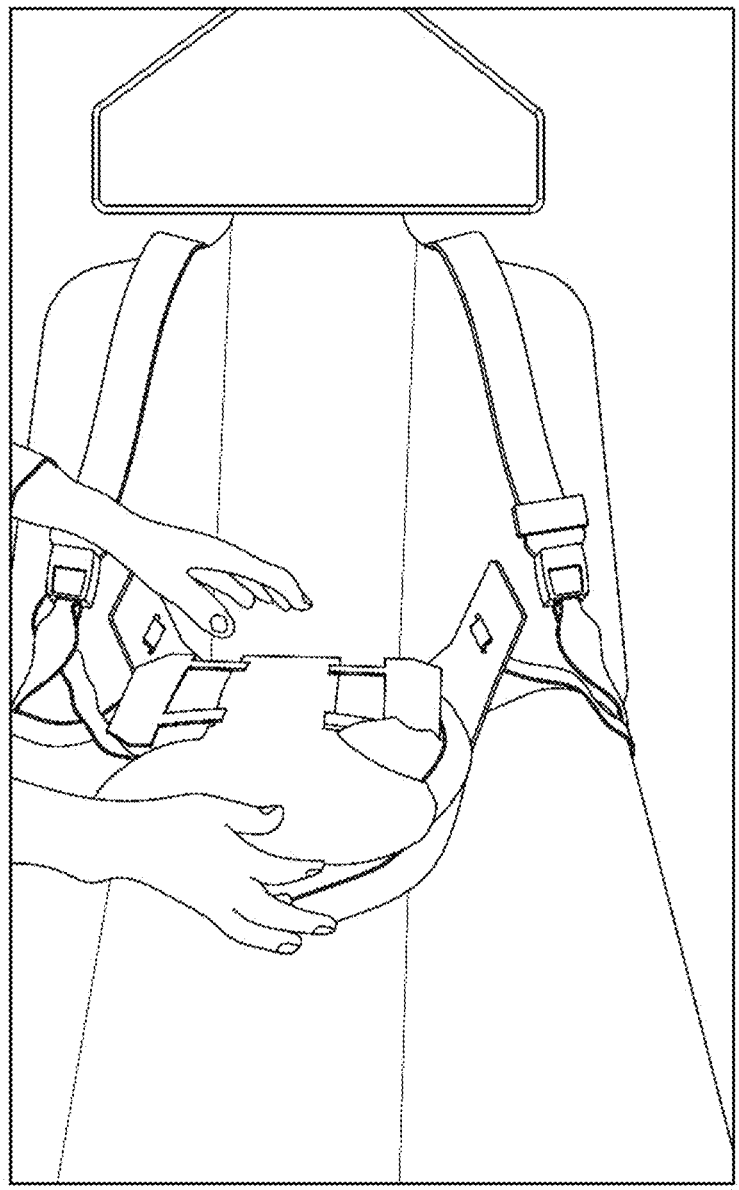
Figure 148:
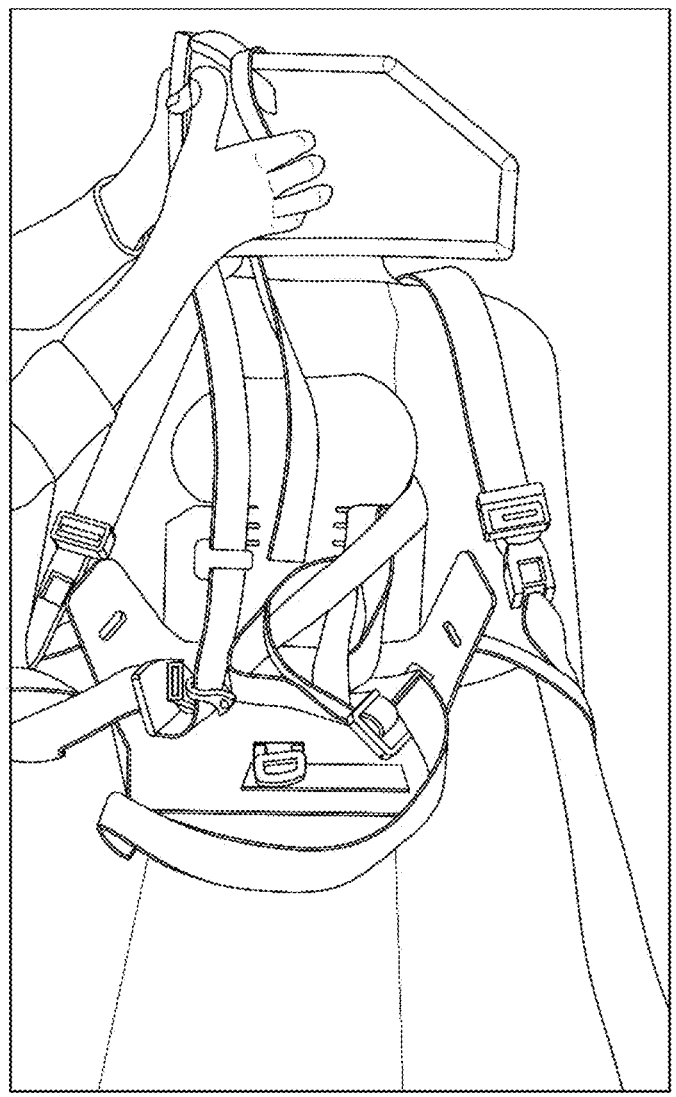
Figure 149:
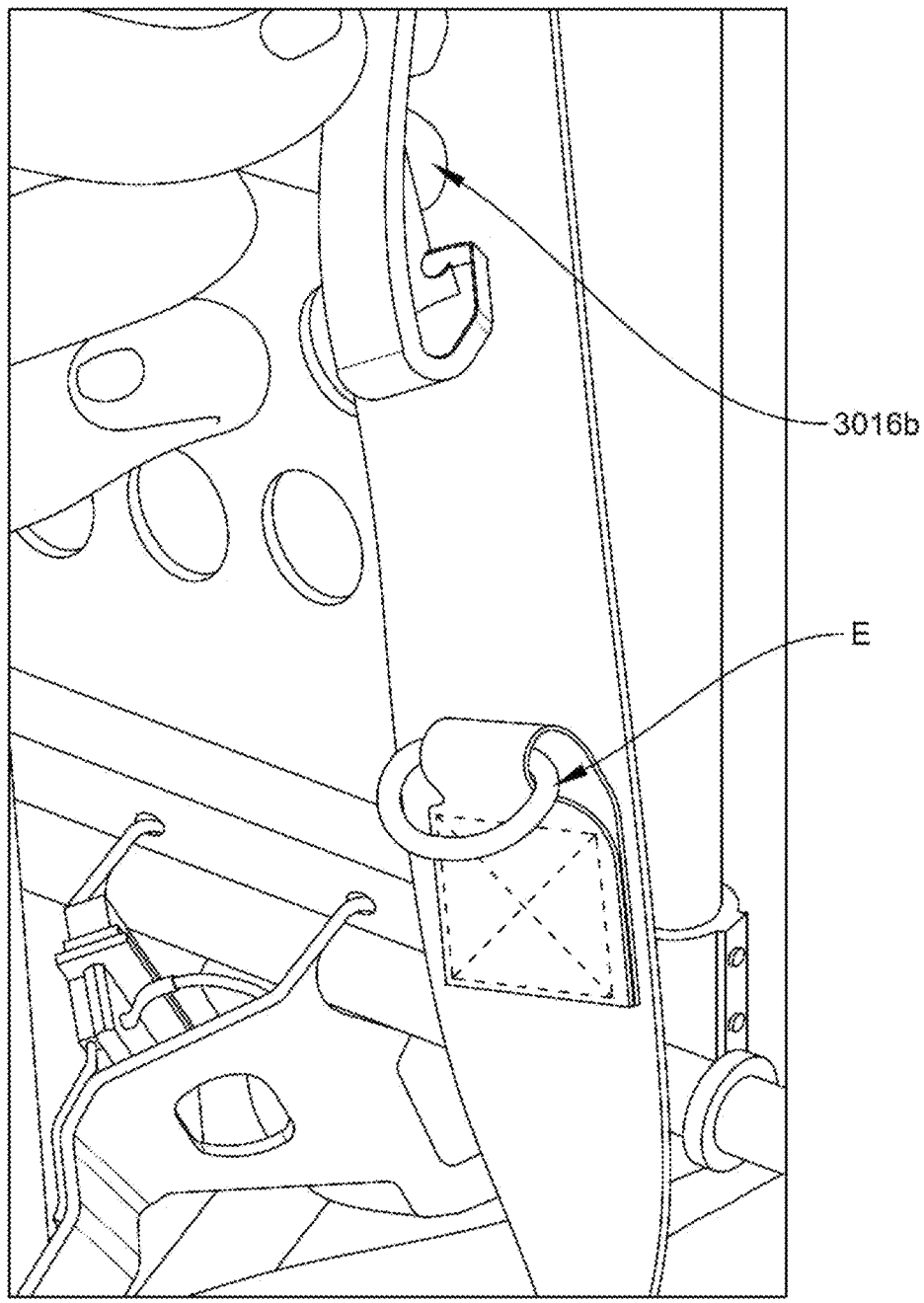
Figure 150:
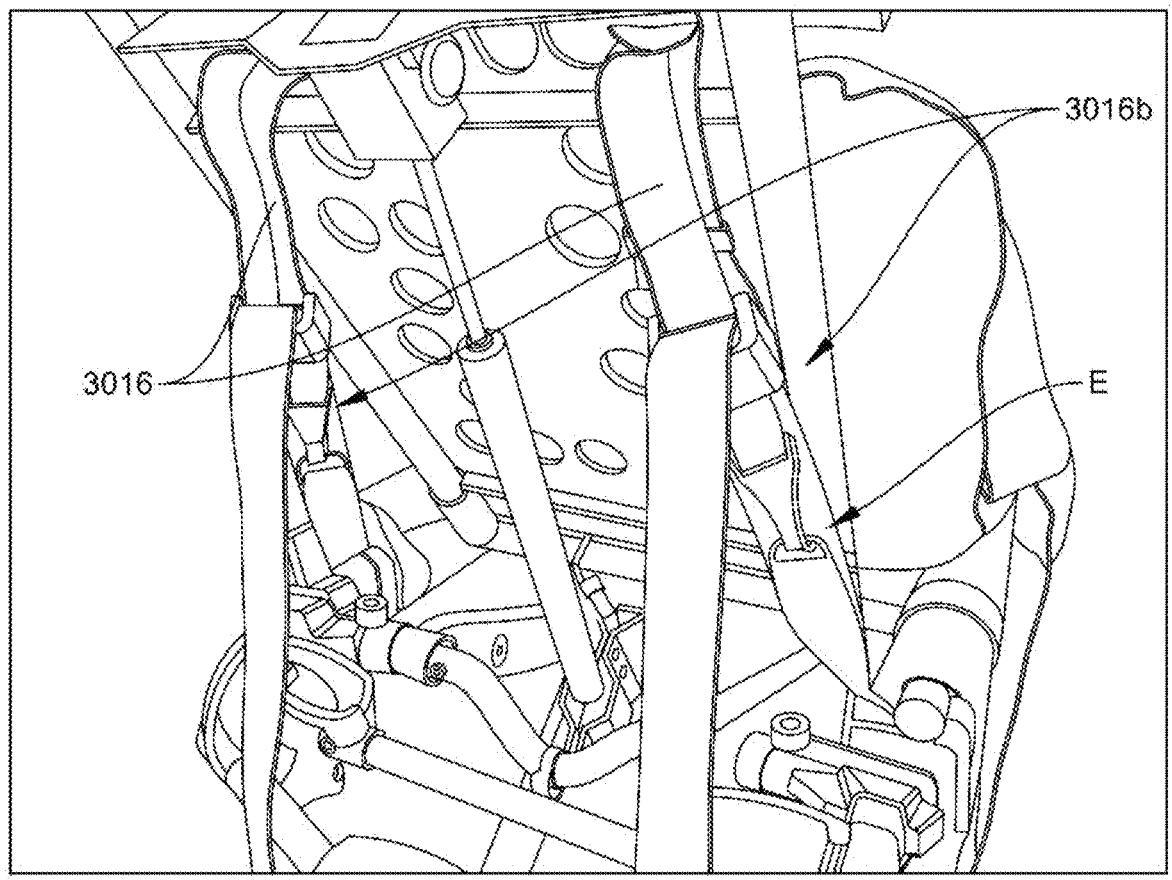
Figure 151:
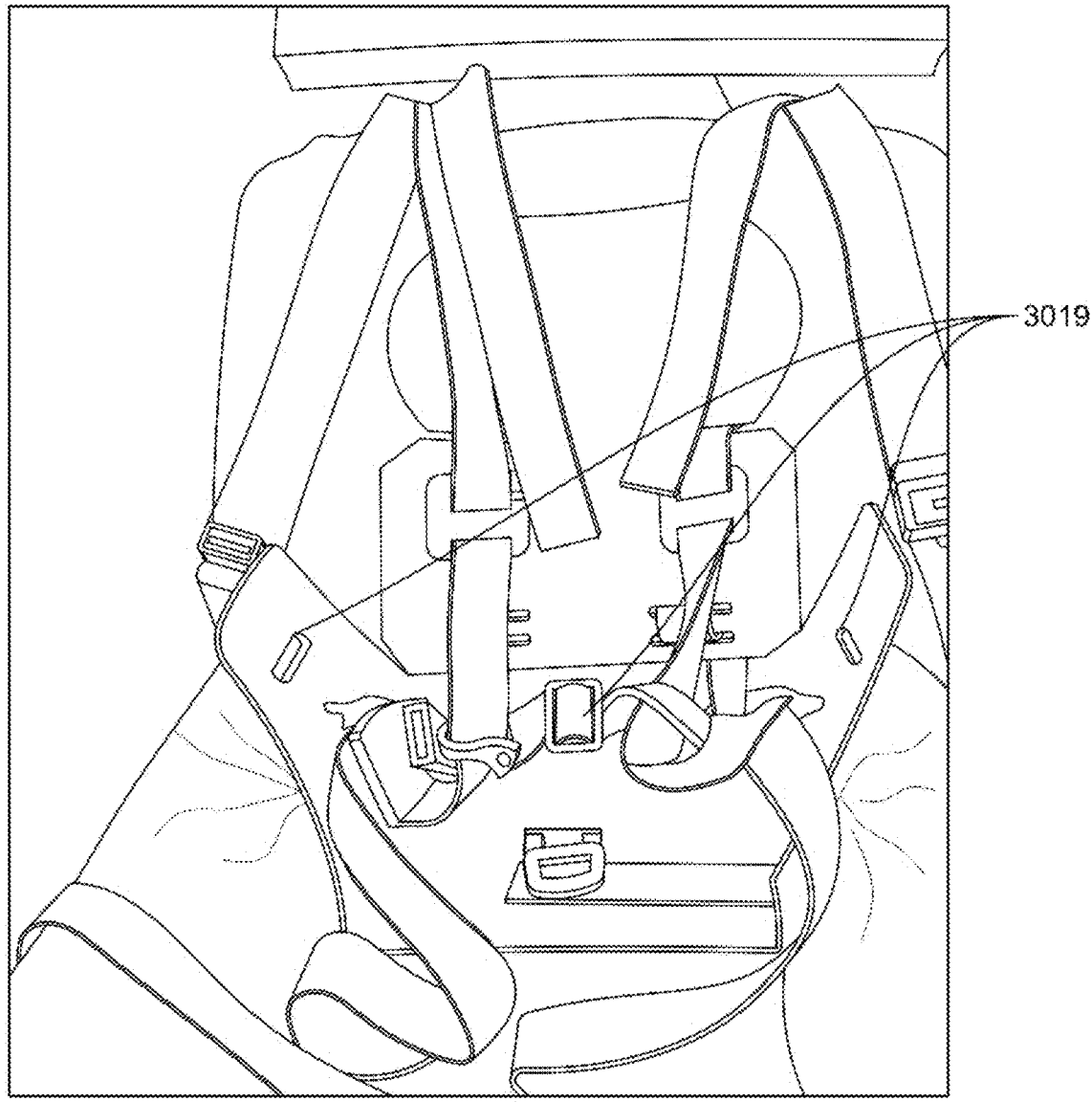
Figure 152:
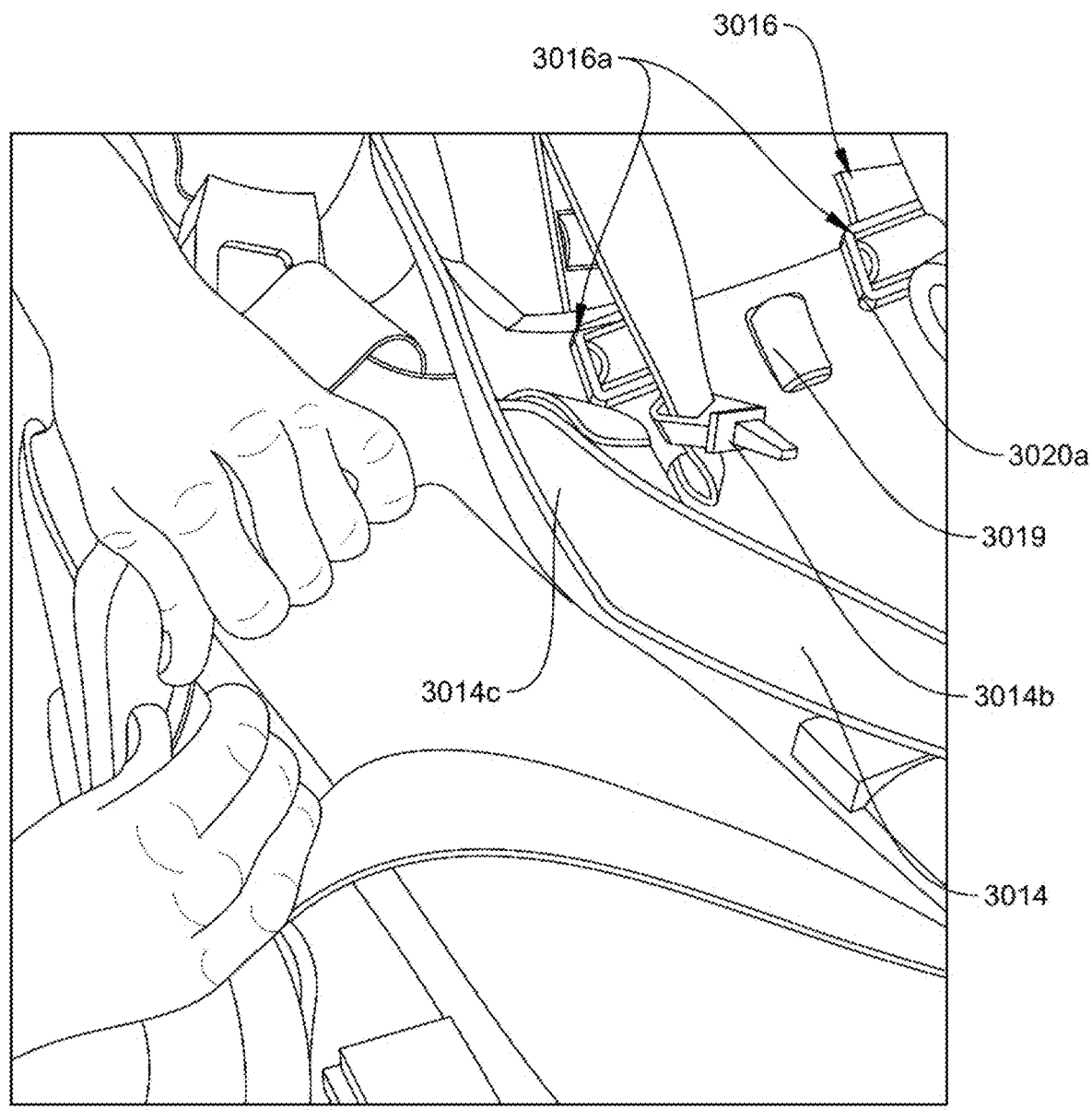
Figure 153:
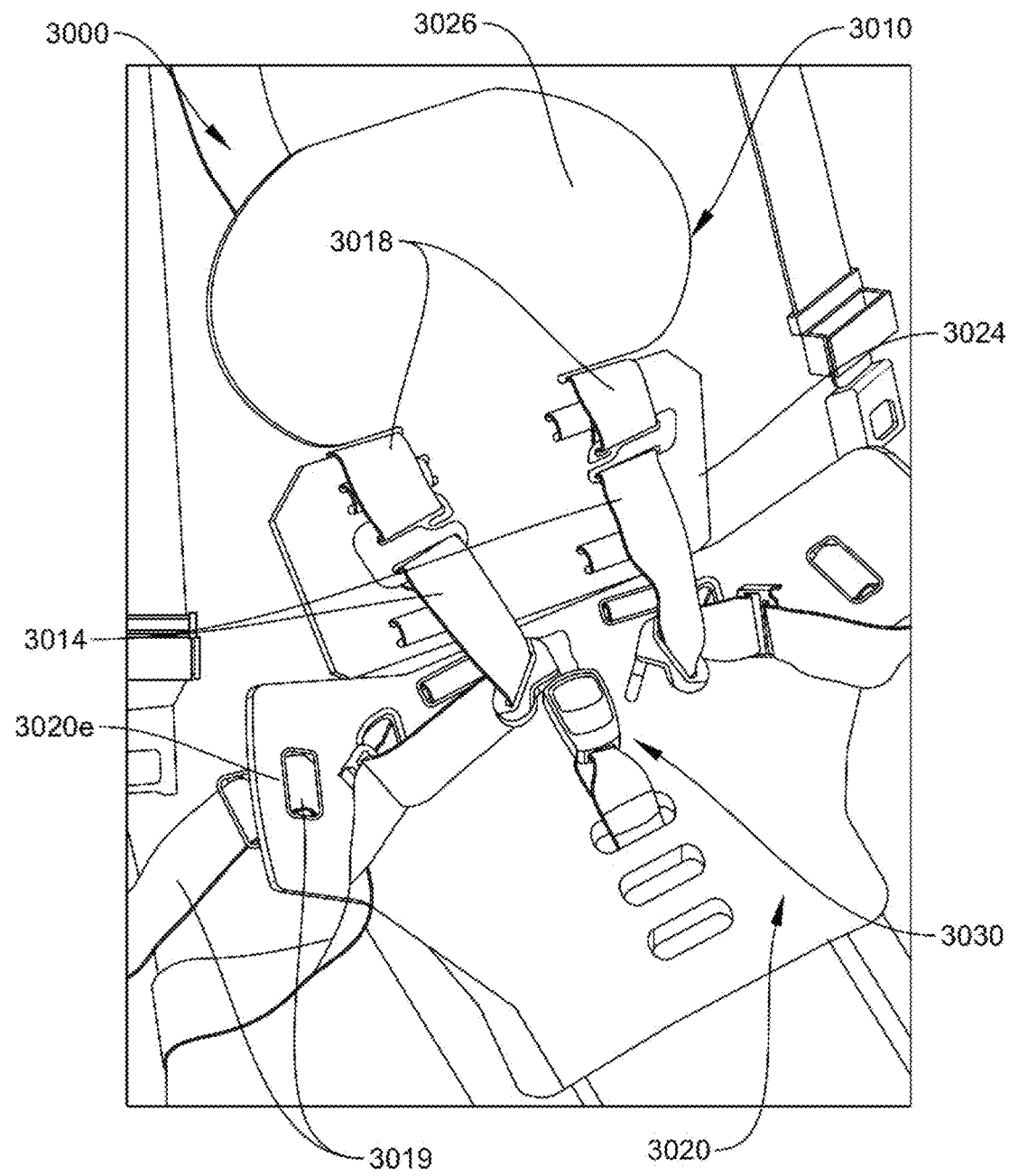
Figure 154:
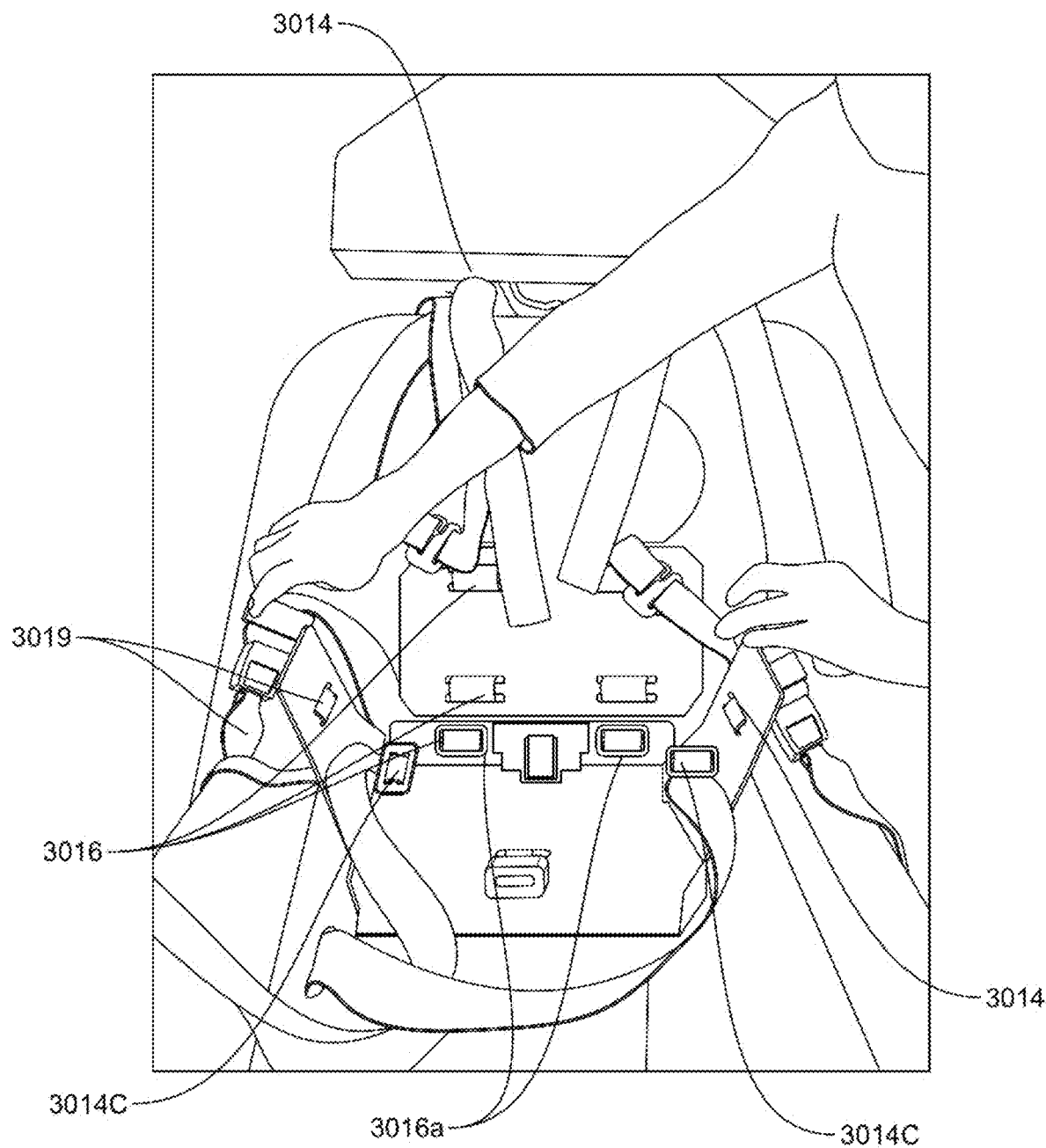
Figure 155:
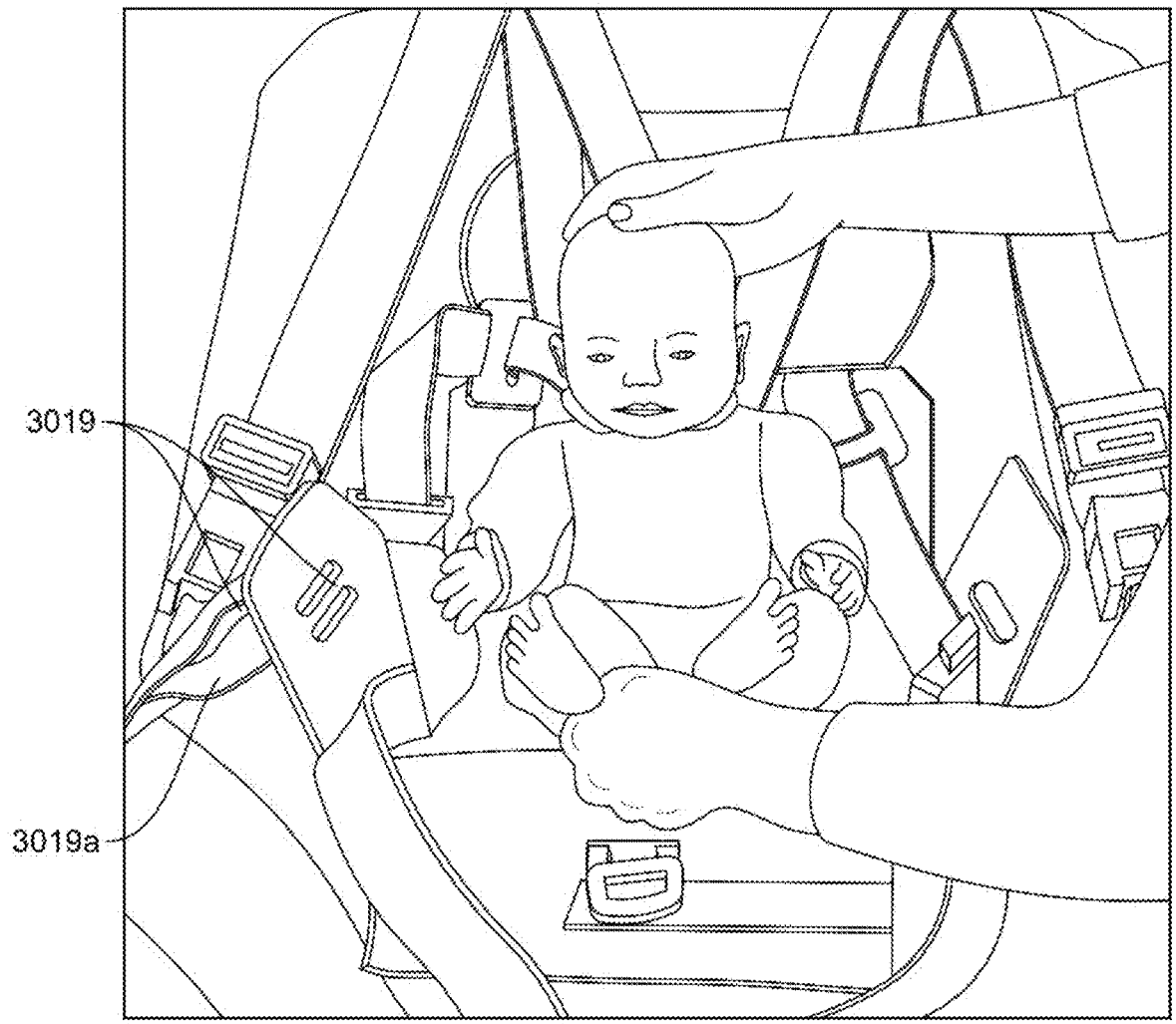
Figure 156:
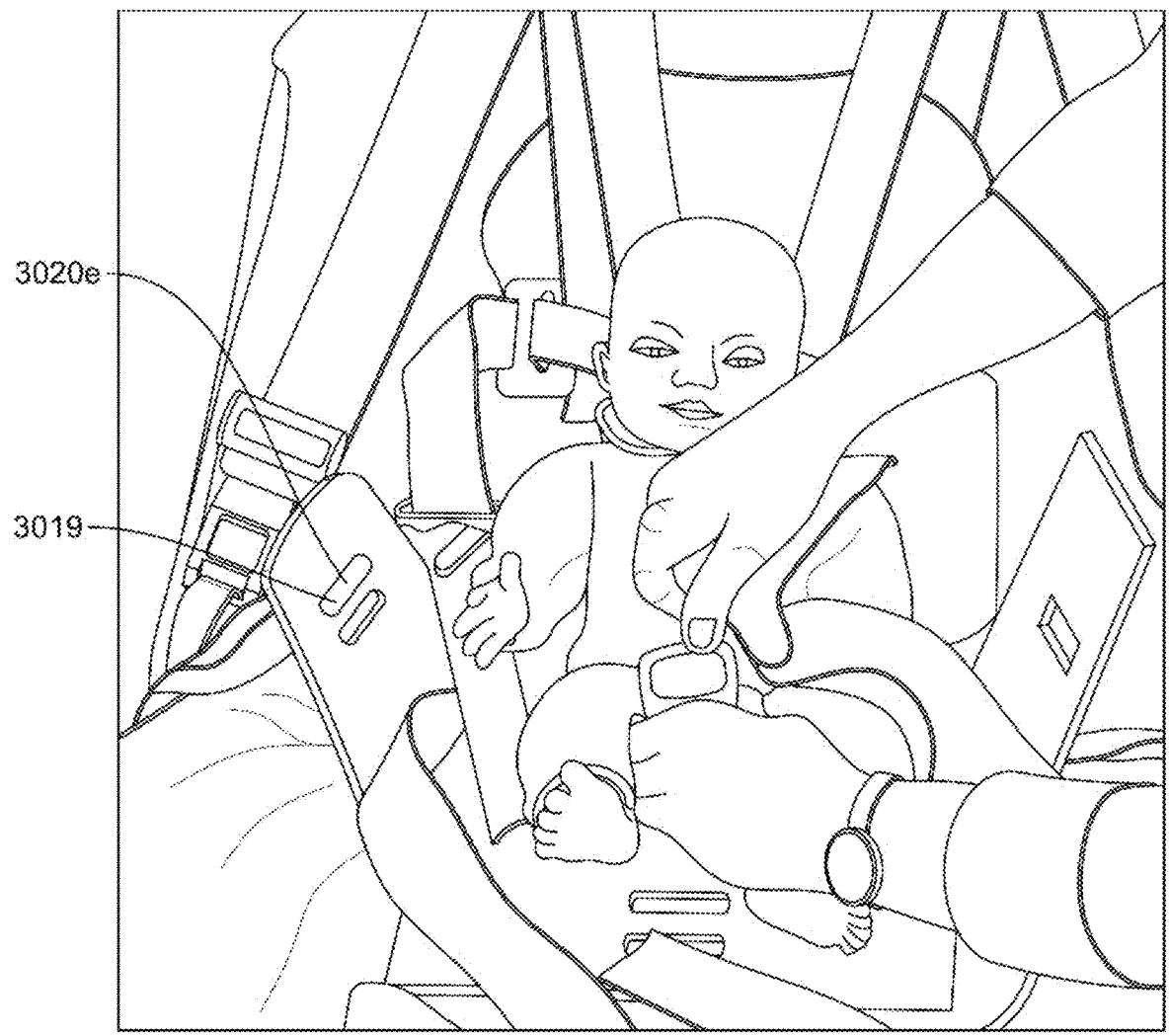
Figure 157:
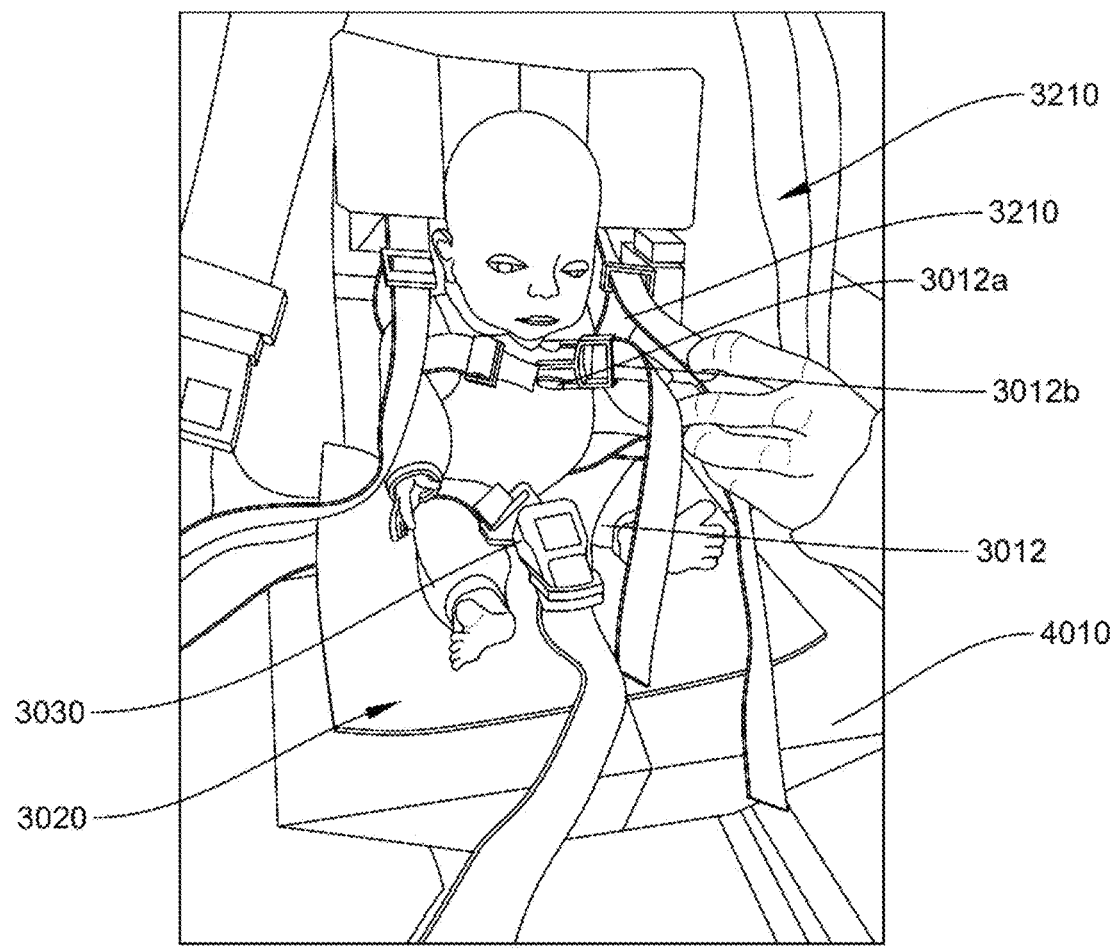
Figure 158:
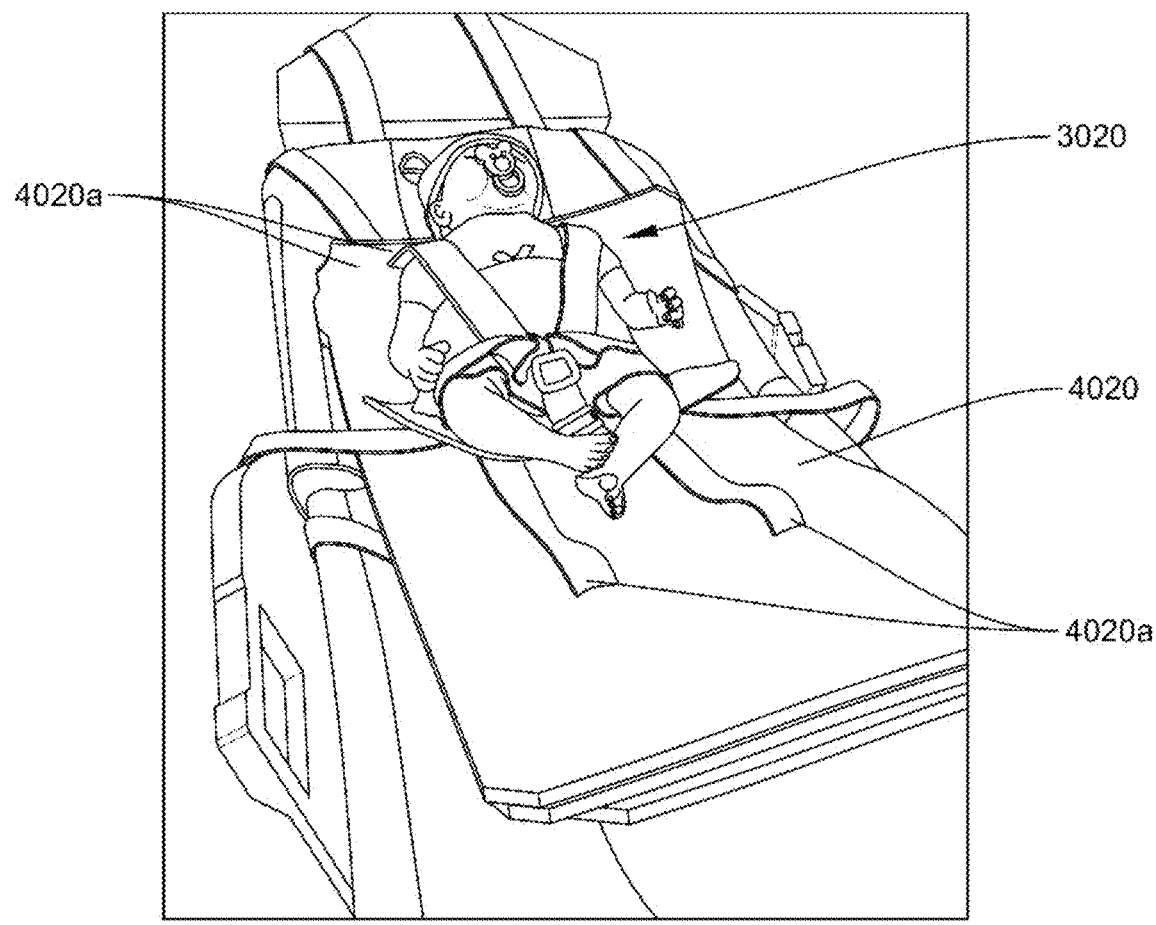

FIG. 103 is a perspective view of a headrest suitable for use with the pediatric restraint assembly;

FIG. 104 is a right side elevation view of the headrest of FIG. 103, which is a mirror image of the left side;

FIG. 105 is a front elevation view of the headrest of FIG. 103;

FIG. 106 is a back elevation view of the headrest of FIG. 103;

FIG. 107 is a bottom end view of the headrest of FIG. 103;

FIG. 108 is a top end view of the headrest of FIG. 103;

FIG. 109 is a perspective view of another embodiment of the headrest;

FIG. 110 is a back elevation view of the headrest of FIG. 109;

FIG. 111 is a left side view of the headrest of FIG. 109;

FIG. 112 is a right side view of the headrest of FIG. 109;

FIG. 113 is a bottom end view of the headrest of FIG. 109;

FIG. 114 is a top end view of the headrest of FIG. 109;

FIG. 115 is a perspective view of another embodiment of the headrest;

FIG. 116 is a back elevation view of the headrest of FIG. 115;

FIG. 117 is a left side view of the headrest of FIG. 115;

FIG. 118 is a right side view of the headrest of FIG. 115;

FIG. 119 is a bottom end view of the headrest of FIG. 115;

FIG. 120 is a top end view of the headrest of FIG. 115;

FIG. 121 is a perspective view of the pediatric restraint assembly of FIG. 101 with the headrest of FIGS. 103-108 shown mounted to the shoulder straps of the pediatric restraint assembly;

FIG. 122 is a perspective view of the pediatric restraint assembly of FIG. 101 with the headrest of FIGS. 109-114 shown mounted to the pediatric restraint assembly;

FIG. 123 is a perspective view of the pediatric restraint assembly of FIG. 101 with the headrest of FIGS. 115-120 shown mounted to the pediatric restraint assembly;

FIG. 124 is a perspective view of another embodiment of a pediatric restraint assembly for a pediatric patient;

FIG. 124A is another perspective view of the pediatric restraint assembly of FIG. 124;

FIG. 124B is another close-up perspective view of the pediatric restraint assembly of FIG. 124;

FIG. 125 is an exploded perspective view of the components of the pediatric restraint assembly of FIG. 124;

FIG. 126 is a perspective view of the back panel of the pediatric restraint assembly of FIG. 124;

FIG. 127 is a front elevation view of the back panel of FIG. 126;

FIG. 128 is a side elevation view of the back panel of FIG. 126;

FIG. 129 is a similar view to FIG. 127 but with the strap segment removed;

FIG. 130 is a similar view to FIG. 128 but with the strap segment removed;

FIG. 131 is a bottom end view of the back panel of FIG. 129;

FIG. 132 is a perspective view of the seat panel of the pediatric restraint assembly of FIG. 124;

FIG. 132A is a perspective view of another embodiment of the seat panel;

FIG. 132B is a bottom perspective view of the seat panel of FIG. 132A;

FIG. 132C is a top perspective view of the seat panel of FIG. 132A;

FIG. 133 is a top plan view of the seat panel of FIG. 132;

FIG. 133A is a bottom plan view of the seat panel with integrated anchors, for example, G-hooks;

FIG. 133B is a similar view to FIG. 133A;

FIG. 133C is a bottom perspective view another embodiment of the seat panel with connection points molded or otherwise formed in the bottom of the seat panel;

FIG. 134 is a bottom end view of the back panel of FIG. 129;

FIG. 135 is a right side elevation view (which is a mirror image of the left side) of the back panel of FIG. 129;

FIG. 135A is a perspective view of a pediatric restraint assembly with a cover;

FIG. 135B is a bottom perspective view the pediatric restraint assembly of FIG. 135A;

FIG. 135C is a back perspective view the pediatric restraint assembly of FIG. 135A;

FIG. 136 is a perspective view of yet another embodiment of a pediatric restraint assembly;

FIG. 136A is an enlarged perspective view of the seat panel of the pediatric restraint assembly of FIG. 136;

FIG. 136B is another enlarged perspective view of the seat panel of the pediatric restraint assembly of FIG. 136;

FIG. 136C is an enlarged partial bottom perspective view of the seat panel of the pediatric restraint assembly of FIG. 136;

FIG. 136D is an enlarged perspective view of a modified seat panel of the pediatric restraint assembly of FIG. 136;

FIG. 136E is an enlarged perspective view of a modified buckle restraint of the pediatric restraint assembly of FIG. 136;

FIG. 136F is an enlarged perspective view of a modified seat panel of the pediatric restraint assembly of FIG. 136;

FIG. 136G is an enlarged perspective view of a modified seat panel buckle restraint anchor location of the pediatric restraint assembly of FIG. 136;

FIG. 136H is an enlarged perspective view of a modified seat panel buckle restraint anchor location of the pediatric restraint assembly of FIG. 136;

FIG. 136J is a plan view of another modified buckle restraint of the pediatric restraint assembly of FIG. 136;

FIG. 136K is an enlarged perspective view of the modified buckle restraint of FIG. 136J;

FIG. 137 is a perspective view of yet another embodiment of a pediatric restraint assembly (with the harness straps and anchoring straps removed for clarity);

FIG. 137A is an exploded perspective view of the back panel of the restraint assembly of FIG. 137;

FIG. 137B is another exploded perspective view of the back panel of the restraint assembly of FIG. 137;

FIG. 138 is a patient facing side perspective view of yet another embodiment of a pediatric restraint assembly back panel;

FIG. 138A is an enlarged cross-section of the fastener that joins the panel components together;

FIG. 139 is a back side perspective view of the pediatric restraint assembly back panel of FIG. 138;

FIG. 140 is a perspective view of a pediatric restraint assembly incorporating the back panel of FIG. 138 and a cover;

FIG. 141 is a back perspective view of the pediatric restraint assembly and cover of FIG. 140;

FIG. 142 is an enlarged fragmentary view of the cover of FIGS. 140 and 141;

FIG. 143 is a perspective view of yet another embodiment of a patient restraint assembly;

FIG. 143A is an elevation view of the patient restraint assembly of FIG. 143 illustrating the headrest portions unfolded;

FIG. 143B is an elevation view of the patient restraint assembly of FIG. 143 illustrating the headrest portions folded;

FIG. 143C is an elevation view of the patient restraint assembly of FIG. 143 illustrating one of the headrest portions folded;

FIG. 144 is a perspective view of yet another embodiment of a pediatric restraint assembly;

FIG. 145 illustrates a sequence for folding a pediatric restraint assembly;

FIG. 145A is a perspective view of a folded pediatric restraint assembly;

FIG. 145B illustrates an unrolled strap of the pediatric restraint assembly;

FIG. 145C illustrates a sequence for rolling and retaining the strap;

FIG. 145D is a perspective view of a strap coupler;

FIG. 145E is a perspective view of a color coded harness and anchoring system;

FIG. 146A illustrates a five point harness configuration;

FIG. 146B illustrates a three point harness configuration;

FIG. 146C illustrates an independent limb harness configuration;

FIG. 146D illustrates an independent shoulder and waist harness configuration;

FIG. 147 illustrates the installation process of the pediatric restraint assembly of FIG. 124 on an emergency cot;

FIG. 148 illustrates the installation process of the pediatric restraint assembly of FIG. 124 on an emergency cot;

FIG. 149 illustrates the installation process of the pediatric restraint assembly of FIG. 124 on an emergency cot;

FIG. 150 illustrates the installation process of the pediatric restraint assembly of FIG. 124 on an emergency cot;

FIG. 151 illustrates the installation process of the pediatric restraint assembly of FIG. 124 on an emergency cot;

FIG. 152 illustrates the installation process of the pediatric restraint assembly of FIG. 124 on an emergency cot;

FIG. 153 illustrates the installation process of the pediatric restraint assembly of FIG. 124 on an emergency cot;

FIG. 154 illustrates the installation process of the pediatric restraint assembly of FIG. 124 on an emergency cot;

FIG. 155 illustrates the installation process of the pediatric restraint assembly of FIG. 124 on an emergency cot;

FIG. 156 illustrates the installation process of the pediatric restraint assembly of FIG. 124 on an emergency cot;

FIG. 157 illustrates the installation process of the pediatric restraint assembly of FIG. 124 on an emergency cot using a cushion insert beneath the seat section; and FIG. 158 illustrates the installation process of the pediatric restraint assembly of FIG. 124 on an emergency cot using a large cushion mattress insert beneath the seat section.

DETAILED DESCRIPTION

Figure 1:
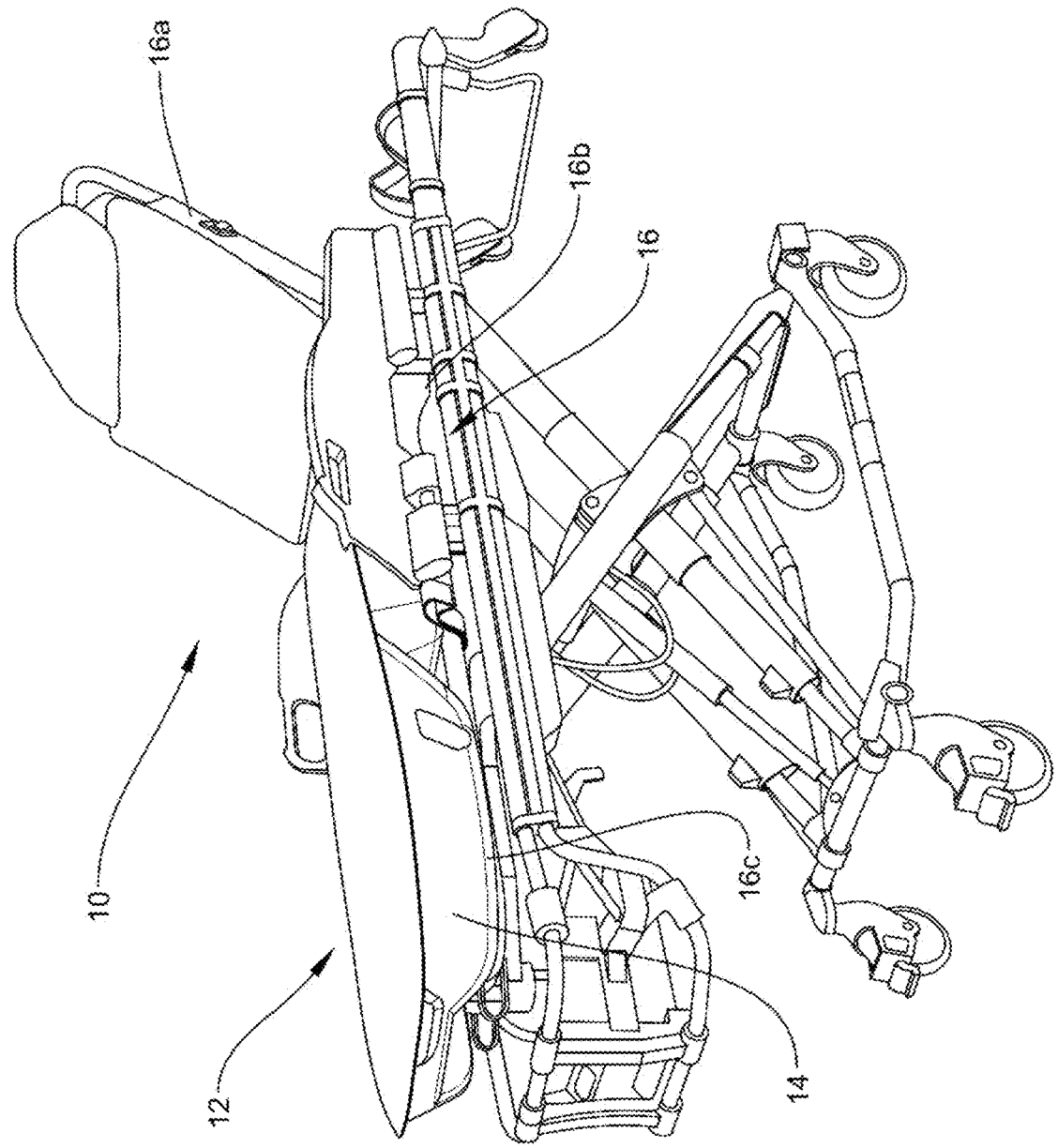
FIG. 1 is a perspective view of a transport apparatus in the form of an emergency cot with a patient support surface system.

Referring to FIG. 1, the numeral 10 generally designates a transport apparatus, such as an emergency cot or stretcher. As will be more fully described below, transport apparatus 10 incorporates a patient support surface system 12 with a patient support surface 14 and optionally one or more features or accessories to enhance the function and comfort of transport apparatus 10.

Figure 2:
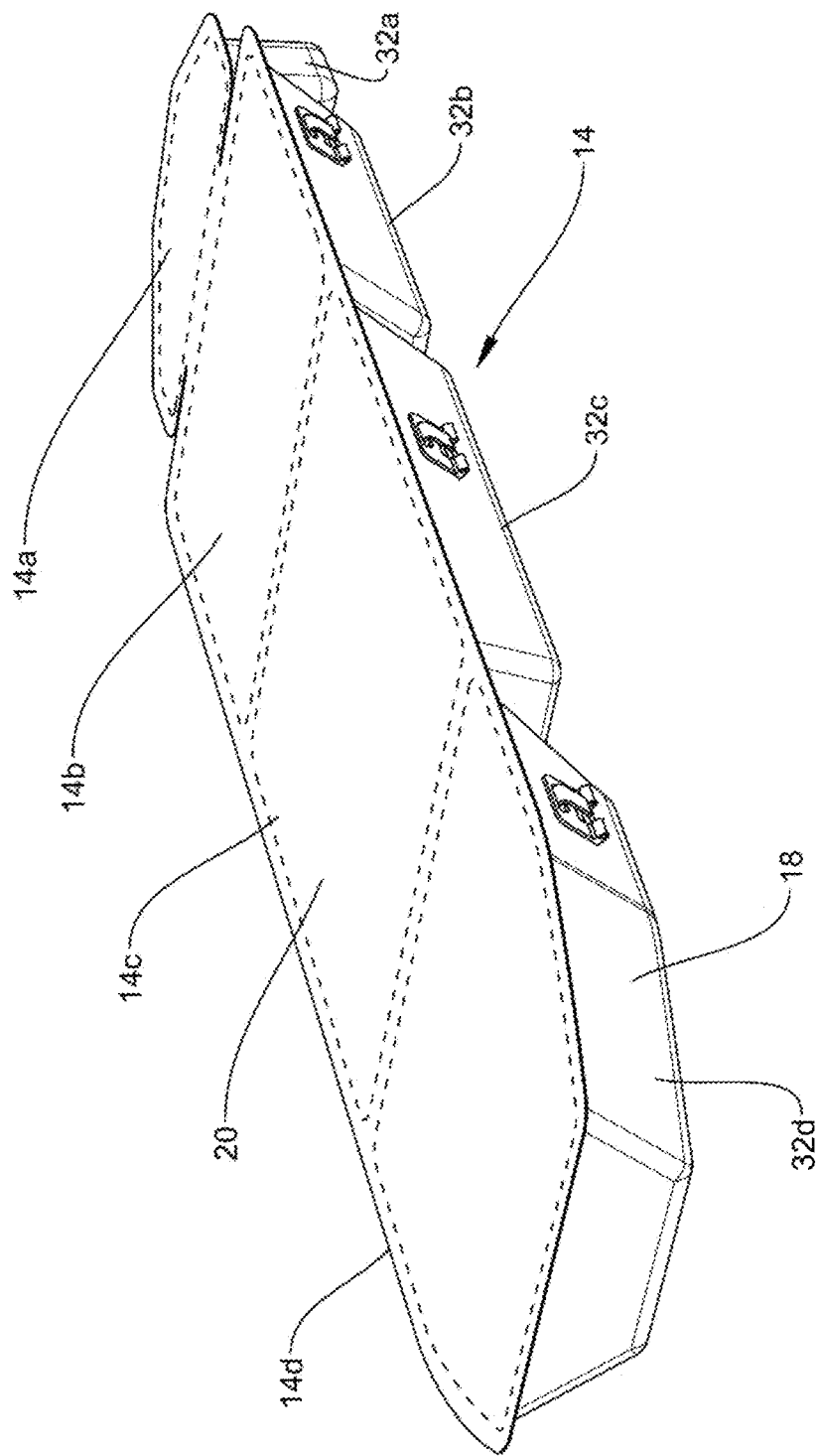
FIG. 2 is perspective view of the patient support surface system of FIG. 1.
Figure 3:
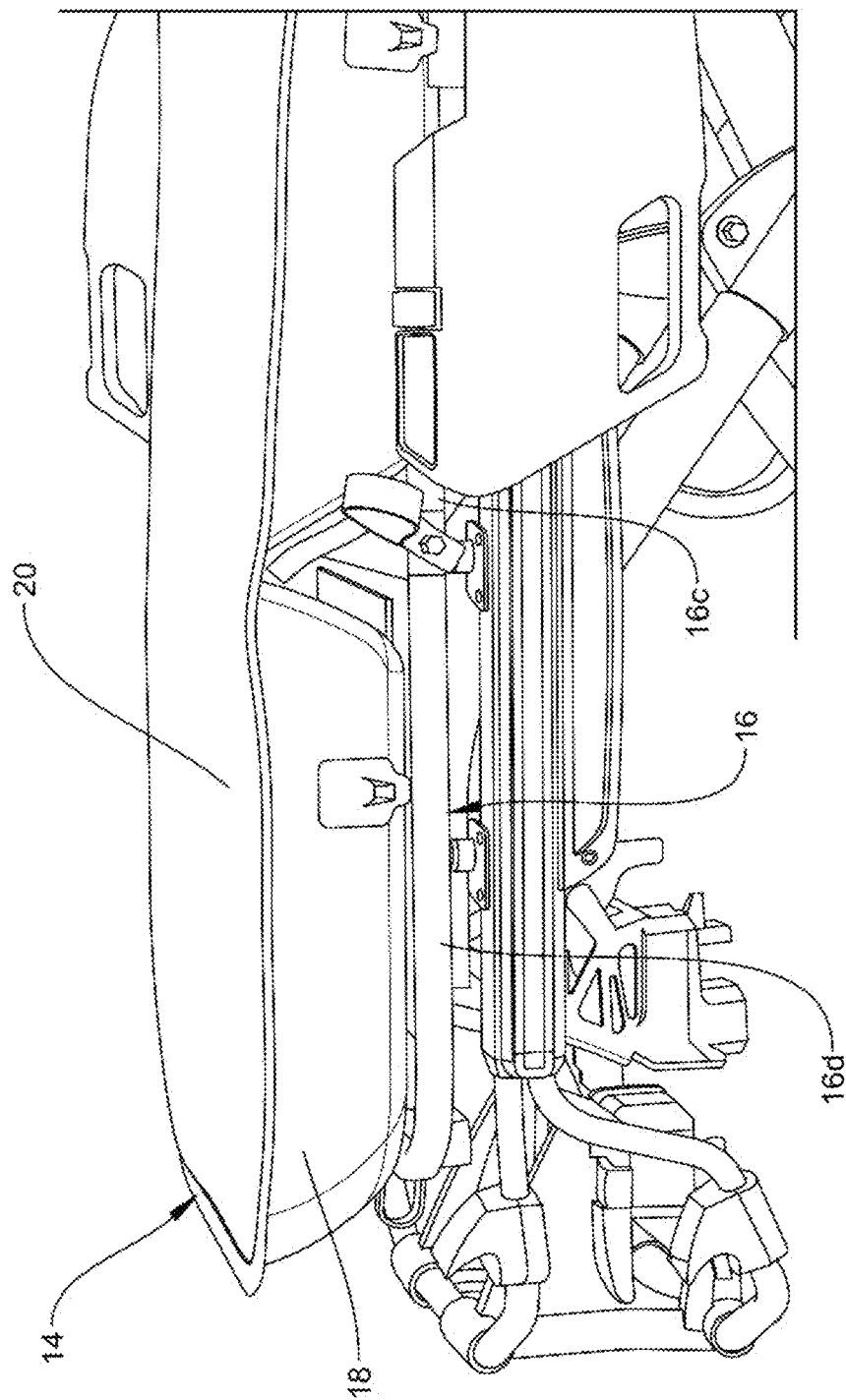
FIG. 3 is an enlarged side elevation view of the foot end of the transport apparatus and the patient support surface system of FIG. 1.

As best seen in FIGS. 1 and 2, patient support surface 14 is segmented into two or more articulateable patient support surface sections—for example, a head section 14a, a back section 14b, a seat section 14c, and a foot section 14d—so that when it is secured to the transport apparatus deck 16, it will fold and unfold as needed, for example, when the deck sections 16a, 16c, 16d (back, leg or foot deck sections) of the deck are tilted or lowered.

Patient support surface 14 is formed by a bottom cover 18 and a top cover 20, which are joined together and respectively form the lower surface and upper surface of the patient support surface. Though it should be understood that the upper surface may or may not form the patient contact surface of the patient support surface, and instead may be covered with a sheet or other cover, including an auxiliary cover, such as a transport cover, as will described below. Bottom cover 18 may be pre-formed from a single sheet of material to form at least two adjacent cavities, with each cavity receiving a cushion section. For example, referring to FIG. 5, in the illustrated embodiment, bottom cover 18 is pre-formed into a multi-cavity shape 22, with four adjacent cavities 22a, 22b, 22c, and 22d. Each cavity 22a, 22b, 22c, and 22d is joined to its adjacent cavity by a living hinge 24a, 24b, 24c, which are formed by the sheet of material forming the bottom cover. In this manner, the patient support surface can be articulated about each living hinge (as the deck is articulated or access is needed beneath the patient support surface as described below).

In one embodiment, the bottom cover 18 is formed from a polymer film and pre-formed by molding, such as thermoforming. Alternately, bottom cover 18 may be formed from blow molding, injection molding, rotational molding, or structural form molding, for example. Suitable materials for bottom cover 18 include urethane films, urethane laminates, urethane coated fabric or textile, or polyolefin or the like.

In one embodiment, the bottom cover 18 is formed from a thick urethane sheet so that when formed (e.g. by thermoforming or the like) into its multi-cavity shape, it can retain its shape (the sides will remain standing vertically) but still remain flexible. In other words, if manually pressed, the side walls of bottom cover 18 would no longer remain vertical; instead, the side walls of bottom cover 18 would easily deflect, bend and/or fold. For example, suitable thicknesses may fall in a range of about 8 to 125 mils, about 10 to 40 mils, or about 20 to 30 mils.

Alternately, the bottom cover may be formed out of a structural polymer material, such as ABS, polyethylene, HIPS, HDPE, PET, or PETG, or the like, or composites thereof, including fiberglass, and, therefore, be relatively rigid. In other words, if manually pressed, bottom cover 18 would still retain its overall shape though portions of the bottom cover, such as the side walls, could deflect.

Figure 5:
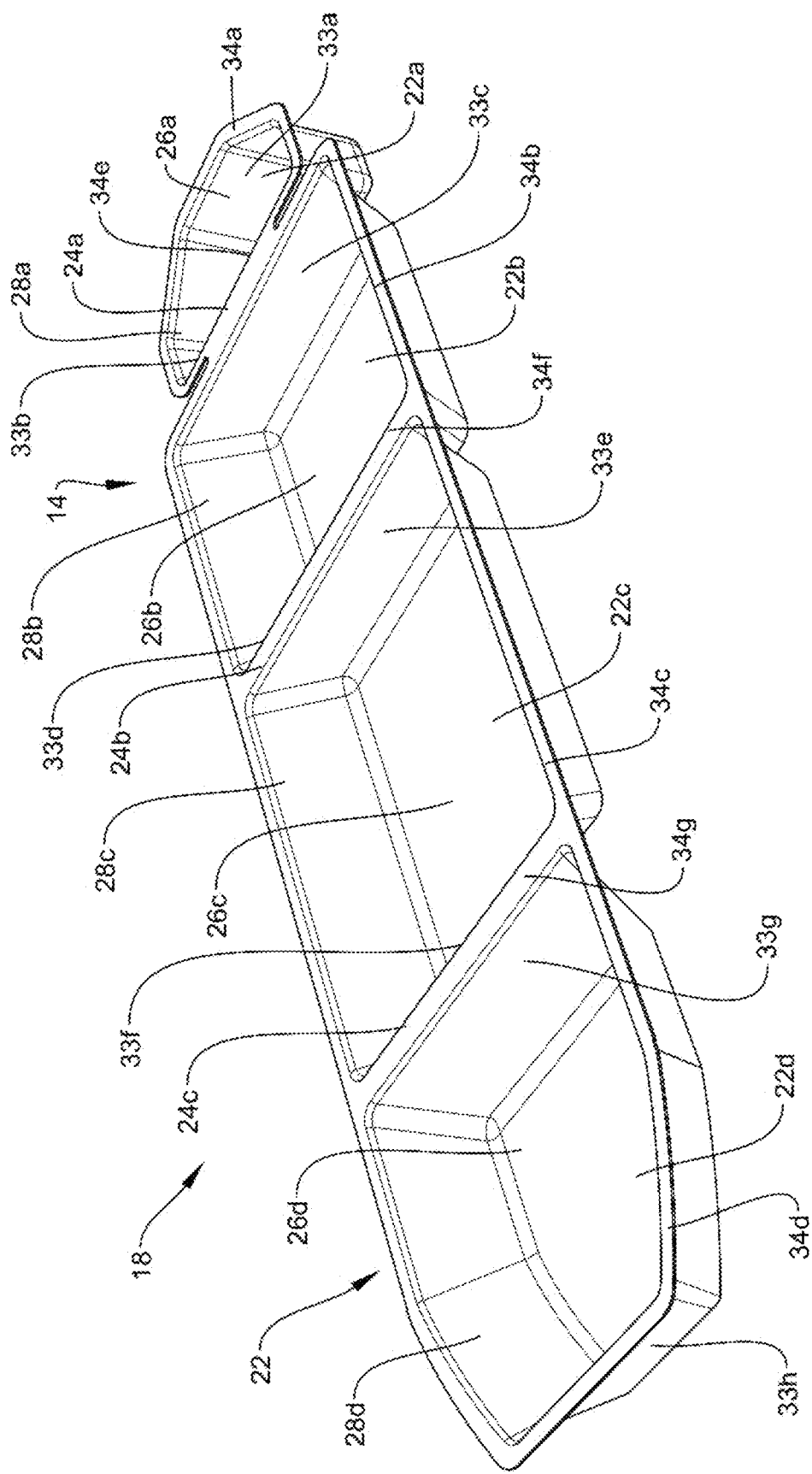
FIG. 5 is a top perspective view of the bottom cover of the patient support surface of the patient support surface system of FIG. 1.

Referring to FIG. 5, when formed into its multi-cavity shape 22, as noted above, bottom cover 18 includes at least two, optionally three, and, in the illustrated embodiment, optionally four cavities 22a, 22b, 22c, and 22d. Cavities 22a, 22b, 22c, and 22d are defined by four recesses 26a, 26b, 26c, and 26d that are formed during the thermoforming process, which define the longitudinal sides 28a, 28b, 28c, and 28d of the cavities and the laterally spaced longitudinal sides of the patient support surface. In addition, recesses 26a, 26b, 26c, and 26d form the laterally extending sides 33a, 33b, 33c, 33d, 33e, 33f, 33g, and 33h of each of the cavities, which are spaced along the longitudinal axis (or length) of the patient support surface 14 (with lateral sides 33a and 33h forming the head end side and foot end side of the patient support surface 14), to receive and retain therein cushion sections 32, such as cushion sections 32a, 32b, 32c, and 32d described below.

Recesses 26a, 26b, 26c, and 26d are formed at spaced intervals along the longitudinal axis and inwardly of the outer perimeter of the sheet that is used to form bottom cover 18, thus leaving an upper outer perimeter edges or lips 34a, 34b, 34c, and 34d around each cavity and shared lateral upper perimeter edges or lips 34e, 34f, and 34g between each of the cavities to form the living hinges (described above) between each of the cavities. Each recess may be tapered so that some or all of their respective sides are angled inwardly to form wedge shaped cavities. For example, the angle of the sides of the recesses may vary from vertical to about 45 degrees.

In another embodiment, one or more of the sides of the recess may tilt inwardly. For example, the lateral width of the bottom of one or more of the respective recesses may be wider than the lateral width at the top of the recess, or it may have a trapezoidal shape—one side vertical and the other angled. In yet another embodiment, the sides may be non-linear—for example, an hour glass shape or V-shape to provide a recess in the side of the patient support surface for a sheet to grasp or provide space for storage or incorporating an accessory—such as a sheet, drape, or a cover, including a warming blanket or cooling blanket, that can be rolled up in the space and then deployed to cover the patient.

To thermoform the bottom cover, the sheet, such as the polymer film or urethane sheet, is heated and drawn down into a mold via a vacuum, or close to a vacuum pressure, to form the separate recesses and cavities and, hence, patient support surface sections. As described more fully below, additional mechanical features may be added into the mold as part of the forming or molding process (such as the female receptacle for the patient support surface-to-deck attachment, expanding bellows for stretching at hinge points, different hinge shapes at each section to accommodate cot movement, formed shapes, such as recesses, for storage access areas). For example, any of the sides (or portion of the side) may be formed with an accordion configuration (with a plurality of folds) to form a bellow that allows the length of the side to stretch without stretching the material. In another embodiment, the bottom cover may be formed from an elastic material, such as rubber, so that the sides can stretch.

Referring again to FIG. 2, top cover 20 is formed from a continuous sheet that extends from the foot end to the head end of the patient support surface, and between the left longitudinal side and the right longitudinal side of the patient support surface, and over each of the cavities. For example, top cover 20 may be formed from a low surface friction material, such as DARTEX or DARTEX-LIKE fabric, Nylon, Nylon weave, to reduce shearing against a patient's skin, but optionally also a material with high chemical/mechanical durability. Other suitable materials for the top cover include sheets formed from a polymer layer, such as a urethane film, urethane laminated/coated fabric, or polyolefin or the like.

Top cover 20 is joined with the bottom cover around the upper perimeter edge or lip of the bottom cover and, further, joined with the bottom cover around the upper perimeter edges or lips of each of the cavities. The top cover may be joined with the bottom cover by stitching and/or sealing, such as formed by welding, including RF welding. Optionally, a seal may be formed by a seam tape that is sewn and glued to the sewn perimeter edges of the top cover and the bottom cover. For example, the top sheet forming the top cover may be sewn to the bottom cover and then seam taped to form corners, thus remain fluid-proof.

In one embodiment, the top cover is formed from a single sheet of material that is only joined to the bottom cover by a seal (e.g. formed by welding, such as RF welding, or gluing) so that the top cover is imperforate—in other words has no holes at any time—and can remain fluid-proof. When the cover is formed from a fluid and gas impermeable material, the chances of any leakage through the top cover is reduced. Further, the cavities form sealed compartments.

Forming the patient support surface from a bottom cover and a top cover, which is formed from a single continuous top sheet (single thin layer of material) allows for a living hinge to act as the flexible joint between the patient support surface sections, giving the patient support surface more durability and simplifying the design. It should be understood that a single continuous sheet formed from multiple layers may also be used. It should also be understood that other types of hinges may be used, such mechanical hinges.

Providing a continuous top sheet (single layer or multi-layer top sheet) as the top cover, and forming hinges within the bottom cover, allows for a simplified top cover that promotes easy cleaning between patients. Further, when unloaded, the top cover 20 may be configured to remain generally flat or planar, though as noted, it may include channels for directing fluid etc. Thus, top cover 20 may be constructed to be free of cracks, crevices, or folds to collect contaminants.

As noted above, the top cover is optionally formed from a material that is impermeable. Optionally, the top cover may be formed from multiple layers or a layer or layers with a coating or coatings to render the top cover impermeable.

Optionally, the material forming the top cover may have no stretch, or be formed from stretch fabric, such as a 2-way stretch fabric or 4-way stretch fabric, to prevent hammocking. In either form (stretch or no stretch), the cover is configured to minimize interference with the immersion of the patient into the cushioning material and, thereby, maximize pressure redistribution of the foam or other cushioning medium used in the cushion sections described below. In one embodiment, the air may be used as part of the cushioning system, with the foam preventing bottoming out in the event of an air loss. To improve the longevity of the patient support surface, the material for the top cover is durable enough to withstand environmental conditions, harsh chemical cleaners, and repeated mechanical abrasion while still being fluid impermeable. As noted above, suitable materials include polymer layers, such as a urethane film, urethane laminated, and/or coated fabric, or a polyolefin, or the like.

As noted above, the top and bottom covers may be RF welded. For example, the top and bottom covers may be RF welded around the perimeter of the patient support surface and then trimmed, rolled under itself, and welded again, or have a separate binder welded on to form a finished edge, thus the patient support surface would remain fluid-proof. As noted above, suitable materials for the top cover and the bottom cover include a urethane film or a urethane coated textile or fabric.

Alternately, as noted above, the top and bottom covers may be sewed and then glued using seam tape to seal them together. The seam tape may be used to cover the joined top and bottom covers (e.g. by stitching) and seal off the raw edge of fabric to remain fluid-proof. In that configuration, the suitable materials for the top cover and bottom cover again include a urethane film, a urethane coated textile or fabric, or polyester.

In another embodiment, the top and bottom covers may be sealed together using binder/bias tape (hot air welded tape). After being sewn together, bias tape may be used to cover the stitching and raw edge of fabric. The top cover could be sewn to the bottom cover and then the edge around the perimeter is covered/sealed with bias tape to make the patient support surface fluid-proof. Again, suitable materials for the top cover and bottom cover include a urethane film, a urethane coated textile or fabric, or polyester.

To avoid ballooning and/or interference with the pressure redistribution performance of the patient support surface (when relying on the cushioning material, e.g. foam, gel, air bladders, 3D cushioning material), the top or bottom cover may include one or more valves to allow pressure above a prescribed level to escape from within the patient support surface. For example, this valve may be a vent or a mechanical pressure relief valve, including umbrella valves or duckbill valves. The vent may be formed from a fluid-proof vent or breathable fabric patch. When formed as a fluid-proof valve, the valve may also be provided in the top cover. A suitable fabric patch for a vent may include polyester, PVC coated polyester, polypropylene, or ePTFE. Further, the vent may be formed from a patch of material that provides air filtration properties to reduce, if not eliminate, any contaminants from entering into the patient support surface.

Optionally, when each compartment is sealed from the adjacent compartment(s), a valve may be provided for each section associated with each sealed cavity of the patient support surface.

In yet another embodiment, the top cover may also be thermoformed, and then joined, such as noted above, with the bottom cover at some point between the upper surface and the lower surface—in other words the top cover may be formed with downwardly depending walls, which are then joined with the upwardly extending walls of the bottom wall. In one embodiment, the bottom cover and the top cover may be inverted. In other words, the thermoformed cover with its plurality of cavities may form the upper side of the patient support surface, and the continuous flat cover may form the lower side of the patient support surface. In this embodiment, the use of an overlying cover, such as the auxiliary cover described below or a standard sheet, over the upper side may be particularly desirable.

Figures 4, 4A:
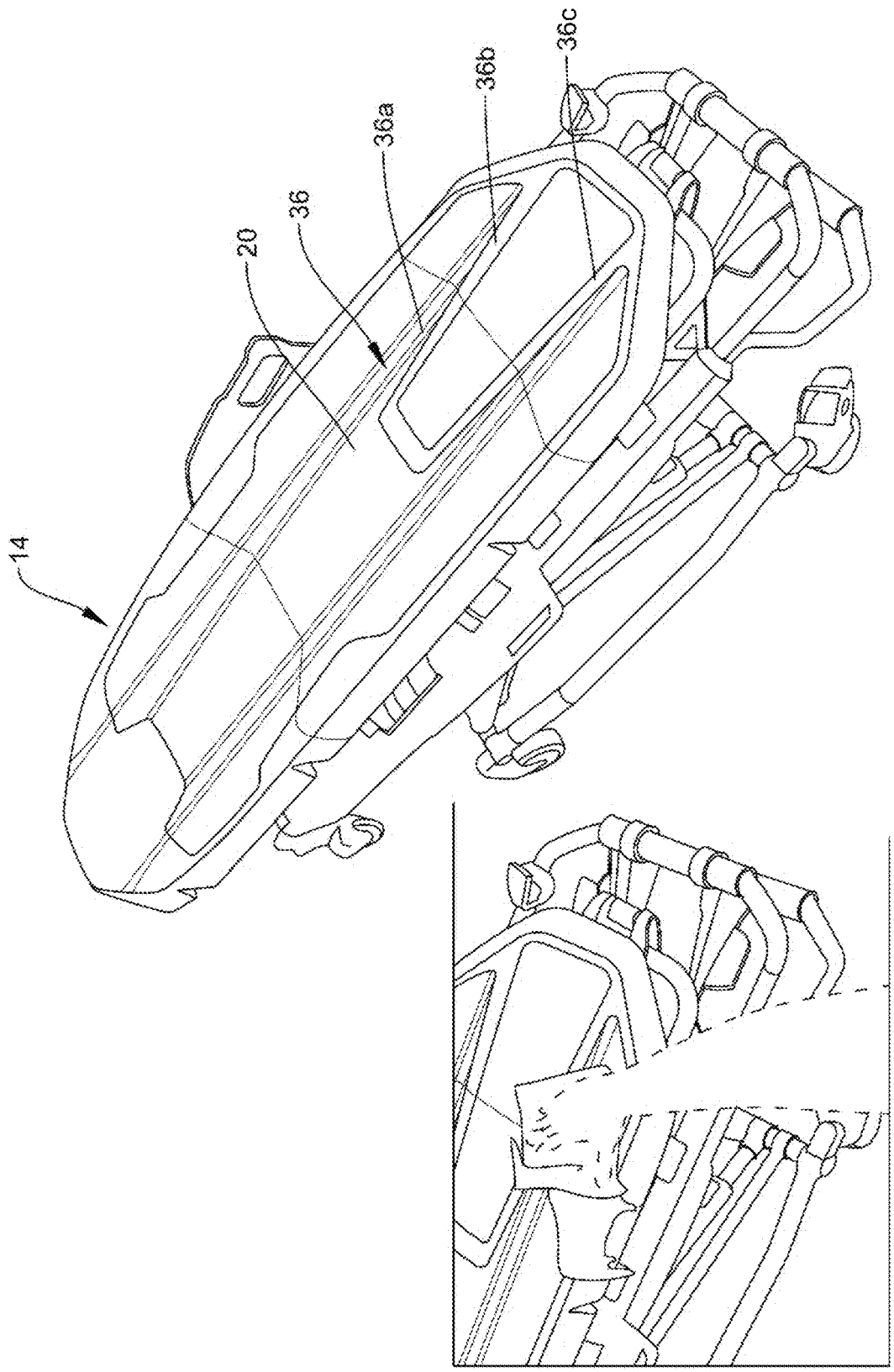
FIG. 4 is a top perspective view of the transport apparatus and the patient support surface system of FIG. 1.
FIG. 4A is a top partial perspective view of the transport apparatus and the patient support surface system of FIG. 1.

Referring to FIG. 4, in one embodiment, top cover 20 may be formed with one or more channels 36, such by thermoforming, embossing, compression molding, or the like. The channels may aid in containing and/or directing fluid and/or may be provided for guides for patient positioning, or simply for aesthetics, such as branding or the like. In the illustrated embodiment, top cover 20 includes a central channel 36a, which optionally extends from the head end or foot end of the patient support surface. An additional group of longitudinally extending channels 36b and 36c may also be provided inwardly of the opposed sides of channel 36a, which extend from the seat section to the foot end of the patient support surface. Additional channels or markings may be provided for patient placement on the transport apparatus. For example, guides for patient positioning on the top cover may also be provided using printed graphics in addition to or in lieu of the channels. Suitable materials for the top cover in this embodiment may include a polymer layer, such as a urethane film, urethane laminated, and/or coated fabric, or polyolefin.

As noted above, each cavity of each patient support section includes a cushion section 32, such as head cushion section 32a, back cushion section 32b, seat cushion section 32c, and foot cushion 32d. Each cushion section 32a, 32b, 32c, and 32d may be formed from one or more cushioning materials that may have uniform properties or optionally vary in their properties along their respective cross-sections to vary the immersion and/or pressure distribution characteristics of the patient support surface. Further, the cushion sections for each patient support surface section may be different to provide different pressure redistribution and/or immersion depending on the portion of the patient's body it is supporting.

For example, each cushion section 32a, 32b, 32c, and 32d (head, back, seat, and foot cushion sections) may be formed from multi-layered foam (vertically and/or horizontally layered), optionally with at least one of the cushion sections being formed with a crib to facilitate patient containment/support. For example, the cushion section for the back section 14b may include a crib to provide lower back support. The cushion section for the foot section 14d may include a crib to provide leg support across its length. Similarly, the seat section cushion section 32c may have a crib to help retain the patient on the patient support surface as well as provide support for the thighs, including by using a wedge, as will be more fully described below. For example, the cribs may be formed from foam, such as polymeric foam, including a polyurethane foam.

As noted above, one or more cushion sections may be formed from multiple layers of cushioning material. By using different layers of cushioning material, the pressure redistribution can be adjusted and customized to suit the portion of the patient's body that is being supported.

Figure 6:
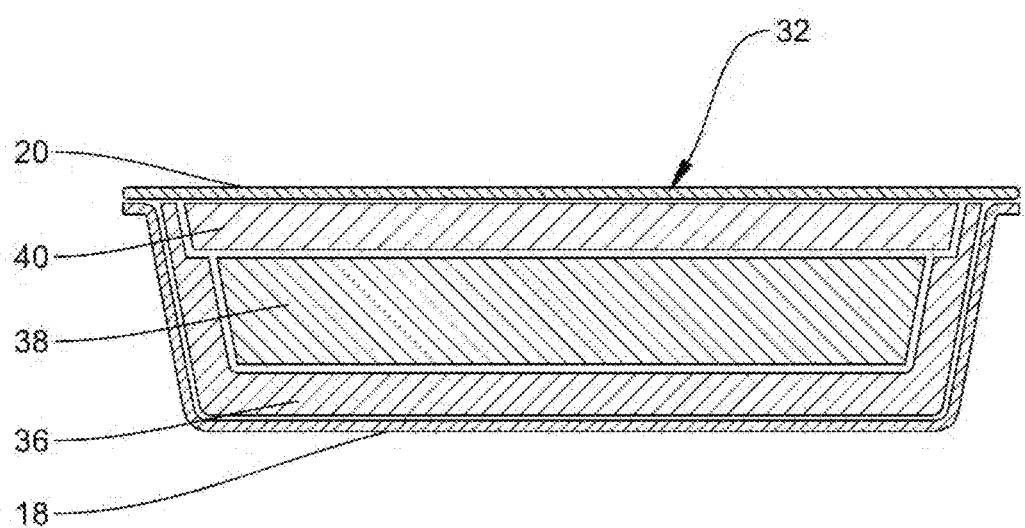
FIG. 6 is a lateral cross-section view of one embodiment of the patient support surface.

Referring to FIG. 6, one or more of the cushion sections may be formed from vertically spaced and varied layers. For example, one or more of the cushion layers 32, such as the seat cushion layer, may include an outer cushion layer 37 (which, as noted, may form a foam crib), a middle cushion layer 38, and a top cushion layer 40. The outer cushion layer 37 may be formed from a cushioning material, such as foam, that has a greater or greatest stiffness (or higher or highest IFD, in the case of foam). The middle cushion layer, which may be the thickest layer, may be formed from a cushioning material, such as foam, that has a medium stiffness (or medium stiffness in the case of foam). The top cushion layer, which may be the thinnest layer may be formed from a cushioning material, such as foam, that has a low firmness (or low ILD in the case of foam) so that it forms the softest layer. For example, the cushion layers may be formed from foam, gel, air cells or bladders, or a combination of two or more or of each. The foam layers may be formed from cast foam, cut foam, or "foam in place".

When the cushion layer or layers are formed from gel, the gel may be a fluid gel (and hence contained in a bladder) or a structural gel, such as formed from a gelastic material, such as gelastic materials formed from a SEB, SEBS, SEP, SEPS, SEEP, SEEPS polymer combined with a mineral oil.

As one example, the gelatinous elastomeric material may be formulated with a weight ratio of oil to polymer of approximately 3.1 to 1. The polymer may be Kraton 1830 available from Kraton Polymers, which has a place of business in Houston, Texas, or it may be another suitable polymer. The oil may be mineral oil, or another suitable oil. One or more stabilizers may also be added. Additional ingredients—such as, but not limited to—dye may also be added. In another example, the gelatinous elastomeric material may be formulated with a weight ratio of oil to copolymers of approximately 2.6 to 1. The copolymers may be Septon 4055 and 4044, which are available from Kuraray America, Inc., which has a place of business in Houston, Texas, or it may be other copolymers. If Septon 4055 and 4044 are used, the weight ratio may be approximately 2.3 to 1 of Septon 4055 to Septon 4044. The oil may be mineral oil and one or more stabilizers may also be used. Additional ingredients—such as, but not limited to—dye may also be added.

In addition to these examples, as well as those disclosed in the aforementioned patents, still other formulations may be used reference is made to application Ser. No. 16/220,589, filed on Dec. 14, 2018, entitled MATTRESS COVER FOR A MATTRESS PROVIDING ROTATION THERAPY TO A PATIENT; Ser. No. 16/220,591, filed on Dec. 14, 2018, entitled PATIENT TURNING DEVICE FOR A PATIENT SUPPORT APPARATUS; Ser. No. 16/585,282, filed on Sep. 27, 2019, entitled PATIENT SUPPORT HAVING BUCKLING ELEMENTS FOR SUPPORTING A PATIENT; Ser. No. 16/585,641, filed on Sep. 27, 2019, entitled PATIENT SUPPORT; Ser. No. 16/585,715, filed on Sep. 27, 2019, entitled PATIENT SUPPORT INCLUDING A CONNECTOR ASSEMBLY; Ser. No. 16/668,894, filed on Oct. 30, 2019, entitled FLUID SOURCE FOR SUPPLYING FLUID TO THERAPY DEVICES; and Ser. No. 16/705,883 filed on Dec. 6, 2019, entitled SUPER-ELASTIC FORMULATION, which are incorporated by reference herein in their entireties. Further, when using gel structures they may have open structural shape configurations (e.g. tubular, grids etc.) the gel may be embedded with foam inserts or vice versa to modify the immersion profile and/or to prevent hottorning out.

For examples of suitable air cells or bladders that may be incorporated into the cushion sections, reference is made to U.S. patent applications Ser. No. 13/022,326, filed Feb. 7, 2011, entitled PATIENT/INVALID HANDLING SUPPORT; Ser. No. 13/022,372, filed Feb. 7, 2011, entitled PATIENT/INVALID HANDLING SUPPORT; Ser. No. 13/022,382, filed Feb. 7, 2011, entitled PATIENT/INVALID HANDLING SUPPORT; Ser. No. 13/022,454, filed Feb. 7, 2011, entitled PATIENT/INVALID HANDLING SUPPORT; Ser. No. 13/548,591, filed Jul. 13, 2012, entitled PATIENT/INVALID HANDLING SUPPORT, all of which are incorporated by reference herein in their entireties. It should be understood these are exemplary only, and that the materials listed above could be used in different configurations.

When forming outer cushion layer 37 with upstanding side walls, as shown in FIG. 6, the side walls create side bolsters to prevent accidental egress, and further can be increased in height for better immersion/envelopment into the central portion or middle of the patient support surface. In one embodiment, the upstanding side walls of outer cushion layer 37 may have a step or ledge so that the top cushion layer 40 can extend over not only the middle cushion layer but also a portion of the upstanding side walls of the crib so as to provide a more gradual transition between the side bolsters (formed by the side walls) and the central portion of the patient support surface, where the greatest immersion occurs.

Figure 7:
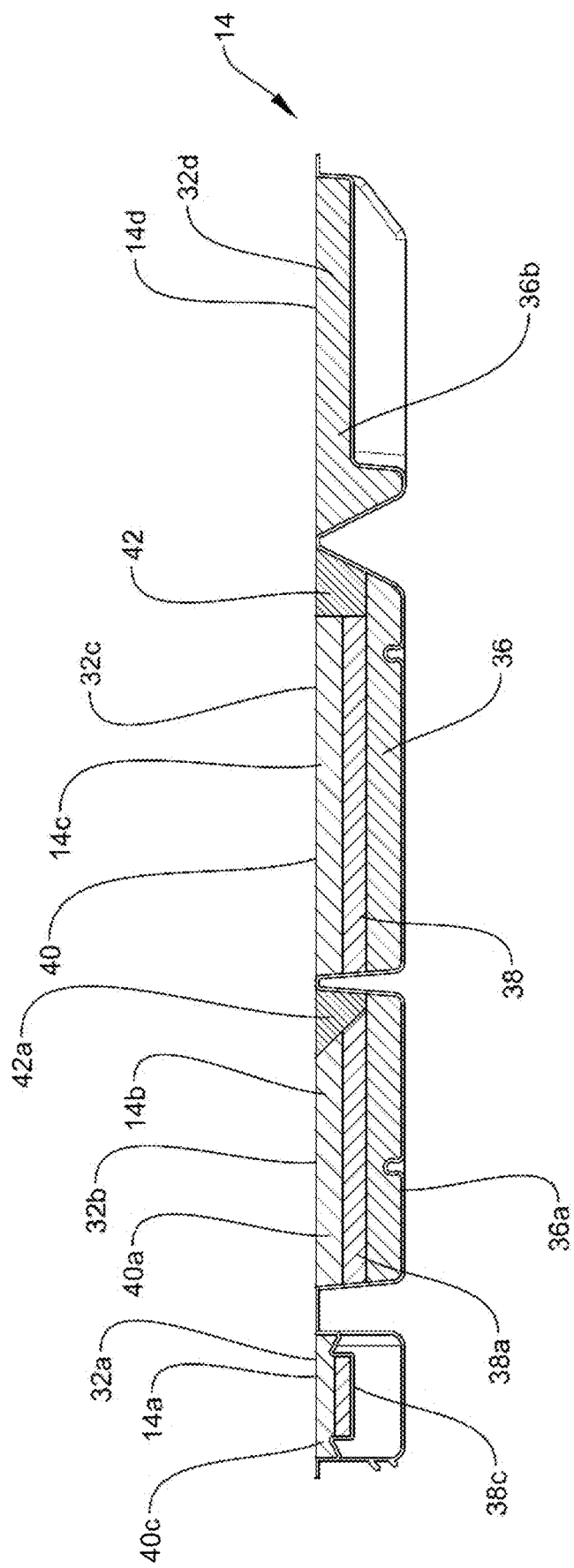
FIG. 7 is a longitudinal cross-section view of one embodiment of the patient support surface.

Referring to FIG. 7, in one embodiment, one or more of the cushion sections (such as cushion sections 32*b* and 32*c*) may have one or more wedges 42, 42*a* of stiffer cushioning material than any of the other cushion layers in the cushion section (other than the crib), which may be located, for example, at their foot end thereof (portion that is closer to the foot end), to reduce patent migration toward the foot end of patient support surface 14. Suitable foam wedges generally are stiffer than all the other cushioning layers, except for the crib. For example, in the case of foam layers, suitable foam wedges have a greater IFD than all the other cushion layers in the cushion section, optionally excluding the crib. For example, suitable foam wedges have an IFD in a range of 30 to 50 IFD, or 30 to 40 IFD. Seat cushion section 32*c* may also be formed in a similar manner to cushion section 32, described above, with an outer cushion layer 37 that forms a crib and two cushion layers 38, 40, and, further, as noted with a wedge 42, Foot cushion 32*d* may be formed from a single layer of cushioning material 37*b*, such as foam, including foam with a similar stiffness to the cribs described herein. Thus, the cushion layers forming the cushion sections may vary both vertically and horizontally, for example, longitudinally. Optionally, these cushioning layers may be arranged in a different arrangement, including where the softer cushion layer is beneath the medium stiffness cushion layers. In some embodiments, the top cushion layer may be the firmest layer.

Figure 8:
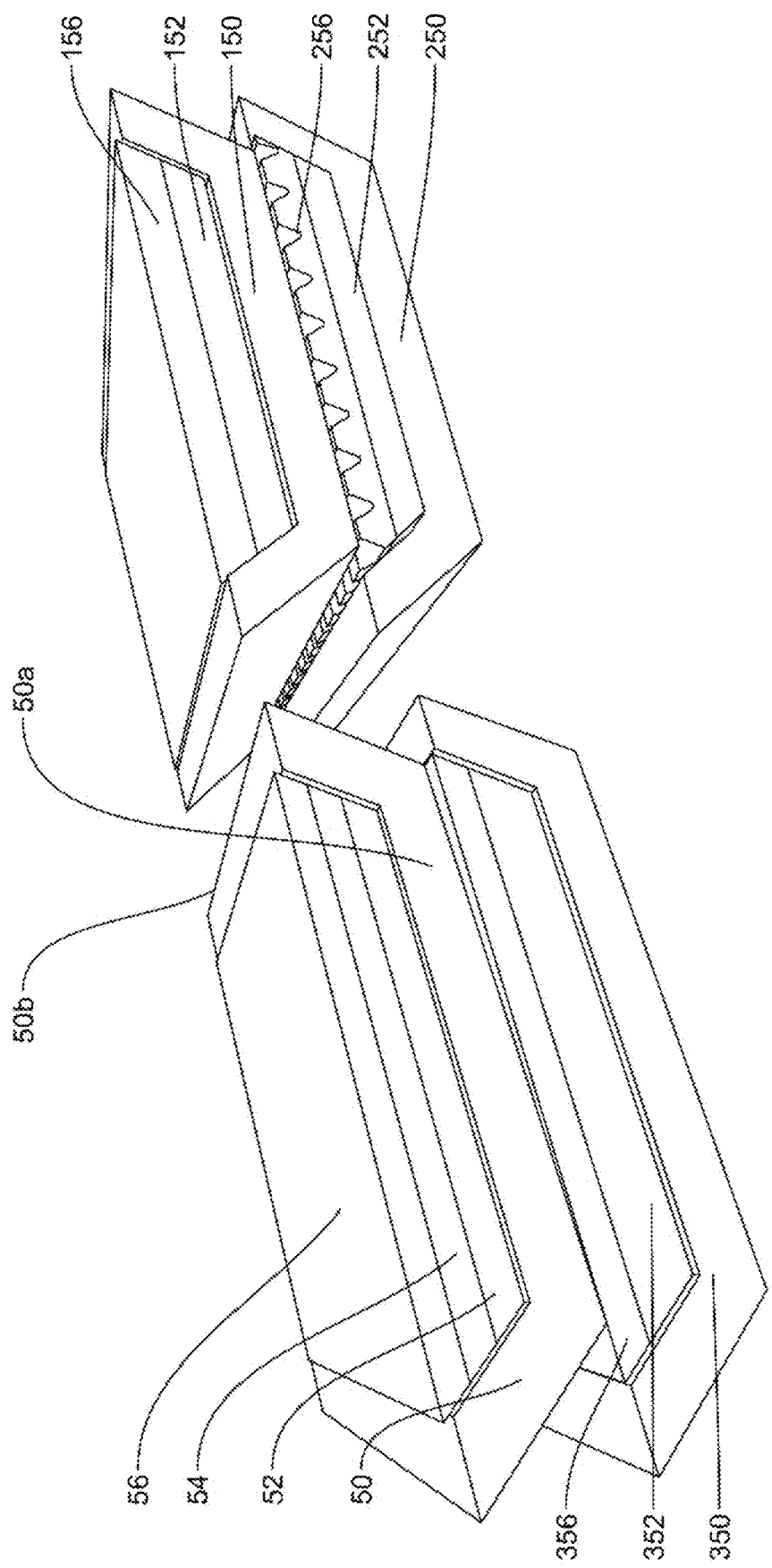
FIG. 8 is a perspective view of several embodiments of the cushion sections of the patient support surface shown in two stacked arrangements.

As noted, one or more of the cushion sections may be formed from an outer foam layer that forms a foam crib. Referring to FIG. 8, in one embodiment, crib 50 includes a base wall 50*a* and two angled side walls 50*b* that diverge away from each other at their upper terminal ends to form a trapezoidal shape cavity or space. The foam used to form the foam crib may have the greatest stiffness of all the layers so that, as noted above, the crib can form side bolsters for the patient supported thereon. The thicker the side walls, the smaller the patient support surface that provides the deep immersion—hence, for smaller patients it may be beneficial to have thicker bolsters to enhance their feeling of security. By the same token for larger patients it may be beneficial to reduce the thickness of the side walls so that the bolsters do not interfere with the patient's immersion into the patient support surface.

Positioned in crib 50 is a plurality of foam layers 52, 54, and 56, each shaped so that their opposed longitudinal edges are wedge shaped, so that when stacked, the foam layers 52, 54, and 56 fill the trapezoidal shape cavity of foam crib 50. Layers 52, 54, and 56 may have the same thickness and, optionally, have the same foam stiffness. Alternately, layers 52, 54, and 56 may have different foam stiffness, such as described above, with each layer having a lower stiffness (i.e. lower IFD) than the layer below it, such that top layer 56 provides the softest layer, which is closest to the patient's body.

In an alternate embodiment, also shown in FIG. 8, foam crib 150, which is of similar construction to foam crib 50, includes two foam layers 152 and 156. Foam layers 152 and 156 are also shaped so that their opposed longitudinal edges are wedged shaped, so that when stacked the foam layers 152 and 156 fill the trapezoidal shaped cavity of foam crib 150. In the illustrated embodiment, layers 152 and 156 have the same thickness and, optionally, have different foam stiffness (i.e. IFD), such as described above, with layer 156 having a lower stiffness than layer 152 below it.

Referring again to FIG. 8, in another embodiment, foam crib 250 (also similar to crib 50) also supports two foam layers 252 and 256, each shaped so that their opposed longitudinal edges are wedged shaped, so that when stacked, the foam layers 252 and 256 fill the trapezoidal shape cavity of foam crib 250. Layers 252 and 256 may have the same overall thickness and, optionally, have the same foam stiffness or different foam stiffness (with each layer 256 having a lower stiffness than the layer 252 below it).

In the illustrated embodiment, foam layer 256 is formed with a layer of foam with portions removed to create a softer layer. For example, in the illustrated embodiment, foam is removed in a pattern, optionally a uniform pattern, to leave a plurality of projections or peaks, for example, often referred to as "convoluted foam," which increases the softness of the foam layer even though it may be formed with foam having the same foam stiffness as foam layer 252. The projections may be formed in a grid pattern or a non-uniform pattern. Alternately, or in addition, holes may be drilled through the layer to further reduce the stiffness and also to allow for airflow through the layer (or layers in the case of multiple layers having transverse holes formed therein).

In yet another embodiment, as seen in FIG. 8, foam crib 350 (also similar to crib 50) also supports two foam layers 352 and 356, each shaped so that their opposed longitudinal edges are wedged shaped, so that when stacked the foam layers 352 and 356 fill the trapezoidal shaped cavity of foam crib 350. Layer 352 has a greater thickness than layer 356, which has a significantly lower foam stiffness than layer 352.

For example, when made from foam, suitable stiffness for the softest upper most foam layer (e.g. layers 40, 56, 156, 256, and 356) may fall in a range of 0 IFD to 20 IFD or in a range of 5 IFD to 20 IFD. Suitable stiffness for the medium stiffness lower foam layers (e.g. layers 38, 54, 56, 156, 256, and 356) may fall in a range of 10 IFD to 40 IFD or in a range of 15 IFD to 35 IFD. Suitable stiffness for the stiff foam crib (e.g. cribs 50, 150, 250, 350) may fall in a range of 40 IFD to 100 IFD or in a range of 50 IFD to 90 IFD. For wedges, as noted above, a suitable stiffness may fall in a range of 30 IFD to 50 IFD or in a range of 30 IFD to 40 IFD.

Figure 8C:
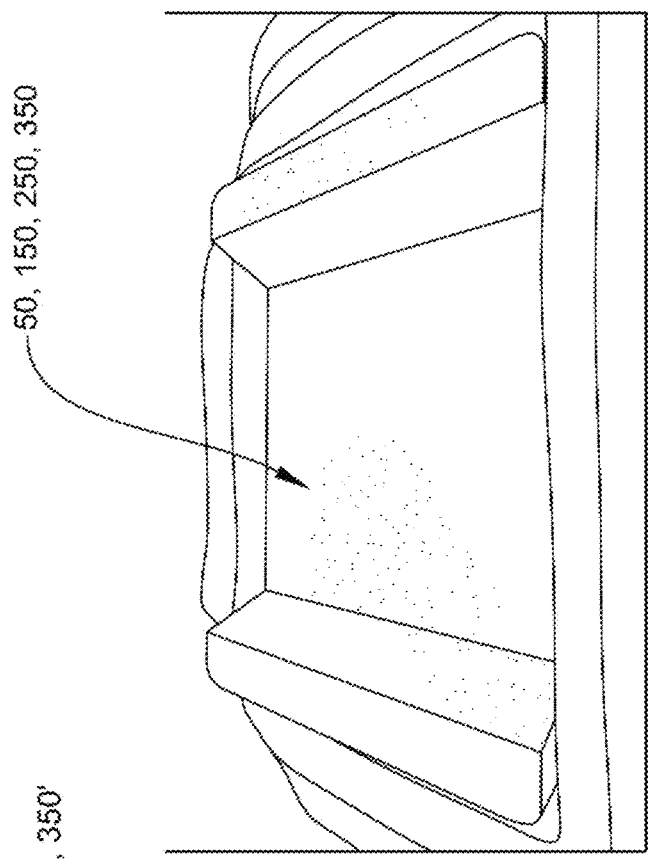
FIG. 8C is a perspective view of another base of one of the cushion sections shown placed in one of the cavities of the bottom cover.
Figure 8B:
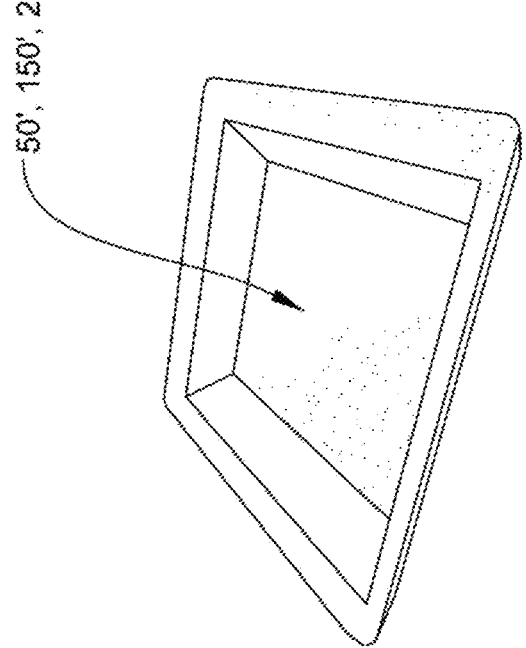
FIG. 8B is another perspective view of the base of the cushion section.
Figure 8A:
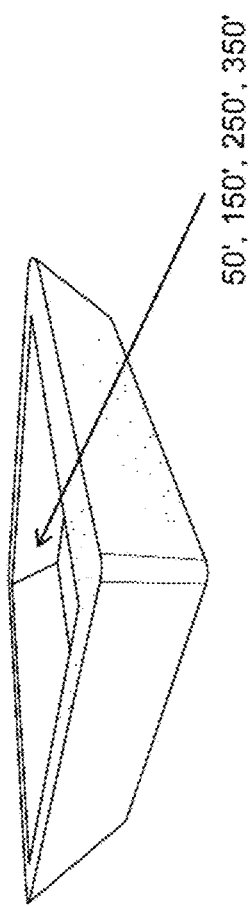
FIG. 8A is a perspective view of the base of one of the cushion sections.

Referring to FIG. 8A-8C, any of the foam cribs noted above, including cribs 50, 150, 250, and 350 may be formed with only longitudinal side walls. As noted above, one or more cushion sections may incorporate a wedge to help prevent patient migration toward the foot end of the patient support surface. To that end, in one embodiment, the wedge may be provided by the crib by forming the cribs 50', 150', 250', and 350' with one or more lateral side walls (that extend perpendicular to the longitudinal side walls) so that the lateral side wall or walls form the wedge, as shown in FIGS. 8B and 8C. The wedge forming lateral side wall(s) may be formed from different foams to provide the increased stiffness to the wedge, as described above.

Figure 9:
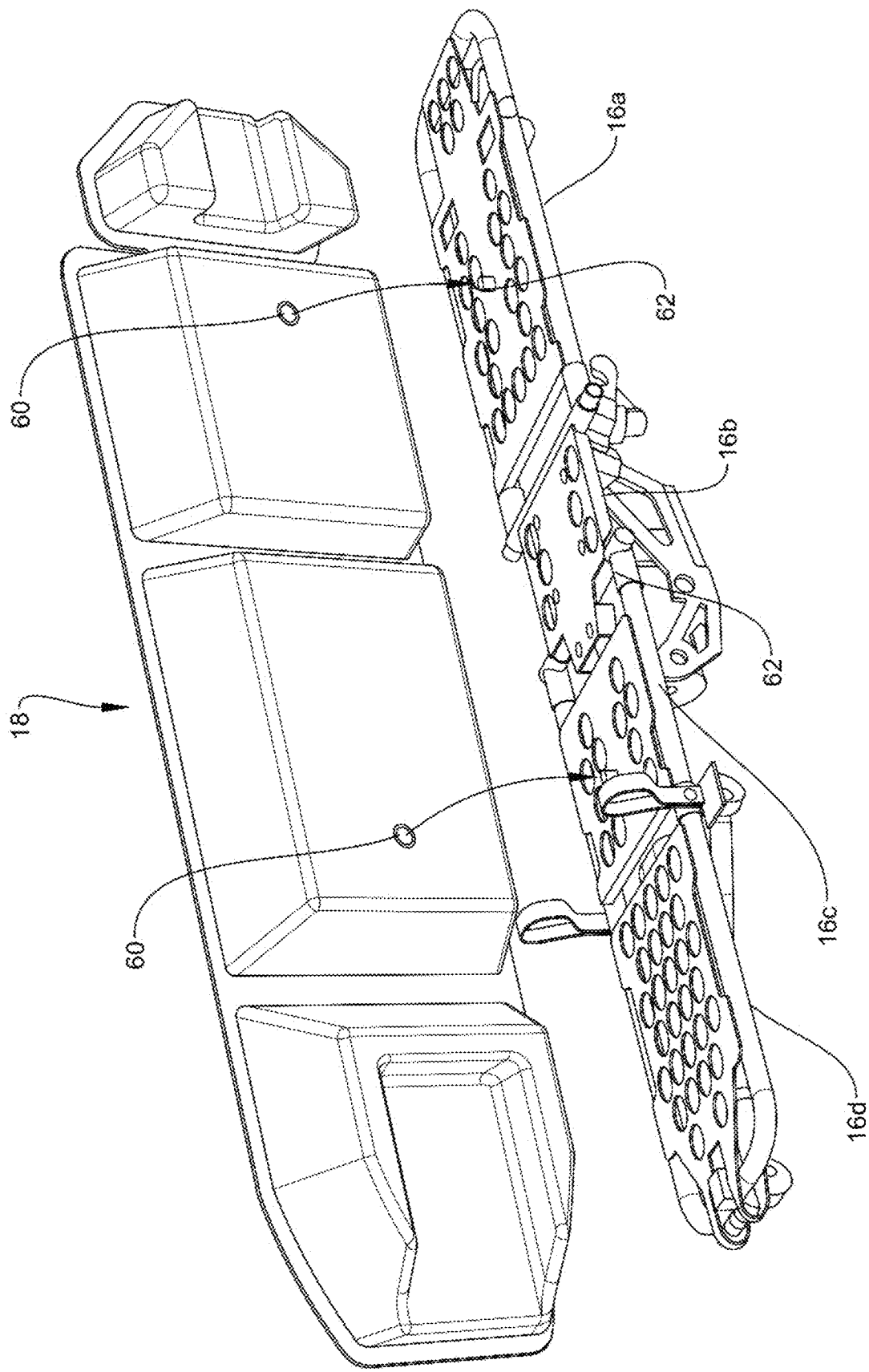
FIG. 9 is a bottom exploded perspective view the patient support surface and deck of the transport apparatus illustrating how the support surface is mounted to the deck.
Figure 11:
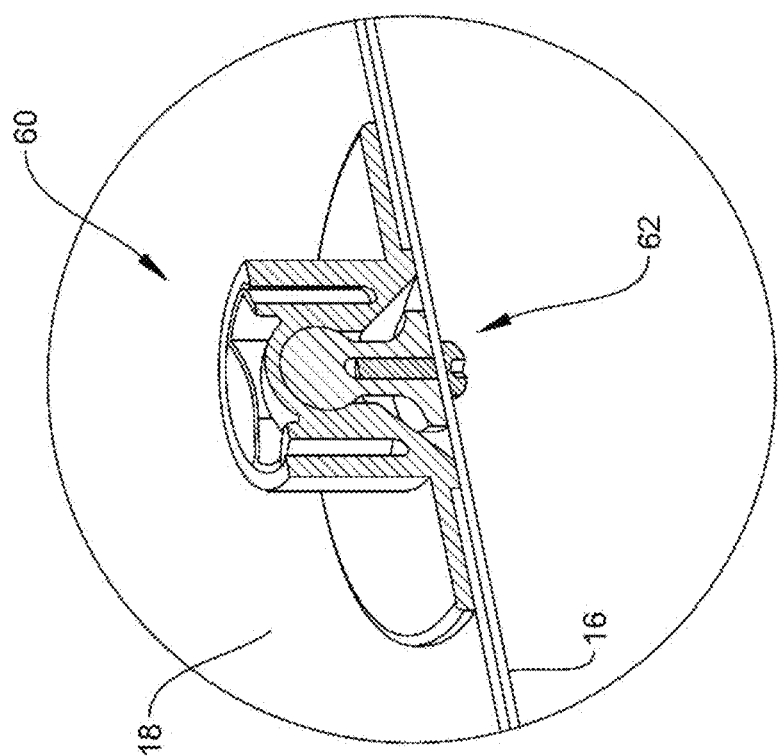
FIG. 11 is a similar partial fragmentary perspective view of the releasable coupler of FIG. 10 releasably coupling the patient support surface to the deck of the transport apparatus.
Figure 10:
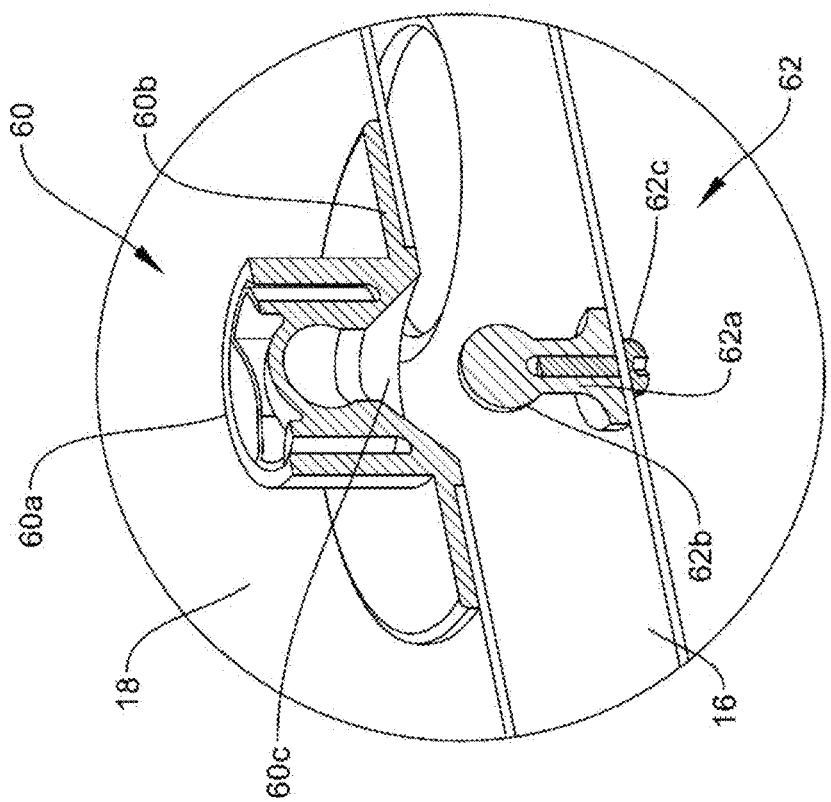
FIG. 10 is a partial fragmentary exploded perspective view of one embodiment of a releasable coupler for releasably coupling the patient support surface to the deck of the transport apparatus as part of the patient support surface system.

Referring to FIG. 9, as noted above, one or more accessories or features may be incorporated, such as by forming or mounting, into or onto the patient support surface. For example, one or more accessories or features may be incorporated, such as by forming or mounting, into or onto the lateral or longitudinal sides of patient support surface.

Referring again to FIG. 9, one or more couplers may be mounted into or onto the bottom side of the patient support surface to couple the patient support surface to the deck of the transport apparatus. In the illustrated embodiment, a pair of couplers 60 are mounted to the bottom surface of patient support surface 14 in bottom cover 18, which form snap fit connections with couplers 62 mounted to or formed in the deck. Optionally, couplers 60 and 62 are configured as male and female couplers that, when engaged, cooperate to releasably couple the patient support surface to the deck.

Further, couplers 60 may be mounted to the bottom surface of patient support surface 14 inwardly of the outer perimeter of bottom cover 18 and within the footprint of the deck sections. By locating the couplers 60 inwardly of the outer perimeter of bottom cover 18 and within the footprint of the deck sections, the risk of bodily fluid intrusion into the patient support surface through couplers 60 is reduced. However, with this configuration the couplers may not be readily visible, at least as viewed from above the patient support surface. Regardless of whether they are easily visible or not, couplers 60, 62 may be configured to provide an indication that the couplers are properly connected. For example, in one embodiment, couplers 60, 62 may be configured to make an audible noise when connected to provide an audible confirmation that the couplers are properly connected.

For example, suitable couplers 60 may each comprise a substantially rigid cup 60a with an annular flange 60b, which forms a socket 60c. Couplers 62 may comprise a post 62a with a ball 62b for receipt in and snap fit engagement with cup 60a to provide a releasable coupler. Cup 60a is substantially rigid but as sufficient resiliency to deflect when ball 62b is inserted into the cup and then return to its original configuration and thereby retain the ball in the cup.

Cup 60a is aligned and, optionally, surface mounted in bottom cover 18 in an opening formed in bottom cover 18. To seal couplers 60 in patient support surface 14, flanges 60b may be glued to the inner surface of bottom cover about the opening (through which the coupler extends) or may be welded, for example using RF welding, or may be formed with the cover during molding of the bottom cover. Couplers 60 and 62 may be each formed from a plastic or a metal.

Couplers 62 may be formed with or secured to the deck 16 by fasteners 62c, such as bolts, which extend through the webs or plates of the respective deck section. It should be understood that the specific construction of the couplers may vary. For example, the couplers 60 and 62 may be reversed—with the male coupler (62) being mounted or formed with the lower surface of bottom cover 18, and the female (60) being formed on the deck, similar to the coupler described below. In addition, as described below, at least one of the couplers may be movable mounted to the deck or to the patient support surface (or both) to accommodate the relative movement that can occur between the deck and the patient support surface, for example, when one or more of the deck sections is being tilted. Thus, one coupler, or set of couplers, may be non-movable, and the other coupler or set of couplers may be movable, or all may be movable.

Alternately, as illustrated in FIGS. 14-14A, one or more couplers 62', which are similar to couplers 62, can be movably mounted to deck 16 so that they accommodate the relative movement between the respective deck section and the patient support surface 14 when the deck section is tilted. For example, in the illustrated embodiment, coupler 62' is mounted in a bracket 66', which mounts to the upper side of the respective deck section, for example, deck sections 16a, 16c, or 16d, and movably mounts the coupler 62' to the deck. For example bracket 66' may include a slot 66a' through which coupler 62' extends and is captured therein by a flange 62c' (from which post 62a' extends). In this manner, coupler 62' can move along slot 66a' when the respective deck section is titled to decouple the shear forces between the patient support surface and the deck when the deck section or sections are articulated.

Figure 13:
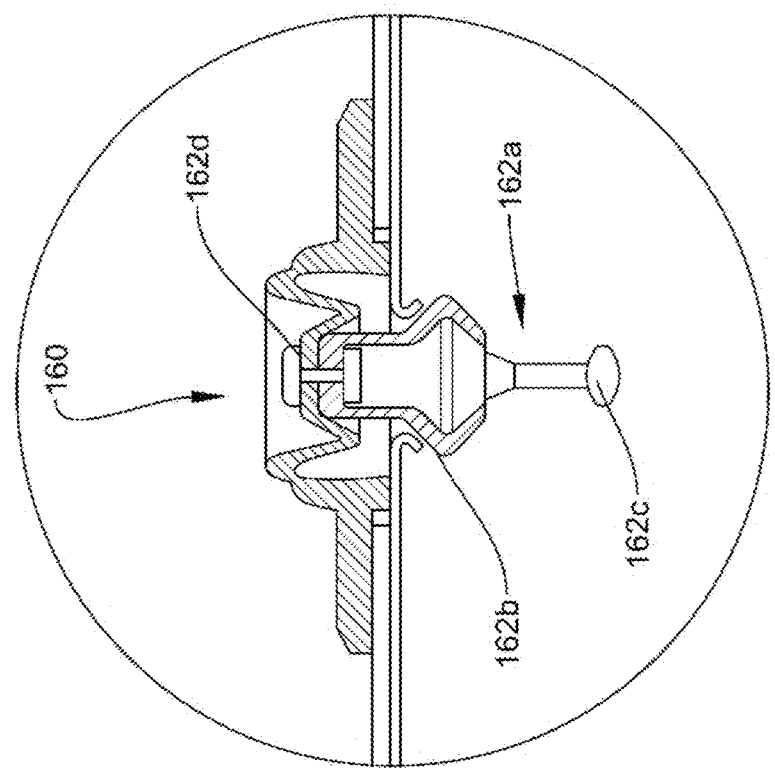
FIG. 13 is a similar partial fragmentary perspective view of the releasable coupler of FIG. 12 releasably coupling the patient support surface to the deck of the transport apparatus.
Figure 12:
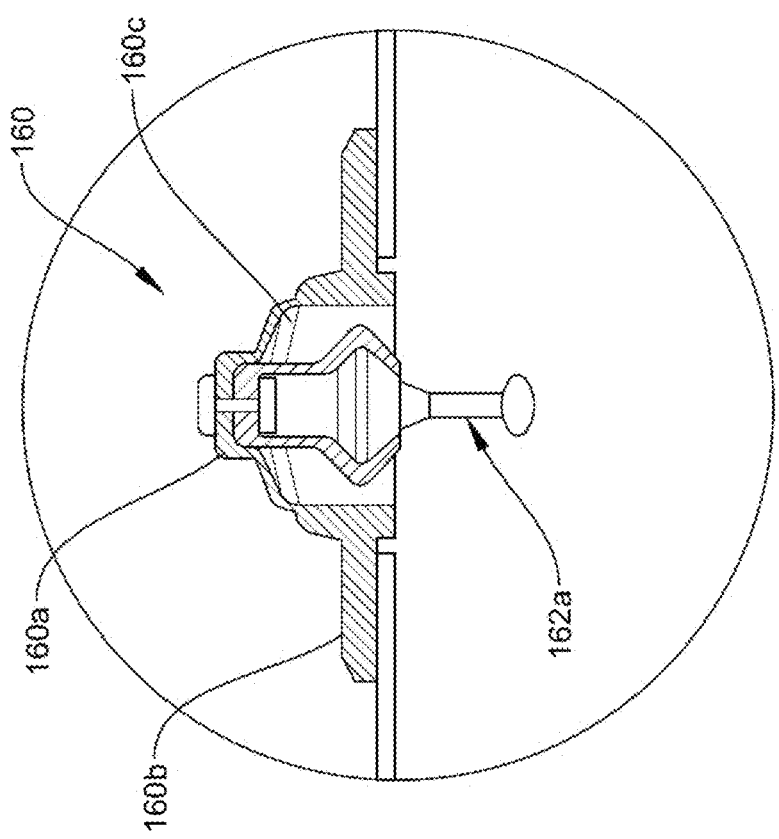
FIG. 12 is a partial fragmentary exploded perspective view of another embodiment of a releasable coupler for releasably coupling the patient support surface to the deck of the transport apparatus.

Referring to FIGS. 12 and 13, in an alternate embodiment of the couplers, couplers 160 are similarly mounted in the bottom cover to couple to the deck but are configured to directly engage the deck. Couplers 160 each include a substantially flexible and deformable cup 160*a* with an annular flange 160*b*, which forms a socket 160*c*. Flanges 160*b* may be similarly glued to the inner surface of bottom cover about the opening (through which the coupler extends) or may be welded, for example using RF welding, or may be formed with the cover during molding of the bottom cover. Though when molded with the cover the post described below may need to be post attached.

Mounted in sockets 160*c* and to cups 160*a* are elongateable posts 162*a*. Posts 162*a* include a compressible annular shoulder 162*b* and an engagement structure 162*c*, such as a ball or annular shoulder, which allows a caregiver to pull the post from its inoperative position (FIG. 12) and stretch the post to its deployed, operative position shown in FIG. 13 for engagement with the deck web or plate.

In the illustrated embodiment, each post 162*a* is secured to its respective cup 160*a* by a fastener 160*d* (such as a plastic rivet) and is movable by pulling on engagement structure 162*c* to move it from its inoperative position to its deployed operative position. When pulled, post 162*a* causes cup 160*a* to collapse or fold (like a bellow) and, as noted, post 162*a* and compressible annular shoulder 162*b* stretch (and hence narrow the width the compressible shoulder). When stretched, post 162*a* and shoulder 162*b* can be pulled through a corresponding opening formed in the deck plate or web. When pulled, the compressible annular shoulder 162*b* narrows and compresses until the compressible annular shoulder 162*b* passes through and below (as viewed in FIG. 13) the opening in the deck, and thereafter expands to trap the post 162*a* and coupler 160 in the deck. To release coupler 160 from the deck, a caregiver may pull on the post once again to narrow the compressible shoulder while lifting the patient support surface of the deck. Suitable materials for couplers 160 include polymers, such as rubber or plastic, including polypropylene, acrylonitrile butadiene styrene (ABS), or the like.

Figure 20:
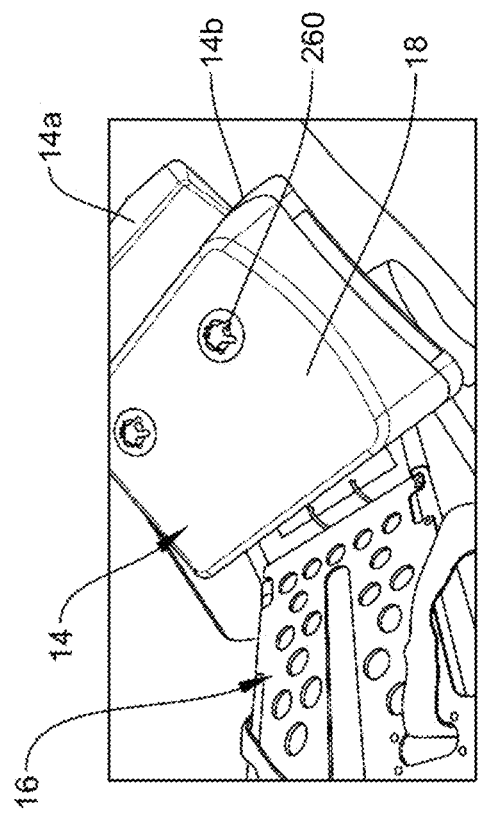
FIG. 20 is a perspective view of another embodiment of releasable couplers mounted to or formed with the bottom side of the patient support surface.
Figure 21:
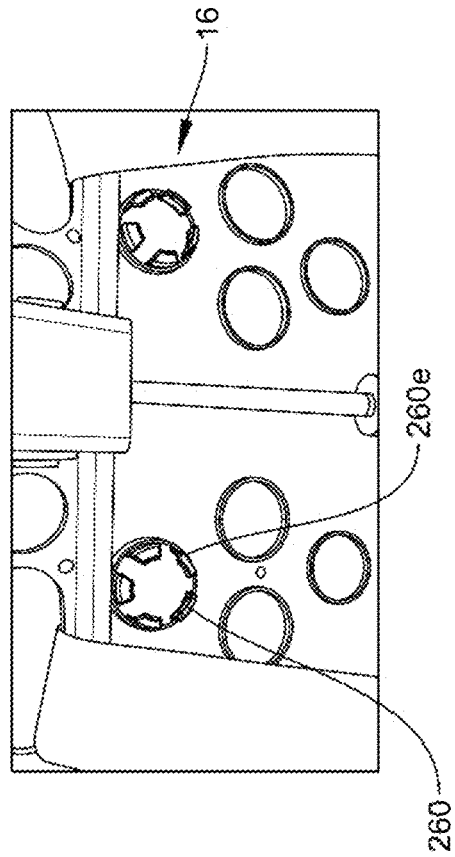
FIG. 21 is an enlarged perspective view of the releasable couplers of FIG. 20 shown coupled to the deck as seen from the underside of the deck.
Figure 22:
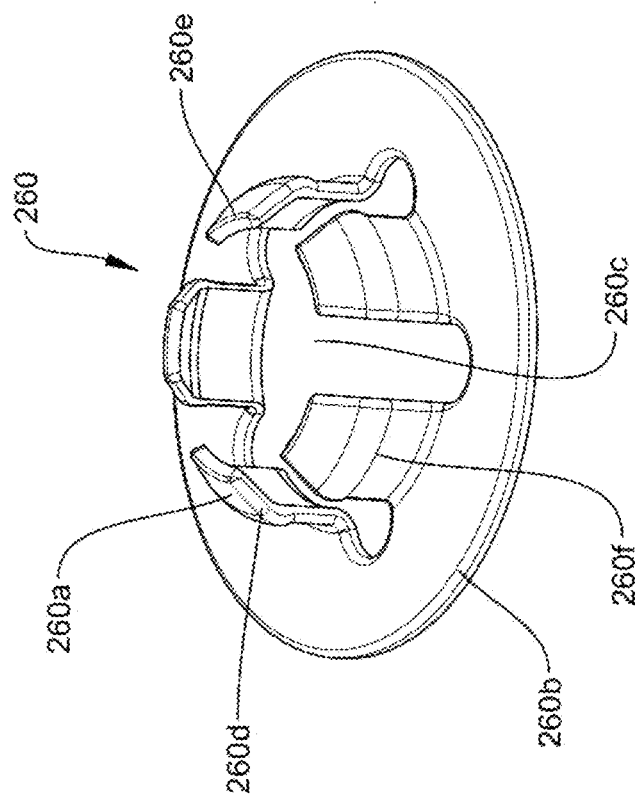
FIG. 22 is an enlarged perspective view of one of the releasable couplers of FIG. 20.

In another embodiment, the couplers may be static—though deformable to engage the deck. For example, as shown in FIGS. 20-22, similar to the previous embodiments, couplers 260 include a cup 260*a*, which forms a socket 260*c*, and an annular flange 260*b*. In the illustrated embodiment couplers 260 are provided at the lower surface of bottom cover 18 so that there may be no openings into the bottom cover. They may be glued or welded or formed with the cover, as described above.

Cup 260*a* is formed from a plurality of annularly or radially spaced fingers 260*d* that extend upwardly from flange 260*b*. Fingers 260*d* include angled distal ends 260*e* and shoulders 260*f* that are sized and arranged so that they that flex inwardly when pressed into the openings in the web of the deck sections and then rebound to their original configuration when the shoulders pass through the opening to thereby releasably couple the patient support surface to the deck. To uncouple the patient support surface, a caregiver may simply lift on the patient support surface with sufficient force to compress the fingers.

As best understood from FIG. 22, one or each patient support surface section may have a pair of couplers 260 to engage a pair of openings in the web of the deck section (as shown in FIG. 21. Suitable materials for couplers 260 include polymers, such as rubber or plastic, including polypropylene, acrylonitrile butadiene styrene (ABS), urethane, such as ELASTOLLAN, or the like.

Figure 23:
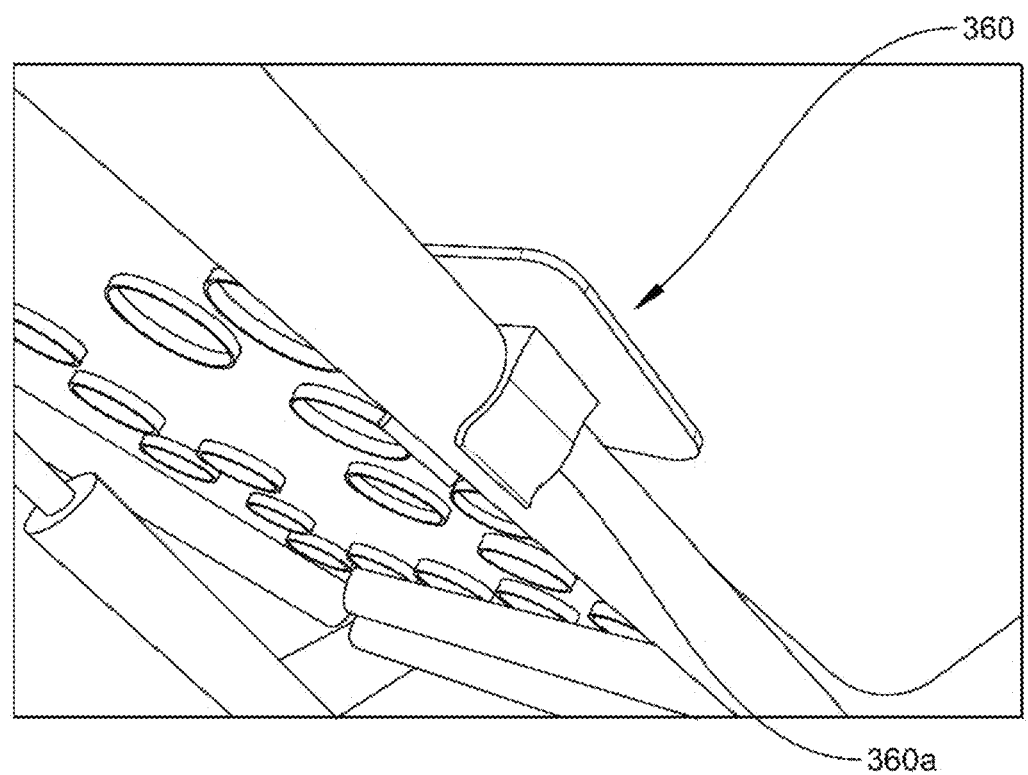
FIG. 23 is an enlarged perspective view of another embodiment of a releasable coupler mounted to or formed with the bottom side of the patient support surface and engaged with the frame of the deck.
Figure 24:
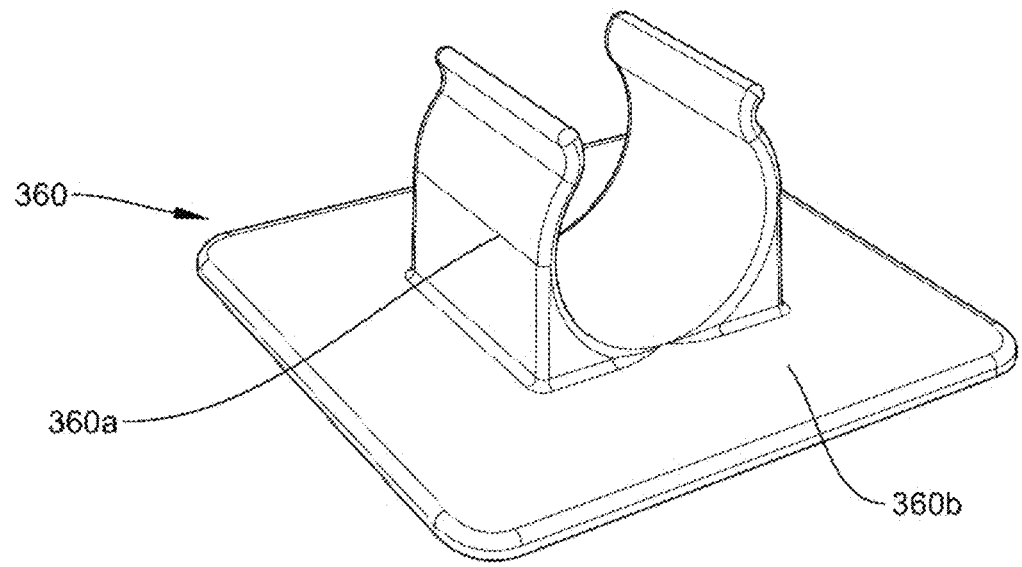
FIG. 24 is an enlarged perspective view of the releasable coupler of FIG. 23.

In another embodiment, as best seen in FIG. 24, releasable coupler 360 may be configured with a pair of fingers 360*a* that extend upwardly from a flange 360*b* to form a C-shaped clip for releasably engaging the deck tubular frame members (FIG. 23). For suitable materials and methods of mounting, reference is made to the above embodiments. Again, the couplers 360 may be mounted inward of the perimeter of the patient support surface, but not within the footprint of the deck sections (instead mounted at the perimeter of the deck footprint), so they are visible from the side of the patient support surface. Even though not forming a blind connection, as in the case of any of the couplers described herein, the couplers may be configured to make an audible noise when connected, so the caregiver can couple the patient support surface without needing to have a visual confirmation—which in an emergency situation may be important.

Figure 19A:
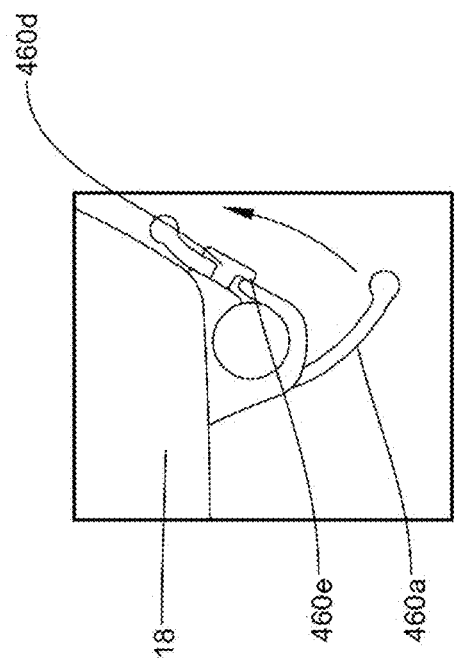
FIG. 19A is an enlarged side view of the releasable coupler.
Figure 19:
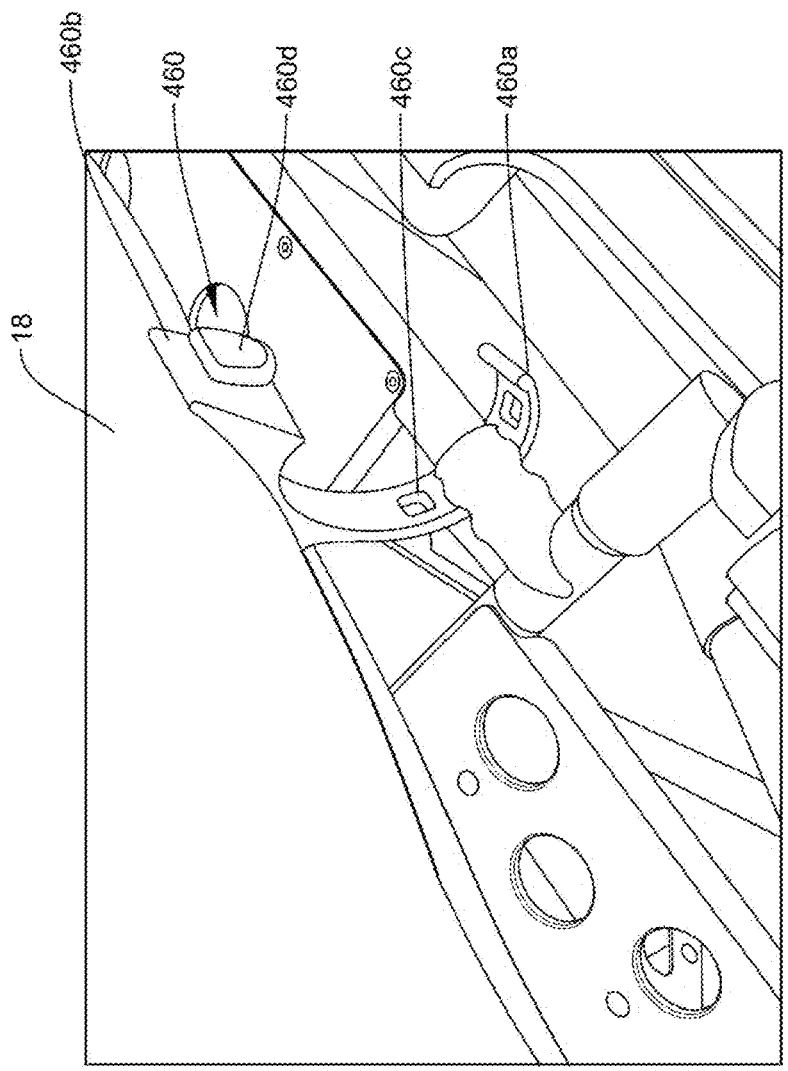
FIG. 19 is an enlarged perspective view of another embodiment of a releasable coupler mounted to or formed with the lateral side of the patient support surface.

In another embodiment, the releasable coupler 460 may be mounted to or formed onto or into the longitudinal side or sides of the patient support surface. For example, referring to FIG. 19, coupler 460 includes a strap 460*a* for wrapping around a portion of the transport apparatus, such as a deck tubular frame member, and a base 460*b*, which is mounted to or formed with the side of the bottom cover 18. For examples of optional methods of mounting base 460*b* to bottom cover 18, reference is made to the above embodiments.

Strap 460*a* extends from one side of base 460*b* on one end and includes one or more openings 460*c* for engagement with a flange 460*d* mounted to the other side of base 460*b* to thereby form a receptacle for receiving a portion of the transport apparatus, as noted. After the strap has been wrapped around the portion of the transport apparatus, such as the deck tubular frame member, the flange can then be inserted into and captured into one of the openings in the strap and thereby releasably couple the patient support surface to the deck. Flange 460*d* may include a lip 460*e* to facilitate retention of the strap on the flange once the flange is passed through the opening. In one embodiment, the strap is formed from an elastic material, such as rubber, so that it can be stretched as it is wrapped around the deck tubular frame and, further, so that the opening can be stretched when pressed on to the flange.

Figure 26:
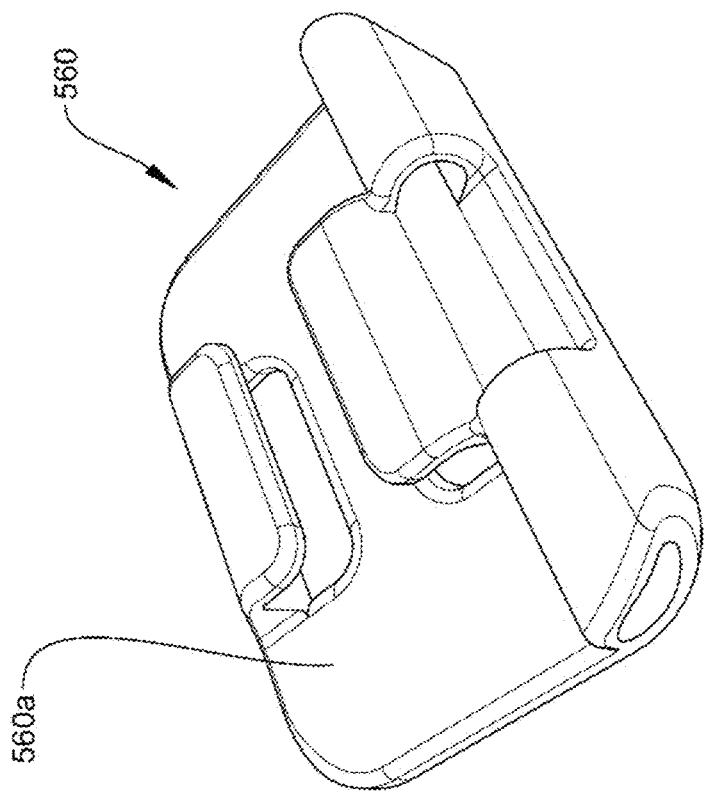
FIG. 26 is another perspective view of the releasable coupler of FIG. 25.
Figure 25:
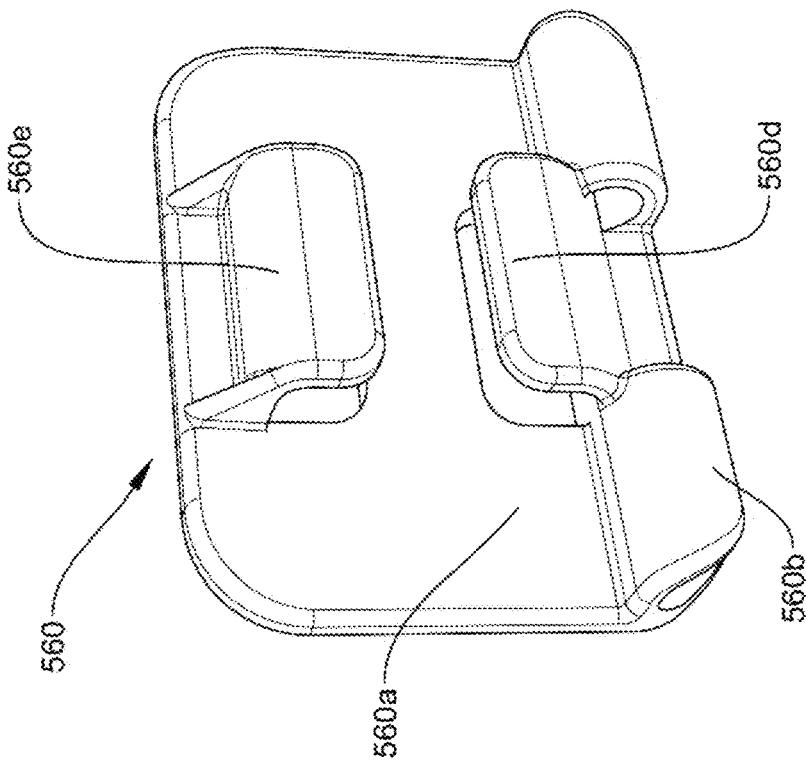
FIG. 25 is an enlarged perspective view of another embodiment of a releasable coupler.
Figure 27:
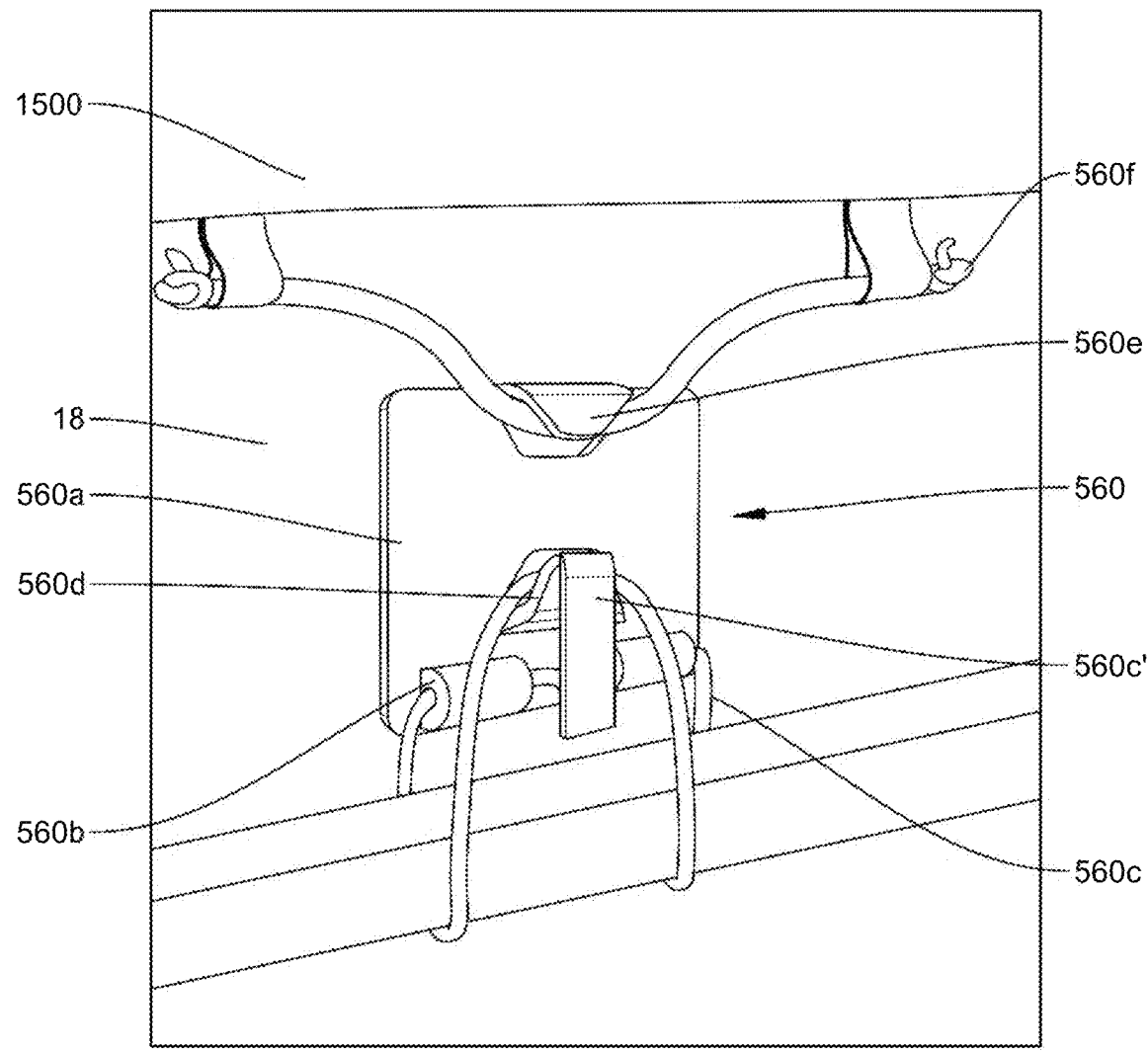
FIG. 27 is a perspective view of the coupler of FIGS. 25 and 26 shown mounted to or formed with the lateral side of the patient support surface.

Referring to FIGS. 25-27, couplers 560, which also may be mounted to the sides of the bottom cover 18, each include a flange 560*a* with one or more retainers 560*b* for retaining and mounting a chord 560*c* to the coupler. For example, retainers 560*b* may comprise a closed section tube or boss with a central transverse passageway for receiving the chord therein. Spaced from the retainers 560*b* is another retainer 560*d*. Retainer 560*d* may have an open section, for example, formed from an L-shaped arm, which can retain the chord 560*c* after it has been wrapped around a portion of the transport apparatus (such as the deck tubular frame member) and thereby releasably couples the patient support surface to the deck. To facilitate use of the chord, chord 560*c* may include a tab 560*c*', which can be color coded, to ease installation and attachment.

In addition, coupler 560 may include another retainer 560*e*, such open sectioned retainer formed by an L-shaped arm, which also extends from flange 560*a* and is spaced above retainer 560*d* for retaining another chord or strap 560*f* of an overlying cover, such as cover 1500 described below.

As noted above, any of couplers described may be formed from plastic or metal, such as a punched steel part. Further, as noted the couplers may be joined to or formed with the bottom cover in a number of different ways, including by an adhesive, RF/ultrasonic welding, heat staking, and also riveting or using other fasteners, or a combination thereof. Further, the couplers may be molded into the bottom cover as part of the forming process, such as thermoforming process. Other couplers include buckle, cleats, hooks, snaps, shock cord, suction cups, or magnetic fasteners (such as FIDLOCK magnetic fasteners), or the like.

For example, magnets can be enclosed within a sewn/welded pocket that is made of high surface friction textile or film. The magnetic force holds the patient support surface to the metal cot deck and the high surface friction fabric prevents the patient support surface from sliding side-to-side during patient transfers.

Different connectors, other than male and female connectors may be used, including any mechanical connector that latches, fastens, clips, press-fits on an existing transport apparatus, such as an EMS cot, with or without modifications. This can be used to ensure compatibility with different transport apparatuses and can eliminate design changes required to the transport apparatus.

In yet other embodiments, the couplers may be tethered to the bottom cover. For example, referring to FIGS. 15-18, couplers 660 may be tethered to bottom cover 18 by straps 662. For example, in the illustrated embodiment the straps 662 may be sewn and/or glued to the central portion of the lower surface of the bottom cover, and the couplers may be attached to the opposed distal or terminal ends of the straps, for example by loops formed in the ends of the straps or buckles. The couplers 660 may be C-shaped clips or brackets formed from a wired frame arm construction, which can be formed from metal or plastic, that are sized to releasably engage the deck tubular frame members (FIG. 16) and provide a snap fit connection therewith.

Referring to FIG. 17, couplers 760, which are similar to couplers 660, but with a solid C-shaped arm construction, may be tethered to opposed sides of bottom cover 18 by straps 762 or other couplers, such as buckles. Straps 762 are mounted at one end to the sides of the bottom cover—again by stitching and/or adhesive, with the couplers 760 attached to the opposed distal or terminal ends of the straps, for example by loops formed in the ends of the straps or by buckles.

Figures 28, 29:
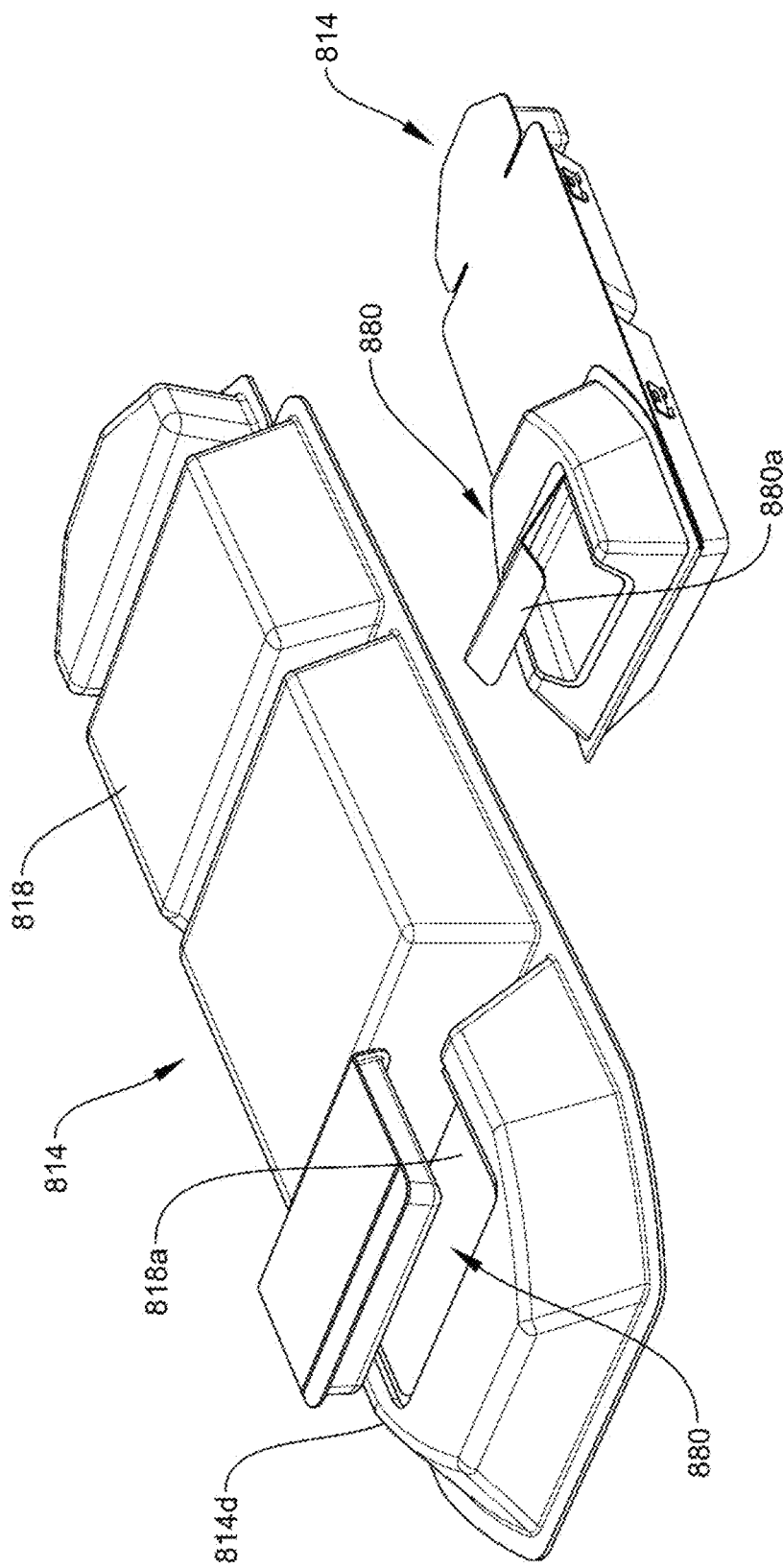
FIG. 28 is an exploded bottom perspective view of another embodiment of the transport apparatus incorporating a storage compartment as part of the patient support surface system.
FIG. 29 is a bottom perspective view of another embodiment of the transport apparatus incorporating a storage compartment as part of the patient support surface system.

Referring to FIG. 28, in one embodiment, patient support surface 814, which may be of similar construction to patient support surface 14, includes one or more recesses formed therein to form or accommodate a storage compartment. For example, areas that do not require as much foam support (for example, the foot, back, head) could have foam removed on the underside of the patient support surface to form cavities or open spaces for the purpose of storing various items/equipment.

In one embodiment, as shown in FIG. 28, a storage compartment 880 is incorporated into patient support surface 814, which may be separately formed from patient support surface 814 and optionally mounted, such as by using adhesive or welding, to patient support surface 814. Alternately, the compartment may be formed with the patient support surface during molding. For example, the patient support surface and storage compartment may be co-injection molded.

Optionally, as shown, compartment 880 may be formed with a folding compartment wall or door 880a to provide access into the compartment, for example, when that section of the patient support surface, which includes the compartment, is folded upwardly, as shown in FIG. 29.

For example, compartment 880 may be located in a recess 818a formed in bottom cover 818 (and corresponding cushioning layer) in the foot section 814d of patient support surface 814. The recess may be formed so that it extends into the patient support surface such that is fully surrounded on all sides by the patient support surface or may extend through the lateral side wall of the cavity of the patient support section, as shown. Folding compartment wall or door 880a may be configured to provide access into the compartment through one or two sides of the compartment, such as shown in FIG. 29. In this manner, when foot section 814d is raised or folded (so that it rests on the seat section of the patient support surface), full access is available to the compartment when the folding wall or door 880a is lifted.

Compartment 880 may be used to store supplies, such as supplies for the caregiver, such as gloves, masks, or the like, or for the patient supported thereon, such as restraints, including the cover and/or pediatric restraint assemblies described below.

In other embodiments described below, the compartment may be separately mounted from the patient support surface and, instead, mounted to the deck of the transport apparatus. In yet other embodiments, as described below, access may be achieved without folding or lifting the patient support surface. When mounted to the deck, the compartment may help retain the patient support surface on the deck, by providing at least a lateral restraint, and in some embodiments a longitudinal restraint or both.

Figure 30:
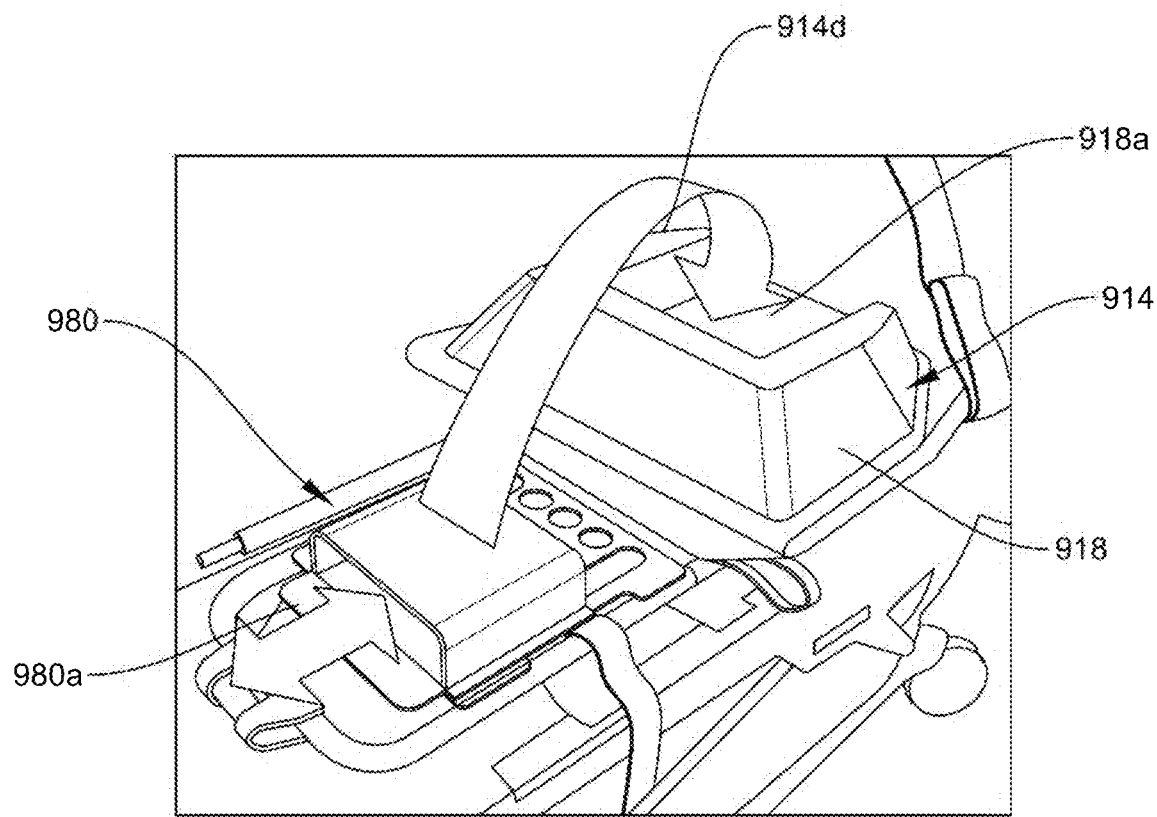
FIG. 30 is a perspective view of the patient support surface mounted to the deck and the foot section folded up to provide access to the compartment, which is mounted to the deck.

As noted, in another embodiment, the compartment may be mounted to the deck of the transport apparatus. For example, referring to FIG. 30, patient support surface 914, which is similar to patient support surface 814, includes a recess 918a in its foot section 914d that extends through its foot end lateral wall and a compartment 980 that is separately mounted from the patient support surface to the deck. For example, compartment 980 may be attached by releasable fasteners to the deck of the transport apparatus. Alternately, the compartment may be formed as part of the deck.

Similar to compartment 880, compartment 980 is formed as a generally rigid box with a folding wall or door 980a, for example at the foot end, which in the illustrated embodiment only provides access into compartment 980 through one wall, for example a side wall, of compartment 980. It should be understood that compartment 980 may be formed with two doors, one as shown, and the other in the top side to provide greater access inside the compartment 980 when the foot end of the patient support surface is raised, as shown. The folding wall or door 980a is sized so that access into compartment 980 may be achieved through the foot end of patient support surface through the recess 918a without folding or lifting the patient support surface. Though, as noted, access can also be provided when lifting or folding the foot section 914d of patient support surface 914.

By attaching the compartment to the deck and nesting the compartment with the patient support surface when in its normal in-use position, the compartment can, therefore, help provide a shear restraint (laterally and/or longitudinally (at least in one direction)) for the patient support surface and thereby help retain the patient support surface on the transport apparatus. At the same time, by extending the recess through the foot end of the patient support surface, the patient support surface will be able to shift as the foot or leg section of the deck is tilted or folded without interference from the compartment. However, it should be understood that access to the compartment or compartments made be provided through openings in the side of the patient support surface.

In another embodiment, the compartment may be provided at the head end of the patient support surface. Referring to FIGS. 31 and 32, patient support surface 1014, which may be of similar construction to the patient support surface 14 described above, includes a compartment 1080 at its head end. For example, as illustrated in FIG. 32, compartment 1080 may be formed by the same sheet that forms the bottom sheet of the back, seat, and foot sections of patient support surface 1014—and hence is formed by the "bottom cover". In this embodiment, head section cavity 1022a, which forms a lid for compartment 1080, is formed by a separate additional sheet that is joined, for example, to the living hinge between the compartment 1080 and back section 1014b of the patient support surface. The head section cavity 1022a is then enclosed and covered by the top sheet 1020. Therefore, the compartment 1080 may be formed by an extension of the bottom cover, while the top of the head section cavity (which holds the head end cushion section) may be formed by an extension of the top cover.

Alternately, compartment 1080 may be formed below the bottom cover 1018. For example, the head section cavity 1022a in patient support surface 1014, which contains the head end cushion section 1024a, may be formed by the same sheet that forms the back, seat, and foot sections of patient support surface 1014—and hence is formed by the "bottom cover". In this alternative embodiment, compartment 1080 may be formed by a separate additional sheet (or molded compartment described below) that is joined, for example, to the living hinge between the head and back sections of the patient support surface.

In either case, the head section cavity 1022a containing the head end section cushion section 1024a may form the lid for compartment 1080, and hence can be lifted or folded to provide access into compartment 1080.

The profile of head section cavity 1022a may be stepped, as shown, so that it partially inserts into and nests with compartment 1080. Optionally, the sheet (bottom cover or separate sheet) forming the head section cavity 1022a may form a friction fit with the inner surface of the compartment 1080 to help retain the head section cavity 1022a coupled with the compartment unless a separation force is applied and they are intentionally separated. Further, the nested arrangement (with or without the friction fit) reduces or prevents egress of fluid into the compartment. Optionally, a compressible seal or gasket may be provided between the head section cavity 1022a and the compartment 1080 to better seal the compartment.

In another embodiment, a releasable latch may be provided to further secure the "lid" of the compartment 1080 in its closed position.

Optionally, as noted, compartment 1080 may be formed from the bottom cover 1018 of patient support surface 1014, and head section cavity 1022a may be formed by an additional sheet 1022a' that is then joined with the bottom cavity in a similar manner described above in reference to the overall construction of bottom cover 18 in the first embodiment. When formed from the bottom cover, compartment 1080 may include an additional insert 1082, formed from a rigid plastic that is inserted into the cavity 1080a formed in bottom cover 1018. Though as will be more full described below, the compartment may be made from just the bottom cover and, therefore, have a more flexible construction and, in some instances, fold or partially collapse, as needed.

Optionally, in either case, a caregiver may hold the head section cavity 1022a of the patient support surface 1014 and lower the head section of the deck, at the same time, separating the compartment from the head section cavity 1022a, to allow the caregiver access to compartment 1080 without raising the head of the patient. Alternately, the caregiver may raise the head section 1014a of the patient support surface and separate the compartment at the head section cavity 1022a, to allow the caregiver access to compartment 1080.

In each of the above embodiments described in reference to FIGS. 31 and 32, the compartment 1080 effectively extends the full width of the head section. In another embodiment, the width of the compartment may be reduced and offset inwardly from the opposed longitudinal sides of the patient support surface, similar to compartments 880 and 980—so that a portion of the head section cavity 1022a straddles the compartment. In this manner, the deck of the transport apparatus may be formed with a recess to accommodate receipt of the compartment so that the head section cavity 1022a can be still be supported by the deck and the caregiver can lower the compartment into the recess of the deck for access. Alternately, the compartment may be simply mounted to the head section of the deck, as described above and below. Further, access to any or each of its sides may be provided, to provide six-sided access into the compartment.

In yet other embodiments, any of the compartments described herein may be provide access for multiple or all sides, including the top or bottom in the case of compartments secured to the patient support surface.

Figure 34:
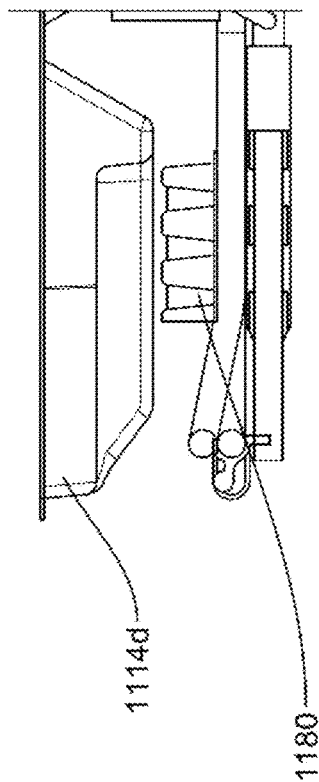
FIG. 34 is a side view of the patient support surface of FIG. 33.
Figure 33:
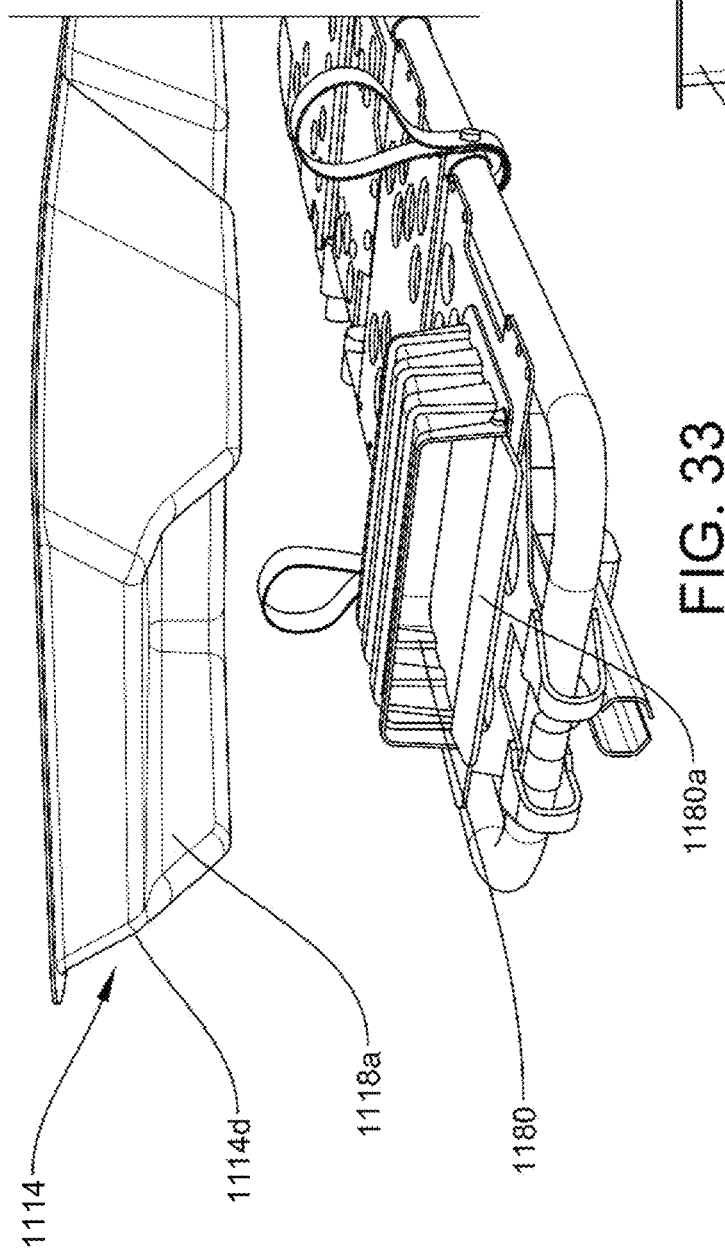
FIG. 33 is a perspective view of another embodiment of the patient support surface incorporating a storage compartment at the foot end of the patient support surface as a part of the patient support surface system, which is accessible from the foot end of the patient support surface.

Referring to FIGS. 33-34, patient support surface 1114, which is similar to patient support surface 914, includes a recess 1118a in its foot section 1114d that extends through its foot end lateral wall and a compartment 1180 that is separately mounted from the patient support surface to the deck. In the illustrated embodiment, compartment 1180 is secured to the deck of the transport apparatus, for example by fasteners or welds or adhesive. Compartment 1180 may be formed from a rigid material, such as metal or plastic material, and may include ribbed portions in its side walls and top wall for reinforcement to form a rigid box. Compartment 1180 optionally also includes a folding wall or door 1180a, which in the illustrated embodiment only provides access into compartment 1180 through the side wall of the compartment, which faces the foot end of the patient support surface. Again, folding wall or door 1180a is sized so that access into the space in compartment 1180 may be achieved through the foot end of the patient support surface through the recess 1118a without folding or lifting the patient support surface.

In other embodiments, the compartment may be accessed through any side of the compartment once the patient support surface is raised. Similarly, the recess in the patient support surface may be extended through either or both of the longitudinal sides of the patient support surface.

In one embodiment, compartment 1180 may be sized (as understood in FIG. 34) so that it remains located in recess 1118a even when the leg section of the deck is tilted downwardly. In other words, in this manner, when the leg section of the deck is tilted downwardly no part of the compartment 1180 is uncovered.

Figure 35A:
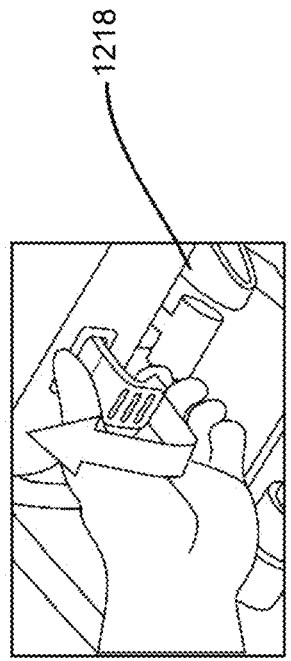
FIG. 35A is an enlarged partial perspective view of the foot end of the patient support surface when the foot section of the patient support surface is raised.
Figure 35B:
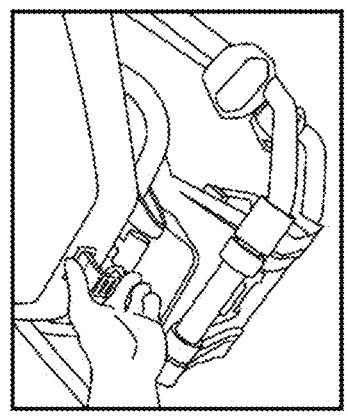
FIG. 35B is another enlarged partial perspective view of the foot end of the patient support surface.
Figure 35:
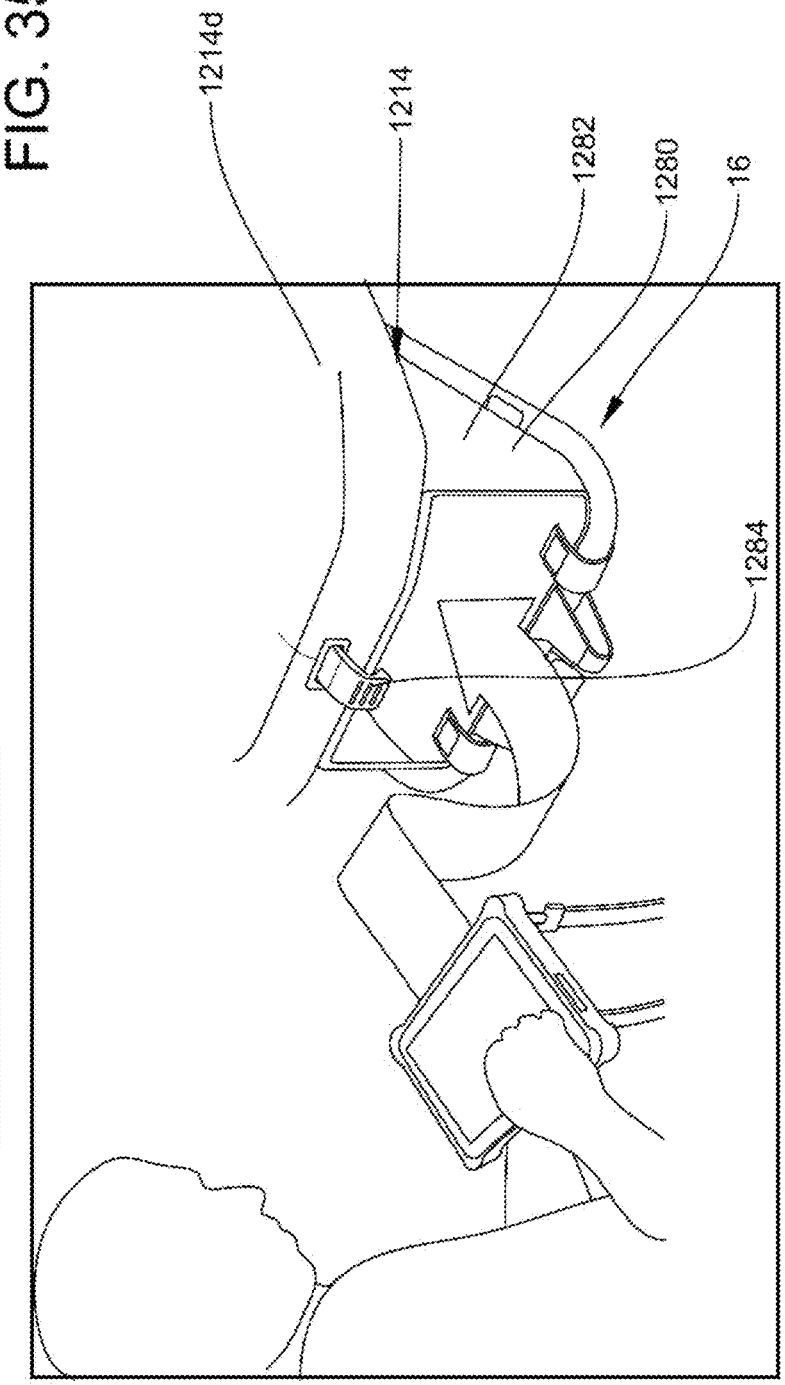
FIG. 35 is a perspective view of another embodiment of the patient support surface incorporating a storage compartment at the foot end of the patient support surface as a part of the patient support surface system, which is accessible from the foot end of the patient support surface when the foot section of the patient support surface is raised.

As noted above, the compartments may be formed with a flexible, collapsible or foldable construction. Referring to FIG. 35, patient support surface 1214, which is similar to patient support surface 14, includes a compartment 1280 mounted between its lower surface, for example, at foot end section 1214d, and deck 16. Compartment 1280 is formed by a flexible pocket 1282 with an upper side connected to the lower surface of the patient support surface and a lower side connected to the deck. The upper and lower sides may be formed from plates of a rigid material and are joined by flexible panels of material, such as a plastic sheet or plastic coated fabric or textiles. In this manner, the compartment may fold and collapse when not being accessed.

Optionally, the upper side of compartment 1280 may be formed with a recess, for example, a recess that extends into a corresponding recess formed in the lower surface of bottom cover 1218, such as described and illustrated in reference to patient support surface 814 or 914. In this manner, at least a portion of the cavity of the compartment may be rigid and fixed in size, and dictated by the recess formed in the lower surface of the patient support surface.

To close the compartment, compartment 1280 may include a releasable latch 1284, such as shown in FIG. 35, mounted to the respective patient support surface section.

Referring to FIG. 36, the numeral 1314 generally designates another embodiment of a patent support surface that incorporates a storage compartment 1380 at the head end of the patient support surface. Storage compartment 1380 is similar to storage compartment 1080 except with an inverted construction. Rather than the head section cavity 1022a forming the lid for the compartment, head section 1314a forms the compartment 1380 (with the cushion section formed in the top wall of the compartment), and the lid or door 1382 is formed by a panel mounted to the compartment 1380 at the lower surface thereof, for example, by a living hinge. Lid 1382 may be configured so that it nests in the cavity 1384 of compartment and, further, to optionally form a friction with the side walls 1386 of the compartment 1380 to retain the lid in its closed position. To open the compartment, panel 1382 may be provided with a pull-tab or strap 1388, which can be formed by webbing that is glued, welded, or otherwise secured to the panel.

As would be understood, access to compartment 1380 is, therefore, available when the head section 1314a of patient support 1314 is lifted off the deck (or the deck section is lowered) and the lid is opened.

Figure 37A:
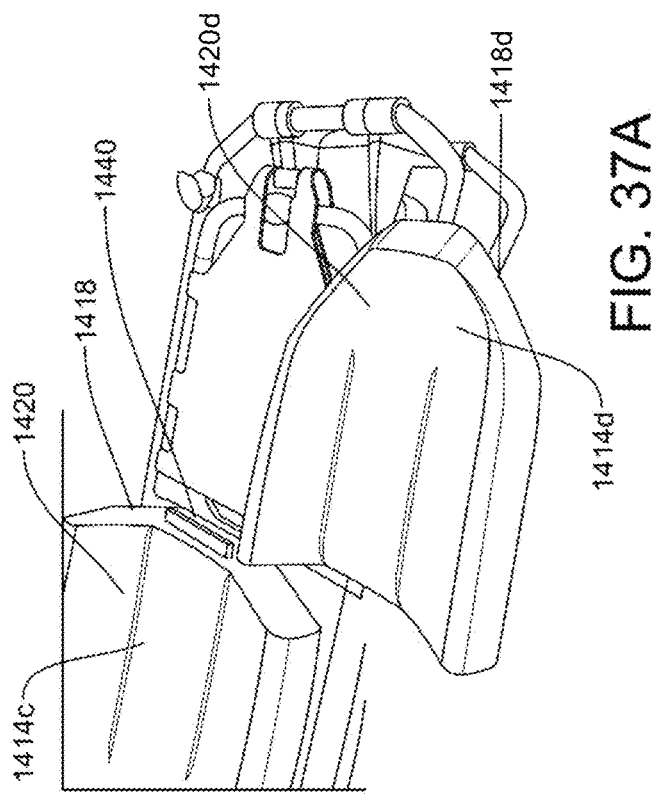
FIG. 37A is a perspective view of the patient support surface of FIG. 37 showing one section of the patient support surface removed.
Figure 37B:
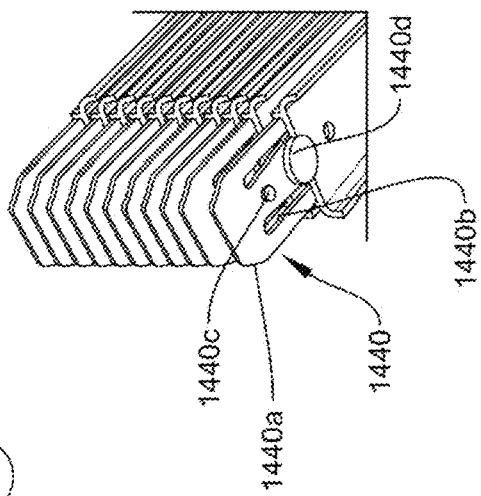
FIG. 37B is an enlarged perspective view of a coupler.
Figure 37:
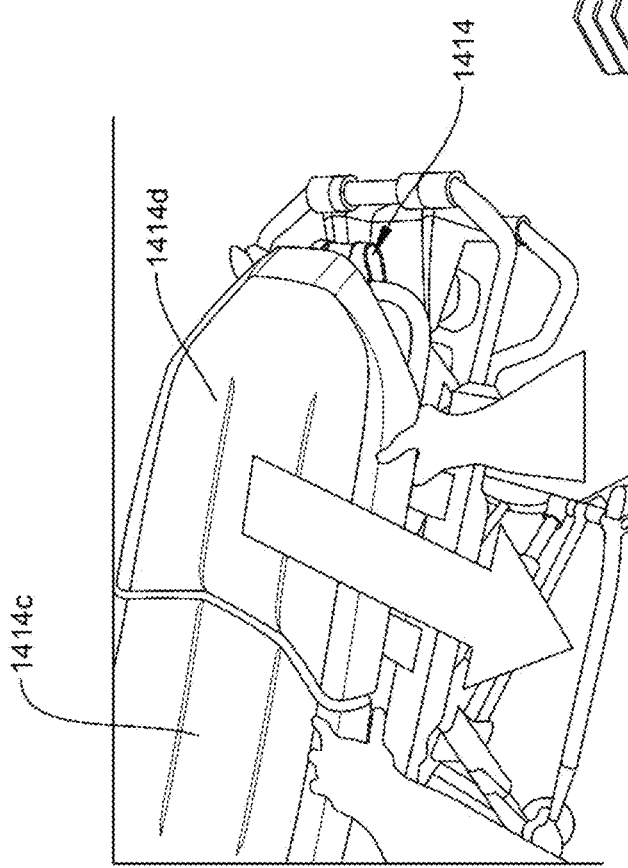
FIG. 37 is a perspective view of another embodiment of the patient support surface incorporating a modular construction to allow sections of the patient support surface to be removed for repair or replacement.

Although described as being formed from a unitary bottom cover, the patient support surface may be formed with one or more separate sections. In other words—the section or sections are formed without the living hinges joining them together. For example, referring to FIG. 37, patient support surface 1414 may be formed with a separate section, for example, foot section 1414d. Foot section 1414d may be formed in a similar manner to patient support surface 14 with a bottom cover 1418d thermoformed into is desired shape with a cavity for receiving a cushion section, but without the living hinge joining to the adjacent section—namely, the seat section. Bottom cover 1418d is then joined with top cover 1420d in a similar manner described above.

To couple the separate section to the adjacent section (in this case the foot section 1414d to seat section 1414c), the two sections have a male/female coupler 1440. For example, in one embodiment, the coupler may be formed by a plate 1440a with a spring arm 1440b and detent 1440c, and a release button 1440d. For example, the release button 1440d may be located between the two sections when the two sections are coupled together. Plate 1440a is mounted to its respective section, such as seat section 1414c, and extends so that it can be inserted into a receptacle (such as a slotted opening) formed in foot section 1414d. The detent 1440c may be a ramped detent so that when the plate is inserted into the receptacle, the ramp will be pressed to allow the spring arm to pass into the receptacle while in a non-engaging position, but once fully inserted will allow the arm and detent to return to their unbiased positon to engage a corresponding notch located in the receptacle and thereby couple to the two sections together. When the release button 1440d is pressed, the detent disengages from the notch, allowing the plate to be removed from the receptacle and thereby decouple the two sections. With a separable patient support section (or sections), the support section can be decoupled for cleaning or replacement.

Various other mechanical devices or mechanisms may be used to join the sections, including, for example, other tongue and groove couplers, Keder rails, zippers, snaps, hook and loop, press-fit friction joints, slotted and keyed. Interchangeable sections allow for specific sections that experience high wear to be serviced and/or changed. Further, one or more sections of the patient support surface may be changed out with a section or sections having different materials and/or different immersion properties, and in some instances different cribs to accommodate larger or much smaller patients. Additionally, the removable section or sections allow the surface to be modified to suit its use—for example, long duration rides vs short rides or based on patient preference or to be compatible with accessories, such as devices that provide treatment to a patient, such as the LUCAS device available from Stryker Corp. of Kalamazoo, Michigan.

As noted in some cases above, suitable materials for any of the storage compartments described above include rigid plastics or flexible panels. Thus, the compartments may be formed as a rigid box or a soft pocket (i.e. waterproof bag), which are similarly formed by thermoforming, molding, sewing, or RF welding. In any of the embodiments, as described the compartments may be integrated or internal to the patient support surface. When separately formed but integrated, the compartment may be attached to the patient support by sewing, gluing, RF/ultrasonic welding, or a combination thereof. Consequently, any or all of the storage compartments may provide fluid impermeable compartments to protect items stored in the compartments from fluid intrusion, and also infection control.

In any of the above, the top cover may be configured to prevent bodily fluid reaching any of the cushion sections. For example, the top covers may incorporate or consist of impermeable coated fabrics or plastic films as part of their construction, thus preventing fluid from passing through the top cover. Suitable materials include DARTEX or DARTEX-LIKE fabric (such as urethane laminated to a knit) or any other laminate combination. Layers of TPU, PVC, PE or PP in film may also be incorporated to form a laminated top cover. As noted above, in any of the above, the top covers may incorporate a channel or channels to direct fluid away from the patient.

In some embodiments, the top cover may be formed with a sleeve with an opening in the side to allow an accessory, such as a support structure, to be inserted into the top cover beneath the upper surface, such as backboard and/or the EMS COVID SHIELD device.

In each case, the material forming the top cover may be a very durable material to allow use of disinfectant, to be machine washed, and/or contain material or materials that have antimicrobial properties, such as MICROBAN, copper, silver, or other antimicrobial materials.

Figure 38:
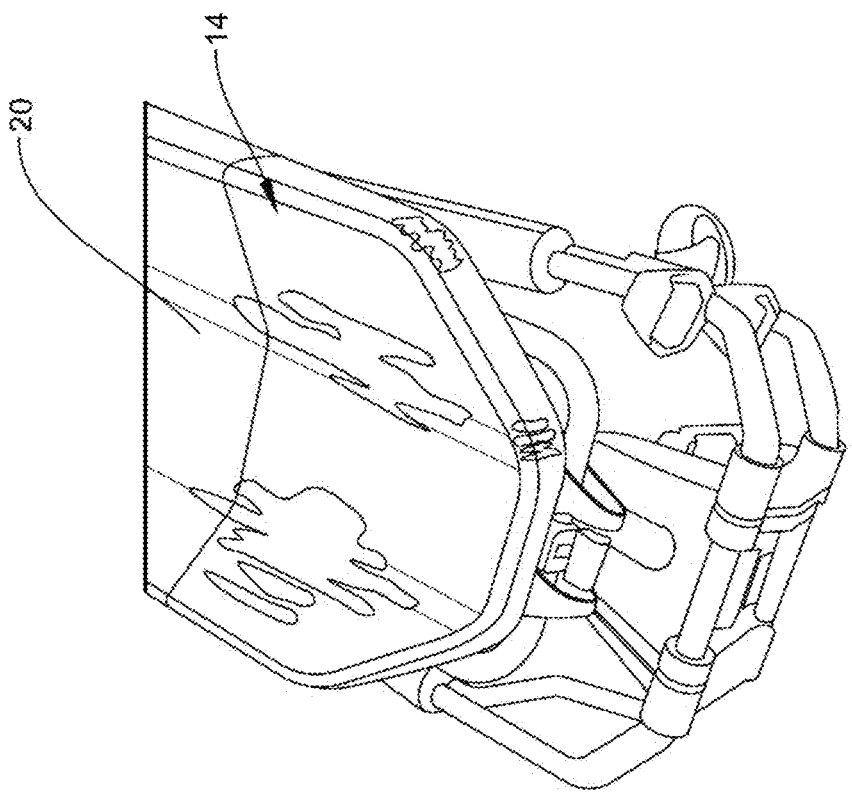
FIG. 38 is a top perspective view of another embodiment of a patient support surface incorporating a wear indicator component.
Figure 38A:
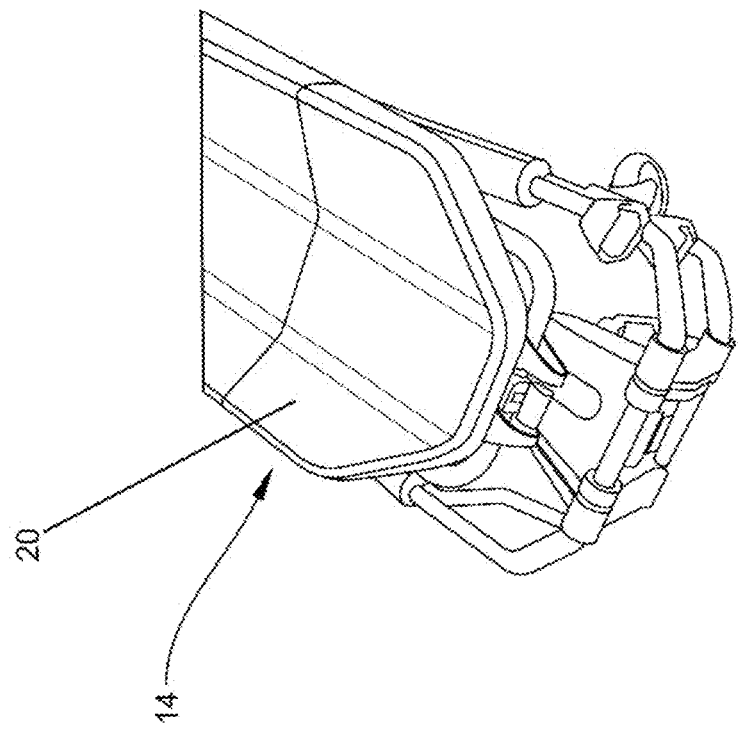
FIG. 38A is another top perspective view of the patient support surface of FIG. 38.

In any of the patient support surfaces described herein, the top cover may incorporate a wear indicator component or be configured to indicate wear. For example, the upper surface of the top cover (e.g. top cover 20) may be formed from a wear material so that when worn, the upper surface will become opaque or translucent (or completely wear off) to allow an underlying or inner colored layer to be visible (such as illustrated in FIG. 38). Once the colored layer is visible, this provides a visual indication that the patient support surface is worn and should be replaced.

For example, any of the top covers of the patient support surfaces, described herein, may be formed from a textile or knitted lamination that has a top colored urethane layer over a clear urethane on top of a different colored woven or knitted layer. As the top colored coating layer is worn away from cleaning and abrasion the colored woven or knitted layer starts showing through while still being protected from fluid ingress by the clear coat urethane layer. Thus, the wearing down of the top colored urethane layer acts as a visual indicator to the user or caregiver that the cover is at the end of its useful life. Suitable materials include DARTEX or DARTEX-LIKE fabric, polyurethane coated fabric, polyolefin. For examples of suitable construction of top cover 20 when configured with a wear indicator or configured to indicate wear, reference is made to copending application Ser. No. 16/935,347, entitled, COVER WITH WEAR DETECTION PROPERTIES, filed Jul. 22, 2020 (P-627A), which is commonly owned by Stryker Corporation of Kalamazoo, Michigan and which is incorporate by reference herein in its entirety.

According to yet another embodiment, any of the patient support surfaces may incorporate a temperature management device or be configured to provide temperature management. For example, the top cover of the patient support surface may incorporate a pneumatic or hydraulic system, which can be used to flow cool or warm fluid through the surface.

For example, a conduit or conduits, such as formed by tubing or channels, may be extended through the cushion sections to allow fluid at controlled temperature to flow through at least portions of, if not throughout, the patient support surface. The conduit or conduits may be coupled to an onboard fluid supply or an external fluid supply, such as the commercially available fluid pump sold under the trademark ALTRIX. In one embodiment, cooled or warm air may be directed into the cushion section, for example between the layers or into a porous layer forming the cushion section, such as 3D fabric.

In another embodiment, the patient support surface may incorporate an electrically powered heating or cooling component, such as a Peltier device, which may be coupled to and powered by the transport apparatus batteries—either directly or via inductive coupling, or a separate battery.

In another embodiment, the patient support surface may incorporate electrical wires, which are coupled to the transport apparatus electrical system or to an onboard battery, which in turn may be inductively couple to the transport apparatus' electrical system, to warm the patient.

In yet another embodiment, the patient support surface may be formed with a phase change material/fabric (PCM), which absorbs heat and releases heat at specific temperatures. For example, it can remain cool to the touch in summer and room temperature in the winter.

In one embodiment, the top cover may be formed from a breathable fabric where airflow of a certain temperature is circulated through the surface to control moisture vapor transmission and patient skin temperature. The system may be powered by an external air pump or fan with a thermal electric device to warm/cool air that plugs into the surface, which is directed through the surface by conduits, such as formed by channels or tubing or material (such as a layer or section of 3D fabric).

In any of the above compartments, electrical connections in electrical communication with the transport apparatus control system and/or onboard power supply (e.g. battery) may be provided and mounted in the compartment for selectively coupling to and powering devices stored and/or simply used to monitor or treat the patient, as well as communicate or record information, such as a handheld computer (e.g. tablet or phone). In addition to providing power, for example, via the onboard power supply of the transport apparatus, the connections can provide data ports as well for coupling to an onboard controller. Optionally, any of the compartments may include an inductive power supply, for example, in a charging station built into the compartment, for recharging a battery or batteries on a hand held device.

In another embodiment, any of the compartments may be configured as or with a chamber, such as a sealed chamber, for treating or cleaning articles or devices, such as gloves, phones, masks, thermometers, etc. For example, the chamber may be configured for cleaning the article or device with UV light, including UVC light, chemicals, such hydrogen peroxide, or heat, for disinfecting the article or device. For example, the compartment may have a sub-compartment with a door to allow access or insertion of the article or device into the chamber of the sub-compartment for treatment in the sub-compartment.

For example, UV lights, such as UV LED lights, may be mounted so that they direct UV light into the chamber (of the sub-compartment or the compartment). For example, the internal surfaces of the chamber's walls may be configured to reflect or transmit the UV light so that the article or device placed therein may be washed with the UV light, optionally from all angles and thereby clean the article or device. Additionally, the chamber walls are formed from materials that do not allow UV light to transmit outwardly from the chamber and instead retain the UV light in the chamber.

Chemicals, such as hydrogen peroxide, may be used to disinfect—and may be stored in a dispenser, such as an aerosol canister, that directs the chemical or chemicals into the chamber and dispenses the chemical or chemicals therefrom based on an input. The input may be a signal or mechanical input from a button or may be a signal from an onboard controller, that is used to control the discharge from the dispenser, which allows a user to select a cleaning option, for example, via a user input device in communication with the onboard controller.

Heat may be applied using heating elements, such as infrared LEDS, which are mounted to direct heat into the chamber. In this case, the chamber may be insulated to allow the chamber to reach the desired temperature relatively quickly and, further, to protect the patient from excessive heat, as well as protect any surrounding devices. The heater may be controlled by the onboard battery supply either via a switch and optional timer, or through the onboard controller.

The chamber may include a platform to support the article or device spaced from the chamber walls to increase the exposed surface areas of the article or device. For example, the platform may be made from a material that is transparent to the UV light so that all sides of the article or device can be treated without repositioning the device.

Figure 39:
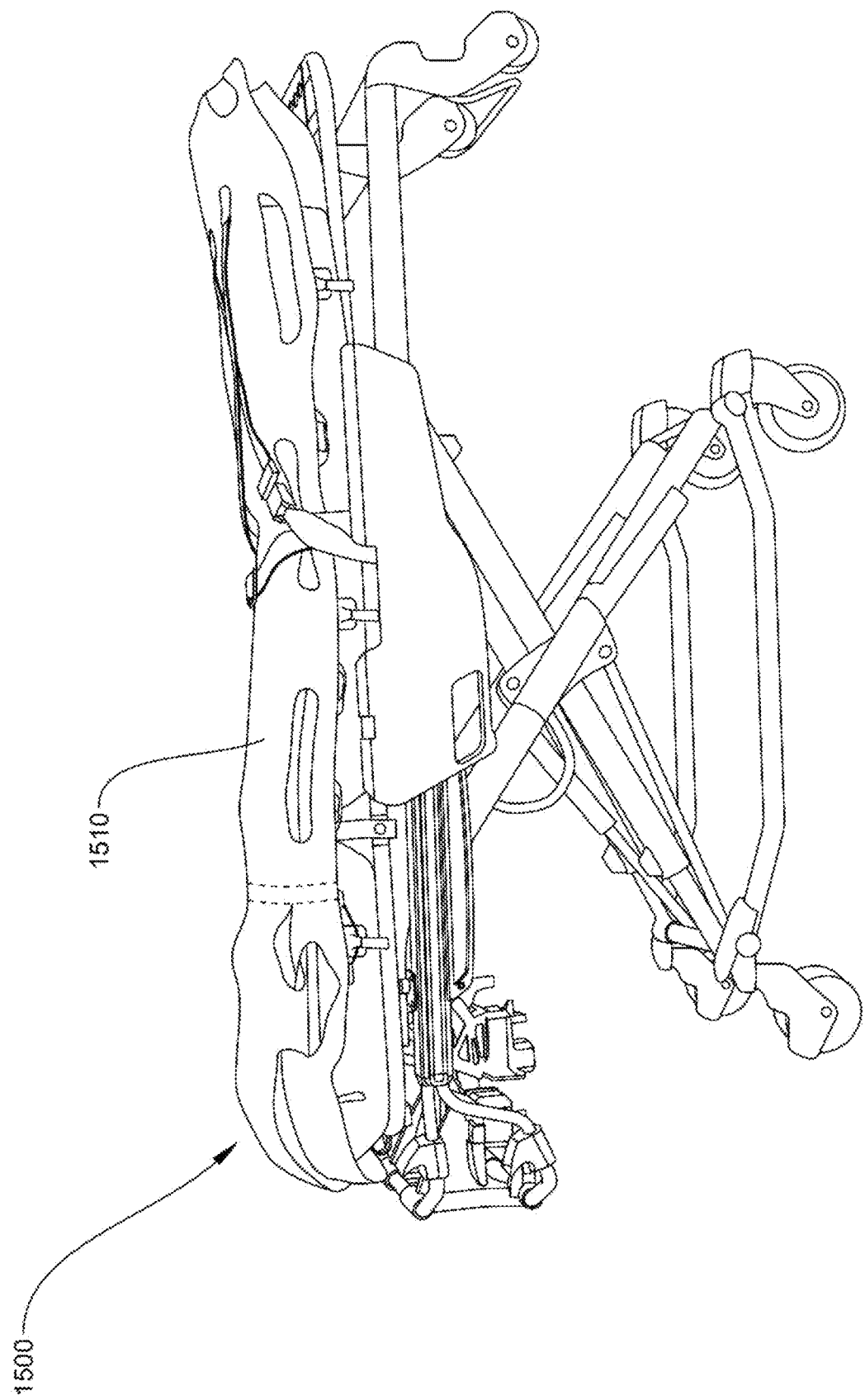
FIG. 39 is a top perspective view of another embodiment of a transport apparatus with a patient support surface system incorporating a cover that can be used to transfer a patient to and from the transport apparatus.

Referring to FIG. 39, the numeral 1500 refers to an auxiliary cover that may be used as part of a patient support surface system, including any of the patient support surface systems and patient support surfaces described above. Auxiliary cover 1500 may be coupled to and secured to the patient support surface using couplers, such as the couplers described above, including couplers 560 (FIG. 27), and then uncoupled and released and, optionally, configured so that it can be used to transport a patient off the patient support surface. Alternately, cover 1500 may retained simply through friction once the patient is supported on the cover, and further when secured by conventional restraints.

Auxiliary cover 1500 may be formed from single layer of fabric or several layers of a fabric or a combination of fabrics assembled together, which are pliable and compliant to provide a comfortable layer for the patient to lay on. The auxiliary cover may be formed from one or more layers that are impermeable, thereby preventing bodily fluid to reach the top of patient support surface to help with the infection prevention aspect of an EMT's or paramedic's work. Lastly, cover 1500 is made from a material that can be washed and/or wiped in place. It could also replace a regular bed sheet as the comfort layer for the patient. Suitable materials for cover 1500 include DARTEX or DATEX like fabric (urethane laminated on to a knit) or any other laminate combination, and incorporate or comprise layers of TPU, PVC, PE, or PP films. Further, cover 1500 may be formed or coated with an antimicrobial, such as MICROBAN, silver, copper or other antimicrobial treatments or suitable materials.

Figure 40:
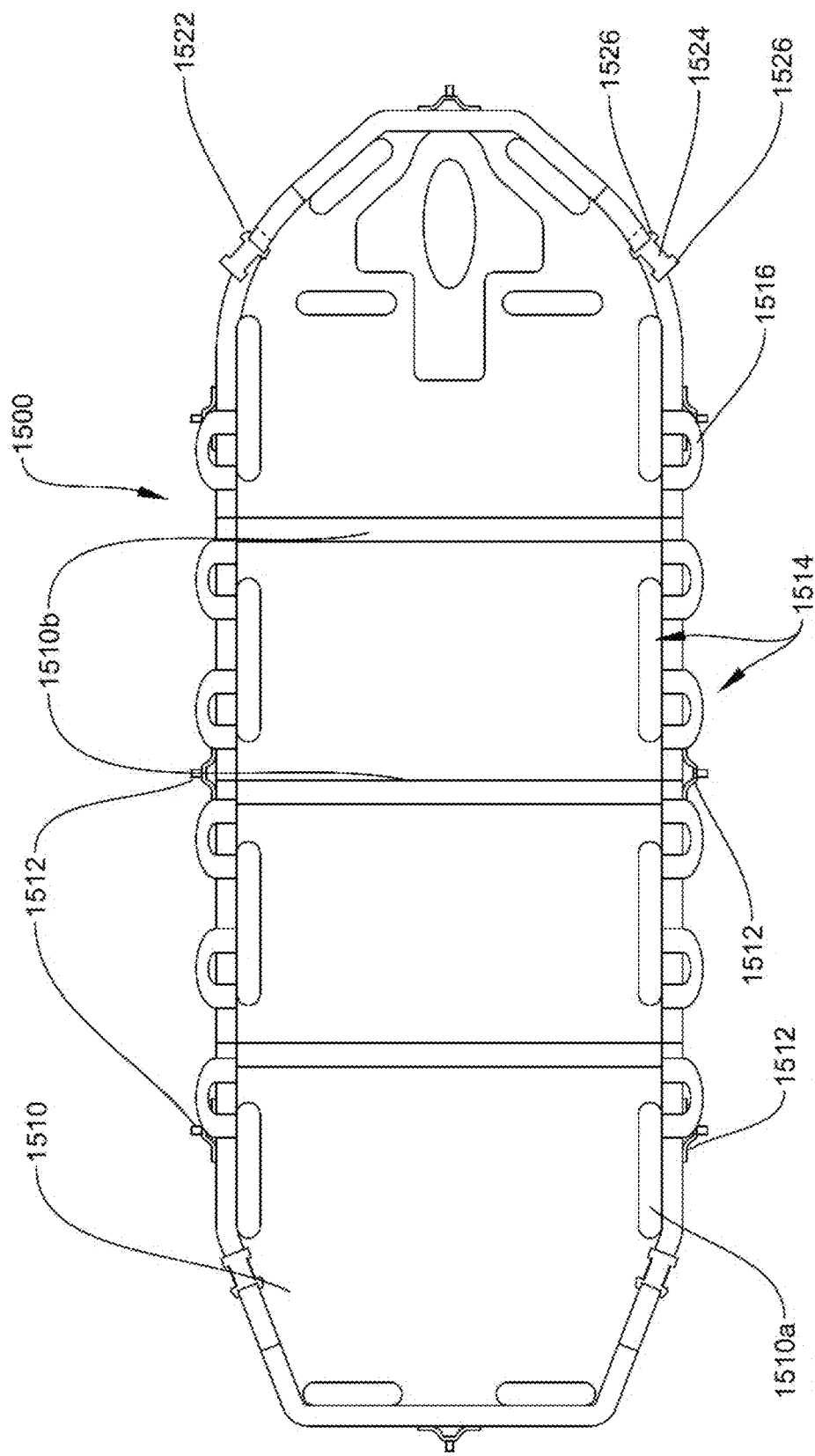
FIG. 40 is a top plan view of one embodiment of the cover.
Figure 42A:
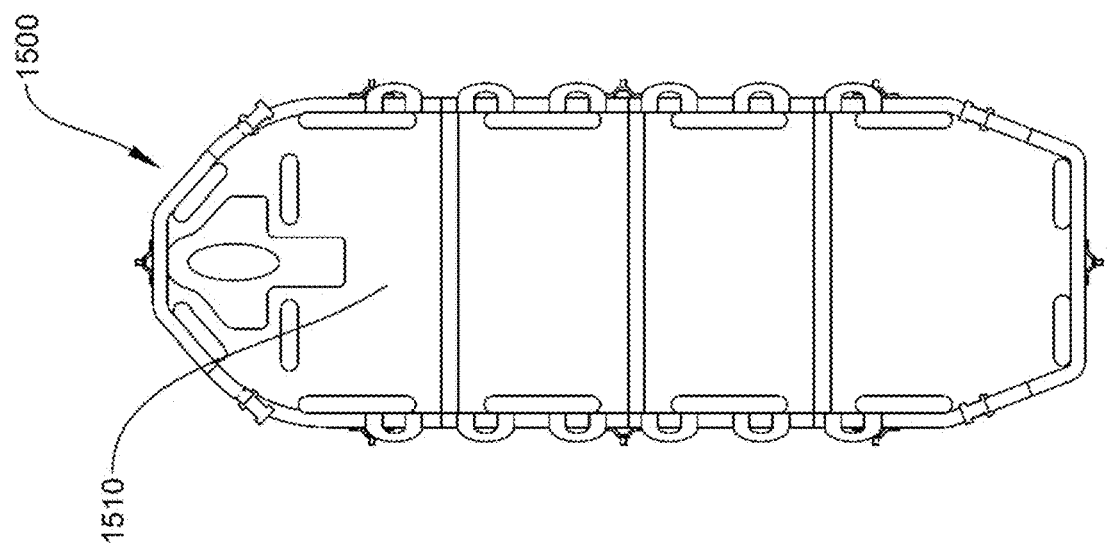
FIG. 42A is a plan view of the cover.
Figure 42:
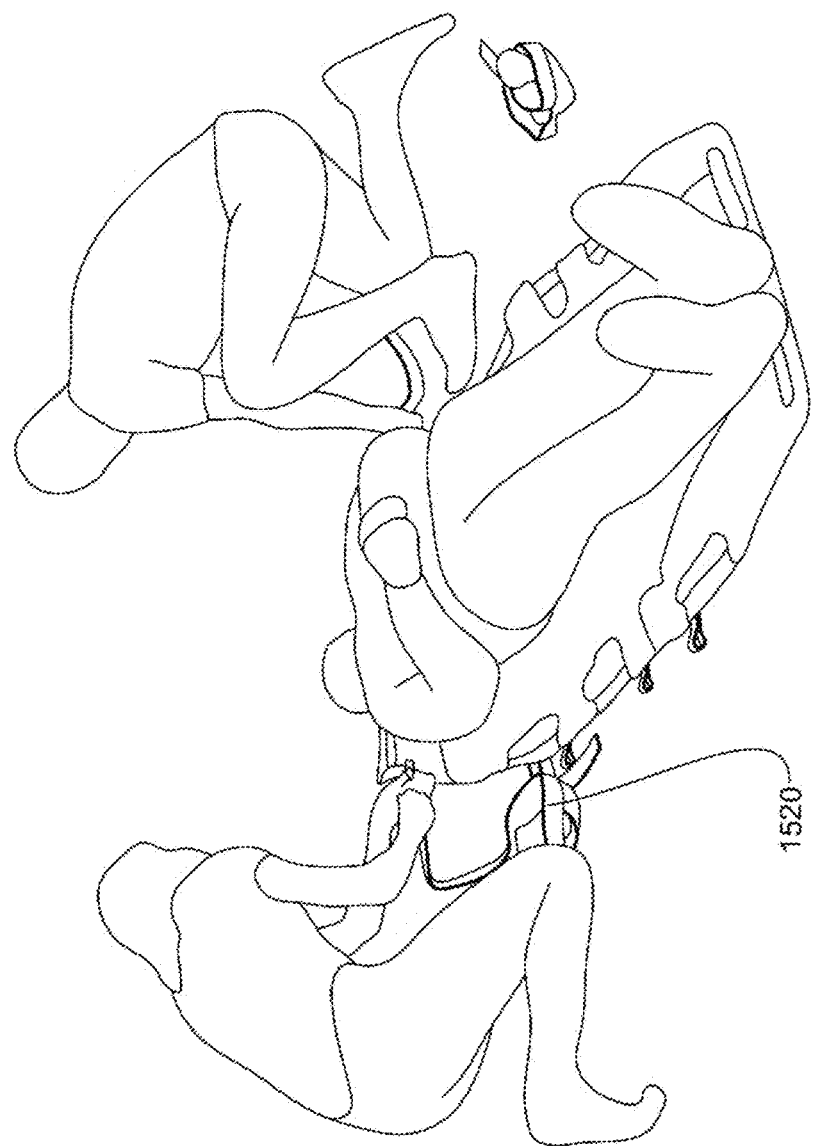
FIG. 42 is an illustration of how the cover can be prepared for transporting the patient once placed under the patient.

In one embodiment, cover 1500 is configured to support the weight of a patient, such as a weight in a range of about 25 lbs. to 700 lbs., about 25 lbs. to 400 lbs., or about 25 lbs. to 350 lbs. Referring to FIGS. 40 and 41, auxiliary cover 1500 includes a panel 1510 of material (or materials) with a plurality of loops 1512 spaced around its perimeter for engagement with the couplers, noted above, such as couplers 560, which are mounted to patient support surface 514. Alternately or in addition, cover 1500 may include male or female couplers for receipt in or receipt of female or male couplers mounted to the patient support surface. Suitable male/female couplers include clips, buckles, snaps, hooks, or the like.

Figure 43:
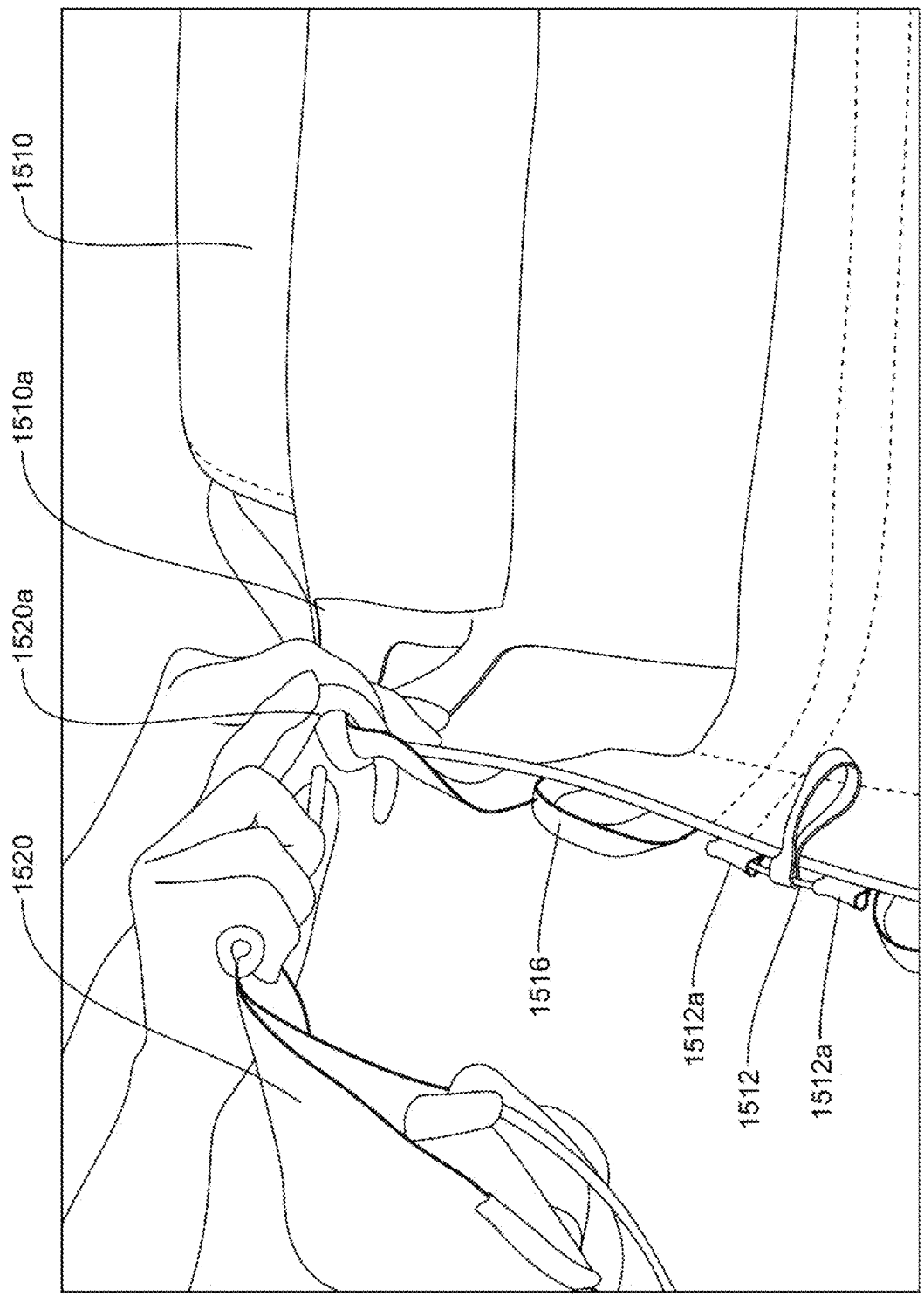
FIG. 43 is partial enlarged view illustrating how a strap can be coupled to the cover to facilitate transporting the patient.

For example, loops 1512 may comprise elastic cords with pull tabs to allow a caregiver to secure cover 1500 to the respective couplers and, further, apply a biasing force to the cover 1500 to keep the cover substantially flat (when unloaded) when supported at least on the patient support surfaces described herein. The loops 1512 may be formed from a closed loop of elastic or a segment of elastic mounted at each of its ends to the panel, for example in small retention loops formed on or in or attached to the panel (see e.g. retention loops 1512*a* in FIG. 43). While reference herein is generally made to patient support surface 514, it should be understood that cover 1500 may be used with any of the patient support surfaces described herein and, further, other patient support surfaces, including conventional patient support surfaces.

In order to facilitate lifting of a patient, auxiliary cover 1500 may include one or more hand-engageable structures formed or mounted to panel 1510. Referring again to FIGS. 40 and 41, the hand-engageable structures may include hand holds 1514 formed by openings 1510*a* in the panel 1510 spaced around the perimeter of panel 1510 and/or straps 1516 that are secured to the panel around its perimeter, which form loops. The openings may be reinforced with ribs (formed in or inserted into the panel) or webbing sewn on the panel at, for example, their outer perimeters or at the outer perimeter of the panel adjacent the openings. Further, the webbing may have loops formed therein for use as hand holds or attachment points for straps 1520, as noted below. The shape of the panel may be generally oval or rectangular, and optionally provided with tapered ends, including rounded tapered ends, at the foot and head ends, where less material may be required. Further the tapered ends may facilitate maintaining the patient flat when being carried, as noted below.

For overall added reinforcement, panel 1510 may include strips of reinforcement 1510*b*, such a ribs or transverse webbing or other strips, extending across its width, which may be formed in or on (such as during molding of panel 1510) or may be post attached by glue, RF welds, or stitches or a combination of one or more. Optionally, this reinforcement may be integrally formed or connected with (e.g. by stitching or gluing or welding) the reinforcement provided around openings 1510*a* and/or along the perimeter edge of panel 1510.

In one embodiment, suitable handholds may be formed from tubular knit coated webbing with tubing in it, which is then sewn into the panel. These may be in lieu of or in addition to the openings noted above. Further, they may be mounted so that they can be located underneath the cover and deployable therefrom, from a non-deployed position to a deployed position.

In any of the above, the hand engageable structures may have a visual indication or indications, such as a color code or label, to indicate where to lift the patient. For example, when straps are used with cover 1500, the visual indication may instruct a caregiver where to attach the straps. These indications may vary for different size patients, different uses (e.g. when needing to pull or drag the patient away), and, as noted below, the number of medics.

For example, panel 1510 may include twelve openings 1510*a* along its sides and ends, allowing three medics or more to lift a patient from the floor onto the transport apparatus. For example, the visual indication may instruct where caregivers should grab (or attach straps) based on the number of medics and/or based on the use of the auxiliary cover. For example, the cover 1500 may be used to lift or pull a patient along a surface. In some situations there may be only two medics on the scene, so cover 1500 may include straps 1520 (e.g. FIG. 43) with conventional releasable buckles 1520*a*, such as carabiner buckles, which can be coupled to the panel to ease lifting by the two medics—though it should be understood depending on the construction of the straps, the straps can be used by more than two medics. At least one end of the straps or both ends may be permanently affixed to the panel. Alternately, as noted, the straps 1520 may be removable and then stowed in the various storage compartments described above or in a storage compartment provided in the auxiliary cover, as described more fully below.

For example, when removably attached, the straps 1520 may be coupled to the panel 1510 at the hand-engageable structures, such as at openings 1510*a* (FIG. 43), using the buckles noted above. Alternately or in addition, panel 1510 may provide dedicated structures for engagement by the straps or engagement by the auxiliary straps noted below. For example, referring to FIG. 40, for example, rigid structures 1522, such as channel-shaped members, may be mounted to the outer perimeter edge of panel 1510, such as by gluing, stitching, welding, molding, or fastening using rivets or the like. For example, rigid structures 1522 may include a female buckle half or tubular section 1524, rectangular or round or other shape, straddled by a pair of projecting lips or flanges 1526, with the female buckle half or tubular section engageable by a male buckle half or clamp mounted to the ends of the straps 1520. Suitable straps may be formed from conventional webbing, such as biothane, nylon webbing, or with a weave or knit formed from various yarn size. Alternately, the straps may be formed from rope.

Figure 47:
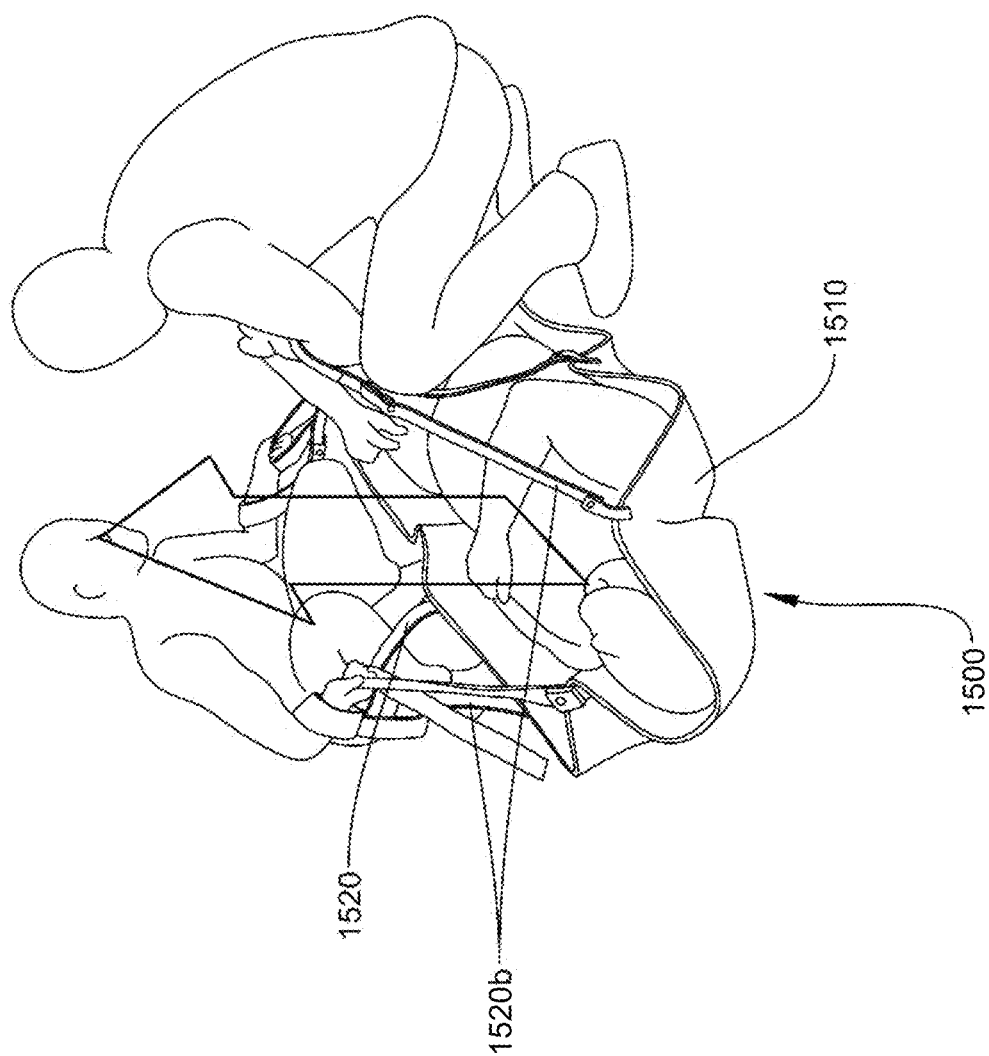
FIG. 47 is an illustration of how the cover can be used with straps to transport a patient.
Figure 48A:
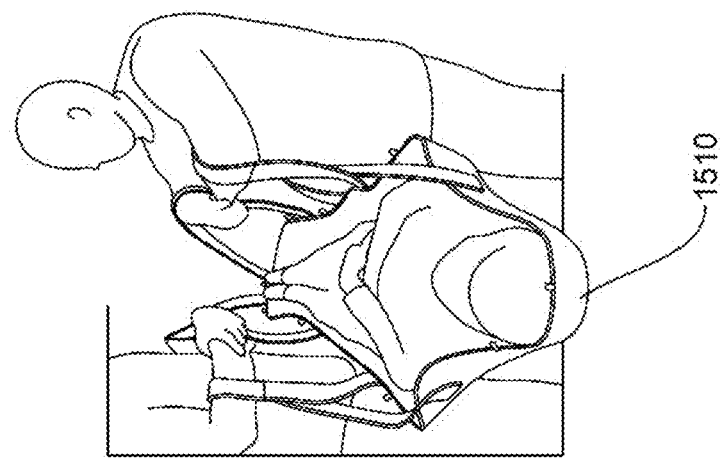
FIG. 48A is a similar illustration to FIG. 48 from a different angle.
Figure 48:
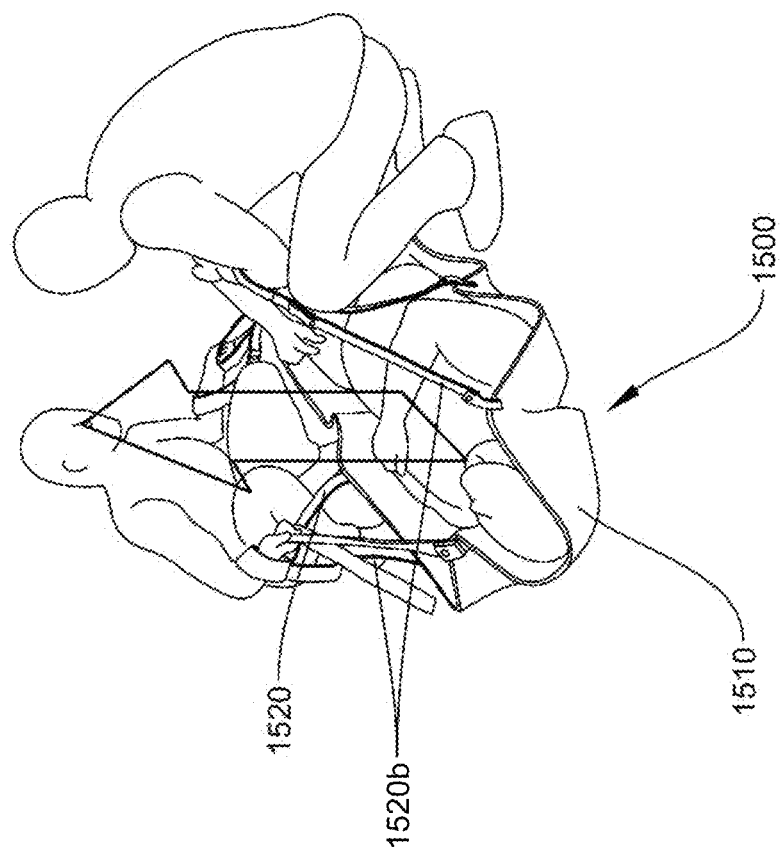
FIG. 48 is a similar illustration to FIG. 47 from a different angle.
Figure 49:
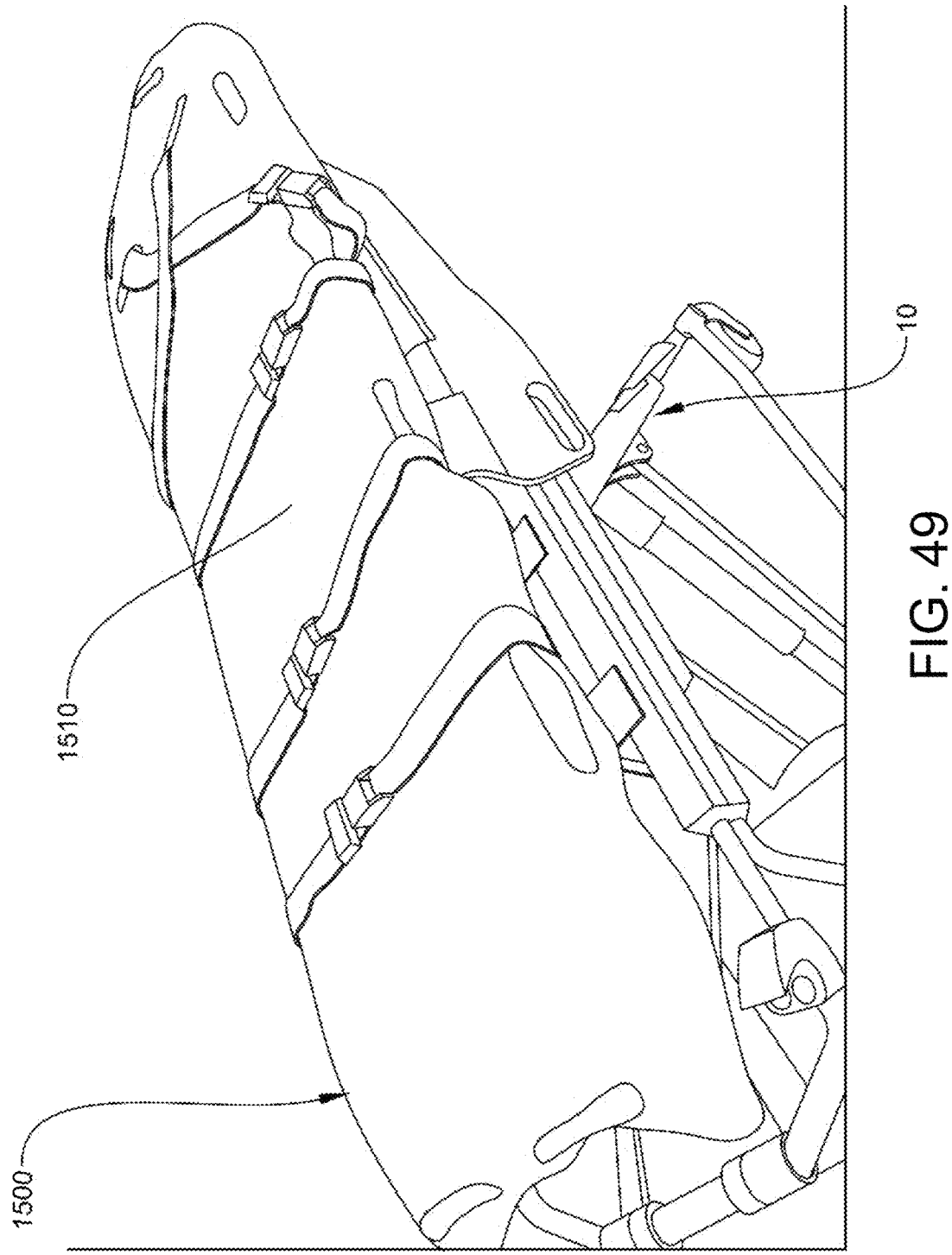
FIG. 49 is a top perspective view of another embodiment of a cover that can be used to transfer a patient to and from the transport apparatus.

In one embodiment, the straps 1520 may include extension straps 1520b (FIGS. 47 and 48) that can be used to engage the panel, for example, closer to the head or feet of the patient, for example at rigid structures 1522. Thus, the straps may have an inverted Y-shaped configuration when attached to panel 1510. The lengths of the extension straps may vary and are optionally selected or adjusted so that a patient can be carried in a generally flat or planar arrangement.

Also, to facilitate lifting, especially of adult patients, straps 1520 may be adjustable and, further, have various loops and/or buckles to adjust their length. In this manner, a medic can adjust the lengths of the straps to suit their height, loop the straps over their arms, and/or buckle the straps to a vest or belt they are wearing.

Figure 44:
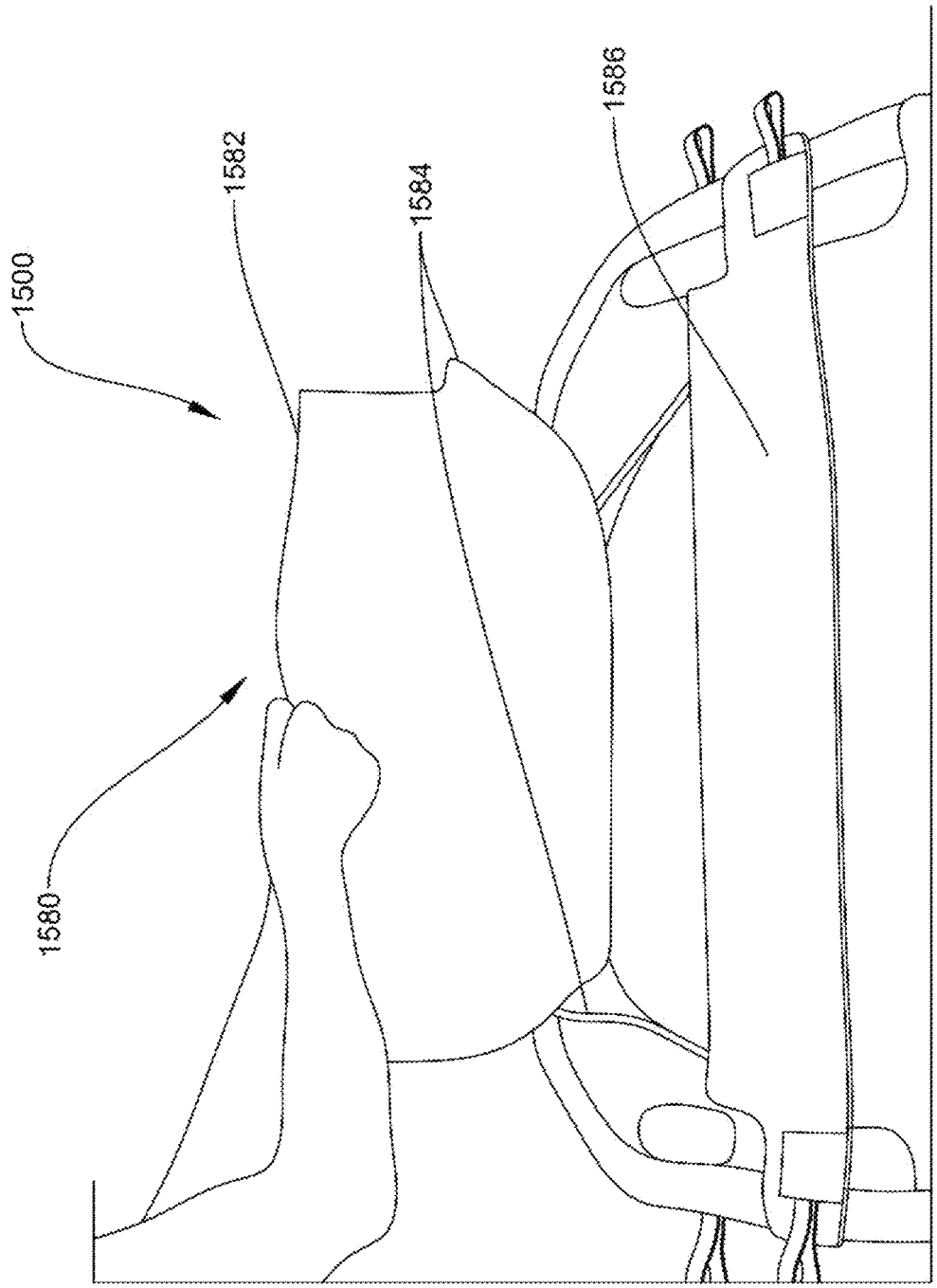
FIG. 44 is a partial enlarged view of the foot end of the cover incorporating a pocket for storage and/or for a patient's feet to prevent migration of the patient down the cover.
Figure 45:
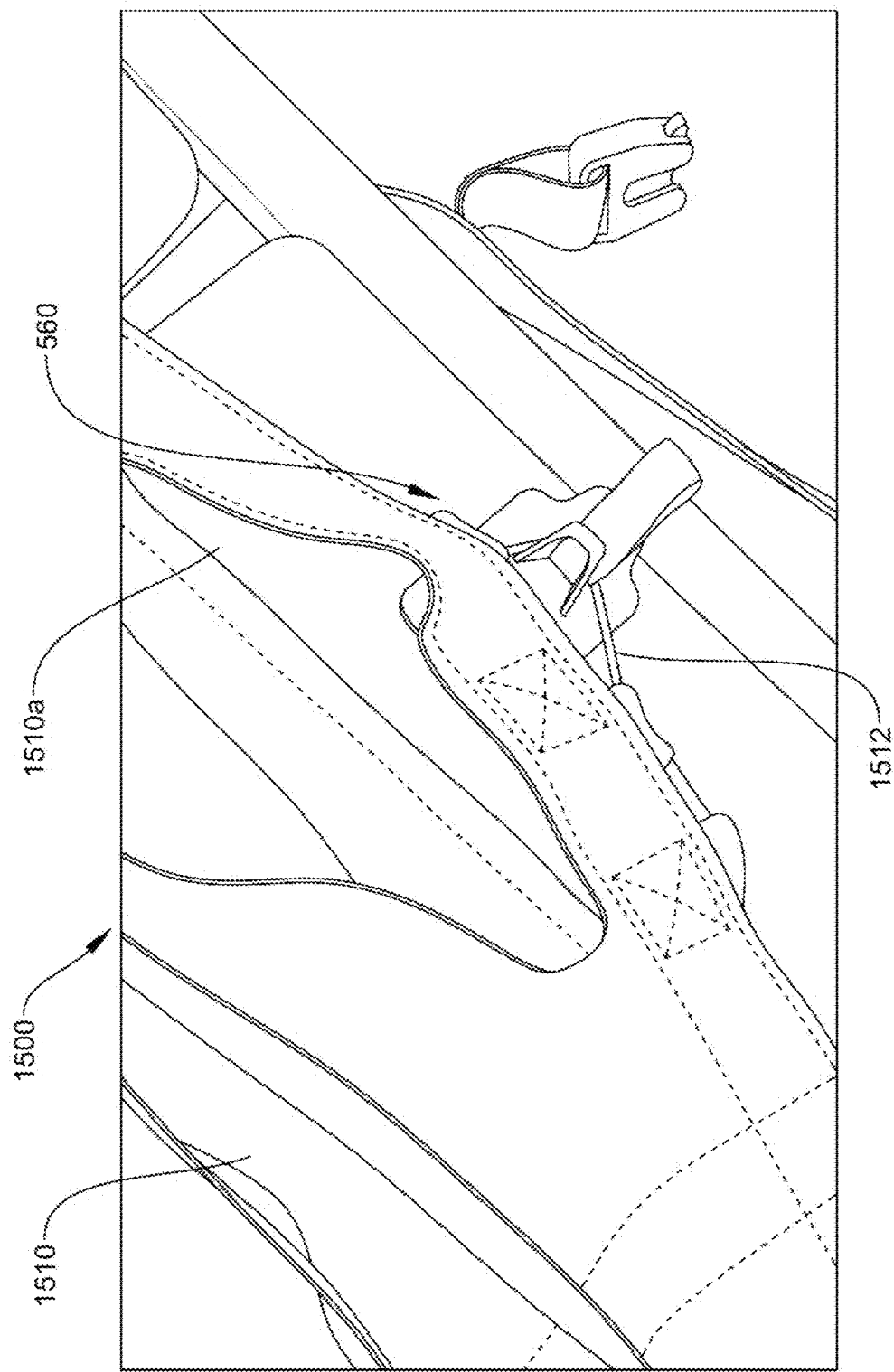
FIG. 45 is a partial enlarged side view of the cover showing how the cover is coupled to the deck frame of the transport apparatus.

In one embodiment, as noted, cover 1500 may incorporate a compartment for storage or to facilitate handling of the patient. Referring to FIG. 44, cover 1500 may include a compartment 1580 at its foot end. For example, compartment 1580 may be formed from a fabric panel or panels of material, for example, the same material forming cover 1500, to form a soft and collapsible compartment, such as a pocket. In the illustrated embodiment, compartment 1580 has a rectangular footprint and is secured on three sides to panel 1510 with its fourth side forming an opening, which allows access therein for the patient's feet or for storage. The fabric panels may be welded, glued, and/or stitched together and similarly welded, glued, and/or stitched to panel 1510.

The compartment may be formed from a top panel 1582, a base panel (formed from panel 1510 or a separate base panel) that is joined with at least two side panels 1584 (for example, triangular or trapezoidal shape panel), and an optional end panel. The panels, as noted, may be formed from the same material as panel 1510, and can, therefore, fold so that the compartment is collapsible, for example, by folding it about its side and end panels (e.g. the side and end panels may be formed as bellows). When formed from a separate base panel, compartment 1580 may be mounted to panel 1510 by releasable fasteners, such as snaps, zippers, magnets, or the like, so that it is removable.

Compartment 1580 may also include an additional panel (of material similar to the cover 1500) that forms a flap 1586 that can be secured to the base of the compartment 1580 (e.g. panel 1510 or the separate base panel) and can close the opening so that the compartment 1580 can be used for storage. For example, flap 1586 may be secured in its closed position by one or more buckles, or a strap or straps with one or more buckles. However, it should be understood the flap may be eliminated, and instead the pocket may be closed by couplers mounted to the top panel edge that engage similar couplers mounted to the cover panel 1510 or by the use of other straps or elastic cords.

Alternately, or in addition, as noted, the pocket may be sized to extend over a patient's feet so that the patient's feet can be inserted into the pocket when open to help prevent migration of the patient toward the foot end of the cover 1500 and/or simply to cover the feet of the patient, for example when their feet are dirty.

Figure 50:
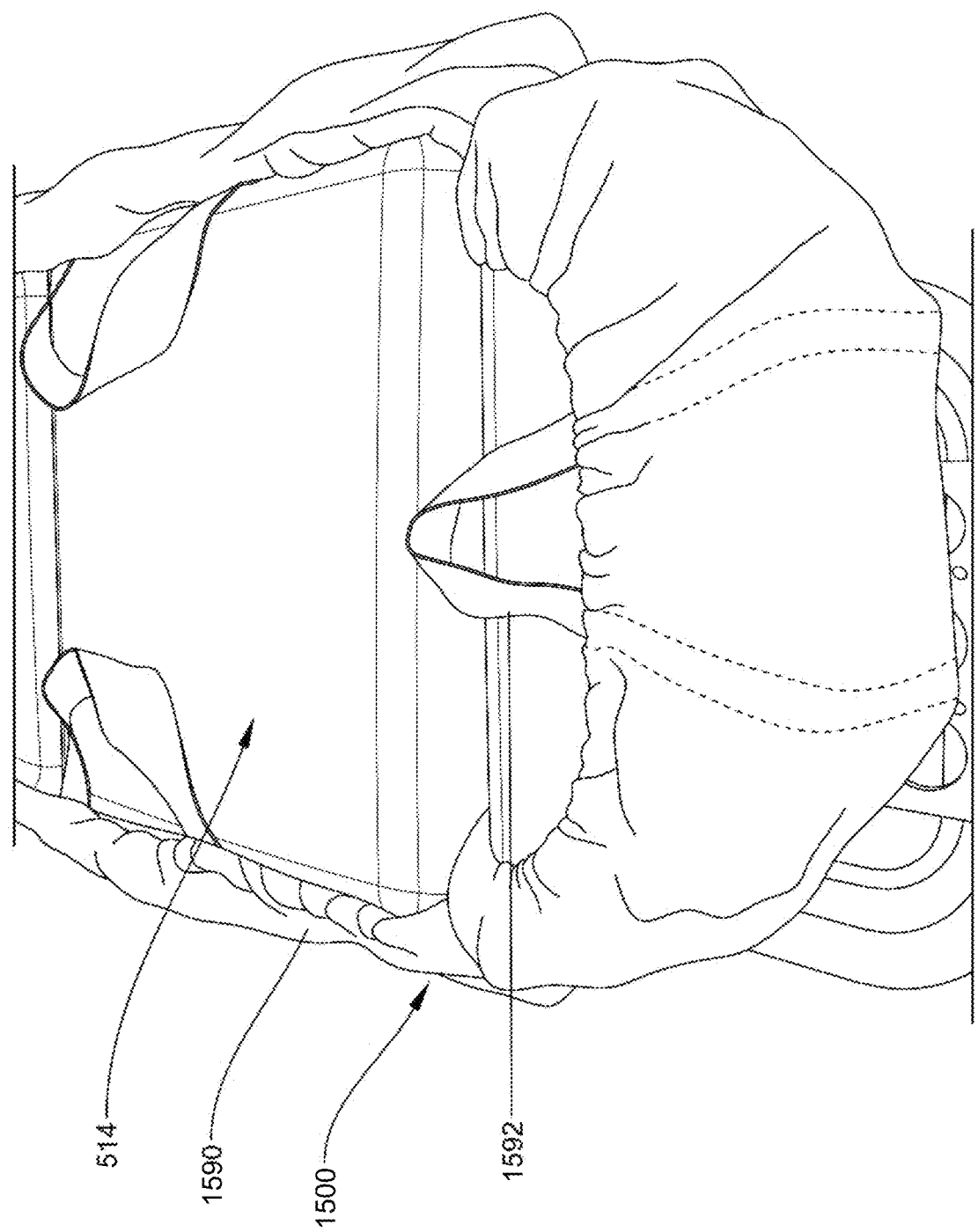
FIG. 50 is a bottom perspective view of another embodiment of a cover that can be placed over a patient support surface and cinched to hold it in place.

In one embodiment, in addition to, or in lieu of, using couplers 560, auxiliary cover 1500 may be releasably secured to the patient support surface using an extension or extensions, such as formed by a portion or portions of the panel itself or another sheet of material secured to the panel. The extension or extensions extend under the patient support surface and are tightened or cinched by, for example, straps or a cord, including an elastic cord, including a cord with a cord lock (to adjust the length of the cord), that extends through the extension or extensions. For example, referring to FIG. 50, panel 1510 may include a skirt 1590 formed from a separate sheet of material, such as nylon, that is secured to the panel 1510, for example, around the panel's outer perimeter by stitching, lacing, gluing, or FR welding. The skirt may be removably attached, for example, by snaps, lacing, a zipper or zippers, or the like.

Referring again to FIG. 50, skirt 1590 may include handles 1592 to assist in handling of the skirt and also to facilitate raising the skirt up and over the patient. By flipping the skirt over onto the patient, it may be sized to cover at least the feet of the patient and may be used to cover at least part of the patient or the patient's entire torso and legs. Therefore, the skirt may also be used to help retain the patient on cover 1500.

In any of the auxiliary covers or top covers of the patient support surface, the covers may be washable, including machine washable, and/or simply be wiped down in place. Therefore, it may be desirable to form the auxiliary covers and/or the top covers from material that resists multiple-wipe down cycles or machine washing without degradation, including material that resists degradation from a wide variety of cleaners (bleach, AHP, Phenolic, alcohol). Suitable materials include DARTEX or DARTEX-like fabric (urethane laminated to a knit) or any other laminate combination, including materials formed with TPU, PVC, PE or PP layers or film.

In other embodiments, the compartment or another compartment, such as a pocket or bag, may be attached to the side of cover 1500, which can hang on the side of the transport apparatus, and can be used to carry equipment, such as straps (e.g. restraints, patient lifts), waste, or the like.

In some embodiments, auxiliary cover 1500 may be formed with a sleeve with an opening in the side (e.g. at its perimeter) to allow an accessory, such as a support structure, to be inserted into the cover beneath the upper surface, such as backboard and/or the EMS COVID SHIELD device.

Figure 51:
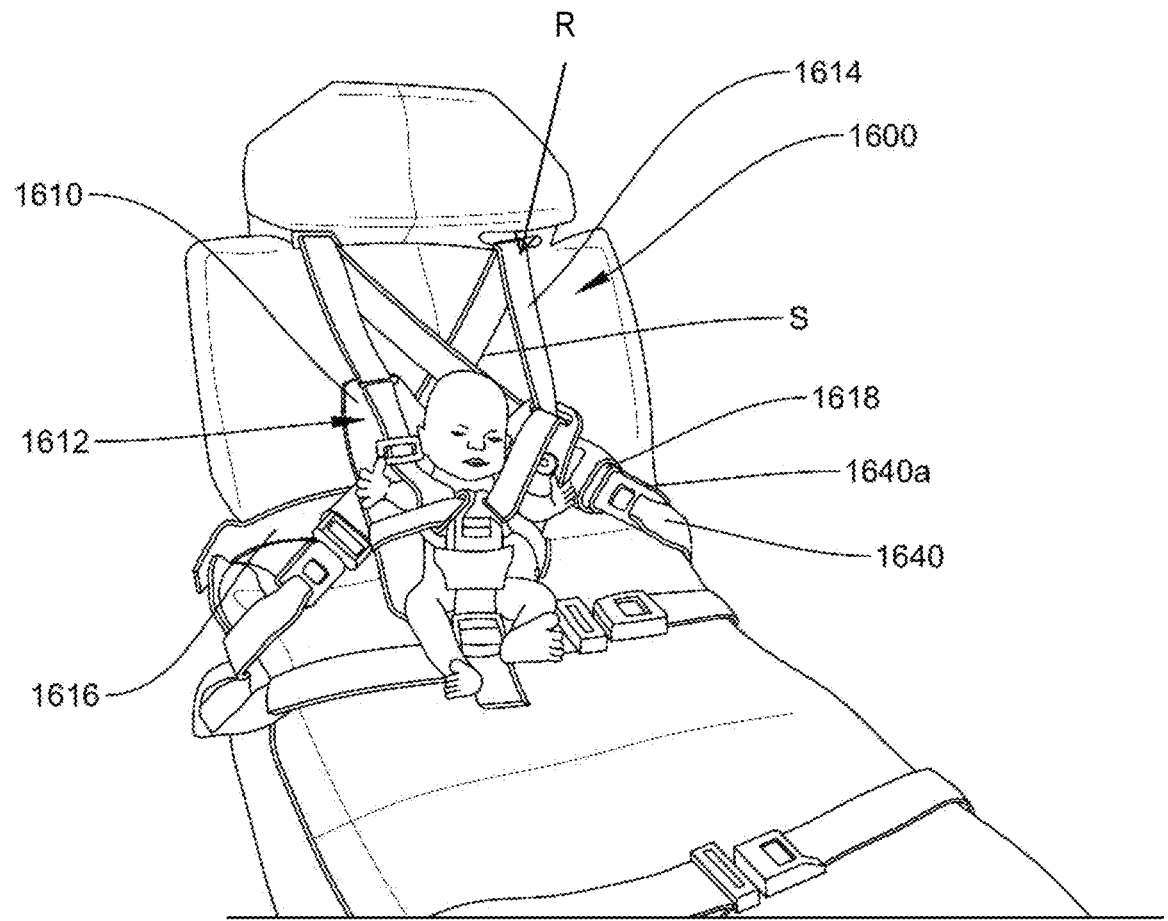
FIG. 51 is a perspective view of another embodiment of a transport apparatus incorporating a patient support surface system with a pediatric restraint assembly for a pediatric patient.
Figure 52B:
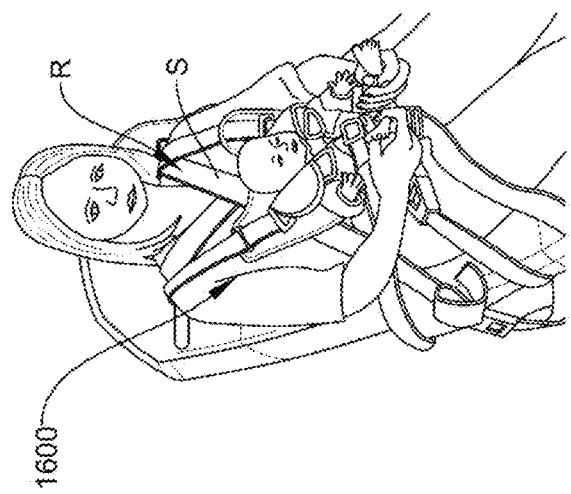
FIG. 52B illustrates the ability of the pediatric restraint assembly to be reconfigured to be mounted over an adult patient supported on the same transport apparatus.
Figure 52A:
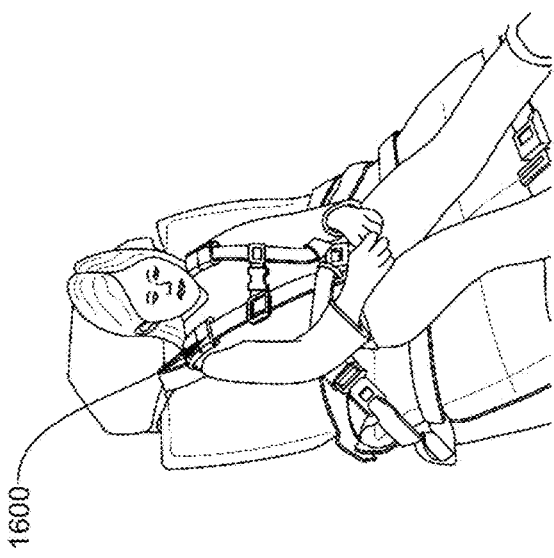
FIG. 52A illustrates the ability of the pediatric restraint assembly to be reconfigured to pediatric patients of different sizes.
Figure 52:
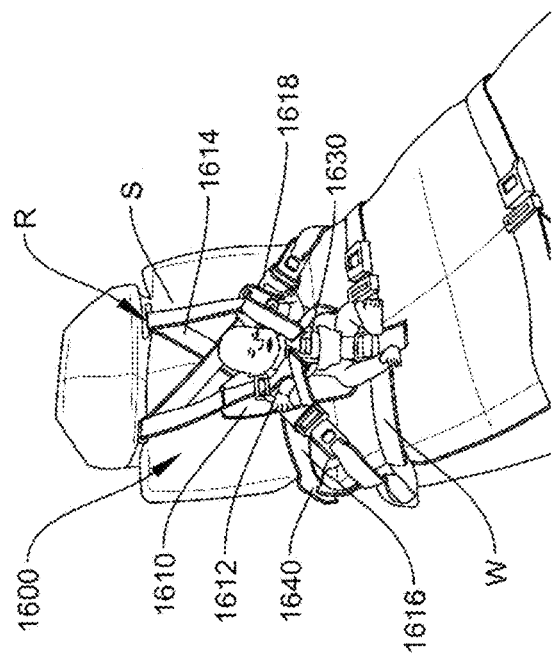
FIG. 52 illustrates the ability of the pediatric restraint assembly to be reconfigured to be mounted over an adult restraint.
Figure 53:
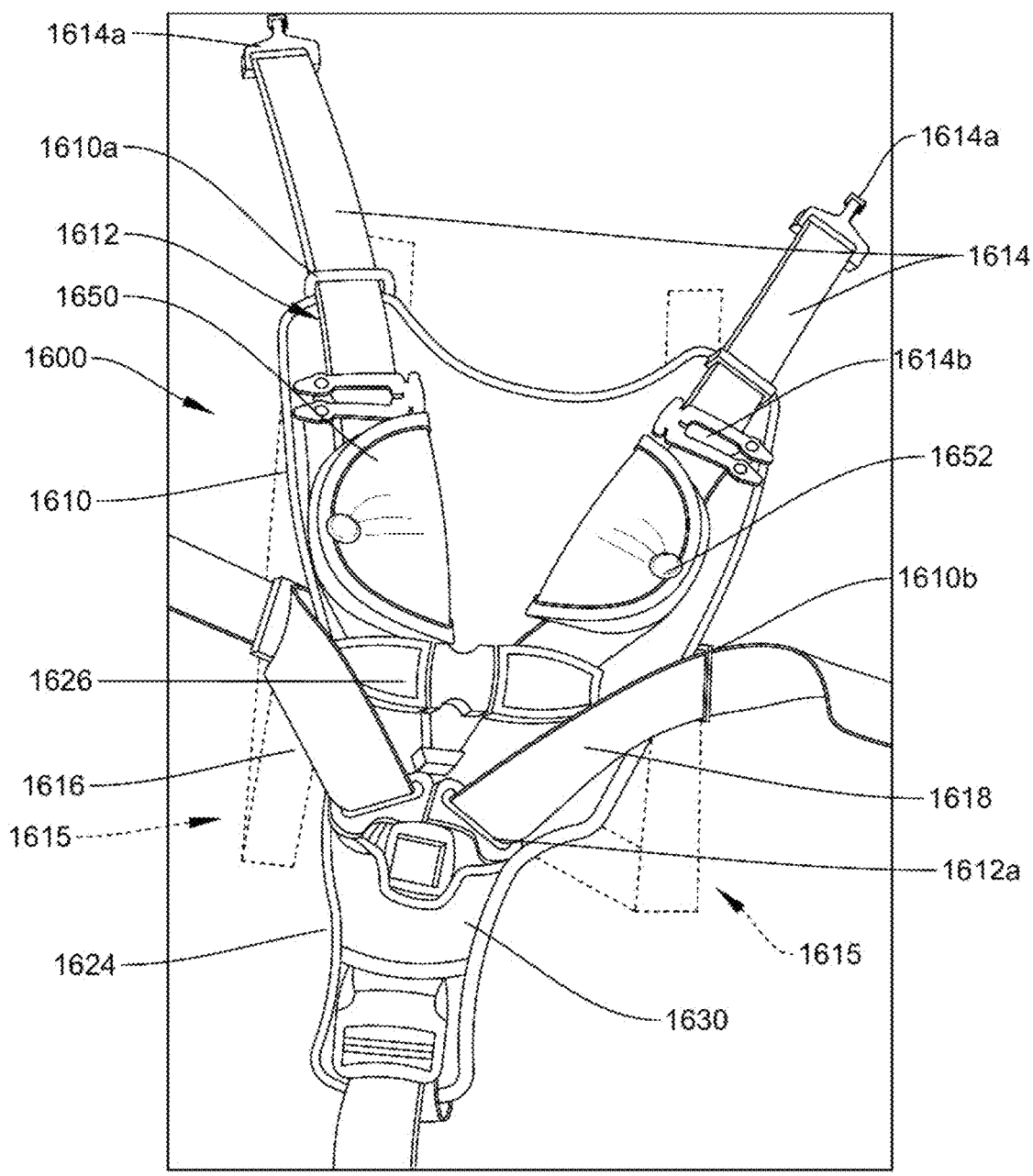
FIG. 53 is a plan view of the pediatric restraint assembly.

Referring to FIGS. 51-53, the numeral 1600 generally refers to a pediatric restraint assembly for use in conjunction with an existing adult restraint R, for example, an adult EMS cot restraint (such as RUGGED restraint available from Stryker), which is configured for restraining pediatric patients, but may be used for small adults. Although illustrated in the context of an emergency cot, it should be understood that pediatric restraint assembly 1600 may be used with other transport apparatuses, including in vehicles, such as cars, airplanes, helicopters, or trains, for, example.

As described below, pediatric restraint assembly 1600 may form a five point harness that is configured so that it can accommodate infant patients and child patients, as well and small adult patients. For example, pediatric restraint assembly 1600 may accommodate patients that weigh in a range of about 4 to 99 lbs. Further, although mounted to an existing adult restraint or harness (in some embodiments), pediatric restraint assembly 1600 may be configured so that it can be used while the adult restraint or harness R is being used as well, as shown in FIG. 52. Alternately, instead of mounting to an adult restraint, pediatric restraint assembly 1600 may be mounted to the transport apparatus via strap extensions that are secured to the transport apparatus in a similar manner as a conventional adult restraint but without the adult restraint buckle, and in some cases without any adjustment buckles given that the adjustment may be made with the pediatric restraint assembly 1600.

Referring again to FIG. 51, pediatric restraint assembly 1600 includes a panel 1610 and a plurality of straps 1612 coupled thereto for securing the panel 1610 to the transport apparatus, in some cases directly and in others, as noted, via the adult restraint R. As will be more fully describe below, pediatric restraint assembly 1600 may be secured to the patient support at five anchor points—two shoulder anchor points, two waist anchor points, and one leg anchor point.

In the illustrated embodiment, each strap 1612 is coupled to panel 1610 via shoulder loops 1610*a* provided at the shoulder end of panel 1610 and waist loops 1610*b* provided at waist height locations on panel 1610 to form shoulder strap portions 1614 and waist strap portions 1616, 1618. A coupler, such as a buckle 1612*a*, is slidably mounted along each strap 1612 between the shoulder and waist loops to releasaby engage a three-point buckle described below. Each of the straps 1612 may be adjustable using various forms of buckles or clips to accommodate different sized patients and, further, to keep the hips of the patient aligned with fowler/seat joint (joint between sections 16*a* and 16*b* of deck 16).

Figure 59:
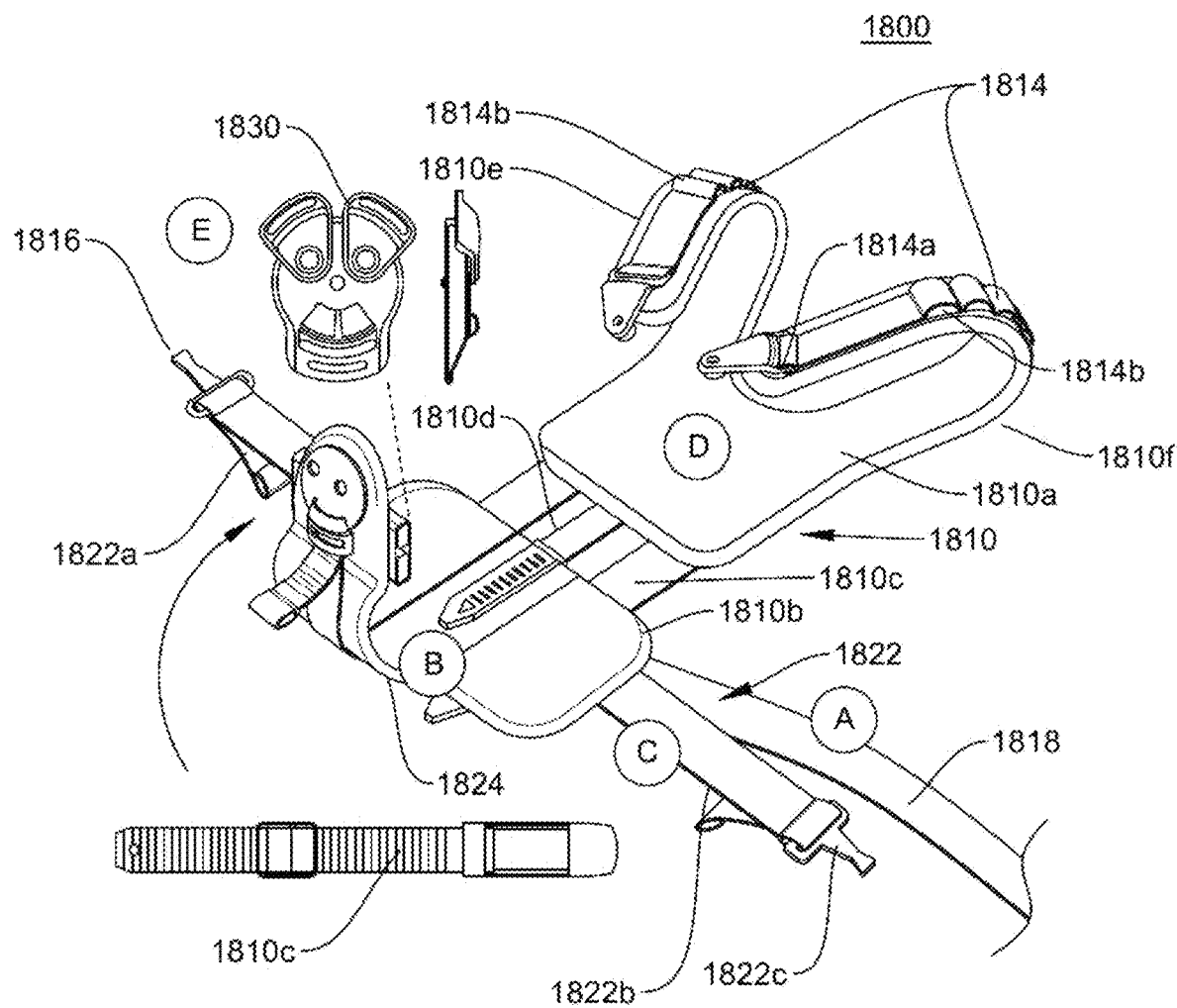
FIG. 59 is a perspective view of yet another embodiment of the pediatric restraint assembly.

In the illustrated embodiment, panel 1610 is shaped to form a leg portion 1624 that extends between the patient's legs and supports a three-point buckle restraint 1630 mounted thereto for receipt of buckles 1612*a*. Buckle restraint 1630 may be secured to leg portions 1624 by a strap and buckle to allow adjustment of buckle restraint 1630 relative to panel 1610. As will be more fully described below, the leg portion of panel 1610 may be separate from the panel and coupled instead just to the shoulder straps (such as shown in FIG. 59) so that it provides a greater range of adjustment. Alternately, the panel may be adjustable in length, as will be described in reference to FIG. 59.

As noted above pediatric restraint assembly 1600 couples to an adult restraint R, already attached to the transport apparatus. In the illustrated embodiment, as noted, straps 1612 form shoulder strap portions 1614 with each releasably coupling on one end to the shoulder straps S (FIG. 51) of the adult restraint R at shoulder anchor points provided on the adult restraint shoulder straps S via, for example, buckles 1614*a*. Thus, the adult restraint R may provide the shoulder anchor points for the pediatric restraint assembly.

The type of anchor points and buckles though may vary. Further, the anchor points may each form a single anchor point or multiple anchor points, or may be adjustable. For example, one or more loops may be added to the shoulder straps S, with the ends of shoulder strap portions 1614 including a hook, such as a carabiner or G hook, to engage the loops. For example, a strip of multiple loops may be provided on each adult restraint shoulder strap S to provide multiple different anchor points along each adult restraint shoulder strap S.

In another embodiment, a COBRA buckle or other type of buckle may be used to releasably couple shoulder strap portions 1614 to the anchor points, for example, where the female or male part is attached to each adult restraint shoulder strap S, and the other male or female part is attached to the end of shoulder strap portions 1614.

In yet another embodiment, each shoulder strap S may each have a coupler mounted thereto by a strap (to the strap S) that allows the free end of each shoulder strap portion 1614 to be fed into the coupler and secured therein. Suitable couplers include cam buckles.

In an alternate embodiment, VELCRO strips may be used to mount an anchor point to the adult restraint straps S to provide repositionable anchor points.

In other embodiments, friction based mechanisms may be used. For example, D-ring fasteners may be mounted to each adult restraint shoulder strap S, which are then engaged by a releasable clasp mounted to each shoulder strap portions 1614. Other mechanisms that may be used to releasably couple shoulder strap portions 1614 to straps S include fasteners that use magnets to secure closure cams or catches or fasteners that use magnets and frictional material, such as FIDLOCK magnetic mechanisms, available from FIDLOCK GMBH.

In yet other embodiments, a slot and key/button fastener arrangement may be used, where each adult restraint shoulder strap S includes a strip of metal or polymer (e.g. plastic) with a plurality of holes with keys (or the strap S itself may have a plurality of through holes). Shoulder strap portions 1614 may each include a button or hook (metal or polymer (e.g. plastic)) to engage a respective hole, and optional key, thereby providing another releasable fastener and, further, one that includes multiple positions to provide adjustment.

In one embodiment, each of the above anchor points may be provided on the adult restraint shoulder straps S around their shoulder height and further, optionally, between the head section and the back section of the patient support surface (such as in any of the above described patient support surfaces) so that they do not interfere with the use of the adult restraint R. In this configuration, an adult can be restrained in restraint R while the pediatric restraint assembly is used, such as shown in FIG. 52.

Figure 51A:
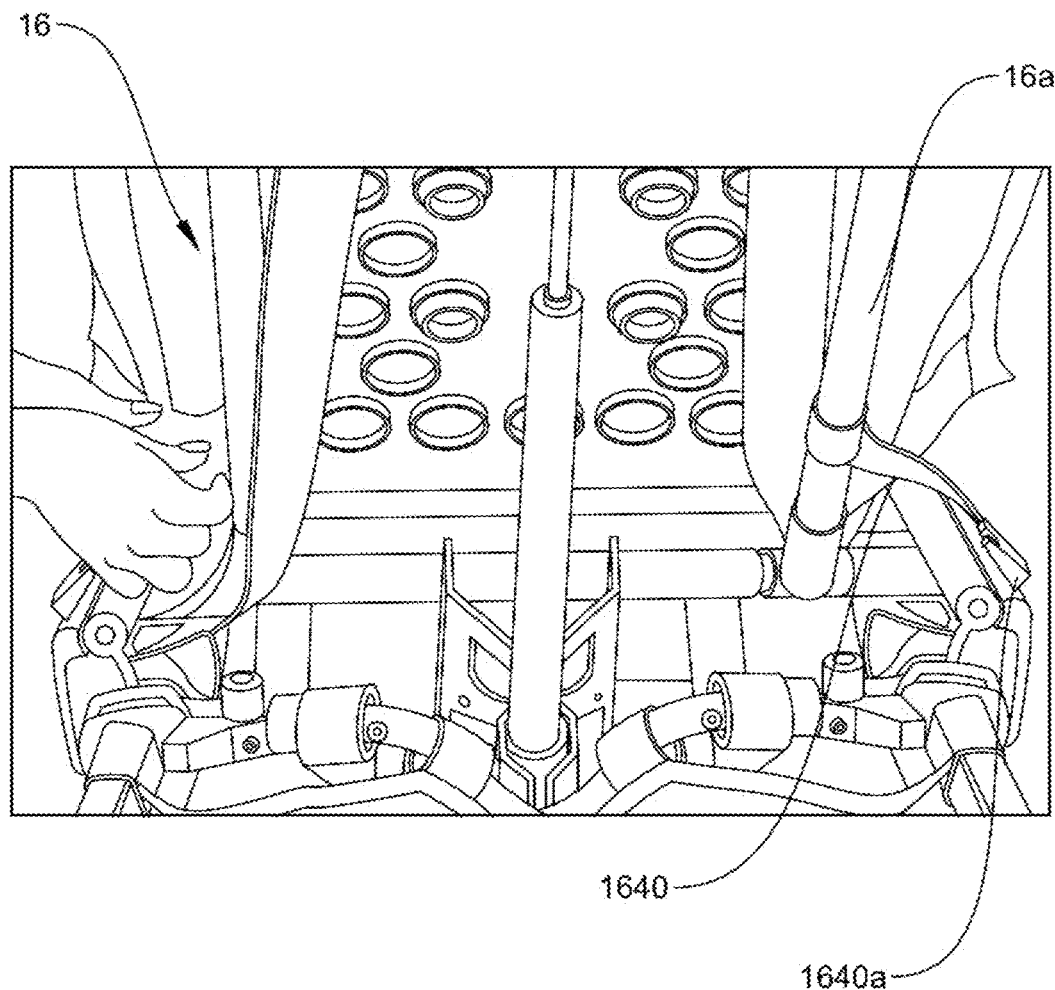
FIG. 51A is a back perspective view of the transport apparatus and pediatric restraint assembly of FIG. 51 illustrating additional anchor points for the pediatric restraint assembly.

In addition to securing pediatric restraint assembly 1600 to the adult restraint R, pediatric restraint assembly 1600 is also secured to the transport apparatus 10 via additional anchor points mounted directly to the transport apparatus 10. For example, as best seen in FIG. 51A, the additional anchor points may include straps 1640 with buckles 1640*a* mounted to transport apparatus 10. Straps 1640 may be secured to transport apparatus 10 by looping around the frame of the deck 16, and then releasably couple at their opposed ends via buckles 1640*a* to corresponding buckles on the ends of waist strap portions 1616 and 1618 of straps 1612.

Straps 1640 are located on the deck frame of the back section 16*a* (commonly referred to as the "Fowler section") of deck 16 adjacent the hinges to the seat section 16*b* (and hence are mounted to the moving portion of the deck) and serve as the pediatric restraint assembly waist anchor points. For examples of other fasteners and arrangements for coupling waist strap portions 1616 and 1618 to straps 1640, and to provide adjustability, reference is made to the above description regarding straps S and shoulder strap portions 1614.

Referring again to FIG. 51, a fifth anchor point for the pediatric restraint assembly 1600 is the leg anchor point, which is formed by the adult restraint waist strap W. The leg portion 1624 may be looped around adult restraint waist strap W to secure the leg end portion of panel 1610 to the transport apparatus when the adult restraint waist strap W is buckled, as shown in FIG. 51.

To secure a patient in the pediatric restraint assembly 1600, shoulder strap portions 1614 also include another buckle 1626, with the female portion mounted to one shoulder strap portion and the male portion mounted to the other shoulder strap portion, which is typically located over the chest of the patient. Further, buckle 1626 is optionally slidably mounted to the respective shoulder strap portions 1614, again to help adjust to smaller or larger patients and also to provide greater access to the patient when needed. In addition, each shoulder strap 1614 may include a clip 1614*b*, such as a sliding clip, which can be used to tighten the shoulder straps close to the patients shoulders. In another embodiment, the various straps may be fed through a template that helps a caregiver place the straps in their appropriate position, as will be more fully described below.

Panel 1610 may be formed from a variety of materials, including reinforced or unreinforced fabric or sheets of flexible material, such as nylon, and, further, may be padded, for example, with foam inserts or a foam layer, to provide at least some cushioning for the patient. When formed from an unreinforced fabric or the like without a foam layer, the panel, therefore, may not hold its shape. Consequently, it will not absorb energy or effectively transfer any energy to the adult restraint or transport apparatus. When discrete padding (e.g. foam inserts) are provided, then the panel will adsorb energy though still not hold its overall shape. Or stated in another way, the panel will not exhibit any significant resistance to bending or a load or twisting applied thereto. When formed with a foam layer that extends across the width and height of the panel, not only will the panel absorb energy, the panel may also hold its overall shape. But it will not transfer energy to the adult restraint or transport apparatus. As described below in reference to other embodiments, the panels may be made from solid materials, such as plastic and/or metal, which hold their overall shape, absorb energy, and transfer energy to the adult restraint or transport apparatus in varying degrees depending on the flexibility of the panels.

Other cushioning may be provided. For example, each shoulder strap portion 1614 may be provided with cushioning in the form of cushioned sleeves 1650. Sleeves 1650 may be adjustable and wrap around the shoulder strap portions 1614 and include a releasable fastener 1652, such as a snap, VELCRO patches, or the like to allow the sleeve to be removed for cleaning or replacement.

Optionally to secure the pediatric restraint assembly to the transport apparatus, a caregiver will attach the ends of straps 1612 and 1614 to the modified adult restraint straps S at the shoulder height. The additional straps 1640, which were attached at the back section 16a of deck 16, for example, at the lowest point on the back section's left and right side, will serve as the pediatric restraint assembly's waist anchor point. Waist straps 1616 and 1618 are then buckled to straps 1640. Then, the adult waist strap W is fastened over the open pediatric restraint panel 1610 and leg portion 1624 to secure the pediatric restraint assembly to the transport apparatus.

To secure the pediatric patient, place the patient on top of the open restraint assembly and bring the shoulder strap portions 1614 of the straps 1612 over the patient's shoulders and secure the shoulder strap portions 1614 together with buckle 1626 at the infant's chest. Bring the waist strap portions 1616 and 1618 around the infant and buckle into the three-point buckle restraint 1630 that comes up between the legs. Lastly, tighten all the straps to create a snug and secure fit. The added padding at the shoulder straps can be adjusted to provide extra comfort and support to a small infant's head. Although shown with the pediatric patient facing away from the adult, the pediatric restraint assembly may be used so the pediatric patient faces the adult.

To restrain a larger child, loosen the restraints and raise the shoulder buckles. Next, place the child on top of the open restraint assembly and bring the shoulder strap portions over their shoulders, securing the shoulder strap portions together at the child's chest via buckle 1626. This buckle can be raised or lowered (by sliding along shoulder strap portions 1614) as needed to provide access for specific therapies. Bring the waist strap portions around the child and buckle into the three-point buckle restraint 1630. Lastly, tighten the straps to create a snug and secure fit. The added padding at the shoulder straps can be adjusted to provide extra comfort.

As noted above, another configuration for pediatric restraint assembly 1600 allows a parent to ride on the transport apparatus while holding their child. In this scenario, the adult restraint is secured around the parent consistent with current standard procedure. The pediatric restraint assembly is then attached in the same process previously described, but now on top of the parent.

Optionally, in one embodiment, pediatric restraint assembly 1600 includes adjustable shoulder straps 1615 so that it can be worn by an adult before the adult is placed on the transport apparatus. For example, each of the shoulder straps 1615 may be secured on one end, for example, by stitching, to the upper end of panel 1610 and secured on their other ends, for example by stitching, to the lower end of panel 1610 to thereby form loops with the panel. Each shoulder strap 1615 may include a buckle so that the size of the loops may be adjusted to suit the wearer. Optionally, the straps may be removable.

Figure 56:
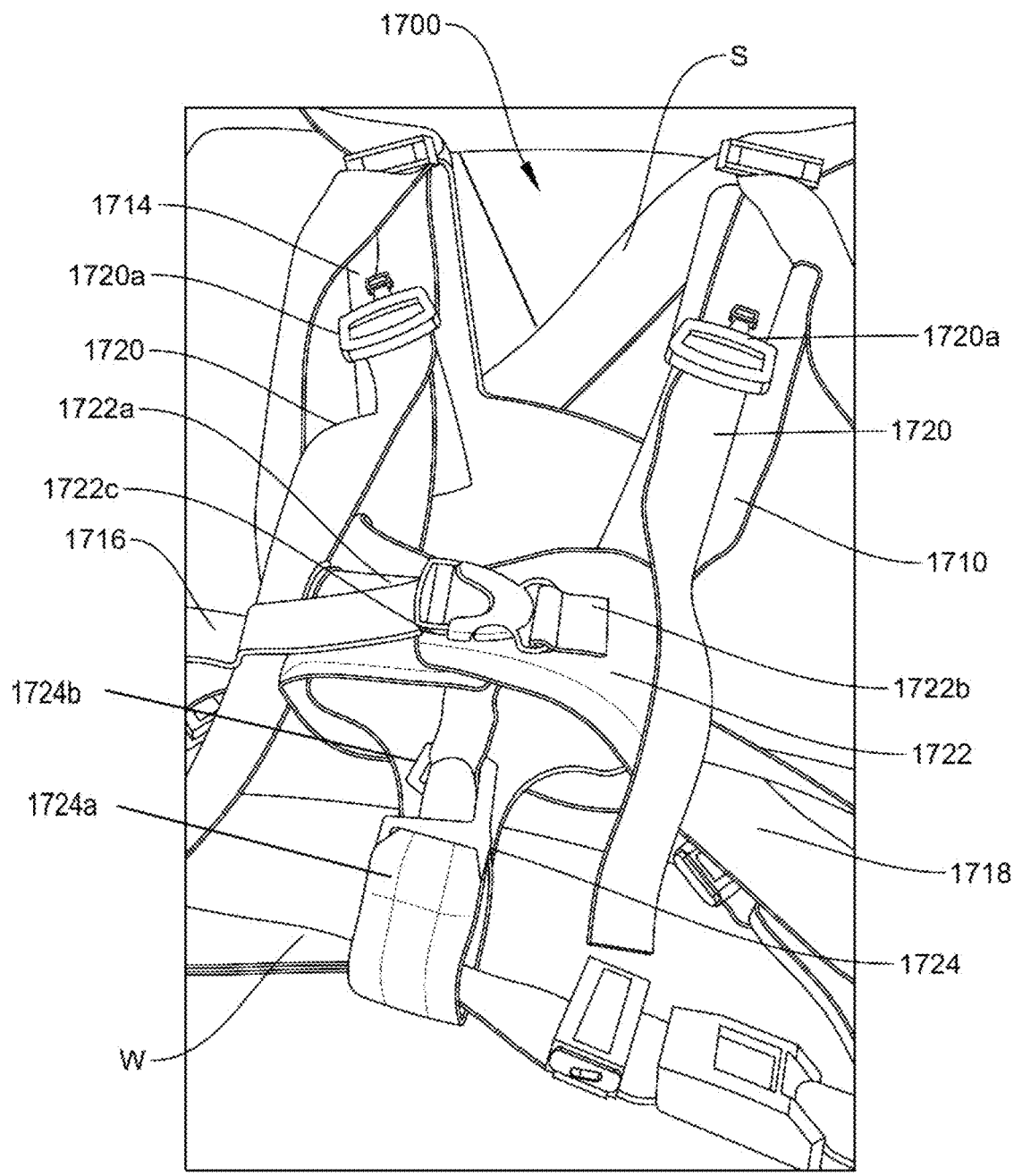
FIG. 56 is a perspective view of another embodiment pediatric restraint assembly.
Figure 57:
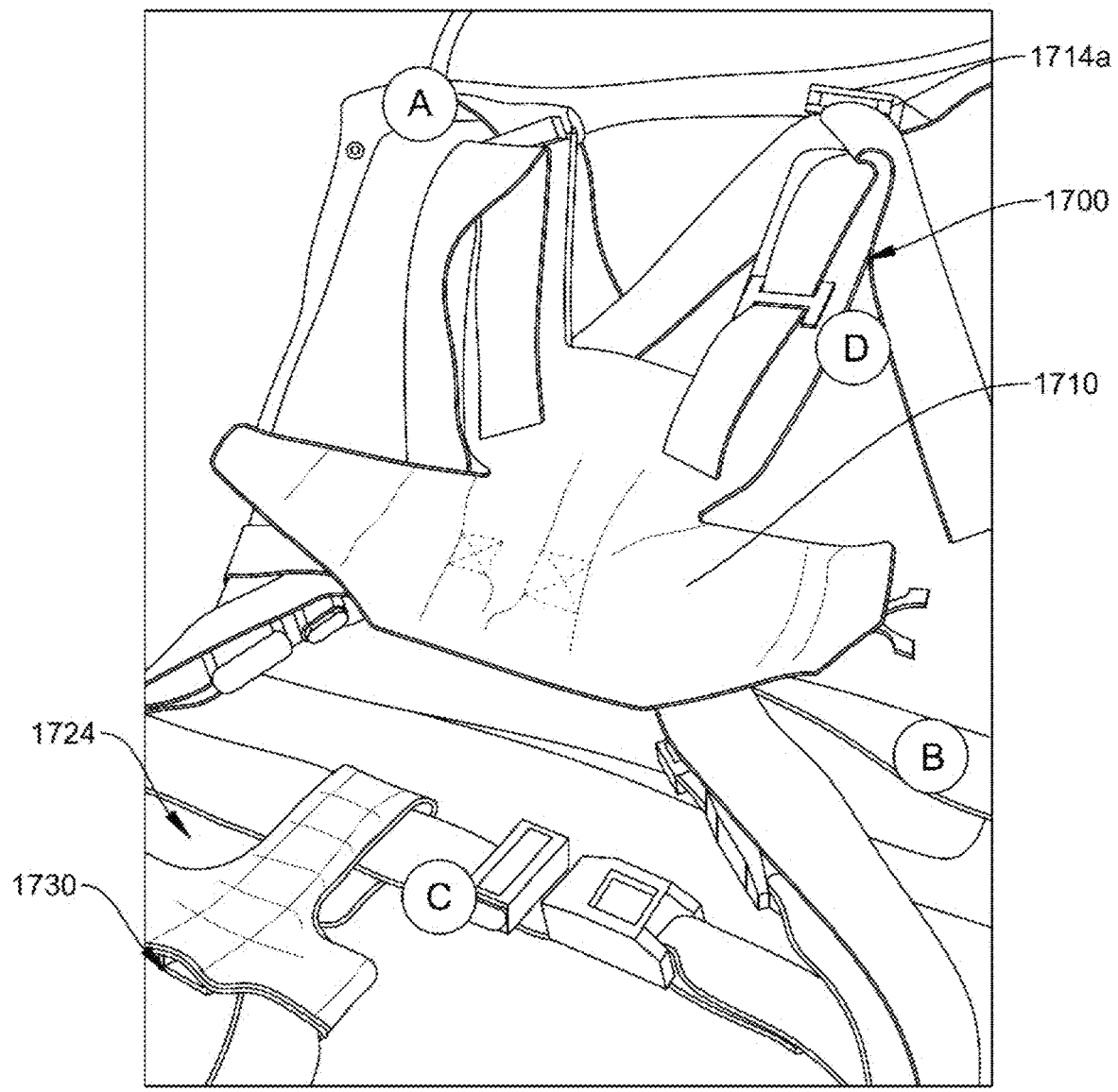
FIG. 57 is another perspective view the pediatric restraint assembly of FIG. 56 shown in an open configuration.
Figure 58:
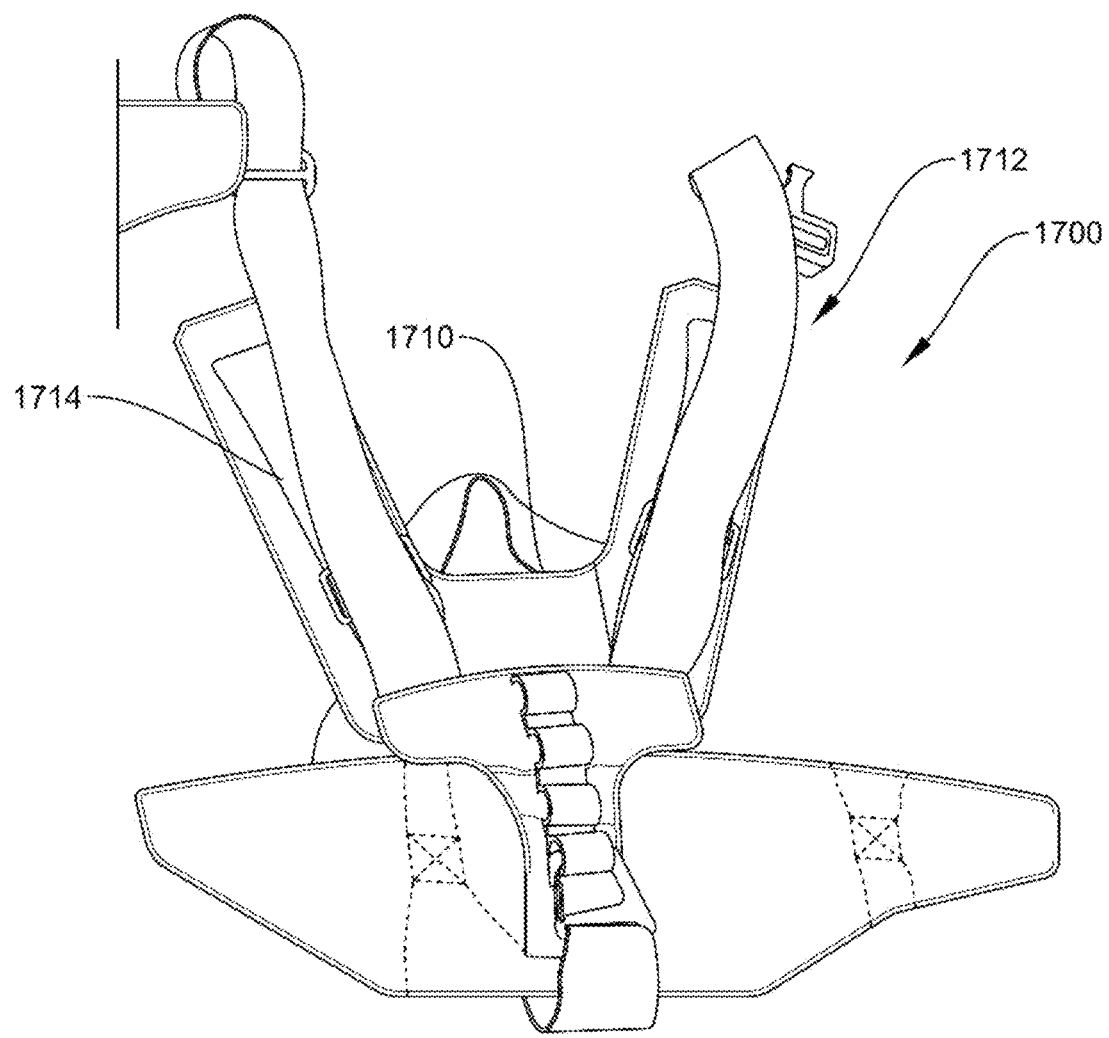
FIG. 58 is another perspective view of the pediatric restraint assembly of FIG. 56.

Referring to FIGS. 56-58, the numeral 1700 refers to another embodiment of a pediatric restraint assembly for use in conjunction with an existing adult restraint R. Similar to restraint assembly 1600, pediatric restraint assembly 1700 may form a five-point harness that is configured so that it can accommodate patients that weigh in a range of about 4 to 99 lbs. In addition, pediatric restraint assembly 1700 is configured so that it can be used while the adult restraint R is being used as well.

Referring again to FIG. 57, pediatric restraint assembly 1700 includes a panel 1710 and a plurality of straps 1712 coupled thereto for releasably securing the panel 1710 to a plurality of anchor points on the transport apparatus. In the illustrated embodiment, each strap 1712 is anchored on one end, for example, by stitching to panel 1710 and includes a coupler, such as an adjustable buckle, on its opposed end for releasable engagement with an anchor point on the transport apparatus.

Similar to the previous embodiment, straps 1712 include shoulder straps 1714 and waist straps 1716 and 1718. Suitable couplers may include adjustable buckles to allow the length of the respective straps to be adjusted. Similar to the previous embodiment, shoulder straps 1714 include couplers 1714a to releasably engage anchor points on straps S of adult restrain R. Waist straps 1716 and 1718 are secured at one end to panel 1710, for example, by stitching and, likewise, include on their opposed ends buckles for releasably engaging straps 1740 secured to the frame of the deck, similar to straps 1640 described above.

In the illustrated embodiment the leg portion is formed from a separate panel 1724, which includes a strap 1724a for looping around waist strap W of adult restraint R and a coupler 1724b for engaging one of several anchor points provided on panel 1724 to allow the position of the leg portion to be adjusted to suit the patient, based on height and/or weight of the patient. For example, the anchor points may be provided by a plurality of loops formed on a strap mounted to the outside of panel 1724.

Additionally, panel 1724 includes a pair of straps 1720 with adjustable couplers 1720a, such as buckles, that releasably couple to the anchor points on the shoulder straps S along with shoulder straps 1714 to provide a shoulder restraint for the patient. Suitable buckles for the anchor points may include COBRA buckle.

As a result, each of the straps 1712 and 1720 are adjustable and may be adjustable using various forms of buckles to accommodate different sized patients and, further, to keep the hips of the patient aligned with fowler/seat joint (joint between sections 16a and 16b of deck 16).

The type of anchor points and buckles though may vary. Further, the anchor points may each form a single anchor point or multiple anchor points, and/or may be adjustable. For example, one or more loops may be added to the shoulder straps S, with the ends of shoulder straps 1714 including a hook, such as a carabiner or G hook to engage the loops. For example, a strip of multiple loops may be provided on each adult restraint shoulder strap S to provide multiple different anchor points along each adult restraint shoulder strap S. For further examples of suitable couplers and anchor points reference is made to the previous embodiment.

Panels 1710 and 1724 may be formed from a variety of materials, including nylon, and, further, may be padded to provide at least some cushioning for the patient. Additional cushioning may be provided. For example, reference is made to the above embodiment for optional cushioning around the shoulder straps. For further examples of suitable materials and properties of the panels reference is made above to panel 1610.

Panel 1710 may also form or support a waist restraint 1722, which is also adjustable using a buckle. Waist restraint 1722 is formed from two straps 1722*a* and 1722*b*, with each having a male or female component of a buckle 1772*c* for releasable connection. The straps may extend over the panel, where the panel overlaps and lies between the buckle and the patient (see e.g. FIG. 56), or may extend from the panel and over the patient, for example, in the case of a larger patient.

As shown, therefore, the panels 1710 and 1724 are separate and may be spaced apart so that they have a distance of about ¾ inches to about 24 inches—depending on the size of the patient. Or they may positioned so that they abut or overlap so that they have an abutting or overlapping relationship with 0 (zero) separation.

Referring to FIG. 59, an alternate embodiment of the pediatric restraint assembly 1800 includes a panel 1810 that is adjustable along its length. For example, panel 1810 may be formed from an upper panel 1810*a* and a lower panel 1810*b*, which may be joined together by a pair of extendible tethers 1810*c*, such as elastic tethers. Upper panel 1810*a* forms a back panel, while lower panels forms a seat panel. To retain the upper and lower panels (1810*a* and 1810*b*) in a fixed relationship, after their spacing has been adjusted (and the overall panel 1810 is at its desired length), panel 1810 may include an adjustable retaining device, such as ratcheted strap 1810*d*, for example, ratcheting buckles and straps available from M2 Inc. of Vermont. Thus, the panels are separate and may be spaced apart so that they have a distance of about ¾ inches to about 24 inches—depending on the size of the patient. Or they may positioned so that they have an abutting relationship with 0 separation.

Similar to the previous embodiments, pediatric restraint assembly 1800 includes leg portion 1824 for extending between the legs of the patient, which supports a buckle restraint 1830 for receiving therein male couplers 1814*a* provided on the ends of shoulder straps 1814. Suitable buckles are available from FIDLOCK GMBH.

Pediatric restraint assembly 1800 also includes waist anchor straps 1816 and 1818 that extend from lower panel 1810*b* and include couplers for engaging straps, such as straps 1640, mounted to the frame of the transport apparatus deck (see FIG. 51A). For example, waist straps may be mounted at their ends to lower panel 1810*b*, for example, by stitching, similar to the previous embodiment.

To tighten the restraint around a patient, lower panel 1810*b* may also form or support a waist restraint 1822, which is also adjustable using a buckle. Waist restraint 1822 is formed from two straps 1822*a* and 1822*b*, which extend from lower panel 1810*b*, with each having a male component of a buckle 1822*c* for insertion into buckle restraint 1830.

In the illustrated embodiment, adjustment to the distance of panel 1810 from the anchor point on the adult restraint R may be provided by providing multiple attachment points on shoulder straps. For example, as shown, shoulder straps 1814 may include a plurality of loops 1814*b* formed thereon for coupling to straps (not shown), which in turn couple to the anchor point provided on the adult shoulder straps S, as would be understood from the above description, to thereby secure restraint assembly 1800 to the transport apparatus.

Panel 1810 may similarly include cushioning, and further include extensions 1810*e* and 1810*f* that extend under the shoulder straps to provide integrated cushioning for the patient.

Figure 54:
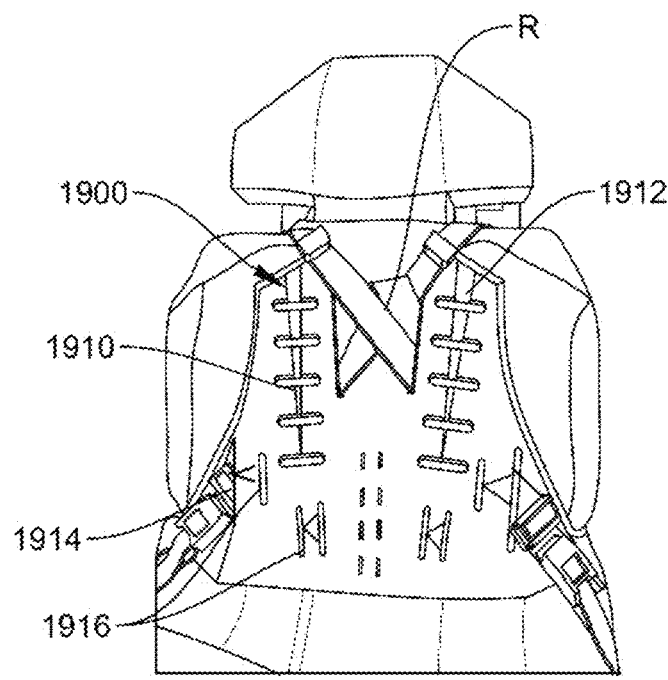
FIG. 54 is an elevation view of a transport apparatus incorporating an adult harness cover over the standard adult restraint harness with guides and indicia in the form of color coding to assist a caregiver on how to connect the pediatric restraint assembly to the transport apparatus.
Figure 54A:
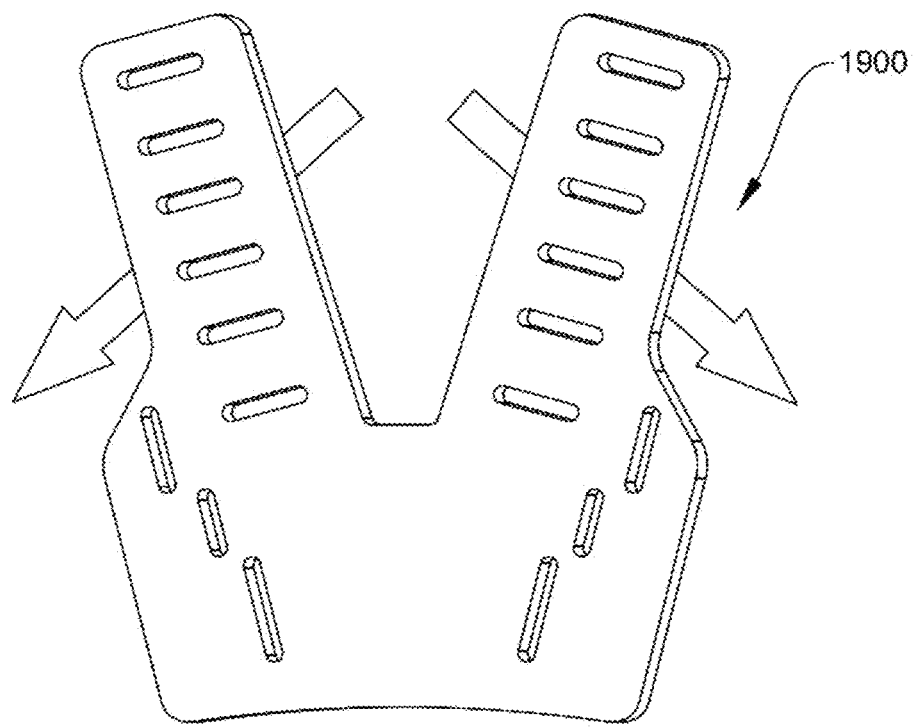
FIG. 54A is an elevation view of another embodiment of the harness cover that uses other indicia to help guide a caregiver on how to connect the pediatric restraint assembly to the transport apparatus.
Figure 55:
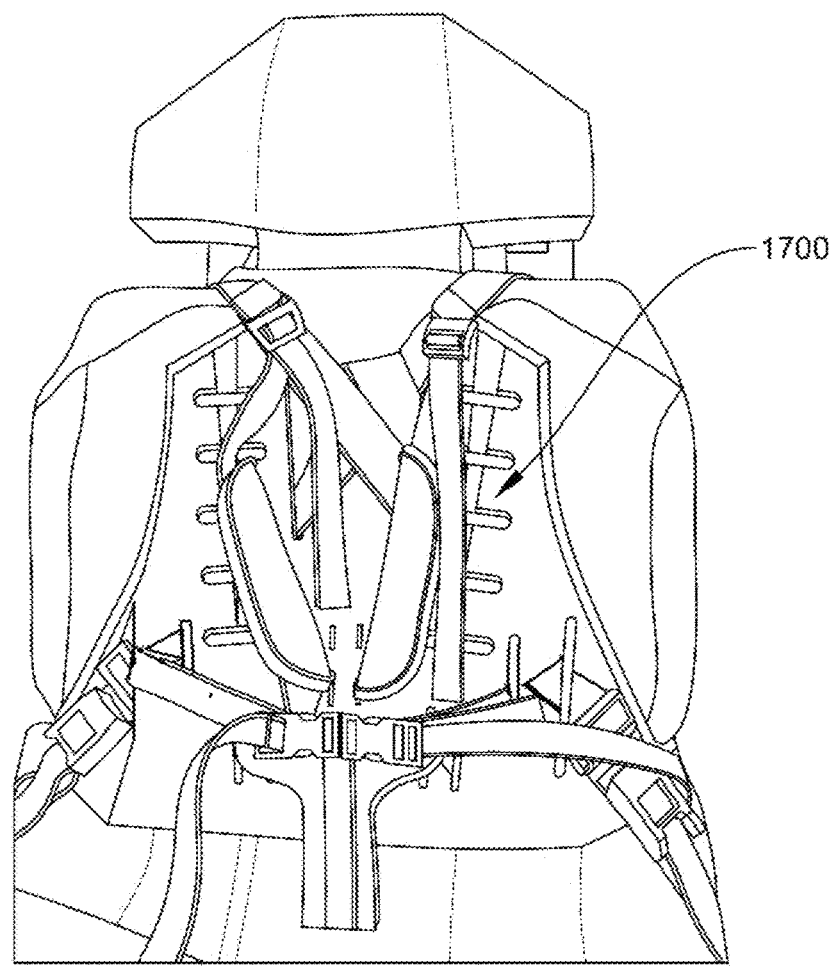
FIG. 55 is a similar view illustrating the pediatric harness secured to the support apparatus over the adult harness cover.

Any of the pediatric restraint assemblies described herein may be used in conjunction with a guide on how to attach the assembly for a given patient, for example, based on weight, height, and/or age. Referring to FIGS. 54, 54A, and 55, a harness cover 1900 may be configured as a guide or template to assist a caregiver in securing the pediatric restraint assembly to the transport apparatus. For example, harness cover 1900 may be formed from a sheet 1910 of material, such as HYPALON coated material, with multiple slots 1912, 1916 formed therein that provide an indication of where the straps of the pediatric restraint assembly should be fed into based on the weight or height of the patient, as indicated by color-coding or indicia (e.g. see FIG. 54A) or both.

In the illustrated embodiment, slots 1912 are vertically arranged to provide an indication of where the shoulder straps of the pediatric restraint assembly (e.g. restraint assembly 1700) should be fed into for coupling to the shoulder anchor points on the shoulder straps S of adult restraint R. Similarly, slots 1916 are arranged horizontally to provide an indication of where the waist straps of the pediatric restraint assembly should be fed into for coupling to the waist anchor points on, for example, straps 1640.

By threading the straps through the slots, the cover 1900 in effect shortens and hence tightens the straps on (and brings the straps closer to) the body of the patient.

For further details of deck 16, and other structures of the transport apparatus, for example of an emergency cot, not specifically mentioned or described herein, reference is made to U.S. Pat. Nos. 5,537,700 and 7,398,571, and published Application No. WO 2007/123571, commonly owned by Stryker Corporation, which are herein incorporated by reference in their entireties.

Figure 60:
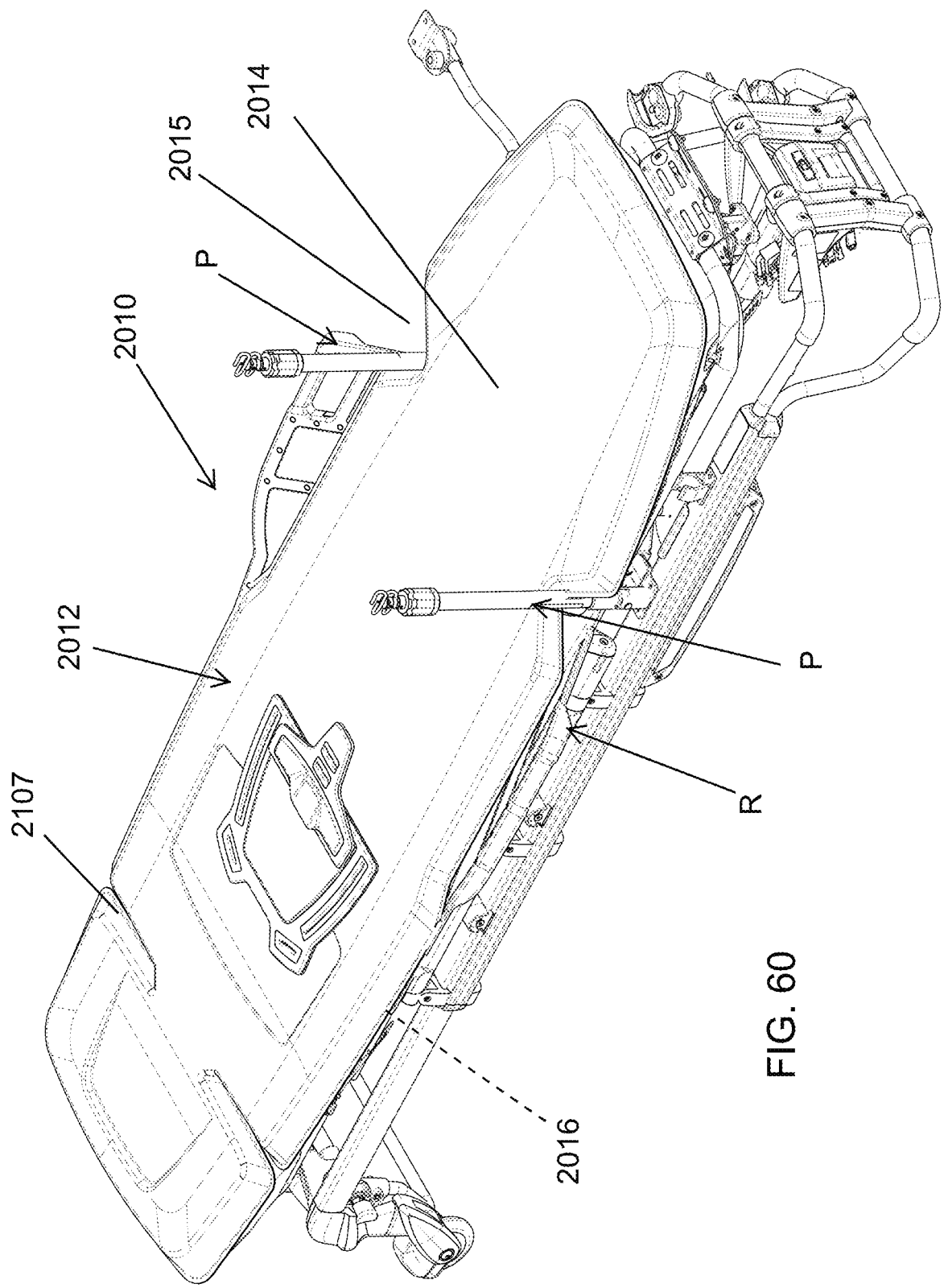
FIG. 60 is a perspective view of a transport apparatus in the form of an emergency cot with a patient support surface system.

Referring to FIG. 60, the numeral 2010 generally designates a transport apparatus, such as an emergency cot or stretcher. As will be more fully described below, transport apparatus 2010 incorporates a patient support surface system 2012 with a patient support surface 2014 and optionally one or more features or accessories to enhance the function, comfort of, and/or use of, and/or to ease ingress into and egress from transport apparatus 2010.

As best seen in FIGS. 62-64, patient support surface 2014 is segmented into two or more articulateable patient support surface sections—for example, a head section 2014*a*, a back section 2014*b*, a seat section 2014*c*, and a leg and foot section 2014*d*—so that when it is secured to the transport apparatus deck 2016 (FIG. 60, as well as FIGS. 70 and 71), it will fold and unfold as needed, for example, when the underlying and corresponding deck sections (back, leg or foot deck sections) are tilted or lowered.

Patient support surface 2014 is formed by a top cover 2018 and a bottom cover 2020, which are joined together and respectively form the lower surface (deck facing side) and upper surface (patient facing side) of the patient support surface. Though it should be understood that the upper surface may or may not form the patient contact surface of the patient support surface, and instead may be covered with a sheet or other cover, including an auxiliary cover, such as a transport covert.

Bottom cover 2020 may be pre-formed from a single sheet of material into a shape that forms at least two adjacent cavities, with each cavity 2022a, 2022b, 2022c, and 2022d receiving a cushion section. Each cavity 2022a, 2022b, 2022c, and 2022d is joined to its adjacent cavity by a living hinge 2024a, 2024b, 2024c, which are formed by the sheet of material forming the bottom cover, so that the patient support surface can be articulated about each living hinge (as the deck is articulated or access is needed beneath the patient support surface as described below). Optionally, as noted below, one or more hinges may include bellows and/or be reinforced by a plastic hinge insert.

Additionally, to further facilitate folding of the leg and foot section 2014d, patient support surface 2014 may include inwardly extending recesses 2015 on its opposed lateral sides, which extend inwardly from the outer perimeter of the patient support surface 2014 between leg and foot section 2014d and seat section 2014c. In the illustrated embodiment, recesses 2015 comprise wedge shaped recesses and are sized to accommodate and reduce, if not eliminate, interference with IV poles (P) that can be mounted to the frame 2016a (see FIG. 70), which supports transport apparatus deck 2016 and also supports side rails R. For more details of suitable side rails R, reference is made to Stryker's XPS Siderails.

Additionally or alternately, recesses 2015 are sized to provide access to straps S, which may be mounted to the leg and foot section 2014d (FIG. 70) to assist when folding the seat and leg and foot sections ("knee gatch"). In addition to providing access, recesses 2015 may also provide an indication (either visual or tactile) to a caregiver, such as EMS personnel, of where to grab the straps S—which may be especially helpful during an emergency situation, commonly associated with the use of EMS cots.

Similarly, to facilitate folding of the head section 2014a, recesses 2017 may be provided on opposed lateral sides of support surface 2014 (FIGS. 60 and 65), which extend inwardly from the outer perimeter of the patient support surface 2014 between head and back sections 2014a, 2014b. In the illustrated embodiment, due to their close proximity to the neck and shoulders of a patient (when properly positioned on patient support surface 2014), recesses 2017 may be configured to accommodate restraint straps, such as X-Restraints available from Stryker, and optionally configured to help retain the straps in place.

In one embodiment, recesses 2017 comprise narrow wedge shaped recesses, which may be sized to create an interference fit with the restraint straps to hold them in place. In one embodiment, optionally support surface bottom cover 2020 may form or include a high friction surface in recesses 2017 to further help retain the straps. Alternately or in addition, each recess may have an offset (e.g. a recess within recess 2017) to seat the strap in the offset or may simply include a lip inside each recess 2017, which extends from one or both sides of the bottom cover 2020 and spaced from the distal end of the recess, for example at least by the width of the strap, to help retain the strap in the recess 2017.

Referring to FIG. 65, patient support surface 2014 may also include recesses 2019 on its opposed lateral sides in seat section 2014c, which extend inwardly from the outer perimeter of the patient support surface 2014. In the illustrated embodiment, recesses 2019 are located and sized to reduce, if not eliminate interference with side rails R (see FIGS. 70 and 71). Additionally, due to their location, recesses 2019 may provide an indication (e.g. visual and/or tactile) to a patient where the patient can sit, lift their legs, and rotate to be properly aligned on patient support surface 2014.

In the illustrated embodiment, recesses 2019 are shallow and, further, adjacent and in communication with recesses 2015.

Referring again to FIGS. 61 and 62, as described above in reference to the previous embodiments, top cover 2018 may be formed from a continuous sheet that extends from the foot end to the head end of the patient support surface, and between the left longitudinal side and the right longitudinal side of the patient support surface, and over each of the cavities. For example, top cover 2018 may be formed from low surface friction materials, such as DARTEX or DARTEX-LIKE fabric, Nylon, Nylon weave, to reduce shearing against a patient's skin, but optionally also high chemical/mechanical durability. Other suitable materials for the top cover include sheets formed from a polymer layer, such as a urethane film, urethane laminated/coated fabric, or polyolefin.

In other embodiments, the top cover may comprise or include a region or regions of high friction to reduce the chances of a patient sliding on the patient support surface 2014.

Top cover 2018 is joined with the bottom cover 2020 around the upper perimeter edge or lip of the bottom cover and, further, joined with the bottom cover around the upper perimeters edges or lips of each of the cavities. The top cover may be joined with the bottom cover by stitching and/or sealing, such as formed by welding, including RF welding.

In the illustrated embodiment, the upper side 2036 of patient support surface 2014 is shaped so that it has a raised perimeter rim 2036a that extends around the outer perimeter of each section 2014a, 2014b, 2014c, and 2014d and defines therein the central support region of support surface 2014. The central support region includes a recess head region 2036b and a body region 2036c, which extends from the head region to the foot region and is straddled by the raised perimeter rim 2036a. Thus, rim 2036a may form a liquid barrier to help retain fluid in the central support region.

The body region 2036c may be shaped to provide an indication of where the torso and/or legs should be place. The head region may be more recessed than the body region to help cradle the head and/or a head pillow supported thereon. Optionally, the surface topography of the upper surface of the body region and head region (and the underlying cushions) may be configured to generally follow the shape of an average person's body, such as described in U.S. patent application Ser. No. 15/834,155, filed on Dec. 7, 2017, which is commonly owned by Stryker Corp. of Kalamazoo, Michigan and which is incorporated by reference in its entirety herein.

Recessed body region 2036c may include a recessed cavity 2036d for receiving a back plate 2036f, which may be formed from a rigid material, such as plastic and used to provide a region of increased stiffness under the patient's chest, for example, for applying CPR to the patient supported on transport apparatus 2010. The back plate 2036f may be secured to the support surface in recessed cavity 2036*d* by straps or fasteners or may be molded therein. Optionally, back plate 2036*f* may simply rest on the support surface 2014, for example in the recessed cavity 2036*d*. Alternately, the patient support surface 2014 may be formed with a recess extending in from one or both lateral sides to allow a back plate to be inserted just below the upper surface of patient support surface 2014.

Optionally, back plate 2036*f* may configured to work with Stryker's LUCAS chest compression apparatus. For example, back plate 2036*f* may have engagement surfaces for engagement by the LUCAS device or may be configured like the LUCAS Back Plate, with upwardly curved opposed ends to generally follow a patient's torso, with each opposed ends having an engagement bar for engagement by the LUCAS device and with a high friction underside, for example, formed on the surface of the underside or by anti-slip tape applied to the underside.

As noted in the above referenced and incorporated application, the top cover is optionally formed from a material that is impermeable. Optionally, the top cover may be formed from multiple layers or a layer or layers with a coating or coatings to render the top cover impermeable. Further, the top cover 2018 may be formed with graphics (lines, patterns, color coding, a human form graphic (e.g. outline of person), etc.) to guide a user on proper placement of a patient on patient support surface 2014. Further, as noted in the above, the central body portion may be formed with one or more channels to direct any fluid to a designated location on the central support region and, optionally, further be contained thereon or discharged via a channel or channels formed therein into a container (e.g. located beneath top cover 2018) via a drain formed in the support surface. To that end, the foot end and head of support surface may have the highest elevations, which are then straddled by the perimeter rim to contain fluid on patient support surface 2014.

In yet another embodiment, the top cover may also be thermoformed, and then joined, such as noted above, with the bottom cover at some point between the upper surface and the lower surface—in other words the top cover may be formed with downwardly depending walls, which are then joined with the upwardly extending walls of the bottom wall, such as shown in FIGS. 61 and 62.

Optionally, as described above in reference to the other embodiments, bottom cover 2020 may be formed from a thick urethane sheet so that when formed (e.g. by thermoforming or the like) into its multi-cavity shape, it can retain its shape (the sides will remain standing vertically) but still remain flexible. In other words, if manually pressed, the side walls of bottom cover 2020 would no longer remain vertical; instead, the side walls of bottom cover 2020 would easily deflect, bend and/or fold.

For example, although not shown, each cushion section (head, back, seat and foot cushion sections) may be formed from multi-layered foam (vertically and/or horizontally layered), optionally with at least one of the cushion sections being formed with a crib to facilitate patient containment/support. In the illustrated embodiment, the cushion is formed from cushioning material, such as multi-layered foam, which is sufficiently soft to allow patient support surface 2014 to conform around the patient and in effect cradle the patient. For example, recesses 2019 could be sized so that when side rails R are moved from their lowered, stowed positions to their raised position, the side rails R raise and urge at least a portion of the raised perimeter rims 2036*a*, adjacent the seat section 2104*c* of patient support surface 2014, to curl upward and cradle a patient supported thereon. Additionally, the shape of recesses 2019 may be tapered so that at its outermost point, the side rails are not encumbered by the patient support surface 2014 but as the side rails move upward and inwards toward the mattress, the side rails force the outer edge (e.g. rim 2036*a*) of patient support surface 2014 to curl or fold up and cradle the patient, as noted.

In the illustrated embodiment, as best seen in FIGS. 63 and 64, bottom cover 2020 may incorporate one of more folds of material to form bellows 2025 at, for example, hinge 2024*b*, which allows the back section ("Fowler") of the transport apparatus and patient support surface 2014 to move over its full range of motion while still supporting the patient.

Referring to FIGS. 63 and 64, as noted above, one or more accessories or features may be incorporated, such as by forming or mounting, into or onto the patient support surface. For example, in illustrated embodiment, bottom cover 2020, which as noted may be molded, may be formed with one or more recesses 2021 at its corners and/or underside to form hand holds or hand recesses to allow better access to the fowler bar when pushing or pulling on the transport apparatus. Additionally, as will be more fully described below, patient support surface 2014 may also incorporate other recesses, for example, of different shapes and sizes for forming or receiving compartments for storage etc. or for receiving devices therein, such as DVT pumps and/or boots or X-ray cassettes.

Figure 63A:
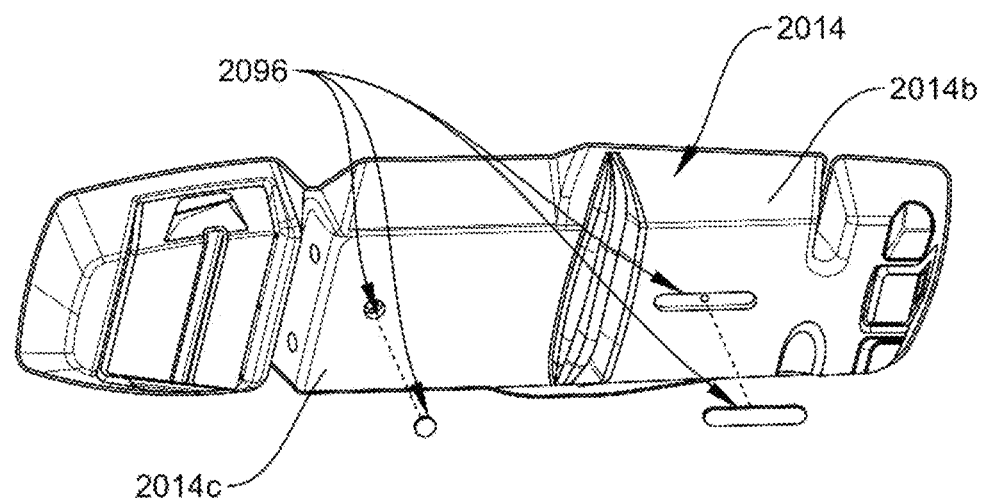
FIG. 63A is an exploded bottom perspective view of the patient support surface of FIG. 63 illustrating two couplers for releasably coupling the patient support surface to the deck of the transport apparatus.
Figure 63B:
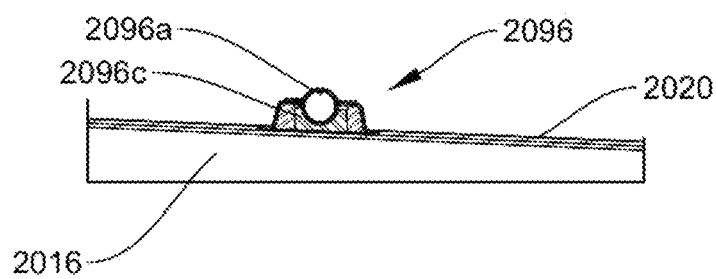
FIG. 63B is a cross-section of the patient support surface taken through one of the couplers.

Optionally, patient support surface 2014 may be coupled to the underlying deck via one or more couplers. Referring to FIG. 63A, in the illustrated embodiment, patient support surface 2014 may incorporate one of more couplers 2096 that releasably couple the support surface to the transport apparatus deck 2016, but which are configured to permit relative longitudinal movement there between, at least in the back section 2014*b* of patient support surface 2014. For example, in the illustrated embodiment, seat section 2014*c* incorporates a coupler in the form of a magnet, which is mounted in bottom cover 2020, for engagement with a corresponding coupler, for example a metal coupler mounted to the deck.

Figure 63C:
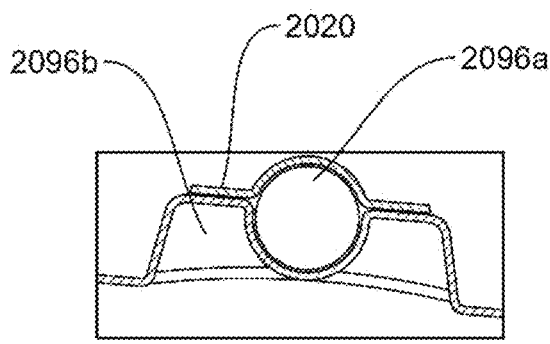
FIG. 63C is an enlarged cross-section of one of the male couplers.

As best seen in FIG. 63C, a spherical magnet 2096*a* may be mounted to support surface 2014 in a recess 2096*b* between two layers, such as an outer urethane layer and an inner urethane layer forming bottom cover 2020. The recess is sized so that magnet 2096*a* may be fully recessed in the bottom surface of cover 2020 and, further, so that a mating coupler (which is mounted to the deck), in this instance, a female coupler in the form of a metal cup 2096*c* (FIG. 63D) can be received in the recess. In this manner, the support surface 2014 can lay flat on the floor when not in use without anything protruding from the underside of the mattress. This results in a very cleanable design because there are no seams or edges given that everything sealed internally to the mattress.

Figure 63D:
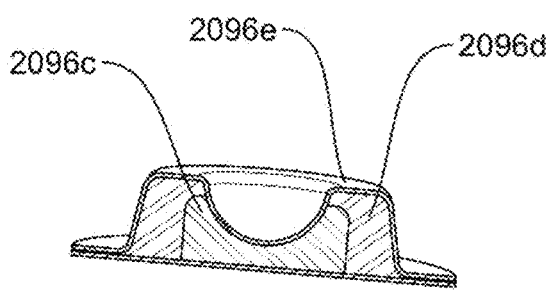
FIG. 63D is an enlarged cross-section of one of the female couplers.

As best seen in FIG. 63D, metal cup 2096*c* may be insulated around the outside with plastic 2096*d* and sealed within a urethane layer 2096*e* for cleanability as well. Thus, when support surface 2014 is placed on the deck, the magnetic ball will be attracted to and finds its way into the cup to thereby be secured in place. The plastic insulation prevents "false" latches on the side of the cup so the magnet will only be attracted to the inside of the cup. The female receptacle(s) may be attached to the cot via mechanical means such as adhesive, strapped, rivets or other fasteners. This could also be retrofitted with the hook and loop fasteners, but this would not eliminate the cleanability issues with hook and loop fasteners.

The magnetic holding force holds it in the normal direction, and interlocking ball and cup hold it mechanically in the shear direction to accommodate patient transfers when the patient is not strapped to the cot.

Figure 63E:
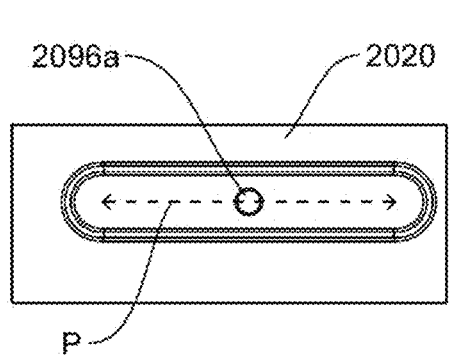
FIG. 63E is an enlarged bottom plan view of another of the male couplers.
Figure 63F:
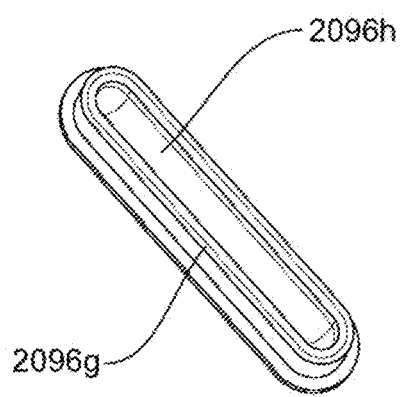
FIG. 63F is an enlarged perspective view of the female couplers that cooperates with the male coupler of FIG. 63E.
Figure 73:
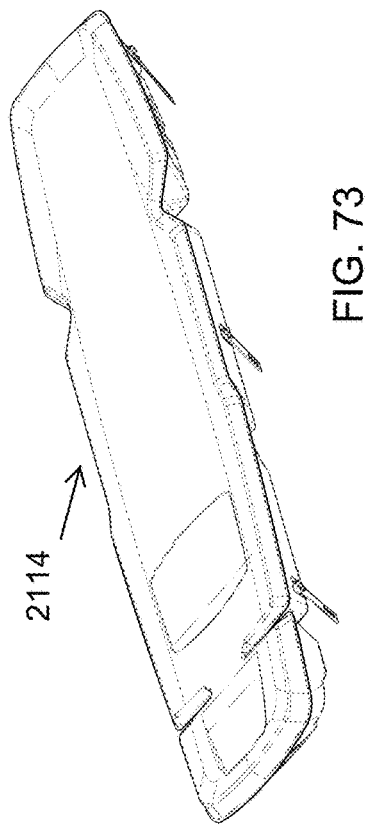
FIG. 73 is a third top perspective view of the patient support surface system of FIG. 70.
Figure 75:
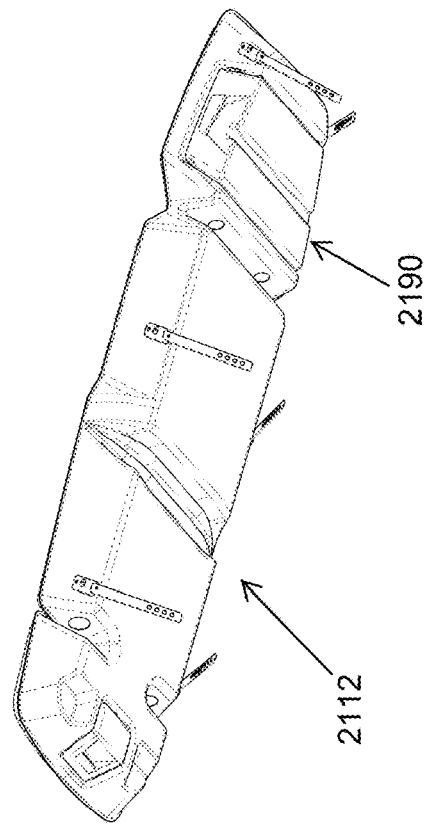
FIG. 75 is another bottom perspective view of the patient support surface system of FIG. 70.
Figure 72:
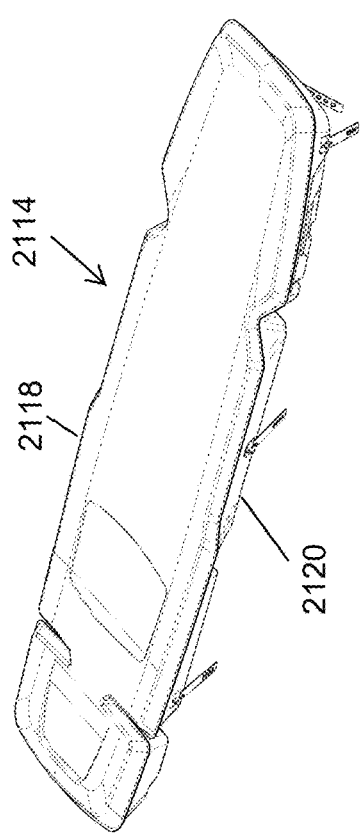
FIG. 72 is another top perspective view of the patient support surface system of FIG. 70.

Referring to FIGS. 63E and 63F, coupler 2096, which is mounted to the back section 2014*b* of patient support surface 2014, may also be movably mounted to surface 2014 so that it allows for movement of the surface 2014 relative to deck 2106. In the illustrated embodiment, coupler 2096 also includes spherical magnet 2096*a* mounted between two layers of urethane forming cover 2020 but is allowed to move longitudinally between the two urethane layers along a path P. Spherical magnet 2096*a* is seated in and engaged with a channel shaped female metal coupler 2096*g*, which is of similar construction to cup 2096*c*, but rather than having a semi-spherical recess has an elongated semi-circular recess 2096*h* that forms the channel along which magnet 2096*a* can move to allow relative movement between the surface 2014 and deck 2016, while still maintaining its magnetic holding force and shearing force in the lateral direction thereby coupling the surface 2014 and deck 2016 together. For further details of how channel shaped female metal coupler 2096*g* is mounted and sealed, reference is made to cup 2096*c*.

For further details of the optional construction of patient support surface 2014, reference is made to the above embodiments.

Referring again to FIGS. 70 and 71, the numeral 2112 designates another embodiment of a patent support system that includes a patient support surface 2114 similar to patient support surface 2014 but with added storage and functionality.

Figure 82:
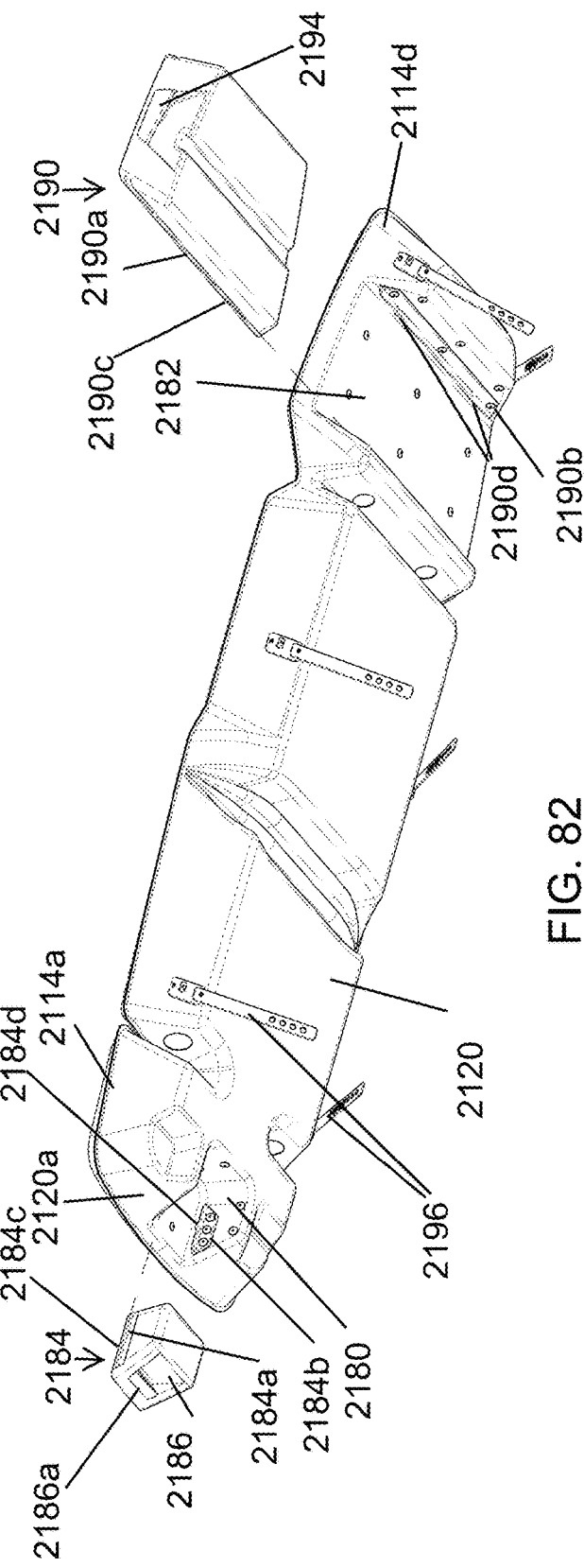
FIG. 82 is a bottom exploded perspective view of the patient support surface system of FIG. 76.

In the illustrated embodiment, support surface 2114 also includes a top cover 2118 and a bottom cover 2120. For further optional details of top cover 2118 reference is made to top cover 2018 and the top covers described above. Bottom 2120 may also be similar to bottom cover 2020 (and to those also described in the other embodiments) but includes additional recesses 2180 and 2182 (FIG. 82). Recess 2180 is formed at the head end of head section 2114*a*, and recess 2182 formed in leg and foot section 2114*d*. As will be more fully described below, recesses 2180 and 2182 may be configured to provide storage.

As best seen in FIG. 82, recess 2180 is configured to hold a compartment 2184. Optionally, compartment 2184 may be formed by the same sheet that forms the bottom cover—and hence is formed by the "bottom cover"—or may be formed as a separate compartment and mounted, such as by using adhesive, fasteners, welding, or rails (as described), in recess 2180 of bottom cover 2120 of patient support surface 2114. Suitable fasteners may include snaps, bayonet like fingers or projections, or buttons or the like. Alternately, as noted, the compartment 2184 may be formed with the patient support surface (e.g. with bottom cover 2120) during molding. For example, the patient support surface and storage compartment may be co-injection molded.

Optionally, as shown, compartment 2184 may be mounted using rails and may be formed with a folding compartment wall or door 2186 to provide access into the interior 2188 of compartment 2184. Door 2186 may provide access while that section of the patient support surface, which includes the compartment, is still resting on the deck (when recess 2180 extends through the end wall as noted below) or when folded upwardly. Optionally, door 2186 may include a handle, which may include a latch to close and secure the door in its closed position or release the door from its closed position. For example, the handle may comprise a movable handle, e.g. sliding or pivoting, which is spring loaded in its closed position, with the latch formed on and extending upwardly from the door to engage a corresponding recess formed in the compartment above the door.

In the illustrated embodiment, compartment 2184 is located in recess 2180 formed in bottom cover 2120 (and corresponding cushioning layer) of the head section 2114*a* of patient support surface 2114. Recess 2180 may be formed so that it extends from the bottom side into the patient support surface 2114 such that is fully surrounded on all sides by the patient support surface or may extend through the end wall 2120*a* of the head end section, as shown. When fully surrounded on all sides, door 2186 may be located in the bottom side of the compartment and then accessed when the head section is lifted up from the deck, as noted.

Figure 81:
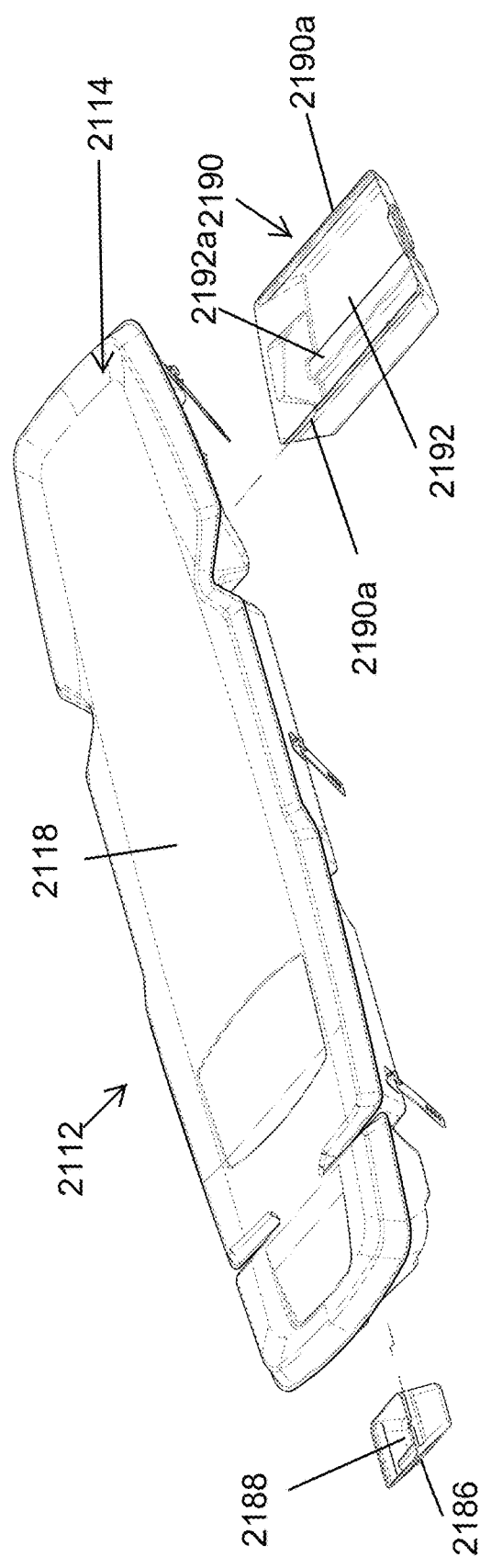
FIG. 81 is a top exploded perspective view of the patient support surface system of FIG. 76.

Folding compartment wall or door 2186 may be configured to provide access into the compartment through one side of the compartment, such as understood from FIGS. 81 and 82, or through the side and bottom (e.g. with an L shaped door).

Optionally, compartment 2184 may be movably and, optionally, removably mounted in recess 2180. For example, as noted, compartment 2184 may be movably by a pair of rails 2184*a* that are mounted to or formed on opposing sides of compartment 2184 and which engage and slide on a pair of rails 2184*b* mounted to the support surface 2114 (e.g., to bottom cover 2120) inside recess 2180. In the illustrated embodiment, rails 2184*b* are mounted in recess 2180 by fasteners. For example, recess 2180 may be formed or provided with a rigid liner, such as a rigid plastic liner that provides a mounting surface of the rails.

To reduce the unintentional full withdrawal of compartment 2184 from recess 2180, the rails 2184*a* and 2184*b* may each include a ridge 2184*c*, 2184*d*, which either act as stops once the ridges are aligned or simply increase the resistance so that the compartment can be fully extracted for cleaning, repair, or replaced when a sufficient pull force is applied to overcome the friction.

Compartment 2184 may be used to store supplies, such as supplies for the caregiver, such as gloves, masks, or the like, or for the patient supported thereon, such as restraints, including the cover and/or pediatric restraint assemblies described below.

As noted above in reference to the other embodiments, the compartment may be separately mounted from the patient support surface and, instead, mounted to the deck of the transport apparatus. When mounted to the deck, the compartment can help retain the patient support surface on the deck, by providing at least a lateral restraint, and in some embodiments a longitudinal restraint or both.

As best understood from FIG. 82, compartment 2184 may be formed as a separate, generally rigid box with solid walls on opposed sides and on its bottom side. Optionally, when movably mounted in patient support surface 2114, the top side of the box may be open to provide access to the top, and door 2186 may be eliminated and instead be configured as solid wall. Handle 2186*a* may remain as a fixed handle so that it can be used simply to provide a gripping or engagement surface to pull compartment 2184 along rails 2184*b*, as noted above.

By attaching the compartment to the deck and nesting the compartment with the patient support surface when in its normal in-use position, the compartment can, therefore, help provide a shear restraint (laterally and/or longitudinally (at least in one direction)) for the patient support surface, and thereby help retain the patient support surface on the transport apparatus. At the same time, by extending the recess through the head end of the patient support surface, the patient support surface will be able to shift as the head section of the deck is tilted or folded without interference from the compartment. However, it should be understood that access to the compartment or compartments may also be provided through openings in the side of the patient support surface.

Referring again to FIG. 82, the foot end recess 2182 may also form or receive a compartment 2190. Again, compartment 2190 may be formed by the same sheet that forms the bottom sheet of the back, seat, and foot sections of patient support surface 2014—and hence is formed by the "bottom cover"—or formed as a separate compartment.

In this embodiment, compartment 2190 is formed as a separate, rigid compartment and configured as a drawer. As will be more fully described below, the compartment may be at least partially bifurcated, for example, by a divider to form two storage spaces or may be formed by two separate compartments, stacked side by side, and/or back to back, as will be described in reference to FIGS. 84-94.

As noted, in the illustrated embodiment, compartment 2190 is configured as a drawer. In this particular embodiment, compartment 2190 is configured as a single drawer that is mounted in recess 2182 to slide from at least one side of support surface 2114, e.g. while patient support surface is resting on deck 2016, to provide access into storage space 2192 (FIG. 81) of compartment 2190.

Optionally, as shown, compartment 2190 may be configured to slide from either side of patient surface. To that end recess 2182 may be configured as a channel shaped-recess that extends laterally across leg and foot section 2114d and through side walls of the leg and foot section 2114d, as best seen in FIG. 82.

Similar to compartment 2184, compartment 2190 may be formed from a generally rigid box with solid walls on opposed lateral sides, opposed end walls, and on its bottom side, but with an open top side. In this manner, when moved from either side of patient support surface 2114, the open top side of the box provides access to the storage space 2192 (FIG. 81).

To facilitate movement of compartment 2190, compartment may include a handle 2194 on one or both lateral sides so that it can be used simply to provide a gripping or engagement surface to pull compartment 2190 along the rails noted below.

For example, compartment 2190 may be movably mounted by a pair of rails 2190a that are mounted to or formed on opposed sides of compartment 2190 and which engage and slide on a pair of rails 2190b mounted to or formed on the support surface 2114 (e.g. to bottom cover 2120) inside recess 2182. In the illustrated embodiment, rails 2190b are mounted in recess 2182 by fasteners. For example, recess 2182 may be formed or provided with a rigid liner, such as a rigid plastic liner that provides a mounting surface of the rails. Similarly, to reduce the unintentional full withdrawal of compartment 2190 from recess 2182, the rails 2190a and 2190b may each include a ridge 2190c, 2190d, which either act as stops once the upper and lower corresponding ridges are aligned or simply increase the resistance so that the compartment can be full extracted for cleaning, repair, or replaced.

Compartment 2190 may be used to store supplies, such as supplies for the caregiver, such as gloves, masks, or the like, or for the patient supported thereon, such as restraints, including the cover and/or pediatric restraint assemblies described below.

Optionally, as shown, the storage space 2192 may be partially bifurcated into sub-storage spaces by one or more walls or ridges 2192a formed or added to compartment 2190. As described below, the wall or ridge may be removable or may be extended or extendible so that there are two separate storage spaces.

Referring to FIG. 83, in one embodiment, compartment 2190 includes a second wall or ridge 2192b to further compartmentalize space 2192. Optionally, wall 2192b is removable and optionally orientated orthogonal to wall 2192a to divide the space in two four sub-spaces. Further, wall 2192b may extend the full height of the space 2192 so that at least subspaces 2192c and 2192d are isolated from each other.

For further details of the optional construction of patient support surface 2114, reference is made to patient support surface 2014 and the other patient support surfaces described above.

In one embodiment, referring again to FIGS. 70 and 71, one or more couplers 2196 may be mounted to support surface 2114 to secure patient support surface 2114 to deck 2016. In the illustrated embodiment, couplers 2196 are secured to the lateral sides of leg and foot section 2114d, seat section 2114c, and back section 2114b of surface 2114. Optionally, fewer or additional couplers may be provided, including on the head end or lateral sides of head section 2114a.

Figure 74:
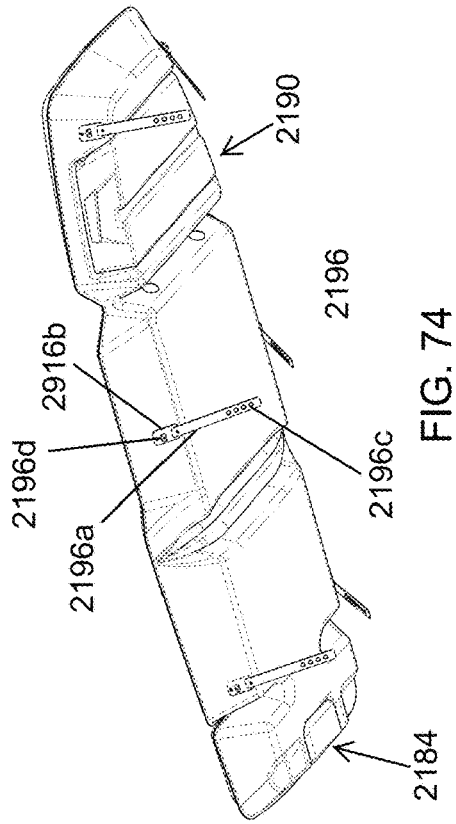
FIG. 74 is a bottom perspective view of the patient support surface system of FIG. 70.
Figure 76:
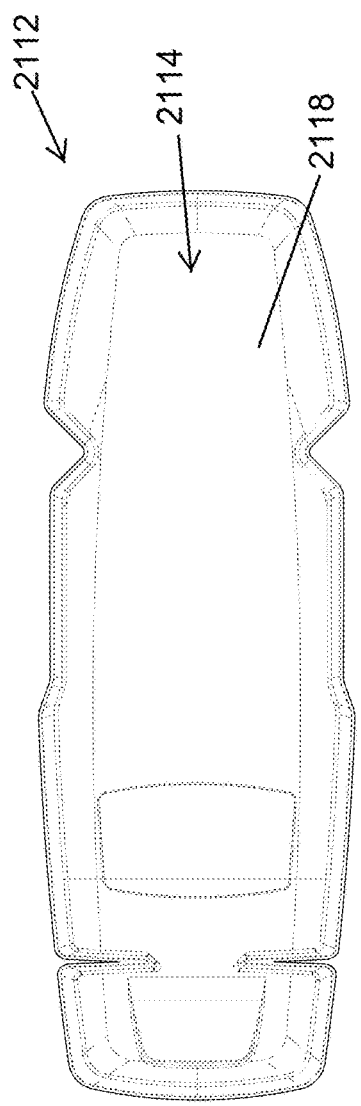
FIG. 76 is a top plan view of the patient support surface system of FIG. 70.
Figure 80:
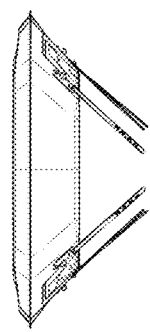
FIG. 80 is a foot end elevation view of the patient support surface system of FIG. 76.
Figure 78:
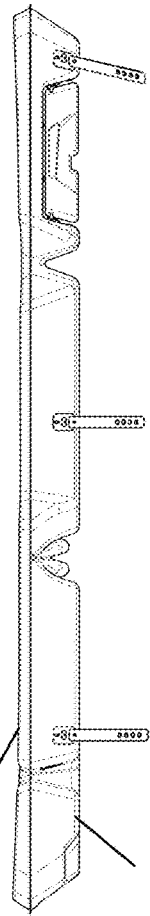
FIG. 78 is a side elevation view of the patient support surface system of FIG. 76.
Figure 79:
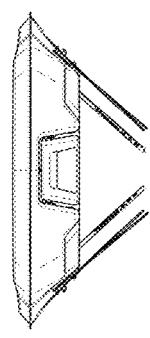
FIG. 79 is a head end elevation view of the patient support surface system of FIG. 76.
Figure 77:
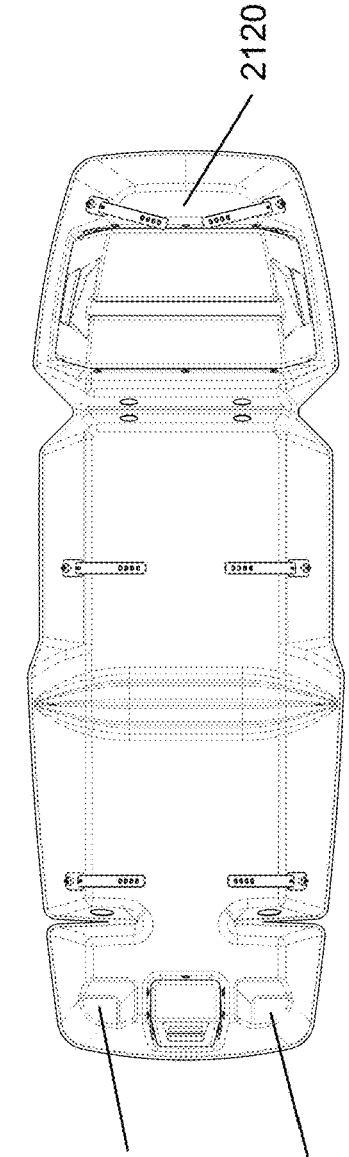
FIG. 77 is a bottom plan view of the patient support surface system of FIG. 76.

In one embodiment, and referring to FIG. 74, couplers 2196 include a tether 2196a secured on one end to bottom cover 2120, by a bracket 2196b, with its free end for wrapping around frame 2016a. In the illustrated embodiment, tether 2196a comprises a strap with one or more openings 2196c on one end for engagement with a button or flange 2196d formed or provided on bracket 2196b after the strap has been wrapped around frame 2016a. In this manner, the straps are adjustable to vary the tension applied to support surface 2114. In one embodiment, the strap is formed from an elastic material, such as rubber, so that it can be stretched as it is wrapped around the deck frame and, further, so that the opening can be stretched when pressed on to the button or flange.

Referring to FIGS. 84-94, the numeral 2212 generally designates another embodiment of a patient support system that includes a patient support surface 2214. Support surface 2214, which may be of similar construction to support surface 2114, includes a top cover 2218 and a bottom cover 2220, and one or more storage compartments. In the illustrated embodiment, bottom cover 2220 includes a recess 2282, similar to recess 2182, but which supports a compartment assembly 2290 that is formed from two vertically stacked compartments 2290a and 2290b that are mounted together and then mounted in recess 2282.

Figure 93:
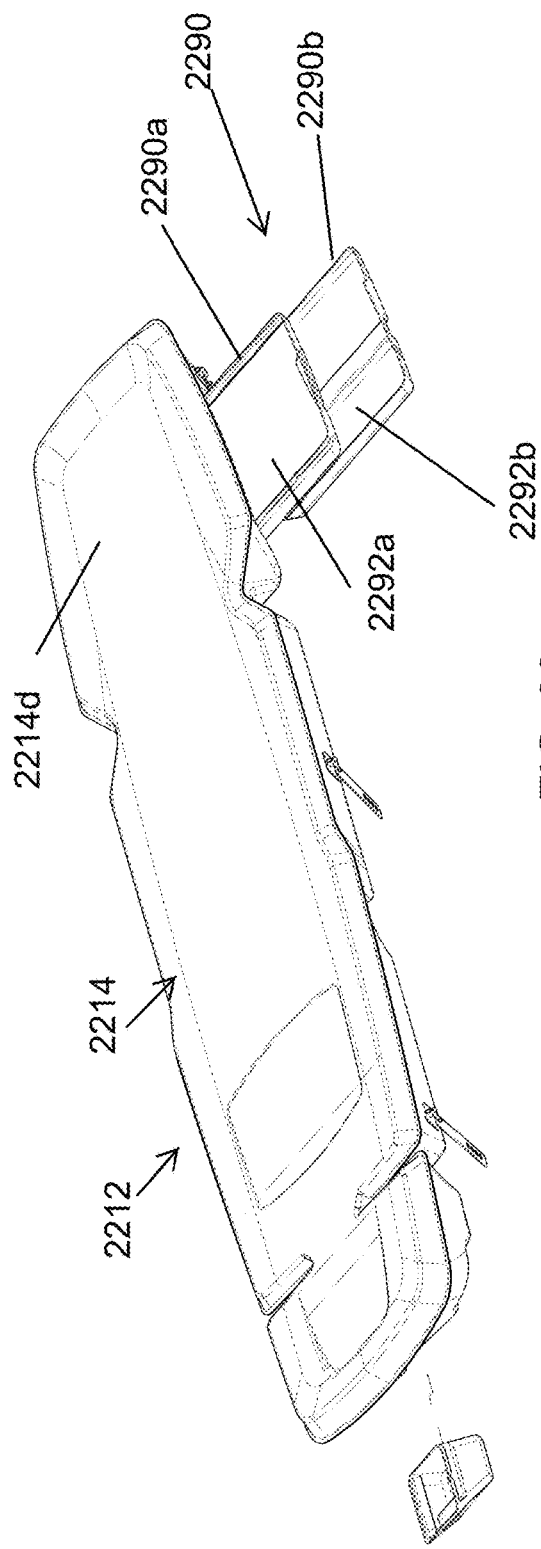
Figure 94:
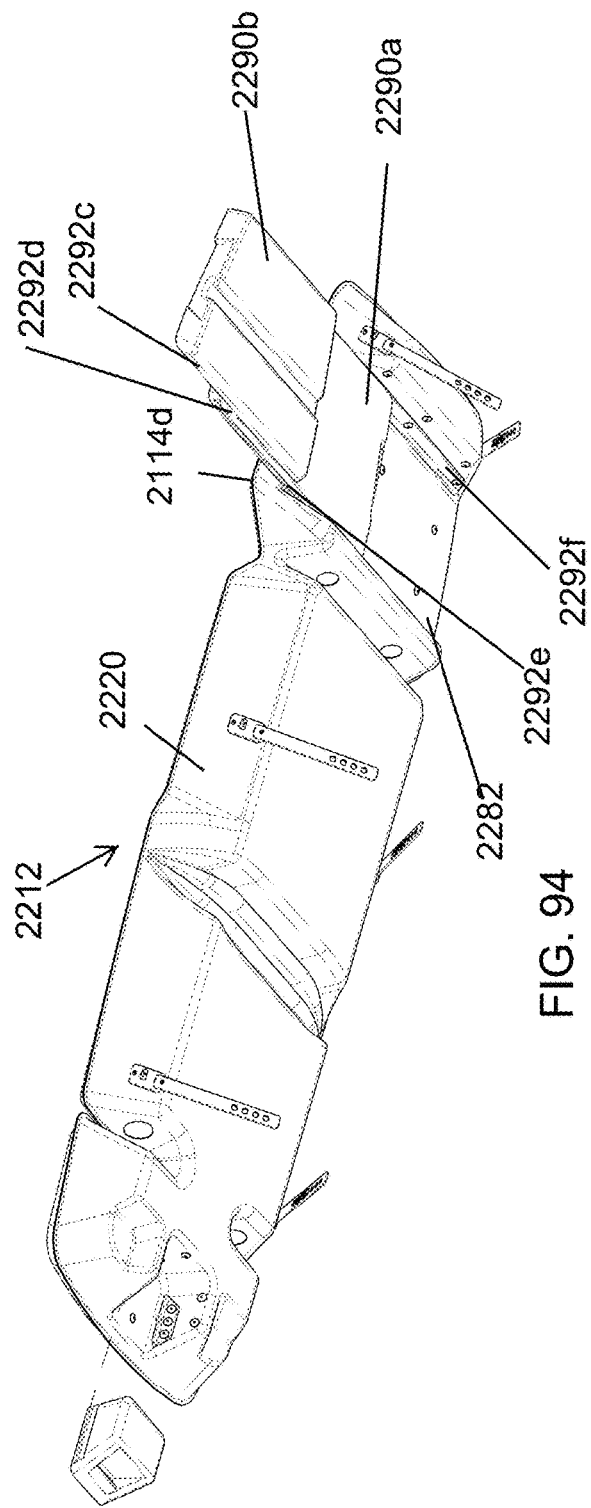
Figure 96:
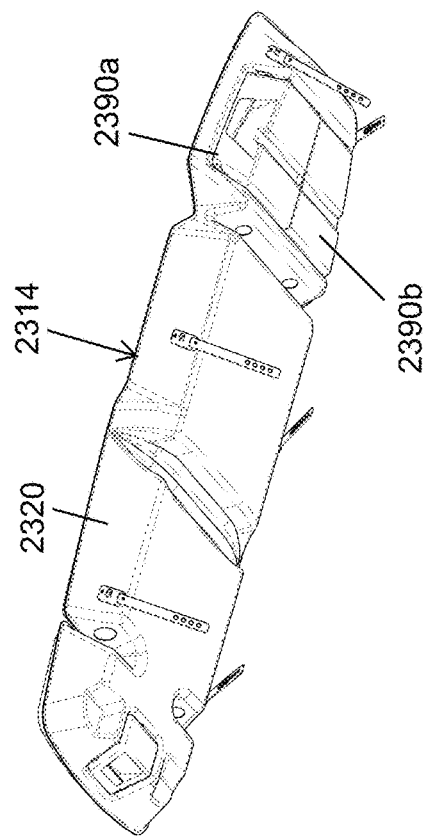
Figure 95:
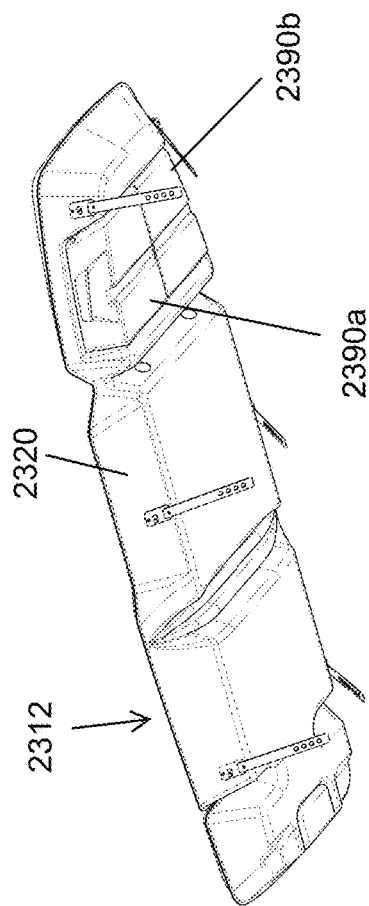

As best seen and understood from FIGS. 93 and 94, compartments 2290a and 2290b are coupled together so that they cooperate together to provide two separate, stacked storage spaces 2292a and 2292b. For example, storage compartment 2290b may be formed or provided with rails 2292c that engage and slide on rails 2292d formed or provided on the opposed lateral sides of compartment 2190a, which in turn is mounted by rails 2292e on rails 2292f provided or formed on opposed sides of recess 2282, in a similar fashion to compartment 2190.

For further optional details of support surface 2214 and the compartments 2290a, 2290b, and optional couplers and other compartments that may be incorporated into surface 2214, reference is made to support surfaces 2014 and 2114, and the other support surface systems described above.

Referring to FIGS. 95-100, the numeral 2312 designates yet another embodiment of a patient support system. Patient support system 2312 includes a patient support surface 2314, which may be of similar construction to the support surfaces described above, and several storage spaces described below. In the illustrated embodiment, bottom cover 2320 includes a recess 2382, similar to recesses 2182 and 2282, but which supports two back-to-back compartments 2390a, 2390b, which are supported so that they can be independently deployed from under surface 2314 from each side of the surface 2314 to allow access into storage spaces 2392a, 2392b of compartments 2390a, 2390b at the same. Similar to compartment 2190, each compartment 2390a, 2390b is formed with or provided with a pair of rails 2392c, 2392d on its opposed side for engagement with and sliding support on rails 2392e, 2393f formed or mounted in recess 2382 to thereby form drawers.

As best seen and understood from FIGS. 97 and 98, each compartment 2390a and 2390b can be deployed from a respective side of surface 2314 independent from the other compartment. Although illustrated as having the same footprint, one compartment may have a larger footprint than the other and, therefore, extend more than halfway across leg and foot section 2314d. Further, while illustrated as being supported on the same pair of rails, separate rails may be formed or mounted in recess 2382 for each compartment.

Additionally, while shown as having a dividing ridge or wall to at least partially bifurcate the storage spaces, one or both ridges or walls may be eliminated or additional walls may be added as described and illustrated above. Further, one or each compartment 2390a, 2390b may have a nested stacked drawer within the compartment to provide three or four compartments. Optionally, the drawers may be configured as side-by-side drawers that extend the full width of the support surface or may be configured as back-to-back and side-by-side to form four or more drawers.

In one embodiment, one or more the compartments may have a slide-out lid that closes the open compartment to form a work surface, but then can be returned from its deployed position (as a work surface) to its stowed position allowing access to the compartment.

The material for forming any of the compartments, rails, and/or doors may include plastic, metal, or a combination of both or composites.

For further details of support surface 2314, including of the couplers and other compartments that may be incorporated into surface 2314, reference is made to support surfaces 2014, 2114, 2214, and the support surfaces described above.

As noted above, the couplers described may be formed from elastic, plastic or metal, such as a punched steel part. Further, as noted the couplers may be joined to or formed with the bottom cover in a number of different ways, including by an adhesive, RF/ultrasonic welding, heat staking, and also riveting or using other fasteners, or a combination thereof. Further, the couplers may be molded into the bottom cover as part of the thermoforming process. Other couplers include buckle, cleats, hooks, snaps, shock cord, suction cups, or magnetic fasteners (such as FIDLOCK magnetic fasteners), or the like. For examples of other optional methods of coupling the patient support surfaces to the deck or frame, reference is made to the above descriptions.

Different connectors, other than male and female connectors may be used, including any mechanical connector that latches, fastens, clips, press-fits on an existing transport apparatus, such as an EMS cot, with or without modifications. This can be used to ensure compatibility with different transport apparatuses and can eliminate design changes required to the transport apparatus.

For example, as described in reference to the embodiment shown in FIGS. 60-69, magnets can be used. Magnets may be enclosed within a sewn/welded pocket that's made of high surface friction textile or film. The magnetic force holds the patient support surface to the metal cot deck and the high surface friction fabric prevents the patient support surface from sliding side-to-side during patient transfers. For example, the upper surface of the top cover 2018 may formed, such as by molding or casting (e.g. cast urethane plastic), with a pattern formed therein to provide the region or regions of higher friction.

As noted in some cases above, suitable materials for any of the storage compartments described above include rigid plastics or flexible plastic or fabric panels. Thus, the compartments may be formed as a rigid box or a soft pocket (i.e. waterproof bag), which are similarly formed by thermoforming, molding, sewing, or RF welding. In any of the embodiments, as described the compartments may be integrated or internal to the patient support surface. When separately formed but integrated, the compartment may be attached to the patient support by sewing, gluing, RF/ultrasonic welding or a combination thereof. Consequently, any or all of the storage compartments may provide fluid impermeable compartments to protect items stored in the compartments from fluid intrusion, but also infection control.

In each case, the material forming the top covers may be a very durable material to allow use of disinfectant, to be machine washed, and/or or contain material or materials that have antimicrobial properties, such as MICROBAN, copper, silver, or other antimicrobial materials.

For examples of suitable couplers that may be used to secure the patient support surface to the transport apparatus and/or to secure accessories to the patient support surface, reference is made to the other embodiments described herein.

Referring to FIG. 101, the numeral 2600 generally refers to a pediatric restraint assembly for use in conjunction with an existing adult restraint, for example, an adult EMS cot restraint (such as RUGGED restraint available from Stryker), which is configured for restraining pediatric patients, but may be used for small adults. As described below, pediatric restraint assembly 2600 may form a five point harness that is configured so that it can accommodate patients that weigh in a range of about 4 to 99 lbs. Further, although mounted to an existing adult restraint, pediatric restraint assembly 2600 is configured so that it can be used while the adult restraint is being used as well, as shown in the incorporated provisional application. Alternately, instead of mounting to an adult restraint, pediatric restraint assembly 2600 may be mounted to the transport apparatus via strap extensions that are secured to the transport apparatus in a similar manner as a conventional adult restraint but without the restraint buckle, and in some cases without any adjustment buckles given that the adjustment may be made with the pediatric restraint assembly 2600.

Referring again to FIG. 101, pediatric restraint assembly 2600 includes a back panel 2610 and a front panel 2630 and a plurality of straps 2612 coupled thereto for securing the assembly 2600 to the transport apparatus, in some cases directly and in others, as noted, via the adult restraint R. As will be more fully described below, pediatric restraint assembly 2600 is secured to the patient support at five anchor points—two shoulder anchor points, two waist anchor points, and one leg anchor point.

In the illustrated embodiment, each strap 2612 is coupled to back panel 2610 through a shoulder opening 2610a provided at the shoulder end of back panel 2610 to form shoulder strap portions 2614. Depending on the material forming panel 2610, openings 2610a may be reinforced with plastic inserts or grommets. Each strap 2612 is additionally coupled to front panel 2630 through waist openings 2610b provided by loops at waist height locations on front panel 2630 to form waist strap portions 2616, 2618. A buckle 2612a (e.g. buckle tab) is slidably mounted along each strap 2612 along waist strap portions 2616 and 2618 to releasably engage a three-point buckle described below. The upper ends of straps 2612 each include a buckle 2612b (e.g. female buckle half) for engaging the buckle (e.g. male buckle half) mounted to the cot on straps, such as described and show in FIG. 56, for example, in the incorporated provisional patent application. Each of the straps 2612 may be adjustable using various forms of buckles to accommodate different sized patients and, further, to keep the hips of the patient aligned with fowler/seat joint (joint between the seat section and back section of deck 2016).

In the illustrated embodiment, back panel 2610 has an extension to form a leg portion that extends between the patient's legs and supports front panel 2630 and three-point buckle restraint 2632 mounted thereto for receipt of buckles 2612a. The extension may be an extension of the panel or a strap, such as described below. Front panel 2630 supports a three point buckle restraint 2632 to which the extension is buckled to allow adjustment of front plate 2630 and buckle restraint 2632 relative to panel 2610. Alternately or in addition, the back panel itself may be adjustable in length, as described in reference to FIG. 59 of the references provisional patent application.

As noted above pediatric restraint assembly 2600 may couple to an adult restraint, already attached to the transport apparatus. In the illustrated embodiment, as noted, straps 2612 form shoulder strap portions 2614 with each releasably coupling on one end to the shoulder straps of the adult restraint at shoulder anchor points provided on the adult restraint shoulder straps via, for example, buckles 2612b. Thus, the adult restraint may provide the shoulder anchor points for the pediatric restraint assembly 2600.

The ends of waist straps 2616 and 2618 are also looped through openings 2610c formed in back panel 2610 and include buckles 2640 for engaging buckles secured to the transport apparatus by straps (not shown, but see straps 1640 in the above embodiment) that loop around the frame of the deck. For example, the straps may be located on the deck frame of the back section (commonly referred to as the "Fowler section") of the deck adjacent the hinges to the seat section (and hence are mounted to the moving portion of the deck) and serve as the pediatric restraint assembly waist anchor points.

In one embodiment, each of the above anchor points may be provided on the adult restraint shoulder straps (e.g. around their shoulder height) and further, optionally, between the head section and the back section of the patient support surface (such as in any of the above described patient support surfaces) so that they do not interfere with the use of the adult restraint. In this configuration, an adult can be restrained in the cot restraint while the pediatric restraint assembly is used.

In addition to securing pediatric restraint assembly 2600 to the adult restraint, pediatric restraint assembly 2600 may also be secured to the transport apparatus via additional anchor points mounted directly to the transport apparatus in lieu of the buckles mounted to the adult restraint. As noted above, additional anchor points may be provided by straps with buckles mounted to transport apparatus, which are then engaged by buckles 2640.

Referring again to FIG. 100, a fifth anchor point for the pediatric restraint assembly 2600 is the leg anchor point, which is formed by the leg extension of back panel 2610, which in the illustrated embodiment is formed by a strap 2650 that is secured on one end to the lower end of panel 2610 and loops around the adult restraint waist strap, which is then secured to buckle restraint 2632. In this manner, back panel 2610 and front panel 2630 are selectively joined via strap 2650 so that the back panel and the front panel are separate.

Optionally, to better manage and maintain alignment of strap 2650, front panel 2630 may include a pair of openings 2630a, and optionally reinforced openings, through which strap 2650 is threaded and passed through for engagement with buckle restraint 2632.

In each case, the respective buckles may be slidably mounted to the respective straps or strap portions to help adjust to smaller or larger patients and also to provide greater access to the patient when needed. In addition, each waist strap 2616, 2618 and leg strap 2650 may include a pull tab or loop 2660. In addition to easing pulling of the straps, loops 2660 provide tactile indications of touch points/adjustment points.

In addition to loops 2660, each waist strap 2616, 2618 and leg strap 2650 may include a clip 2662, such as a sliding clip, which can be used to keep loose ends of the respective strap tethered (to the strap) to maintain the straps tight and organized.

Panels 2610 and 2630 may be formed from a variety of solid materials (though they may be hollow), including nylon or molded plastic or rubber (or a composite thereof or metal as noted below), that is then over molded with rubber, including foamed rubber, such as low density foam, to provide a cushioned interface. For example, back panel 2610 may over molded with rubber, including foamed rubber, such as low density foam, to provide a cushioned interface both on the side facing the pediatric patient and the side facing the adult. The front panel may be similarly over molded, at least on the side facing the pediatric patient. Additionally, the leg portion of back panel 2610 and of the front panel 2630 may include over molded edges to ensure comfort to the crotch of the pediatric patient. Consequently, the panels hold their overall shape, absorb energy, and transfer energy to the adult restraint or transport apparatus in varying degrees depending on the flexibility of the panels. Or stated another way, the panels will resist being bent or resist loads or twisting applied there to, though to varying degrees depending on the amount of flexibility that is desired.

Figure 102:
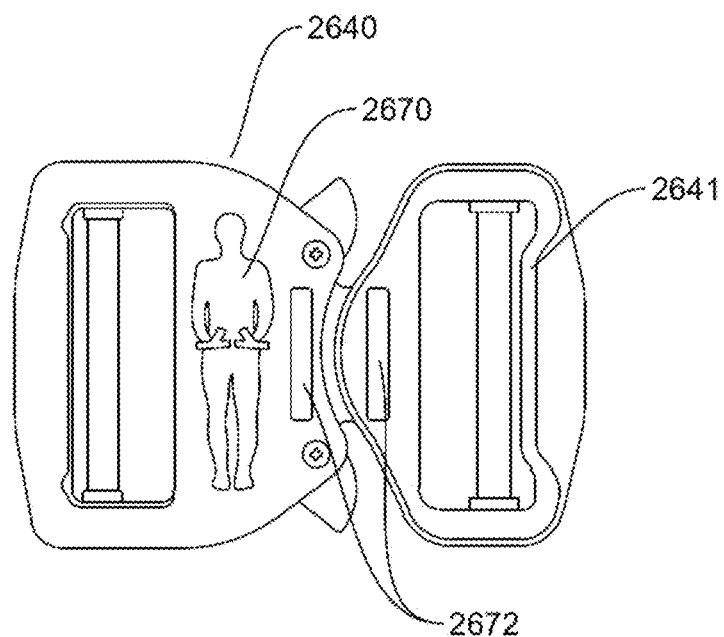
Figure 102A:
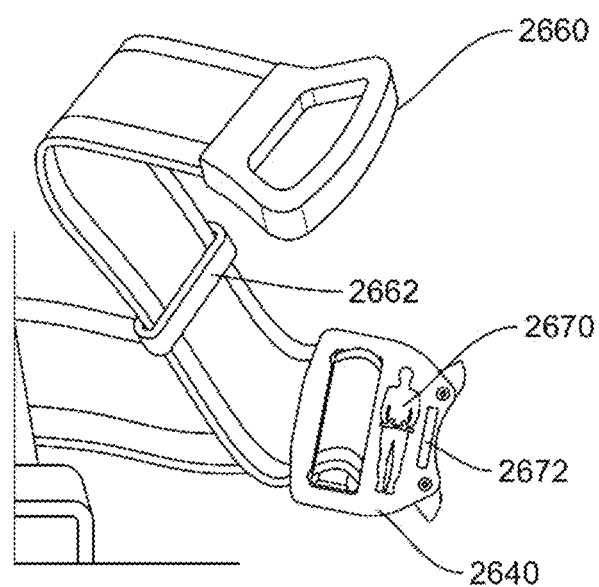

To ease installation and use of restraint assembly 2600, icons and/or color coding can be used on the buckles so that each buckle can be quickly and easily matched up with the correct buckles on the adult restraint or on the cot. For example, referring to FIG. 102, for example each buckle 2640 (2612b) may include an icon 2670 that is a graphical representation of a person and with the location of the strap associated with the buckle illustrated on the icon to provide a visual indication of the placement for the strap relative to the person on the icon to indicate the location for the buckle.

For example, in the illustrated embodiment the strap is shown as a waist buckle for securing the waist of the patient. Consequently, the type of buckle and where is should be placed is understood by any user or caregiver.

In addition, or in lieu thereof, each buckle may include a color icon 2672, such as a color bar, so that a user can match the color icons with the color icon on the buckle on the cot or adult restraint to make sure they are securing the buckle (on the pediatric restraint assembly) to the correct buckle on the cot or adult restraint. In this manner, a user can identify exactly what buckle the restraint assembly buckle should be secured to—including the left or right side waist buckle.

Although only the bar icon is illustrated as color coded, it should be understood that the whole buckle may be color coded or the icon of the person can be color coded.

Reflective elements may also be incorporated into restraint assembly to provide better visibility in low light conditions, including smoke conditions. For example, referring again to FIG. 101, reflective elements 2680 may be provided on straps 2612, and on front panel 2630. Optionally, reflective elements 2680 on straps may include one or more visual marking or indicators 2680*a*, 2680*b* that may be used by a caregiver to determine whether straps have been evenly pulled tight by confirming alignment of the markings.

In one embodiment, the straps 2612 may be color coded so that the color indicates that they are distinct from the cot restraints and, further, may be color coded to designate and help distinguish between left and right straps. For example, the left strap may have one color—or color marking, e.g. trim or pattern, while the right strap may have another color (or trim or pattern) distinct from the left strap color, both of which are different and distinct from the cot restraint strap colors.

To secure the pediatric patient, user places the patient on top of the open restraint assembly and brings the shoulder portions 2614 of the straps 2612 over the patient's shoulders and secures the shoulder strap portions 2614 together with buckle restraint 2632 at the infant's waist. The user then brings the waist strap portions 2616 and 2618 over the infant's waist/hip and couples buckles 2640 to the buckles on the cot at or near the waist of the patient. Then strap 2650 is pulled between the legs of the patient and buckled to buckle restraint 2632. Lastly, tighten all the straps to create a snug and secure fit.

To provide additional support and/or padding to the pediatric patient restraint assembly 2600 may incorporate additional padding. For example, padding can be at the shoulder straps and/or padding can be added support to a small infant's head. For further details of additional padding or cushioning, reference is made to the various headrests and other cushioning described herein.

Referring again to FIG. 101, restraint assembly 2600 includes a head and neck support assembly 2690. Head and neck assembly 2690 includes a transverse body 2690*a*, which extends between and is slidably mounted to assembly 2600 on shoulder straps 2614 by a pair of strap engaging portions 2690*b*. Body 2690*a* may be formed, such as by molding, from a rigid material, such as plastic, or a bendable rigid material, which is then over-molded with rubber or a soft foam to provide a soft exterior surface suitable for use with a pediatric patient's head and/or neck.

Optionally, each strap engaging portion 2690*b* may include a movable latch 2692 for engaging the respective strap to secure the head and neck assembly in position along the respective straps. Each latch 2692 may be formed from a rigid material, such as plastic, and comprise wedge shaped slide that is mounted on pair of pins in tracks formed in body 2690*a* so that it can move toward or away from the respective strap. The slide has a high friction surface, such as knurled surface, which when pressed and moved toward the strap fixes the position of assembly 2690 along the strap. To release the latch, the slide may be simply pulled to thereby release the frictional engagement off the strap.

In another embodiment the latch may be a rotating member mounted about a pair of pins, which has an enlarged lobe that also has a high friction surface, which when pressed toward the strap fixes the position of assembly 2690 along the strap. To release, the latch is then pulled out of engagement with the strap.

To facilitate actuation of the latch, latch 2692 may include a finger recess and/or further may be over-molded with a high friction surface for an easier grip.

Optionally, head and neck restraint assembly 2690 may be combined with one or more additional cushions, including inflatable cushions.

Referring to FIGS. 103 through 108, the numeral 2710 refers to a head cushion assembly that may be used in pairs in conjunction with restraint assembly 2600 to form a headrest. In the illustrated embodiment, cushion assembly 2710 is configured so that it can be used as a left or right side cushion assembly with an elongate cushion 2712 and a mounting structure 2714. Cushion 2712 may be formed from a tubular piece of cushioning material that has a round or rounded cross-section and which is enclosed in a fabric cover 2712*a* formed from a soft material, such as nylon or fabric. For example, the cushioning material may be foam, a foam covered bendable piece of plastic (so the shape of the cushion may be adjusted), super elastic material, or an inflated bladder.

In the illustrated embodiment, mounting structure 2714 is in the form of two panels 2714*a* also of soft material, such as nylon or fabric. Panels 2714*a* are joined at one end with cover 2712*a*, for example, by stitching or welding (or may be formed from extensions of the cover) and secure around straps 2612 by fasteners 2716, which are mounted at their distal edges. For example, suitable fasteners may include Velcro strips, snaps, buttons, or magnets.

Each cushion assembly 2710 may be positioned between pediatric patient's head and a corresponding strap and then secured in place by mounting structure 2714 or, as described below, by clips.

Referring to FIGS. 109-114, the numeral 2810 refers to another embodiment of a head cushion assembly that also may be used in conjunction with the pediatric restraint assemblies described herein, including restraint assembly 2600. In the illustrated embodiment, cushion assembly 2810 is configured so that it can provide cushioning on both the left and right side of the head and includes a generally butterfly shaped cushion 2812. Cushion 2812 may be formed from a single piece of foam or multiple pieces of foam or an inflated bladder or multiple inflated bladders, which is or are enclosed in a soft cover 2812*a*, such as nylon or fabric.

In the illustrated embodiment, cushion assembly 2810 includes a downwardly depending mounting structure 2814 in the form of a panel 2814*a* of soft material, such as nylon or fabric, also similar to or the same as cover 2812*a*. Panel 2814*a* may be formed from an extension of the cover or may be joined to cover 2812*a*, for example, by stitching or welding. Panel 2814*a* is sufficiently long so that it extends behind the back of the patient and is, therefore, held in place by the weight the patient. Alternately, as described below, clips may be mounted to the cushion to secure it to the shoulder straps.

Referring to FIGS. 115-120, the numeral 2910 refers to another embodiment of a head cushion assembly that also may be used in conjunction with the pediatric restraint assemblies described herein, including restraint assembly 2600. In the illustrated embodiment, cushion assembly 2910 is configured so that it can provide cushioning around the patient's head and on both the left and right side of the head. Cushion assembly 2910 includes a generally inverted U-shaped cushion 2912 with a central panel 2912*a* that is generally flat, though it too may be inflated but to a lesser degree than the U-shaped portion of the cushion. Cushion 2912 may be formed from a single piece of foam or an inflated bladder, which is enclosed in a soft cover 2912*b*, such as nylon or fabric.

In one embodiment, two panels of gas impermeable fabrics are welded together by an outer perimeter seam and an inner seam that form the U-shaped cushion, with the an inlet in fluid communication with the U-shaped portion to inflate the cushion. Optionally, it may include one or more valves to allow for self-inflation, for example, once unfolded. As noted above, the central portion 2912*a* may be left uninflated or be in fluid communication with the U-shaped cushion to allow it too to be inflated or have a separate inlet to allow it to be inflated.

In the illustrated embodiment, cushion assembly 2910 also includes a downwardly depending mounting structure 2914 in the form of a panel 2914*a* of soft material, such as nylon or fabric, also similar to or the same as cover 2912*b* (or the panels forming the bladder). Panel 2914*a* may be formed from an extension of the cover (or the panels forming the bladder) or may be joined to cover 2912*b* (or to the panels), for example, by stitching or welding. Again, panel 2914*a* is sufficiently long so that it extends behind the back of the patient and is, therefore, held in place by the weight the patient. Alternately, as described below, clips may be mounted to the cushion to secure it to the shoulder straps.

In any of the above head cushion assemblies, the assemblies may be mounted to the shoulder straps or strap portions of any of the pediatric restraint assemblies, such as shoulder straps 2614, by clips are secured on one end (at or near their hinge) to the head cushion assembly and that fold over the strap and then secure the head cushion assembly in place along the straps and thereby form a headrest. For example, the clips may be constructed by two hinge halves—one back hinge half extending behind the strap and the other top hinge half (formed by a pair of flexible fingers) folding over the strap, which then engages the back hinge half and grips the strap there between. To release for adjustment or removal, the fingers of the top hinge half may be squeezed together to release hold of the back hinge half and in turn the strap.

Referring to FIG. 124, the numeral 3000 generally refers to another embodiment of a pediatric restraint assembly for use in conjunction with transport apparatus and optionally with an existing adult restraint, for example, an adult EMS cot restraint (such as the RUGGED restraint available from Stryker). Although pediatric restraint assembly 3000 is illustrated and described in the context of restraining pediatric patients, it also may be used for small adults similar to the previous embodiments.

Similar to the previous embodiments, pediatric restraint assembly 3000 may form a five point harness that is configured so that it can accommodate patients that weigh in a range of about 4 to 99 lbs. Further, in the illustrated embodiment, pediatric restraint assembly 3000 is configured to couple to an existing adult restraint, and optionally while the adult restraint is being used by an adult as shown in the incorporated provisional application. Alternately, instead of mounting to an adult restraint, pediatric restraint assembly 3000 may be mounted to the transport apparatus via strap extensions that are secured to the transport apparatus in a similar manner as a conventional adult restraint but without the restraint buckle, and in some cases without any adjustment buckles given that the adjustment may be made with the pediatric restraint assembly 3000 by the various buckles described below.

Referring to FIG. 125, pediatric restraint assembly 3000 includes a back panel 3010 and a seat panel 3020 and a plurality of straps 3012 coupled thereto for securing the assembly 3000 to the transport apparatus, in some cases directly and in others, as noted, via the adult restraint R, and for securing the patient to the pediatric restraint assembly 3000. As will be more fully described below, pediatric restraint assembly 3000 may be secured to the patient support at five anchor points—two shoulder anchor points, two waist anchor points, and one leg anchor point.

In the illustrated embodiment, straps 3012 include two sets of straps—restraint assembly anchor straps to anchor the restraint assembly to the transport apparatus and patient restraint straps (which form a patient restraint or harness) to restrain the patient on the restraint assembly. For example, in the illustrated embodiment, straps 3012 include two shoulder/waist straps 3014 (to restrain the patient on the restraint assembly), two back anchor straps 3016 (to anchor the restraint assembly to the transport apparatus), and one seat anchor strap 3019 (to anchor the restraint assembly to the transport apparatus). Back anchor straps 3016 may be threaded through slotted openings 3010*a* formed in back panel 3010 and in slotted openings 3020*a* formed on seat panel 3020 to couple the seat and back panels together and anchor the back panel to the transport apparatus, though it should be understood that the two panels—the back panel and seat panel—may be formed as a single unity panel, as described below.

For example, as best seen in FIGS. 152 and 154, one end of each back anchor strap 3016 may include a buckle 3016*a* to trap one end of the strap and secure the strap to seat panel 3020 in a respective slotted opening 3020*a* in seat panel 3020 (FIG. 152). The other end of each strap 3016 is threaded through slotted openings 3010*a* in panel 3010 to emerge from the back of panel 3010 (as best understood from FIG. 124A) and for attachment to a second buckle 3016*b*, for example, a buckle with a J-coupler, for coupling the assembly 3000 to the EMS restraint as shown in FIGS. 149 and 150. Buckle 3016*b* may comprise an adjustable buckle to adjust the length of strap 3016, for example, when an adult is also sitting on the cot. In the illustrated embodiment, the EMS restraint strap may include an engagement structure E, such as a loop secured thereto, for engagement by buckle 3016*b*.

Referring to FIGS. 125, 127 and 128, each shoulder/waist strap 3014 includes a shoulder buckle 3014*a* secured to each upper end to engage a shoulder anchor strap 3018, for example, via a loop 3018*a*, which is looped through an upper slotted opening 3010*b* (e.g., at shoulder height) formed in the back panel 3010 and then sewn back on itself to form two loops—one to anchor the strap to back panel 3010 and the other for engagement by buckle 3014*a*. Optionally, anchor strap 3018 may include a buckle (similar to buckle 3016*a*) to trap the end of the strap in slotted opening 3010*b* instead to provide a removable anchor strap.

As best seen in FIG. 125, each shoulder/waist strap 3014 also supports a buckle 3014b between its two ends for engaging a three point center or groin buckle restraint 3030 (FIGS. 124 and 125), which located between the legs of a patient when seated on seat panel 3020. Buckle restraint 3030 includes a strap 3030a for extending through one of the slotted openings 3020b (as best suited for the patient) in seat panel 3020 and a buckle 3030b (beneath seat panel) to thereby secure the buckle restraint 3030 and strap 3030a to the seat panel 3020. While three slotted openings 3020b are shown, more or fewer openings may be provided to increase or reduce the adjustability of the restraint assembly.

The other end of each shoulder/waist strap 3014 (after buckle 3014b) is coupled to an adjustment buckle 3014c (FIGS. 124B, 125 and 154), which also includes a strap 3014d (FIG. 125) for extending through a slotted opening 3020c in seat panel 3020 and which is retained therein by a buckle 3014e mounted to strap 3014d (see FIG. 125) located on the underside of the seat panel. Thus, strap 3014d forms a waist anchor strap. Again, several slotted openings 3020c in seat panel 3020 may be provided to adjust the anchor point for waist anchor strap 3014d to accommodate larger patients and increase the adjustability of assembly 3000.

Seat anchor strap 3019 is threaded through a pair of slotted openings 3020d (FIGS. 132, 135B) formed in the central portion of seat panel 3020 and includes buckles 3019a, such as adjustable buckles with J-couplers, adjacent its opposed ends for securing the seat panel to the EMS cot, for example, the anchor points described in reference to the previous embodiment and as understood from FIGS. 150, 153, and 155. Additionally to help better retain and provide a greater downward restraint on the restraint assembly, anchor strap 3019 is also threaded through slotted openings 3020e (see e.g. FIGS. 124, 151, 154, and 155) which are located in the angled sides of seat panel 3020, more fully described below.

As best seen in FIG. 128, back panel 3010 may be divided into two sections—an upper section, which may be configured as a head support, and a lower section that supports the back of the patient. In the illustrated embodiment, back panel 3010 is formed by a unitary panel and divided by two inwardly extending slots or recesses 3022 that bifurcate the panel into lower portion 3024 and upper portion 3026, which as noted may be configured to form a head support. Further, the upper portion and the lower portion may be provided with a hinge 3026c (FIG. 129) so that the upper portion 3026 may be folded over the lower portion 3024, as discussed in reference to FIG. 145. For example, a suitable hinge may a living hinge.

Further, as best seen in lower portion 3024 and upper portion 3026 may each include angled sides 3024a and 3026a to provide some lateral support to the patient, and which may be configured to fold further to make the restraint assembly more compact and have a smaller footprint for easy storage. For example, each upper and lower section of panel 3010 may have a pair of hinges 3026b, such as living hinges or mechanical hinges, between the central panel portion and the side pane portions. For example, the angles A, B (FIG. 131) of the angled sides of the upper and lower sections (as measured from horizontal) may be the same or may be different and fall in a range of 10 to 45 degrees, 15 to 30 degrees or 20 to 25 degrees. It should be understood these angles are just exemplary. Optionally, the pair of hinges for the upper section 3026 may be more closely spaced than the hinges that form the angled sides of the lower section, as see in FIG. 129 so that the respectively angled sides are spaced to cradle the head (to form a headrest) and back respectively.

Similarly, seat panel 3020 may be formed with angled sides 3028, which may also fold about hinges 3028a and are optionally spaced to cradle the hips of a patient. Further, sides 3028 may have intermediate bends or hinges 3028b to allow seat panel to conform to the underlying EMS cot mattress.

Panels 3010 and 3020 may be formed from a variety of materials, including plastic, such as nylon, metal, or rubber (or composites), and may be formed (in whole or in part) by molding, for example by cast molding or injection molding. Optionally, as noted, back panel 3010 and seat panel 3020 may be separately formed and then coupled together, such as described, by straps 3016 or other straps. Thus, the panels may be separate and may be spaced apart so that they have a distance of about % inches to about 24 inches—depending on the size of the patient. Or they may positioned so that they have an abutting or overlapping relationship with 0 separation. Alternately, back panel and seat panel may be formed as a unitary panel, with an optional living hinge between the two portions of the panel.

For example, referring to FIGS. 133A and 133B, seat panel 3020 may be molded or formed from plastic and/or a metal and further formed with integrated anchor points. Referring again to FIGS. 133A and 133B, hooks 3015, such as G-hooks, may be integrated, such as by fasteners 3015a, or simply may be integrated by insert molding.

Referring to FIG. 133C, in another embodiment of seat panel 3020', engagement structures 3015b', such as loops, may be formed in the panel during the panel forming process or post attached, for example, by adhesive or welding, which are then engaged by hooks 3015', such as G-hooks, which are secured to the end of the respective strap. Similar to seat panel 3020, seat panel 3020' may mount hooks 3015' via fasteners 3015a' to the seat panel rather than molding them or bonding them.

Optionally, the seat panel may be formed with reinforcing and/or other retention structures, such as ribs or relief areas. For example, referring again to FIGS. 133A and 133B, the central portion 3021 of the seat panel base may include reinforcing ribs 3021a and a relief area 3021b, which extends around the through-openings, for example, where the buckle restraint is anchored. The size and shape of the ribs and relief area may vary depending on the material and the desired weight capacity of the restraint assembly.

Referring to FIG. 133C, seat panel 3020' may include pairs of ribs 3021a' that reinforced the seat panel but also form a track to help retain the respective strap extending there between in position. Optionally, the seat panel 3020' may also include recesses for receiving any of the buckles extending under the seat panel to thereby optionally provide a flush arrangement where the buckles do not protrude from the seat panel to minimize detection by a person upon whom the restraint assembly rests.

Optionally, a portion or the entire panel (one or both) may be provided with cushioning material, such as shown in FIG. 135A. For example, the panels may be co-molded (e.g. during injection molding) or over molded with a cushioning material, such as rubber or a super elastic material, including foamed rubber, such as low density foam, to provide a cushioned interface. For example, back panel 3010 may over molded with rubber, including foamed rubber, such as low density foam, to provide a cushioned interface both on the side facing the pediatric patient and the side facing the adult. The seat panel may be similarly over molded, at least on the side facing the pediatric patient.

Optionally, both sides of the panels may be provided with cushioning material (e.g. on the pediatric facing side and the adult facing side) (FIG. 135B) to provide a more comfortable interface when the restraint assembly is used at the same time an adult is being transported on the cot. In one embodiment, the cushioning material on either panel may be formed with a surface topography that follows (or at least somewhat follows) the contour of the adult patient's body, e.g., the legs, and/or of the pediatric patient's body to provide a more comfortable interface and possibly reduce any pressure points. As noted the cushioning material may be integrated with the panels, e.g., though molding or by using an adhesive, or may be separate for cleaning or disposal.

In addition or instead, panels 3010 and 3020 may be covered with a cover or covers, which may have cushioning material, to facilitate cleaning or disposal.

Additionally, the various slotted openings in the panels may be reinforced with grommets, including molded plastic or rubber grommets, to protect the straps, such as shown in FIGS. 126, 127, 132, 133, and 135B-135C.

Optionally, in some embodiments, the shoulder anchor straps 3018 may be anchored in upper slotted opening 3010b provided in back panel 3010 by buckles 3018b (FIG. 135C), which for example, may be captured on the back side of back panel 3010 and located in a recess in the cushioning material, such as foam, as seen in FIG. 135C. Similarly, the buckle 3030b on the end of buckle restraint strap 3030a may be located in a recess formed in the cushioning material as shown in FIG. 135B. Buckles 3014e of waist anchor straps 3014d may also be located in recesses provided or formed in the cushioning material (FIG. 135B) and/or in recesses formed in the seat panel as shown and described in reference to FIG. 133C. In this manner, when restraint assembly 3000 is placed on the lap of an adult, the adult will not feel the buckles.

As noted, each of the anchor points, such as slotted openings 3010a, 3010b, 3020a, 3020b, 3020c, and 3020d in the back and seat panels may be provided with grommets, such as plastic grommets, to reduce wear and tear on the strap webbing. The grommets may also be located in recesses formed in the cushioning material, as best seen in FIGS. 135B and 135C.

As noted above, the seat panel may be made from a variety of materials, including metal. Referring to FIGS. 132A-132C, seat panel 312C is formed from a metal plate or substrate that is stamped. Similar to seat panel 3020, seat panel 3120 includes openings 3210a for managing and anchoring the straps, as described above, and a central relief area 3121b, which reinforces the area around the buckle restraint anchor openings. Seat panel 3120 may be similarly covered by a cushioning material, such as foam, by over molding, and, further, formed with a plurality of contours to more closely follow the shape of a patient supported thereon.

Referring to FIG. 136, the numeral 3200 generally refers to another embodiment of a pediatric restraint assembly for use with transport apparatus and optionally for use in conjunction with an existing adult restraint, for example, an adult EMS cot restraint (such as the RUGGED restraint available from Stryker). Similar to the previous embodiments, pediatric restraint assembly 3200 may form a five point harness that is configured so that it can accommodate patients that weigh in a range of about 4 to 99 lbs. Though it should be understood, as in the case of the previous embodiments, as will be more fully described below in reference to FIGS. 146A-146D, other harness configurations may be used.

In the illustrated embodiment, pediatric restraint assembly 3200 is also configured to couple to an existing adult restraint, and optionally while the adult restraint is being used by an adult as shown or may be mounted to the transport apparatus via strap extensions, as described above.

Referring again to FIG. 136, pediatric restraint assembly 3200 includes a back panel 3210 and a seat panel 3220, and a plurality of straps (see previous embodiments) coupled thereto for securing the back panel 3210 to the seat panel 3220 as well as coupling the assembly 3200 to the transport apparatus and/or to the adult restraint R. Additionally, assembly 3200 also includes straps to form a harness for securing a patient thereon which are coupled to seat and back panels in a similar manner as described above. For details of an exemplary five point harness with two shoulder anchor points, two waist anchor points, and one leg anchor point, reference is made to the above descriptions. Similar to some of the above embodiments, the panels are separate and may be spaced apart so that they can have a distance of about % inches to about 24 inches—depending on the size of the patient. Or they may positioned so that they have an abutting relationship (or even an overlapping relationship) with 0 separation.

In the illustrated embodiment, seat panel 3220 also includes a central portion 3221 and two upwardly extending angled sides 3228, which may also fold about hinges 3228a and are optionally spaced to cradle the hips of a patient. Further, sides 3228 may have intermediate bends or hinges 3228b to allow seat panel to conform to the underlying EMS cot mattress. In one embodiment, seat panel 3220 and back panel 3210 are each molded with a rigid fixed configuration (except optionally e.g. the headrest portions 3226a described below).

Sides 3228 may also include flanges 3228c to form arm rests at their upper ends, which may be more suitable for children or small adults. The flanges 3228c may be covered, such as by over molding with a cushioning material to form arm rest cushions 3228c', such as shown in FIG. 136D. Sides 3228 may also form mounting surfaces for mounting brackets 3250, for example with cam arms that frictionally hold straps therein when rotated and clamped in their closed positons. Brackets 3250 may be used to secure the waist anchor straps, depending on the size of the patient, or may be used to secure the seat anchoring straps.

In the illustrated embodiment, seat panel 3220 is reinforced, for example, around the buckle restraint anchor region. For example, the central portion 3221 of seat panel 3220 may have raised or relief potion 3221b arranged so that it can be located between the legs of a patient, which reinforces, as noted the anchor point for the harness buckle restraint 3230. The relief may be wedge-shaped and extend from the free edge of seat panel 3220 to the through slotted opening 3220a.

As best seen in FIGS. 136A and 136B, the strap 3230a of the buckle restraint 3230 may extend through opening 3220a and can be anchored thereto by a buckle 3230b, which in the illustrated embodiment is mounted beneath the relief area and mounted to the underside of seat panel 3220, for example, by fasteners or via an adhesive (FIG. 136C). Buckle 3230b may be similarly formed with a hinged cam arm that uses friction to hold the strap in place once the cam arm is moved to its closed position. In this manner, the length of the buckle restraint strap may be adjusted to suit the size of the patient.

To ease handling of strap 3230a, strap 3230a may have an enlarged distal end 3230d, which may be formed from folding over the end of the strap, which is then secured in place by stitching or glue. In other embodiments, a plastic or rubber tab or other fabric, such as a color coded pierce of webbing, may be secured to the end of the strap by stitching or glue or molded thereon. As described below, the straps or accessories may be color coded to assist a caregiver in using the restraint assembly system.

As best seen in FIG. 136, the shape of the back panel 3210 may vary and the number of openings 3210a may vary to provide anchor points for the various straps and/or allow the various straps described herein to be threaded through the back panel. Further, similar to some of the previous embodiments the back panel may include a headrest that is configured to improve the comfort and/or support of the head of the patient. For example, back panel 3210 may have a headrest 3226 with articulatable headrest portions 3226a on either side, which can be adjusted to cradle the head of the patient. Articulatable headrest portions 3226a may be hinged to a central portion 3227 of headrest 3226 and, further, hinged so that their positions can be fixed at least until a sufficient force is applied to move them, for example using friction hinges 3226b. To facilitate movement of headrest portions 3226a, each headrest portion may include a pull tab 3226c, for example, formed from a rigid plastic flange or a flexible elastomeric or fabric strip formed or attached to the edge of the respective headrest portion.

Referring to FIG. 136D, in another embodiment of seat panel 3220', relief 3221b' includes the slotted opening 3220a' for receiving the strap of the buckle restraint 3230. In this illustrated embodiment, relief 3221b' includes two openings 3220a' so that strap 3230a can loop back though the openings to secure to itself using a buckle 3230b' mounted to the end of strap 3230a. For example, as best seen in FIG. 136E, strap 3230a may include a plurality of engagement structures 3230e, such as loops, for engagement by buckle 3230b', which is mounted to the end of the strap via a loop formed in the end of the strap. Engagement structures 3230e may be formed by a loop of webbing or plastic loops that are sewn or glued at spaced intervals to the strap to provide adjustment to the effective length of the tether formed by the strap.

Referring to FIGS. 136F-H, in another embodiment of seat panel 3220', relief 3221b" includes a plurality of C-shaped openings 3220a" for receiving the strap of the buckle restraint 3230. In this illustrated embodiment, strap 3230a can be inserted through the openings without having to thread the strap through the relief and instead may have a looped end that can be simply slid onto one of the central fingers 3220f" of openings 3220a" (FIG. 136G).

Alternately, as best seen in FIG. 136H, the strap may still be thread through the openings in the relief 3221b" but then captured therein by a buckle 3230b. For example, one of the openings may be slotted opening, which traps the buckle and with the remaining openings allowing the strap to be loped through them to adjust the length of the strap.

Referring to FIGS. 136J and 136K, in an alternate embodiment of strap 3230a', strap 3230a' may have loops 3230e' attached thereto or formed thereon that are sized to allow buckle restraint 3230 to pass through the loops to secure the strap and buckle restraint though one of the openings described above to thereby secure the buckle restraint to the seat panel.

Referring to FIG. 137, the numeral 3300 generally refers to another embodiment of a pediatric restraint assembly. Similar to the previous embodiments, pediatric restraint assembly 3300 may include a five point harness that is configured so that it can accommodate patients that weigh in a range of about 4 to 99 lbs. For a description of the straps that may be used to form the harness in pediatric restraint assembly 3300, reference is made to the above embodiments. Though it should be understood, as in the case of any of the previous embodiments, and as will be more fully described below in reference to FIGS. 146A-146D, other harness configurations may be used.

Referring again to FIG. 137, pediatric restraint assembly 3300 includes a back panel 3310 (with portions removed for clarity) and a seat panel 3320, and a plurality of straps (see previous embodiments) coupled thereto for securing the back panel 3310 to the seat panel 3320, as well as coupling the assembly 3300 to the transport apparatus and/or to the adult restraint R. Thus, the panels are separate and may be spaced apart so that they have a distance of about % inches to about 24 inches—depending on the size of the patient. Or they may be positioned so that they have an abutting relationship with 0 separation.

In the illustrated embodiment, seat panel 3320 also includes a central portion 3321 and two upwardly extending angled sides 3328, which may be rigidly joined with central portion 3321 during molding of seat panel 3320 or mounted by hinges to central portion 3321 to allow them to fold. Sides 3328 are optionally spaced to cradle the hips of a patient. Further, similar to the previous embodiments, sides 3328 may have intermediate bends or hinges to allow seat panel to fold or simply conform to the underlying EMS cot mattress. In one embodiment, seat panel 3320 and back panel 3310 are each molded with a rigid fixed configuration (except optionally e.g. the headrest portions 3326a described below).

Sides 3328 may also include or form flanges 3328c to form arm rests at their upper ends, which may be more suitable for children or small adults. Flanges 3328c may also be covered, such as by over molding, with a cushioning material to form arm rest cushions, similar to cushions 3228c' as shown in FIG. 136D. Sides 3328 and central portion 3321 may also form mounting surfaces for mounting brackets, similar to the previous embodiment.

In the illustrated embodiment, seat panel 3320 is reinforced, for example, around the buckle restraint anchor region by a raised or relief potion 3321b arranged so that it can be located between the legs of a patient, which reinforces, as noted the anchor point for the harness buckle restraint. Seat panel 3320 may also be reinforced by ribs, as partially seen in FIG. 137. The relief may be wedge-shaped and extend from the free edge of seat panel 3320 to the slotted opening 3320a. For further details of relief portion 3320b and ribs and variations thereof, reference is made to the above embodiments.

As best seen in FIG. 137, the shape of the back panel 3310 may vary and the number of openings 3310a may vary to provide anchor points for the various straps and/or allow the various straps described herein to be threaded through the back panel. Further, similar to some of the previous embodiments the back panel may be configured to improve the comfort and/or support of the head of the patient.

For example, back panel 3310 may have a headrest 3326 with articulatable headrest portions 3326a on either side, which can be adjusted to cradle the head of the patient. Articulatable headrest portions 3326a may be hinged to a central portion 3327 of headrest 3326 and, further, hinged so that their positions can be fixed at least until a sufficient force is applied to move them, for example using friction hinges 3326b. To facilitate movement of headrest portions 3326a, each headrest portion may include a pull tab 3326c, for example, formed from a rigid plastic flange or a flexible elastomeric or fabric strip formed or attached to the edge of the respective headrest portion.

In the illustrated embodiment, as best seen in FIG. 137A back panel 3310 may be formed from three sub-panel assemblies-3325a, 3325b, 3325c, with sub-panel assembly 3325a forming the back of the back panel, sub-panel assembly 3325b forming the pediatric patient facing side of the back panel, and sub-panel assembly 3325c forming the core or substrate of the back panel.

Each sub-panel assembly has a central portion that forms the lower back portion and an upper portion that forms the headrest, as well as two headrest portions and, further, has the same overall outline and number of openings so that when aligned and coupled together they form the overall outline of panel 3310 and form openings 3310a, as well as the articulateable head rest portions 3326a.

At least one or both of sub-panels 3325a, 3325b are formed with or from cushioning material to provide padding to panel 3310, including padding on the headrest portions 3326a. For example, sub-panels 3325a, 3325b may be formed, such as by molding, from a dense closed cell foam. Central sub-panels 3325c may be formed from plastic or metal such as by molding, casting or the like, to provide strength and rigidly to back panel 3310. To increase the rigidity, central sub-panel 3325c may be formed with a plurality reinforcing ribs 3311a and relief areas 3311b, which also form recesses 3311c (FIG. 137B) on the opposed side to receive hinges 3326b so that at least the leaves of the hinges may be flush with the surface of sub-panel 3325c.

Sub-panel assembly 3325c may also incorporate engagement structures, such as hooks 3315, which may be mounted via fasteners 3315a, adhesive or maybe molded therein. The sub-panel assemblies are coupled together using fasteners 3310s, such as male posts or nesting screws or the like. The fasteners may be provided only on the inside facing surfaces of sub-panel assemblies 3325a, 3325b (e.g. as shown in FIG. 137A, B) to couple to central sub-panel assembly 3325c via engagement structures 3310r formed or provided on or in the sub-panel assembly components—such that the fasteners do not protrude and are not detectible by a user. Suitable engagement structures may be formed by openings and the surrounding material, including openings surrounded by flexible radially extending fingers, for example, to form snap fit couplings. Alternately, the fasteners may be mounted through the respective sub-panel assembly and optionally recessed in the respective sub-panel assembly components (such as shown in FIG. 138A).

Similarly, sub-panel assemblies 3325a, 3325b may include reinforcements area (such as formed by plate inserts) and/or relief areas, such as areas 3227a to accommodate hooks 3315 and/or reinforce the region where the straps extend into the back panel. In general, each of the sub-panel assemblies 3325a, 3325b may have inwardly facing planar surfaces so that the make close contact with the respective side of the central sub-assembly 3325c.

Optionally either or both sub-panel assemblies 3325a, 3325b may be formed from substrates 3325e that support the cushioning material, such as by being over molded with the cushioning material, such as foam, and also support (via co-molding or bonding via an adhesive or mechanical mounting) or form the fasteners. A suitable substrate may comprise a metal sheet or a plastic sheet, with portions of the substrate projecting from the cushioning material to form the tabs described above.

Referring to FIGS. 138-139, the numeral 3410 designates another embodiment of a back panel that may be used with any of the seat panels described above. In the illustrated embodiment, back panel 3410 is similar to back panel 3310, but is formed by sub-panel assemblies 3425a, 3425b, and 3425c that are coupled together by fasteners 3410s that pass through the sub-panel assemblies 3425a, 3425b to couple to central sub-panel assembly 3425c. Each of the sub-panel assemblies 3425a, 3425b includes recesses around the respective fasteners so that neither the pediatric patient nor the adult holding the pediatric restraint assembly seated on the emergency transport apparatus can detect or feel the fasteners. For example, as best seen in FIG. 138A, fasteners 3410s may comprise nesting screws that extend and join together through or in openings provided in sub-panel assembly 3425c.

In the illustrated embodiment sub-panel assembly 3425a may be configured to cover and conceal all the harness components, such as straps 3016, shoulder anchor straps 3018 and their buckles 3018b, but also provide upper and lower openings 3429a, 3429b so that straps 3016 can exit sub-panel assembly 3425a for connection to the transport apparatus. Further, sub-assembly panel assembly 3425a may be contoured to either simply accommodate the harness components and/or to provide additional cushioning and/or a comfortable contour or for the adult holding the restraint assembly. For further details of the construction of back panel reference is made to the above embodiment and to any previous embodiment for a description of the harness components that may be use.

Referring to FIGS. 140-141, back panel 3410 as well as its associate seat panel 3420 may each include a cover 3400c and 3400c'. As best understood from FIG. 142, each cover 3400c and 3400c' may include an outer sheet 3400d, 3400d' of flexible material, such as a fabric sheet, such as nylon, or the like, and one or more pads 3400p formed from cushioning material, such as foam, including closed cell foam. Optionally the covers may be washable or at least surface cleanable. Pads 3400p may be provided in discrete locations, such as the head section or the lumbar region of the back panel. The pads may be strategically placed where the greatest pressure may occur or may be provided to cover the entire underlying back and/or seat panel.

For example, pads 3400p may be mounted to the outer sheet by stitching or by an adhesive, or the pads may be vacuum coated with the material forming the outer sheet.

To secure the covers 3400c, 3400c' to the underlying back and seat panels, each cover may include a perimeter strip 3400e, for example of elastic material, which is joined with the outer sheet, for example by stitching, welding or glueing, and a pull cord 3400f that extend through, e.g. via a loop or though openings formed in the strip so that the cover can be pulled tight and cinched against the respective panel. Therefore, covers 3400c, 3400c' maybe removable and washable/cleanable as noted.

While illustrated in the context of back and seat panels 3410 and 3420, it should be understood that covers 3400c, 3400c' may be used on any of the restraint assemblies described herein. Further, the pads may supplement the cushioning formed on the respective panels or may be used in lieu thereof. As such, the contouring and/or cushioning may be provided by the pads in the cover or by the cushioning material of the panels themselves or a combination of both.

Referring to FIG. 143, another embodiment of a back panel 3510, which is configured for use alone without the seat panel and which is, therefore, more suitable for larger patients, such as adults. Back panel 3510 may be similarly used with standard emergency cot restraints and to that end include clips on the back of back panel for mounting to similar structures formed or provided on the X frame restraints described above. For example, the clips may be molded or otherwise attached to the back part of the central portion 3521 for securing the back panel to the straps as noted above or directly to the frame of the emergency cot or other transport apparatuses.

As best seen in FIG. 143, back panel 3510 includes a central portion 3521 with a pair of headrest portions 3526*a*, which form a headrest for a person or a patient and which may be coupled to the central portion 3521 via hinges, such as friction hinges, so that the position of the side or headrest portions can be held in place absent a sufficient force to overcome the friction in the hinges, such as described above in reference to the above embodiments.

Central portion 3521 and headrest portions 3526*a* may each may be similarly be formed from a plastic or metal substrate and then covered, such as by over molding or mechanical attachment with a cushioning material, such as describe above in reference to above embodiments.

In the illustrated embodiment, headrest portions 3526*a* may be configured so that when folded there is no interference (by providing triangular cut-outs between them and the central portion), and hence avoiding any bunching of any covers that may be provided over the respective components of the back panel. For example, covers, such as covers 3400*c*, 3400*c'*, may be configured to independently mount to the central portion and to the head rest portions so as not to interfere with to folding of headrest portions 3526*a*.

Lower portion of central portion 3521 may be configured, either by the shape of the substrate or cushioning material provided thereon or both, to form a raised curved region that can provide lower back support to further increase the comfort of a person or patient supported on an emergency cot or transport device. For further details of the optional construction of the back panel reference is made to the above embodiments.

Referring to FIG. 144, the numeral 3700 generally refers to another embodiment of a pediatric restraint assembly. Similar to the previous embodiments, pediatric restraint assembly 3700 forms a five point harness. Pediatric restraint assembly 3700 is also configured to couple to an existing adult restraint, and optionally while the adult restraint is being used by an adult, but may also be mounted to the transport apparatus via strap extensions that are secured to the transport apparatus.

Referring again to FIG. 144, pediatric restraint assembly 3700 is of similar construction to assembly 3000 and includes a back panel 3710 and a seat panel 3720 and a plurality of straps coupled thereto for securing the assembly 3700 to the transport apparatus. Assembly 3700 also include two sets of straps—restraint assembly anchor straps to anchor the restraint assembly to the transport apparatus and patient restraint straps to restrain the patient on the restraint assembly.

Similar to assembly 3000, assembly 3700 includes two back anchor straps 3716 (to anchor the restraint assembly to the transport apparatus), which thread though slotted openings in back panel 3710, and one seat anchor strap 3019 (to anchor the restraint assembly to the transport apparatus) that threads through slotted opening in seat panel 3720. Back anchor straps 3016 are also threaded through slotted openings formed in seat panel 3720 to couple the two panels together. As shown, back panel 3710 may be moved up straps 3716 to accommodate pediatric larger patients.

In the illustrated embodiment, the shoulder/waist straps (not shown, but see straps 3014) couple via adjustable buckles on one end to shoulder anchors straps 3018, which are integrated (e.g., by stitching, glueing or otherwise) to back panel 3710. Similarly, the other end of the shoulder/waist straps are coupled via adjustable buckles to waist anchor straps 3014*d*, which may also be integrated (e.g., by stitching, glueing or otherwise) to seat panel 3720.

Center buckle 3730, to which shoulder/waist straps couple in a similar manner to straps 3014 described above, may be integrated with seat panel 3720 or coupled to seat panel 3720 in a similar manner to buckle 3030 described above.

Seat panel 3720 may be anchored to the EMS cote in a similar manner to seat panel 3020 by way of a seat anchor strap 3719 that is threaded through openings in seat panel 3720.

Like back panel 3010, back panel 3710 may also be formed with two sections—upper and lower sections, with the upper section similarly forming a head support or rest, and the lower section forming a back support. In the illustrated embodiment, the upper section may include slotted openings to tether a head restraint, such as the separate head restraints described above.

In any of the above restraints one or more of the components, including any of the afore mentioned covers, may incorporate antimicrobial treatments, such as MICROBAN or antimicrobial metals, such as silver, copper or the like. Further, the covers may be formed from washable or at least cleanable materials to minimize contamination.

For further details of assembly 3700 and how it may be mounted, reference is made to assembly 3000.

Referring to FIG. 145, any of the restraint assemblies by be configured with multiple hinges to that it can be folded into a more compact configuration. For example, the restraint assemblies headrest portions may first be folded inwardly over the central portion of the headrest and then together fold over the lower portion of the back panel (when a hinge is provided between the upper portion and lower portion of the back panel. Then the folded back panel may be placed on the central portion of the seat panel with the two sides of the seat panel then folded over the folded back panel. In one embodiment the overall height of the restraint assemblies when folded may be less than 10 inches, less than 8 inches, less than 6 inches and in some embodiments about 5 inches or less, depending on the thicknesses of the cushioning material and the substrates.

In other embodiments the back panel may simply fold over the seat panel between sides of the seat panel, such as shown in FIG. 145A. As best seen in FIG. 145A, optionally any of the above restraint assemblies may include one or more straps, including elastic straps, to manage the restraint assembly components when folded. With reference to restraint assembly 3000 in FIG. 145A, the back side of back panel may include a strap 3090 secured at its opposed ends to the back panel by stitching, snaps, releasable fasteners, such as VELCRO patches, buttons or the like so that the strap forms a loop with the back of the panel for receiving there between the harness straps 3014 and buckles and buckle restraint 3030, which may be bundled or rolled together before placing under strap 3090.

Referring FIGS. 145B-145D, one or more the ends of any the harness straps or anchor straps may have a coupler 3092, such as an elastic loop, attached thereto so that when the strap is rolled up it can be retained in its rolled up configuration by coupler 3092 and thereafter inserted under strap 3090.

Optionally, as best seen in FIG. 145D, the end of the strap may have a tactile end or cap 3094 to improve facilitate grabbing and pulling of the strap. For example, the tactile cap may be formed by another material or fabric with a texture to optionally provide a higher coefficient of friction than the strap webbing material. Further, the tactile cap may be color coded and/or otherwise marked. For example, tactile cap 3094 may be marked by an image, formed for example by a heat transfer graphic, to provide a visual indication of which strap it is, which can, therefore, make it easier for a user to follow visual instructions, such as in a user's manual or an app on a hand held device, such as a phone, or a printed label on the back of the restraint assembly.

Coupler 3092 may be similarly color coded or marked with an image 3096, formed for example by a heat transfer graphic. The tactile cap 3094 may be formed, as noted from fabric that is sewn over the end of the strap (whose distal end may be heat treated to stabilize the webbing). Coupler 3092 may be sewn or glue or welded onto the strap adjacent or under the tactile cap.

As noted and illustrated above, one or more of the straps may be color coded to facilitate use of the restraint assembly. As best seen in FIG. 145E, for example, in simplest form, the harness straps HS may be color coded in one color, while the restraint anchor straps AS may be color coded in another color. Optionally, the harness straps may be color coded based on a patient's weight or size (as noted above), with the restraint assembly, therefore, having two or more harness strap sets to accommodate different size patients. Alternately, one set of harness straps may fit a full range of patient sizes, as noted above, and optionally may have markings provided thereon, such as heat transfer images, which can be used as guides for different size patients. Further, as previously described the strap and buckles may be color coded or have markings to indicate which buckles the straps should be inserted into.

As noted above, a variety of harness configurations may be used and/or additional straps map be used. Referring to FIG. 146A, suitable harnesses that can be employed in the pediatric restraints include the five point harness formed by buckle restraint 3030 (FIG. 146A) described above, but may also incorporate a chest strap 3012a (FIG. 157) that releasable joins the shoulder strap portions of straps 3014. In another embodiment, shown in FIG. 146B, a three point harness buckle restraint 3031 be used with separate leg straps, which are respectively anchored to the seat panel. In this manner, the harness straps may be independently adjusted. The shoulder straps may be joined by a chest strap 3012a and optionally may be extended to allow the restraint assembly to be carried by a person's shoulders.

In yet another embodiment, rather than having a centrally anchored harness, the restraint assembly may use separate straps 3012b, 3012c for each limb, such as shown in FIG. 146C, with each strap anchored to the respective back or seat panels and having its own buckle to secure the strap around the respective limb and also provide for adjustment. In yet another embodiment, the shoulder and wait straps may be separate, with the shoulder straps joined by a chest strap 3012a (FIG. 146D), and the waist straps (and buckle restraint anchor strap, which also may be referred as crotch strap) are coupled to a three way buckle restraint 3032. Similar to the previous embodiment, it may provide more access to the abdomen of the patient.

In each case the various straps may be adjustable to accommodate a wide range of patient weights and heights as noted above.

Referring to FIGS. 147-156, to secure the pediatric restraint assembly to the cot, patient, the user places the restraint assembly on the seat section of the cot mattress adjacent the back or "Fowler" section of the mattress. The user then unfolds (when using a foldable version and assuming it is folded) the restraint assembly and then secures the back anchor straps to the EMR restraint engagement structures E (FIGS. 149 and 150). Then the user then couples the opposed ends of the seat anchor strap (e.g. 3019) to the anchor points provided on the cot deck frame (FIGS. 151 and 152). Once the restraint assembly is anchored to the cot, the user then pulls the shoulder/waist straps 3014 apart (FIG. 154) and places the patient on top of the open restraint assembly (FIG. 155) and brings the shoulder/waist straps 3014 over the patient's shoulders. After positioning the center buckle restraint 3030 between the patient's legs, the user then secures the shoulder/waist straps 3014 to the center buckle restraint 3030 (FIG. 156). The user then tighten all the straps to create a snug and secure fit.

As noted above, back panel 3010 may also include an integral head support formed by upper portion3026. Upper portion3026 may be formed with a cushion or cushions, such as by molding or applying using an adhesive, to the face of the upper portion3026, such as shown in any one of head restraints 2710, 2810, or 2910, to thereby provide a cushioned head cradle.

Although illustrated with back and seat panels being immediately adjacent each other, back panel may be moved up the back anchor straps to accommodate larger pediatric patients, as shown in FIG. 144. Further one or more the anchor straps may be integrally formed with the respective panels.

Optionally, referring to FIGS. 157 and 158, any of the above restraint assemblies may be mounted to the emergency cot mattress over an insert 4010 or 4020. Insets 4010 and 4020 may be formed from foam and provided added cushion to the patient supported therein. Each insert may include one or more openings to thread any of the anchoring straps there through to better secure the insert under the patient. For example, insert 4020 is configured as a large cushion to accommodate a wider range of patients and also provide multiple openings 4020a to receive the various straps based on the side of the patient.

In a similar manner as described above, to ease installation and use of any of the restraint assemblies, icons and/or color coding be used on the buckles so that each buckle can be quickly and easily matched up with the correct buckles on the adult restraint or on the cot. Similarly, as noted the straps may be color coded—for left and right side, for example. For further details, reference is made to the previous embodiment. Additionally, reflective elements may also be incorporated into restraint assembly to provide better visibility in low light conditions, including smoke conditions.

As noted above, the pediatric restraint assemblies may couple to an adult restraint, already attached to the transport apparatus. As described in some embodiments, the shoulder/waist straps may releasably couple to the shoulder straps of the adult restraint at shoulder anchor points provided on the adult restraint shoulder straps via, for example, buckles.

In other embodiments, the shoulder/waist straps are isolated from the restraint anchors straps, with the shoulder/waist and crotch straps anchoring to the restraint panels, while the restraint panels are anchored to the emergency cot or transport apparatus either directly and/or via the adult harness straps. Thus, the adult harness restraint may provide the anchor points for the pediatric harness straps or the restraint assembly anchor straps. Suitable anchor points depend on the coupler being used to couple the strap to the adult harness and may include loops, folded webbing with eyelets, which are sewn on the strap of the harness or the strap may comprise tubular webbing, have D rings secured thereto via a folded strip of webbing (sewn thereto). Optionally, the webbing of the strap may be folded and sewn together to form a loop. A cable may be used and formed as loop that is secured to the adult harness straps by a folded strip of webbing, which is sewn or otherwise attached to the strap.

As noted in some embodiments, the waist end of shoulder/waist straps 3014 secure to the seat panel adjacent the seat strap 3019, which anchors the seat panel to straps that may be located on the deck frame of the back section (commonly referred to as the "Fowler section") of the deck (e.g. adjacent the hinges to the seat section (and hence are mounted to the moving portion of the deck)), which therefore serve as the pediatric restraint assembly waist anchor points.

Each of the straps may be adjustable using various forms of buckles to accommodate different sized patients and, further, to keep the hips of the patient aligned with fowler/seat joint (joint between the seat section and back section of the deck). In each case, the respective buckles may be slidably mounted to the respective straps or strap portions to help adjust to smaller or larger patients and also to provide greater access to the patient when needed. In addition, any of the straps may include a pull tab or loop (see previous embodiment for examples).

In addition to easing pulling of the straps, as noted, tactile caps or tabs or loops can provide tactile indications of touch points/adjustment points and be formed from fabric or rubber or plastic and may be sewn on, glued on, welded on, or molded on to the respective strap ends. For example, as described above a fabric may be mounted to the end of one or more straps. Optionally, the end of the strap may be folded back over itself and then secured in place by a polyethylene (PE) board, which loops around the folded over and then shrink wrapped. The end of the strap may be folded over multiple times and then shrink wrapped to increase the thickness and stiffness of the end of the strap. The shrink wrap may be at the distal end of the strap or spaced from the end so that the folds of the strap can form a loop—again increasing the tactile characteristic of the end of the strap.

In one embodiment a clip, such a molded plastic or metal clip, with protruding portions may be sewn or shrink wrapped on the end of the strap to enhance the grip of a user when pulling on the strap.

In addition to the loops, each strap may include a clip (not shown), such as a sliding clip, which can be used to keep loose ends of the respective strap tethered (to the strap) to maintain the straps tight and organized.

While numerous embodiments have been shown and described, it should be understood that one or more features of one embodiment may be substituted or added to another embodiment. For example, as noted, various harnesses may be used and various buckles and strap arrangements may be used to secure the pediatric patient to the panel or panels and various buckles and strap arrangements may be used to anchor the restraint assemblies to the adult restraint (harness) and/or the transport apparatus. A variety of different materials may be used for the panels (e.g. back and seat panels or front panels), and various cushioning features or accessories may be incorporated into the various restraint assemblies.

For further details of a suitable patient support, such as for deck 16, and other structures of the transport apparatus, for example of an emergency cot, not specifically mentioned or described herein, reference is made to U.S. Pat. Nos. 5,537,700 and 7,398,571, and published Application No. WO 2007/123571, commonly owned by Stryker Corporation, which are herein incorporated by reference in their entireties.

The terms "head-end" and "foot-end" used herein are location reference terms and are used broadly to refer to the location of the cot that is closer to the portion of the cot that supports the head of a person and the portion of the cot that supports the feet of a person, respectively, and should not be construed to mean the very ends or distal ends of the cot.

While several forms of the support surface have been shown and described, other forms will now be apparent to those skilled in the art. For example, one or more of the features of one patient support surface may be incorporated into another patient support surface. Similarly, other features from other transport apparatuses cots may be incorporated into transport apparatus 10. Examples of other features that may be incorporated herein are described in U.S. Pat. Nos. 7,398,571; 7,100,224; 5,537,700; 6,701,545; 6,526,611; 6,389,623; and 4,767,148, and U.S. Publication Nos. 2005/0241063 and 2006/0075558, which are all incorporated by reference herein in their entireties.

Therefore, it will be understood that the embodiments shown in the drawings and described above are merely for illustrative purposes, and are not intended to limit the scope of the invention.

We claim:

1. A pediatric restraint system comprising:
a pediatric restraint assembly for securing to a soft compliant support structure of a patient transport apparatus, the patient transport apparatus comprising an emergency stretcher or cot including a longitudinal length and including a frame operable to support the soft compliant support structure, the patient transport apparatus including an adult harness assembly operable to couple to the frame of the patient transport apparatus, said pediatric restraint assembly comprising:
a back section formed from a material to hold its overall shape;
a seat section formed from a material to hold its overall shape;
a connector joining said back section with said seat section and maintaining said back section in a contacting relationship or in a spaced relationship with said seat section;
a child restraint mounted relative to said back and seat sections;
a plurality of connecting members releasably connecting said pediatric restraint assembly to the adult harness assembly, wherein the plurality of connecting members comprise straps extending from a top of the back section and upwardly along the longitudinal length toward an upper portion of the patient transport apparatus, and down a rear side of the patient transport apparatus where the straps directly couple to the adult harness assembly;
wherein the adult harness assembly is usable independently of the pediatric restraint assembly; and
a coupler coupling said seat section of said pediatric restraint assembly to the frame of the patient transport apparatus, wherein said child restraint is not coupled directly to the frame.

2. The pediatric restraint system according to claim 1, wherein said child restraint comprises a five point harness.

3. The pediatric restraint system according to claim 2, wherein said seat section includes opposed upwardly extending sides.

4. The pediatric restraint system according to claim 3, wherein straps thread through said opposed upwardly extending sides.

5. The pediatric restraint system according to claim 2, wherein said straps of said plurality of connecting members form said five point harness.

6. The pediatric restraint system according to claim 1, wherein said adult harness assembly has a first set of coupling points for coupling to the patient transport apparatus and a second set of coupling points; and wherein said plurality of connecting members are configured to releasably connect said pediatric restraint assembly to said second set of coupling points on said adult harness assembly.

7. The pediatric restraint system according to claim 6, wherein said straps releasably couple to a buckle restraint to form a five point harness.

8. The pediatric restraint system according to claim 7, wherein said straps thread through said back and seat sections.

9. The pediatric restraint system according to claim 6, wherein said frame releasably couples to said first set of coupling points of said adult harness assembly.

10. The pediatric restraint system of claim 6, wherein the first set of coupling points correspond to a first set of anchor points for coupling to the patient transport apparatus, and wherein the second set of coupling points correspond to a second set of anchor points.

11. The pediatric restraint system according to claim 1, wherein said connector comprises an adjustable connector, and wherein said contacting or spaced relationship is adjustable.

12. The pediatric restraint system according to claim 11, wherein said connector comprises a strap.

13. The pediatric restraint system according to claim 11, wherein said connector comprises a sliding link.

14. The pediatric restraint system according to claim 1, wherein said adult harness assembly has multiple anchor points spaced from the frame of the patient transport apparatus, and at least a first group of said plurality of connecting members of said pediatric restraint assembly releasably coupling to said multiple anchor points of said adult harness assembly, whereby said pediatric restraint assembly is at least in part coupled to the frame of the patient transport apparatus via said adult harness assembly.

15. The pediatric restraint system according to claim 14, wherein said frame forms at least two anchor points for a second group of said plurality of connecting members of said pediatric restraint assembly.

16. The pediatric restraint system according to claim 1, wherein said contacting or spaced relationship comprises a distance in a range of 0 to 24 inches.

17. The pediatric restraint system according to claim 1, wherein when said back section is folded onto said seat section, said back section nests with said seat section.

18. The pediatric restraint system according to claim 1, wherein the plurality of connecting members include the connector for joining the back section with the seat section.

19. The pediatric restraint system according to claim 1, wherein the adult harness assembly includes a set of pediatric restraint connecting members, and wherein the plurality of connecting members releasably connect said pediatric restraint assembly to the set of pediatric restraint connecting members.

20. A method of securing a pediatric patient to a patient transport apparatus, the patient transport apparatus comprising an emergency stretcher or cot having a longitudinal length and having a frame, a patient support supported by the frame, said method comprising:
  providing an adult harness assembly;
  coupling the adult harness assembly to the patient support and the frame;
  providing a pediatric restraint assembly including:
    a back section formed from a material to hold its overall shape;
    a seat section formed from a material to hold its overall shape;
    a connector joining the back section with the seat section and maintaining the back section in a contacting relationship or in a spaced relationship with the seat section;
    a child restraint mounted relative to the back section and the seat section;
  coupling the pediatric restraint assembly to the adult harness assembly via a plurality of connecting members releasably connecting said pediatric restraint assembly to the adult harness assembly, wherein the plurality of connecting members comprise straps extending from a top of the back section and upwardly along the longitudinal length toward an upper portion of the patient transport apparatus, and down a rear side of the patient transport apparatus where the straps directly couple to the adult harness assembly;
  wherein the adult harness assembly is usable independently of the pediatric restraint assembly; and
  coupling the pediatric restraint assembly to the frame, wherein said coupling the pediatric restraint assembly to the frame includes coupling the seat section of the pediatric restraint assembly to the frame, wherein the child restraint is not coupled directly to the frame.

* * * * *